United States Patent
Baldwin et al.

(10) Patent No.: US 8,163,743 B2
(45) Date of Patent: Apr. 24, 2012

(54) 4-CARBOXAMIDE INDAZOLE DERIVATIVES USEFUL AS INHIBITORS OF PI3-KINASES

(75) Inventors: Ian Robert Baldwin, Stevenage (GB); Kenneth David Down, Stevenage (GB); Paul Faulder, Stevenage (GB); Simon Gaines, Stevenage (GB); Julie Nicole Hamblin, Stevenage (GB); Katherine Louise Jones, Stevenage (GB); Joelle Le, Stevenage (GB); Christopher James Lunniss, Stevenage (GB); Nigel James Parr, Stevenage (GB); Timothy John Ritchie, Stevenage (GB); Christian Alan Paul Smethurst, Harlow (GB); Yoshiaki Washio, Stevenage (GB)

(73) Assignee: GlaxoGroupLimited, Greenford, Middlesex (GB)

( * ) Notice: Subject to any disclaimer, the term of this patent is extended or adjusted under 35 U.S.C. 154(b) by 0 days.

(21) Appl. No.: 12/994,246

(22) PCT Filed: Jun. 3, 2009

(86) PCT No.: PCT/EP2009/056837
§ 371 (c)(1),
(2), (4) Date: Jan. 14, 2011

(87) PCT Pub. No.: WO2009/147187
PCT Pub. Date: Dec. 10, 2009

(65) Prior Publication Data
US 2011/0112070 A1    May 12, 2011

Related U.S. Application Data

(60) Provisional application No. 61/058,978, filed on Jun. 5, 2008, provisional application No. 61/158,423, filed on Mar. 9, 2009.

(51) Int. Cl.
*C07D 231/56*    (2006.01)
*C07D 401/04*    (2006.01)
*A61K 31/416*    (2006.01)
*A61K 31/4439*   (2006.01)
*A61P 11/00*     (2006.01)

(52) U.S. Cl. .............. 514/234.5; 514/338; 514/405; 544/140; 546/275.4; 548/360.1

(58) Field of Classification Search .............. None
See application file for complete search history.

(56) References Cited

U.S. PATENT DOCUMENTS
2004/0009968 A1 *  1/2004  Binch et al. .............. 514/217.05

FOREIGN PATENT DOCUMENTS
| EP | 1679308 | * | 7/2006 |
| WO | WO 03/064397 | * | 8/2003 |
| WO | WO 2007/126841 | * | 11/2007 |
| WO | WO 2007/132171 | * | 11/2007 |

* cited by examiner

*Primary Examiner* — Fiona T Powers
(74) *Attorney, Agent, or Firm* — Robert J. Smith

(57) ABSTRACT

The invention is directed to certain novel compounds. Specifically, the invention is directed to compounds of formula (I) and salts thereof. The compounds of the invention are inhibitors of PI3-kinase activity.

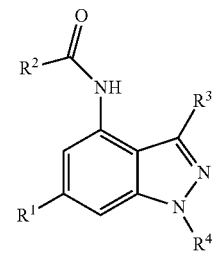

(I)

11 Claims, No Drawings

4-CARBOXAMIDE INDAZOLE DERIVATIVES USEFUL AS INHIBITORS OF PI3-KINASES

This application is a 371 of International Application No. PCT/EP2009/056837, filed 3 Jun. 2009, which claims the benefit of U.S. Provisional Application Nos. 61/158,423, filed 9 Mar. 2009, and 61/058,978, filed 5 Jun. 2008, which are incorporated herein in their entireties.

FIELD OF THE INVENTION

The present invention is directed to certain novel compounds which are inhibitors of the activity or function of the phosphoinositide 3'OH kinase family (hereinafter PI3-kinases), processes for their preparation, pharmaceutical compositions comprising the compounds, and the use of the compounds or the compositions in the treatment of various disorders. More specifically, the compounds of the invention are inhibitors of the activity or function of, for example, PI3Kδ, PI3Kα, PI3Kβ and/or PI3Kγ. Compounds which are inhibitors of the activity or function of PI3-kinases may be useful in the treatment of disorders such as respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

BACKGROUND OF THE INVENTION

Cellular membranes represent a large store of second messengers that can be enlisted in a variety of signal transduction pathways. In relation to function and regulation of effector enzymes in phospholipids signaling pathways, class I PI3-kinases (e.g. PI3 Kdelta) generate second messengers from the membrane phospholipid pools. Class I PI3Ks convert the membrane phospholipid $PI(4,5)P_2$ into $PI(3,4,5)P_3$, which functions as a second messenger. PI and PI(4)P are also substrates of PI3K and can be phosphorylated and converted into PI3P and $PI(3,4)P_2$, respectively. In addition, these phosphoinositides can be converted into other phosphoinositides by 5'-specific and 3'-specific phophatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate $(PI(4,5)P_2)$ to produce phosphatidylinositol-3-phosphate (PI3P), phosphatidylinositol-3,4-bisphosphate $(PI(3,4)P_2)$, and phosphatidylinositol-3,4,5-trisphosphate $(PI(3,4,5)P_3)$, respectively. Class II PI3Ks can phosphorylate PI and PI4P. Class III PI3Ks can only phosphorylate PI (Vanhaesebroeck et al. (1997), above; Vanhaesebroeck et al., Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

Scheme A: Conversion of $PI(4,5)P_2$ to $PI(3,4,5)P_3$

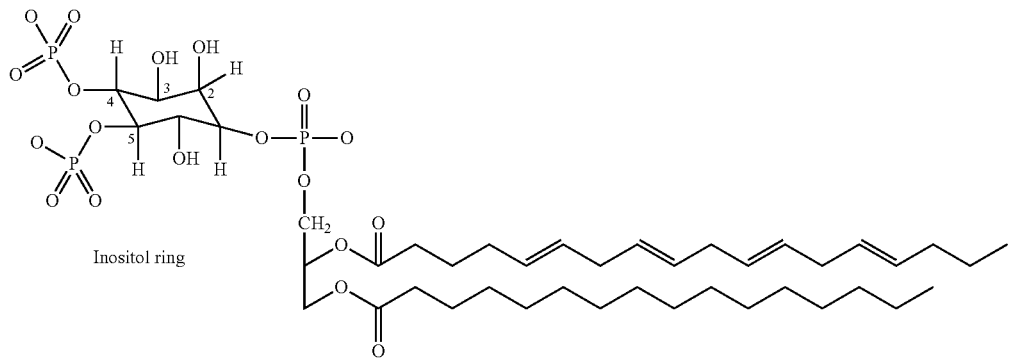

PtdIns(4,5)P₂

↓ PI3K

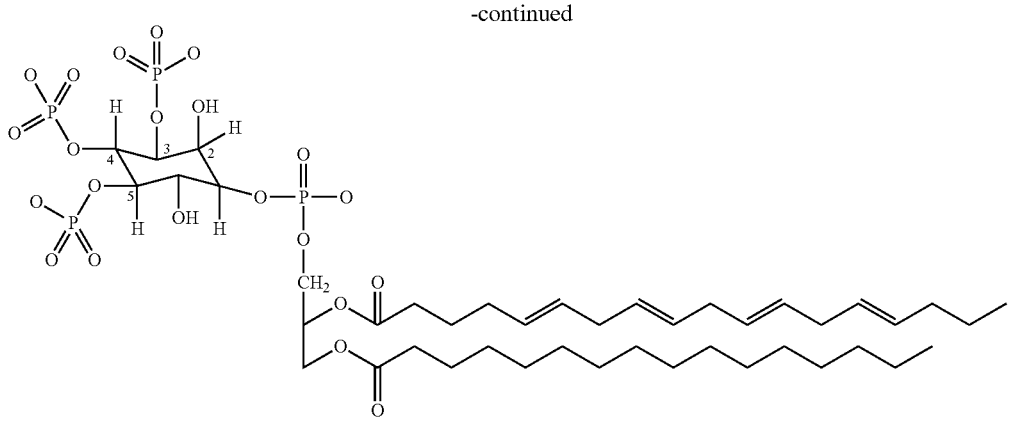

PtdIns(3,4,5)P₃

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3)P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, and are capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation is believed to be involved in a wide range of cellular responses including cell growth, differentiation, and apoptosis (Parker, Current Biology, 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pagès et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the IC$_{50}$ values of wortmannin against each of the various Class I PI3-kinases are in the range of 1-10 nM. Similarly, the IC$_{50}$ values for LY294002 against each of these PI3-kinases is about 15-20 μM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)P$_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

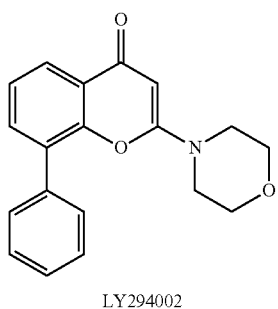

LY294002

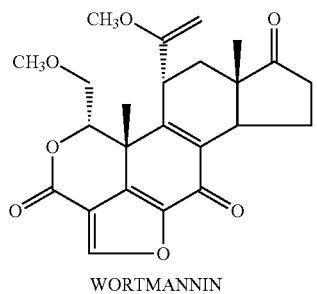

WORTMANNIN

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns(4,5)P2 into Ins(3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5)P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonist (LABA) in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutic benefit for allergic indications such as asthma, allergic rhinitis and atopic dermatitis.

The role of PI3Kδ in B cell proliferation, antibody secretion, B-cell antigen and IL-4 receptor signalling, B-cell antigen presenting function is also well established Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus. Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (Sadhu et al. J. Immunol. (2003) 170(5) p. 2647-54). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that PI3Kδ inhibition should not globally inhibit neutrophil functions required for innate immune defence. PI3Kδ's role in neutrophils offers further scope for treating inflammatory diseases involving tissue remodeling such as COPD or rheumatoid arthritis.

In addition, there is also good evidence that class Ia PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110α (PIK3CA gene) have been associated with various other tumors such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered novel compounds which are inhibitors of PI3-kinase activity. Compounds which are PI3-kinase inhibitors may be useful in the treatment of disorders associated with inappropriate PI3-kinase activity, for example in the treatment and prevention of disorders mediated by PI3-kinase mechanisms. Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

In one embodiment, compounds of the invention may show selectivity for PI3-kinases over other kinases. For example, the compounds of the invention may show selectivity for PI3-kinases over DNA-dependent protein kinase (DNA-PK).

In one embodiment, compounds of the invention may show selectivity for PI3Kδ over other PI3-kinases. For example, the compounds of the invention may show selectivity for PI3Kδ over PI3Kα and/or PI3Kβ.

SUMMARY OF THE INVENTION

The invention is directed to certain novel compounds. Specifically, the invention is directed to compounds of formula (I)

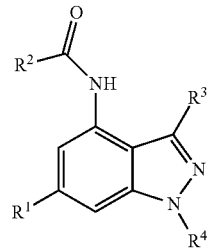

wherein $R^1$, $R^2$, $R^3$ and $R^4$ are as defined below, and salts thereof.

The compounds are inhibitors of PI3-kinase activity. Compounds which are PI3-kinase inhibitors may be useful in the treatment of disorders associated with inappropriate PI3-kinase activity, such as asthma and chronic obstructive pulmonary disease (COPD). Accordingly, the invention is further directed to pharmaceutical compositions comprising a compound of formula (I) or a pharmaceutically acceptable salt thereof. The invention is still further directed to methods of inhibiting PI3-kinase activity and treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation for the compounds of the invention.

DETAILED DESCRIPTION OF THE INVENTION

In one embodiment, the invention is directed to compounds of formula (I)

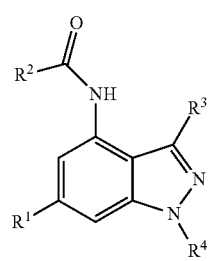

wherein $R^1$ is phenyl substituted by one or two substituents independently selected from $C_{1-6}$alkyl, —$OR^5$, halo, —CN, —$COR^6$, $CO_2R^7$, —$CONR^8R^9$, —$NR^{10}R^{11}$, —$NHCOR^{12}$, —$SO_2R^{13}$, —$(CH_2)_m SO_2NR^{14}R^{15}$, —$NHSO_2R^{16}$, and 5-membered heteroaryl wherein the 5-membered heteroaryl contains one or two heteroatoms independently selected from oxygen and nitrogen; or pyridinyl optionally substituted by one or two substituents independently selected from $C_{1-6}$alkyl, —$OR^{17}$, halo, —$SO_2R^{18}$, —$SO_2NR^{19}R^{20}$, —$NHSO_2R^{21}$ and —$NHCOR^{24}$;

$R^2$ is —$(CH_2)_n$-phenyl optionally substituted by —CN or —$NR^{22}R^{23}$; 5- or 6-membered heteroaryl wherein the 5- or 6-membered heteroaryl contains one or two heteroatoms independently selected from oxygen, nitrogen and sulphur and is optionally substituted by $C_{1-6}$alkyl, halo or —$(CH_2)_q NR^{25}R^{26}$; or $C_{3-6}$cycloalkyl optionally substituted by phenyl;

$R^3$ is hydrogen or fluoro;

$R^4$ is hydrogen or methyl;

$R^7$, $R^{17}$, $R^{19}$, $R^{20}$, $R^{22}$, $R^{23}$, $R^{27}$, $R^{28}$ and $R^{29}$ are each independently hydrogen or $C_{1-6}$alkyl;

$R^5$ is hydrogen, $C_{1-6}$alkyl or —$CF_3$;

$R^6$, $R^{12}$, $R^{13}$, $R^{18}$, $R^{33}$ and $R^{34}$ are each independently $C_{1-6}$ alkyl;

$R^8$ and $R^9$ are each independently hydrogen or $C_{1-6}$alkyl, or $R^8$ and $R^9$, together with the nitrogen atom to which they are attached, are linked to form a 5- or 6-membered heterocyclyl optionally containing an oxygen atom;

$R^{10}$ and $R^{11}$ are each independently hydrogen or $C_{1-6}$alkyl, or $R^{10}$ and $R^{11}$, together with the nitrogen atom to which they are attached, are linked to form a 5- or 6-membered heterocyclyl optionally containing an oxygen atom;

$R^{14}$ and $R^{15}$ are each independently hydrogen, $C_{1-6}$alkyl, $C_{3-6}$cycloalkyl or —$(CH_2)_p$phenyl, or $R^{14}$ and $R^{15}$, together with the nitrogen atom to which they are attached, are linked to form a 5- or 6-membered heterocyclyl optionally containing an oxygen atom;

$R^{16}$ is $C_{1-6}$alkyl; or phenyl optionally substituted by $C_{1-6}$alkyl;

$R^{21}$ is $C_{3-6}$cycloalkyl; $C_{1-6}$alkyl optionally substituted by —$CF_3$; phenyl optionally substituted by one or two substituents independently selected from $C_{1-6}$alkyl, —$OR^{27}$, —$CO_2R^{28}$ and halo; —$(CH_2)_uNR^{35}R^{36}$; or 5-membered heteroaryl wherein the 5-membered heteroaryl contains one or two heteroatoms independently selected from oxygen, nitrogen and sulphur and is optionally substituted by one or two substituents independently selected from $C_{1-6}$alkyl;

$R^{24}$ is $C_{1-6}$alkyl optionally substituted by —$OR^{29}$;

$R^{25}$ and $R^{26}$, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl, $C_{3-6}$cycloalkyl, halo, oxo, phenyl optionally substituted by halo, pyridinyl, —$(CH_2)_rOR^{30}$, —$(CH_2)_sNR^{31}R^{32}$, —$COR^{33}$ and —$SO_2R^{34}$;

$R^{30}$ is hydrogen, $C_{1-6}$alkyl or —$(CH_2)_t$phenyl;

$R^{31}$ and $R^{32}$, together with the nitrogen atom to which they are attached, are linked to form a 6-membered heterocyclyl optionally containing an oxygen atom;

$R^{35}$ and $R^{36}$, together with the nitrogen atom to which they are attached, are linked to form a 5- or 6-membered heterocyclyl wherein the 5- or 6-membered heterocyclyl optionally contains an oxygen atom or a further nitrogen atom and is optionally substituted by one or two substituents independently selected from $C_{1-6}$alkyl;

m, n, p, q, r, s and t are each independently 0, 1 or 2; and u is 1 or 2;

and salts thereof (hereinafter "compounds of the invention").

In another embodiment, the invention is directed to compounds of formula (IA)

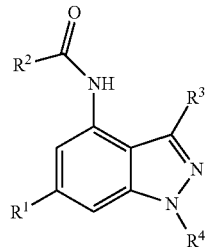

(IA)

wherein $R^1$ is phenyl substituted by one or two substituents independently selected from $C_{1-6}$alkyl, —$OR^5$, halo, —CN, —$COR^6$, $CO_2R^7$, —$CONR^8R^9$, —$NR^{10}R^{11}$, —$NHCOR^{12}$, —$SO_2R^{13}$, —$(CH_2)_mSO_2NR^{14}R^{15}$, —$NHSO_2R^{16}$, and 5-membered heteroaryl wherein the 5-membered heteroaryl contains one or two heteroatoms independently selected from oxygen and nitrogen, or pyridinyl optionally substituted by one or two substituents independently selected from $C_{1-6}$alkyl, —$OR^{17}$, halo, —$SO_2R^{18}$, —$SO_2NR^{19}R^{20}$, —$NHSO_2R^{21}$ and —NH$COR^{24}$;

$R^2$ is —$(CH_2)_n$-phenyl optionally substituted by —CN or —$NR^{22}R^{23}$, 5- or 6-membered heteroaryl wherein the 5- or 6-membered heteroaryl contains one or two heteroatoms independently selected from oxygen, nitrogen and sulphur and is optionally substituted by $C_{1-6}$alkyl, halo or —$(CH_2)_qNR^{25}R^{26}$, or $C_{3-6}$cycloalkyl optionally substituted by phenyl;

$R^3$ is hydrogen or fluoro;

$R^4$ is hydrogen or methyl;

$R^7$, $R^{17}$, $R^{19}$, $R^{20}$, $R^{22}$, $R^{23}$, $R^{27}$, $R^{28}$ and $R^{29}$ are each independently hydrogen or $C_{1-6}$alkyl;

$R^5$ is hydrogen, $C_{1-6}$alkyl or —$CF_3$;

$R^6$, $R^{12}$, $R^{13}$, $R^{18}$, $R^{33}$ and $R^{34}$ are each independently $C_{1-6}$alkyl;

$R^8$ and $R^9$ are each independently hydrogen or $C_{1-6}$alkyl, or $R^8$ and $R^9$, together with the nitrogen atom to which they are attached, are linked to form a 5- or 6-membered heterocyclyl optionally containing an oxygen atom;

$R^{10}$ and $R^{11}$ are each independently hydrogen or $C_{1-6}$alkyl, or $R^{10}$ and $R^{11}$, together with the nitrogen atom to which they are attached, are linked to form a 5- or 6-membered heterocyclyl optionally containing an oxygen atom;

$R^{14}$ and $R^{15}$ are each independently hydrogen, $C_{1-6}$alkyl, $C_{3-6}$cycloalkyl or —$(CH_2)_p$phenyl, or $R^{14}$ and $R^{15}$, together with the nitrogen atom to which they are attached, are linked to form a 5- or 6-membered heterocyclyl optionally containing an oxygen atom;

$R^{16}$ is $C_{1-6}$alkyl, or phenyl optionally substituted by $C_{1-6}$alkyl;

$R^{21}$ is $C_{3-6}$cycloalkyl, $C_{1-6}$alkyl optionally substituted by —$CF_3$, or phenyl optionally substituted by one or two substituents independently selected from $C_{1-6}$alkyl, —$OR^{27}$, —$CO_2R^{28}$ and halo;

$R^{24}$ is $C_{1-6}$alkyl optionally substituted by —$OR^{29}$;

$R^{25}$ and $R^{26}$, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl, $C_{3-6}$cycloalkyl, halo, oxo, phenyl optionally substituted by halo, pyridinyl, —(CH$_2$)$_r$OR$^{30}$, —(CH$_2$)$_s$NR$^{31}$R$^{32}$, —COR$^{33}$ and —SO$_2$R$^{34}$;
R$^{30}$ is hydrogen, C$_{1-6}$alkyl or —(CH$_2$)$_t$phenyl;
R$^{31}$ and R$^{32}$, together with the nitrogen atom to which they are attached, are linked to form a 6-membered heterocyclyl optionally containing an oxygen atom, and
m, n, p, q, r, s and t are each independently 0, 1 or 2;
and salts thereof.

In another embodiment, the invention is directed to compounds of formula (IB)

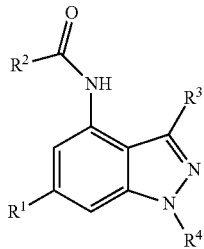

(IB)

wherein
R$^1$ is phenyl substituted by one or two substituents independently selected from C$_{1-6}$alkyl, —OR$^5$, halo, —CN, —COR$^6$, CO$_2$R$^7$, —CONR$^8$R$^9$, —NR$^{19}$R$^{11}$, —NHCOR$^{12}$, —SO$_2$R$^{13}$, —(CH$_2$)$_m$SO$_2$NR$^{14}$R$^{15}$, —NHSO$_2$R$^{16}$, and 5-membered heteroaryl wherein the 5-membered heteroaryl contains one or two heteroatoms independently selected from oxygen and nitrogen, or
pyridinyl optionally substituted by one or two substituents independently selected from C$_{1-6}$alkyl, —OR$^{17}$, halo, —SO$_2$R$^{18}$, —SO$_2$NR$^{19}$R$^{20}$ and —NHSO$_2$R$^{21}$;
R$^2$ is —(CH$_2$)$_n$-phenyl optionally substituted by —CN or —NR$^{22}$R$^{23}$, 5- or 6-membered heteroaryl wherein the 5- or 6-membered heteroaryl contains one or two heteroatoms independently selected from oxygen, nitrogen and sulphur and is optionally substituted by C$_{1-6}$alkyl or halo, or C$_{3-6}$cycloalkyl optionally substituted by phenyl;
R$^3$ is hydrogen or fluoro;
R$^4$ is hydrogen or methyl;
R$^7$, R$^{17}$, R$^{19}$, R$^{20}$, R$^{22}$ and R$^{23}$ are each independently hydrogen or C$_{1-6}$alkyl;
R$^5$ is hydrogen, C$_{1-6}$alkyl or —CF$_3$;
R$^6$, R$^{12}$, R$^{13}$ and R$^{18}$ are each independently C$_{1-6}$alkyl;
R$^8$ and R$^9$ are each independently hydrogen or C$_{1-6}$alkyl, or R$^8$ and R$^9$, together with the nitrogen atom to which they are attached, are linked to form a 5- or 6-membered heterocyclyl optionally containing an oxygen atom;
R$^{10}$ and R$^{11}$ are each independently hydrogen or C$_{1-6}$alkyl, or R$^{10}$ and R$^{11}$, together with the nitrogen atom to which they are attached, are linked to form a 5- or 6-membered heterocyclyl optionally containing an oxygen atom;
R$^{14}$ and R$^{15}$ are each independently hydrogen, C$_{1-6}$alkyl, C$_{3-6}$cycloalkyl or —(CH$_2$)$_p$phenyl, or R$^{14}$ and R$^{15}$, together with the nitrogen atom to which they are attached, are linked to form a 5- or 6-membered heterocyclyl optionally containing an oxygen atom;
R$^{16}$ and R$^{21}$ are each independently C$_{1-6}$alkyl, or phenyl optionally substituted by C$_{1-6}$alkyl; and
m, n and p are each independently 0, 1 or 2;
and salts thereof.

In a further embodiment, the invention is directed to compounds of formula (IC)

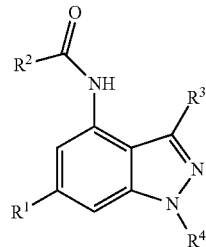

(IC)

wherein
R$^1$ is phenyl substituted by one or two substituents independently selected from C$_{1-6}$alkyl, —OR$^5$, halo, —CN, —COR$^6$, CO$_2$R$^7$, —CONR$^8$R$^9$, —NR$^{10}$R$^{11}$, —NHCOR$^{12}$, —(CH$_2$)$_m$SO$_2$NR$^{14}$R$^{15}$, —NHSO$_2$R$^{16}$, and 5-membered heteroaryl wherein the 5-membered heteroaryl contains one or two heteroatoms independently selected from oxygen and nitrogen; or pyridinyl substituted by one or two substituents independently selected from C$_{1-6}$alkyl, —OR$^{17}$, halo, —SO$_2$R$^{18}$, —SO$_2$NR$^{19}$R$^{20}$, —NHSO$_2$R$^{21}$ and —NHCOR$^{24}$;
R$^2$ is —(CH$_2$)$_n$-phenyl optionally substituted by —CN or —NR$^{22}$R$^{23}$; 5- or 6-membered heteroaryl wherein the 5- or 6-membered heteroaryl contains one or two heteroatoms independently selected from oxygen, nitrogen and sulphur and is substituted by C$_{1-6}$alkyl, halo or —(CH$_2$)$_q$NR$^{25}$R$^{26}$; or C$_{3-6}$cycloalkyl optionally substituted by phenyl;
R$^3$ is hydrogen or fluoro;
R$^4$ is hydrogen or methyl;
R$^7$, R$^{17}$, R$^{19}$, R$^{20}$, R$^{22}$, R$^{23}$, R$^{27}$, R$^{28}$ and R$^{29}$ are each independently hydrogen or C$_{1-6}$alkyl;
R$^5$ is hydrogen, C$_{1-6}$alkyl or —CF$_3$;
R$^6$, R$^{12}$, R$^{18}$, R$^{33}$ and R$^{34}$ are each independently C$_{1-6}$alkyl;
R$^8$ and R$^9$ are each independently hydrogen or C$_{1-6}$alkyl, or R$^8$ and R$^9$, together with the nitrogen atom to which they are attached, are linked to form a 5- or 6-membered heterocyclyl optionally containing an oxygen atom;
R$^{10}$ and R$^{11}$ are each independently hydrogen or C$_{1-6}$alkyl, or R$^{10}$ and R$^{11}$, together with the nitrogen atom to which they are attached, are linked to form a 5- or 6-membered heterocyclyl optionally containing an oxygen atom;
R$^{14}$ and R$^{15}$ are each independently hydrogen, C$_{1-6}$alkyl, C$_{3-6}$cycloalkyl or —(CH$_2$)$_p$phenyl, or R$^{14}$ and R$^{15}$, together with the nitrogen atom to which they are attached, are linked to form a 5- or 6-membered heterocyclyl optionally containing an oxygen atom;
R$^{16}$ is C$_{1-6}$alkyl; or phenyl optionally substituted by C$_{1-6}$alkyl;
R$^{21}$ is C$_{3-6}$cycloalkyl; C$_{1-6}$alkyl optionally substituted by —CF$_3$; phenyl optionally substituted by one or two substituents independently selected from C$_{1-6}$alkyl, —OR$^{27}$, —CO$_2$R$^{28}$ and halo; —(CH$_2$)$_u$NR$^{35}$R$^{36}$; or 5-membered heteroaryl wherein the 5-membered heteroaryl contains one or two heteroatoms independently selected from oxygen, nitrogen and sulphur and is optionally substituted by one or two substituents independently selected from C$_{1-6}$alkyl;
R$^{24}$ is C$_{1-6}$alkyl optionally substituted by —OR$^{29}$;
R$^{25}$ and R$^{26}$, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from C$_{1-6}$alkyl, C$_{3-6}$cycloalkyl, halo, oxo, phenyl optionally substituted by halo, pyridinyl, —(CH$_2$)$_r$OR$^{30}$, —(CH$_2$)$_s$NR$^{31}$R$^{32}$, —COR$^{33}$ and —SO$_2$R$^{34}$;

R$^{30}$ is hydrogen, C$_{1-6}$alkyl or —(CH$_2$)$_t$phenyl;

R$^{31}$ and R$^{32}$, together with the nitrogen atom to which they are attached, are linked to form a 6-membered heterocyclyl optionally containing an oxygen atom;

R$^{35}$ and R$^{36}$, together with the nitrogen atom to which they are attached, are linked to form a 5- or 6-membered heterocyclyl wherein the 5- or 6-membered heterocyclyl optionally contains an oxygen atom or a further nitrogen atom and is optionally substituted by one or two substituents independently selected from C$_{1-6}$alkyl;

m, n, p, q, r, s and t are each independently 0, 1 or 2; and u is 1 or 2;

and salts thereof.

In one embodiment, R$^1$ is phenyl substituted by one or two substituents independently selected from C$_{1-6}$alkyl, —OR$^5$, halo, —CN, —COR$^6$, CO$_2$R$^7$, —CONR$^8$R$^9$, —NR$^{10}$R$^{11}$, —NHCOR$^{12}$, —SO$_2$R$^{13}$, —(CH$_2$)$_m$SO$_2$NR$^{14}$R$^{15}$, —NHSO$_2$R$^{16}$, and 5-membered heteroaryl wherein the 5-membered heteroaryl contains one or two heteroatoms independently selected from oxygen and nitrogen, or pyridinyl optionally substituted by one or two substituents independently selected from C$_{1-6}$alkyl, —OR$^{17}$, halo, —SO$_2$R$^{18}$, —SO$_2$NR$^{19}$R$^{20}$ and —NHSO$_2$R$^{21}$. In another embodiment, R$^1$ is phenyl substituted by one or two substituents independently selected from C$_{1-6}$alkyl, —OR$^5$, halo, —CN, —COR$^6$, CO$_2$R$^7$, —CONR$^8$R$^9$, —NR$^{19}$R$^{11}$, —NHCOR$^{12}$, —(CH$_2$)$_m$SO$_2$NR$^{14}$R$^{15}$, —NHSO$_2$R$^{16}$, and 5-membered heteroaryl wherein the 5-membered heteroaryl contains one or two heteroatoms independently selected from oxygen and nitrogen; or pyridinyl optionally substituted by one or two substituents independently selected from C$_{1-6}$alkyl, —OR$^{17}$, halo, —SO$_2$R$^{18}$, —SO$_2$NR$^{19}$R$^{20}$, —NHSO$_2$R$^{21}$ and —NHCOR$^{24}$. In another embodiment, R$^1$ is phenyl substituted by —OR$^5$. In another embodiment, R$^1$ is pyridinyl optionally substituted by one or two substituents independently selected from C$_{1-6}$alkyl, —OR$^{17}$, halo and —NHSO$_2$R$^{16}$. In another embodiment, R$^1$ is pyridinyl optionally substituted by —OR$^{17}$. In another embodiment, R$^1$ is pyridinyl substituted by two substituents independently selected from C$_{1-6}$alkyl, halo and —NHSO$_2$R$^{21}$. In another embodiment, R$^1$ is pyridinyl substituted by C$_{1-6}$alkyl, for example C$_{1-4}$alkyl such as methyl, and —NHSO$_2$R$^{21}$. In another embodiment, R$^1$ is pyridinyl optionally substituted by halo, for example chloro, and —NHSO$_2$R$^{21}$. In a further embodiment, R$^1$ is pyridinyl substituted by —OR$^{17}$ and —NHSO$_2$R$^{21}$.

The skilled artisan will appreciate that when R$^1$ is pyridinyl substituted by —OR$^{17}$ wherein R$^{17}$ is hydrogen, the R$^1$ group may be drawn as the corresponding keto tautomer. For example, 2-hydroxypyridinyl may be drawn as follows:

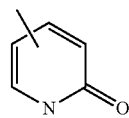

All such tautomeric forms are included whether such tautomers exist in equilibrium or predominantly in one form.

In one embodiment, R$^2$ is —(CH$_2$)$_n$-phenyl optionally substituted by —CN or —NR$^{22}$R$^{23}$, 5- or 6-membered heteroaryl wherein the 5- or 6-membered heteroaryl contains one or two heteroatoms independently selected from oxygen, nitrogen and sulphur and is optionally substituted by C$_{1-6}$alkyl or halo, or C$_{3-6}$cycloalkyl optionally substituted by phenyl. In another embodiment, R$^2$ is —(CH$_2$)$_n$-phenyl optionally substituted by —CN or —NR$^{22}$R$^{23}$, 5- or 6-membered heteroaryl wherein the 5- or 6-membered heteroaryl contains one or two heteroatoms independently selected from oxygen, nitrogen and sulphur and is substituted by C$_{1-6}$alkyl, halo or —(CH$_2$)$_q$NR$^{25}$R$^{26}$, or C$_{3-6}$cycloalkyl optionally substituted by phenyl. In another embodiment, R$^2$ is 5- or 6-membered heteroaryl wherein the 5- or 6-membered heteroaryl contains one or two heteroatoms independently selected from oxygen, nitrogen and sulphur and is optionally substituted by C$_{1-6}$alkyl or halo. In another embodiment, R$^2$ is 5- or 6-membered heteroaryl wherein the 5- or 6-membered heteroaryl contains one or two heteroatoms independently selected from nitrogen and sulphur and is optionally substituted by C$_{1-6}$alkyl or halo. In another embodiment, R$^2$ is 5-membered heteroaryl wherein the 5-membered heteroaryl contains one or two heteroatoms independently selected from nitrogen and sulphur and is optionally substituted by C$_{1-6}$alkyl. In another embodiment, R$^2$ is thiazolyl optionally substituted by C$_{1-6}$alkyl, for example C$_{1-4}$alkyl such as methyl. In another embodiment, R$^2$ is pyridinyl. In another embodiment, R$^2$ is 5- or 6-membered heteroaryl wherein the 5- or 6-membered heteroaryl contains one or two heteroatoms independently selected from oxygen, nitrogen and sulphur and is optionally substituted by C$_{1-6}$alkyl or —(CH$_2$)$_q$NR$^{25}$R$^{26}$. In another embodiment, R$^2$ is 5- or 6-membered heteroaryl wherein the 5- or 6-membered heteroaryl contains one or two heteroatoms independently selected from oxygen, nitrogen and sulphur and is substituted by —(CH$_2$)$_q$NR$^{25}$R$^{26}$. In a further embodiment, R$^2$ is thiazolyl substituted by —(CH$_2$)$_q$NR$^{25}$R$^{26}$.

In one embodiment, R$^3$ is hydrogen.

In one embodiment, R$^4$ is hydrogen. In a further embodiment, R$^4$ is methyl.

In one embodiment, R$^5$ is hydrogen, C$_{1-4}$alkyl such as methyl or isopropyl, or —CF$_3$. In a further embodiment, R$^5$ is hydrogen.

In one embodiment, R$^6$ is C$_{1-4}$alkyl such as methyl.

In one embodiment, R$^7$ is hydrogen.

In one embodiment, R$^8$ and R$^9$ are each independently hydrogen or C$_{1-4}$alkyl such as methyl or ethyl. In a further embodiment, R$^8$ and R$^9$, together with the nitrogen atom to which they are attached, are linked to form pyrrolidinyl.

In one embodiment, R$^{10}$ and R$^{11}$ are each independently C$_{1-4}$alkyl such as methyl. In a further embodiment, R$^{10}$ and R$^{11}$, together with the nitrogen atom to which they are attached, are linked to form morpholinyl.

In one embodiment, R$^{12}$ is C$_{1-4}$alkyl such as methyl.

In one embodiment, R$^{13}$ is C$_{1-4}$alkyl such as methyl.

In one embodiment, R$^{14}$ and R$^{15}$ are each independently hydrogen, C$_{1-4}$alkyl such as methyl, C$_{3-6}$cycloalkyl such as cyclopropyl, or —(CH$_2$)$_q$phenyl. In another embodiment, R$^{14}$ and R$^{15}$, together with the nitrogen atom to which they are attached, are linked to form a 5- or 6-membered heterocyclyl optionally containing an oxygen atom. In another embodiment, R$^{14}$ and R$^{15}$, together with the nitrogen atom to which they are attached, are linked to form pyrrolidinyl. In a further embodiment, R$^{14}$ and R$^{15}$, together with the nitrogen atom to which they are attached, are linked to form morpholinyl.

In one embodiment, R$^{16}$ is C$_{1-4}$alkyl such as methyl. In a further embodiment, R$^{16}$ is phenyl optionally substituted by C$_{1-4}$alkyl such as methyl.

In one embodiment, R$^{17}$ is C$_{1-4}$alkyl such as methyl.

In one embodiment, R$^{18}$ is C$_{1-4}$alkyl such as methyl.

In one embodiment, R$^{19}$ and R$^{20}$ are each hydrogen.

In one embodiment, R$^{21}$ is C$_{3-6}$cycloalkyl, C$_{1-6}$alkyl optionally substituted by —CF$_3$, or phenyl optionally substituted by one or two substituents independently selected from $C_{1-6}$alkyl, —$OR^{27}$, —$CO_2R^{28}$ and halo. In another embodiment, $R^{21}$ is $C_{1-6}$alkyl, or phenyl optionally substituted by $C_{1-6}$alkyl. In another embodiment, $R^{21}$ is $C_{1-4}$alkyl such as methyl. In another embodiment, $R^{21}$ is phenyl. In another embodiment, $R^{21}$ is $C_{3-6}$cycloalkyl, $C_{1-6}$alkyl, for example $C_{1-4}$alkyl, optionally substituted by —$CF_3$, or phenyl optionally substituted by one or two substituents independently selected from $C_{1-6}$alkyl, —$OR^{27}$, —$CO_2R^{28}$ and halo. In another embodiment, $R^{21}$ is $C_{1-4}$alkyl such as methyl optionally substituted by —$CF_3$, or phenyl optionally substituted by one or two substituents independently selected from —$OR^{27}$ and halo. In another embodiment, $R^{21}$ is $C_{1-4}$alkyl such as methyl optionally substituted by —$CF_3$. In another embodiment, $R^{21}$ is phenyl optionally substituted by one or two substituents independently selected from —$OR^{27}$ and halo. In a further embodiment, $R^{21}$ is phenyl substituted by —$OR^{27}$.

In one embodiment, $R^{22}$ and $R^{23}$ are each independently $C_{1-4}$alkyl such as methyl.

In one embodiment, $R^{24}$ is $C_{1-4}$alkyl optionally substituted by —$OR^{29}$.

In one embodiment, $R^{25}$ and $R^{26}$, together with the nitrogen atom to which they are attached, are linked to form a 6-membered heterocyclyl optionally containing an oxygen atom or a further nitrogen atom, wherein the 6-membered heterocyclyl is optionally substituted by one or two substituents independently selected from $C_{1-4}$alkyl and oxo. In another embodiment, $R^{25}$ and $R^{26}$, together with the nitrogen atom to which they are attached, are linked to form a 6-membered heterocyclyl optionally containing an oxygen atom, wherein the 6-membered heterocyclyl is optionally substituted by one or two substituents independently selected from $C_{1-4}$alkyl. In another embodiment, $R^{25}$ and $R^{26}$, together with the nitrogen atom to which they are attached, are linked to form a 6-membered heterocyclyl optionally containing an oxygen atom, wherein the 6-membered heterocyclyl is optionally substituted by one or two methyl groups. In a further embodiment, $R^{25}$ and $R^{26}$, together with the nitrogen atom to which they are attached, are linked to form morpholinyl substituted by two methyl groups.

In one embodiment, $R^{27}$ is $C_{1-4}$alkyl such as methyl.

In one embodiment, $R^{28}$ is hydrogen.

In one embodiment, $R^{29}$ is hydrogen.

In one embodiment, $R^{35}$ and $R^{36}$, together with the nitrogen atom to which they are attached, are linked to form a 6-membered heterocyclyl wherein the 6-membered heterocyclyl optionally contains a further nitrogen atom and is optionally substituted by one or two substituents independently selected from $C_{1-6}$alkyl.

In one embodiment, m is 0 or 1.

In one embodiment, n is 0 or 2.

In one embodiment, p is 1.

In one embodiment, q is 1.

In one embodiment, u is 2.

It is to be understood that the present invention covers all combinations of substituent groups described hereinabove.

In one embodiment, the invention is directed to compounds according to formula (ID)

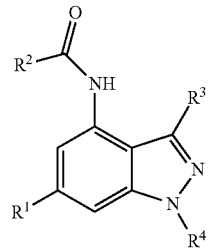

wherein
$R^1$ is pyridinyl substituted by —$OR^{17}$ and —$NHSO_2R^{21}$;
$R^2$ is thiazolyl substituted by —$(CH_2)_q NR^{25}R^{26}$;
$R^3$ is hydrogen;
$R^4$ is hydrogen or methyl;
$R^{17}$ and $R^{27}$ are each independently $C_{1-4}$alkyl;
$R^{21}$ is $C_{1-4}$alkyl optionally substituted by —$CF_3$, or phenyl optionally substituted by one or two substituents independently selected from —$OR^{27}$ and halo;
$R^{25}$ and $R^{26}$, together with the nitrogen atom to which they are attached, are linked to form morpholinyl substituted by two methyl groups; and
q is 1;
and salts thereof.

Compounds of the invention include the compounds of Examples 1 to 116 and 118 to 131 and salts thereof.

In one embodiment, the compound of the invention is:
6-bromo-N-[6-(4-hydroxyphenyl)-1H-indazol-4-yl]-2-pyridinecarboxamide;
N-[6-(3-hydroxyphenyl)-1H-indazol-4-yl]cyclohexanecarboxamide;
N-[6-(3-hydroxyphenyl)-1H-indazol-4-yl]-2-pyridinecarboxamide;
N-[6-(3-hydroxyphenyl)-1H-indazol-4-yl]-3-phenylpropanamide;
4-cyano-N-[6-(3-hydroxyphenyl)-1H-indazol-4-yl]benzamide;
3-(dimethylamino)-N-[6-(3-hydroxyphenyl)-1H-indazol-4-yl]benzamide;
(1R,2R)—N-[6-(3-hydroxyphenyl)-1H-indazol-4-yl]-2-phenylcyclopropanecarboxamide;
N-[6-(3-hydroxyphenyl)-1H-indazol-4-yl]-2-furancarboxamide;
N-[6-(3-hydroxyphenyl)-1H-indazol-4-yl]cyclopropanecarboxamide;
N-{6-[5-(aminosulfonyl)-3-pyridinyl]-1H-indazol-4-yl}-2-methyl-1,3-thiazole-4-carboxamide;
N-(6-{3-[(aminosulfonyl)methyl]phenyl}-1H-indazol-4-yl)-2-methyl-1,3-thiazole-4-carboxamide;
2-methyl-N-{6-[5-(methyloxy)-3-pyridinyl]-1H-indazol-4-yl}-1,3-thiazole-4-carboxamide;
3-(4-{[(2-methyl-1,3-thiazol-4-yl)carbonyl]amino}-1H-indazol-6-yl)benzoic acid;
N-(6-{6-chloro-5-[(phenylsulfonyl)amino]-3-pyridinyl}-1H-indazol-4-yl)-2-methyl-1,3-thiazole-4-carboxamide;
N-{6-[4-(acetylamino)phenyl]-1H-indazol-4-yl}-2-pyridinecarboxamide;
N-(6-{3-[(methylsulfonyl)amino]phenyl}-1H-indazol-4-yl)-2-pyridinecarboxamide;
N-[6-(3-{[(4-methylphenyl)sulfonyl]amino}phenyl)-1H-indazol-4-yl]-2-pyridinecarboxamide;
N-{6-[3,4-bis(methyloxy)phenyl]-1H-indazol-4-yl}-2-pyridinecarboxamide;

N-{6-[3-(4-morpholinyl)phenyl]-1H-indazol-4-yl}-2-pyridinecarboxamide;
N-(6-{3-[(methylamino)carbonyl]phenyl}-1H-indazol-4-yl)-2-pyridinecarboxamide;
N-{6-[3-(2-furanyl)phenyl]-1H-indazol-4-yl}-2-pyridinecarboxamide;
N-{6-[4-(2-furanyl)phenyl]-1H-indazol-4-yl}-2-pyridinecarboxamide;
N-[6-(3-{[(phenylmethyl)amino]sulfonyl}phenyl)-1H-indazol-4-yl]-2-pyridinecarboxamide;
N-[6-(3-cyanophenyl)-1H-indazol-4-yl]-2-methyl-1,3-thiazole-4-carboxamide;
2-methyl-N-{6-[3-(methylsulfonyl)phenyl]-1H-indazol-4-yl}-1,3-thiazole-4-carboxamide;
N-[6-(3-chloro-2-fluorophenyl)-1H-indazol-4-yl]-2-methyl-1,3-thiazole-4-carboxamide;
2-methyl-N-(6-{3-[(1-methylethyl)oxy]phenyl}-1H-indazol-4-yl)-1,3-thiazole-4-carboxamide;
N-{6-[3-(ethyloxy)-2-fluorophenyl]-1H-indazol-4-yl}-2-methyl-1,3-thiazole-4-carboxamide;
N-[6-(3-fluorophenyl)-1H-indazol-4-yl]-2-methyl-1,3-thiazole-4-carboxamide;
N-(6-{3-[(diethylamino)carbonyl]phenyl}-1H-indazol-4-yl)-2-methyl-1,3-thiazole-4-carboxamide;
N-(6-{3-[(dimethylamino)carbonyl]phenyl}-1H-indazol-4-yl)-2-methyl-1,3-thiazole-4-carboxamide;
2-methyl-N-(6-{3-[(methylamino)sulfonyl]phenyl}-1H-indazol-4-yl)-1,3-thiazole-4-carboxamide;
N-[6-(3-acetylphenyl)-1H-indazol-4-yl]-2-methyl-1,3-thiazole-4-carboxamide;
N-[6-(2,3-difluorophenyl)-1H-indazol-4-yl]-2-methyl-1,3-thiazole-4-carboxamide;
2-methyl-N-{6-[3-(4-morpholinylsulfonyl)phenyl]-1H-indazol-4-yl}-1,3-thiazole-4-carboxamide;
2-methyl-N-(6-{3-[(trifluoromethyl)oxy]phenyl}-1H-indazol-4-yl)-1,3-thiazole-4-carboxamide;
2-methyl-N-{6-[3-(1-pyrrolidinylcarbonyl)phenyl]-1H-indazol-4-yl}-1,3-thiazole-4-carboxamide;
2-methyl-N-{6-[3-(1-pyrrolidinylsulfonyl)phenyl]-1H-indazol-4-yl}-1,3-thiazole-4-carboxamide;
N-{6-[3-(acetylamino)phenyl]-1H-indazol-4-yl}-2-methyl-1,3-thiazole-4-carboxamide;
N-{6-[3-(aminocarbonyl)phenyl]-1H-indazol-4-yl}-2-methyl-1,3-thiazole-4-carboxamide;
N-(6-{3-[(cyclopropylamino)sulfonyl]phenyl}-1H-indazol-4-yl)-2-methyl-1,3-thiazole-4-carboxamide;
N-{6-[3-(dimethylamino)phenyl]-1H-indazol-4-yl}-2-methyl-1,3-thiazole-4-carboxamide;
N-[6-(3-methylphenyl)-1H-indazol-4-yl]cyclopropanecarboxamide;
N-[6-(4-hydroxyphenyl)-1H-indazol-4-yl]cyclopropanecarboxamide;
N-[6-(4-hydroxyphenyl)-1H-indazol-4-yl]cyclohexanecarboxamide;
N-[6-(4-hydroxyphenyl)-1H-indazol-4-yl]-2-pyridinecarboxamide;
3-(dimethylamino)-N-[6-(4-hydroxyphenyl)-1H-indazol-4-yl]benzamide;
N-[6-(4-hydroxyphenyl)-1H-indazol-4-yl]-3-phenylpropanamide;
(1R,2R)—N-[6-(4-hydroxyphenyl)-1H-indazol-4-yl]-2-phenylcyclopropanecarboxamide;
N-[6-(4-hydroxyphenyl)-1H-indazol-4-yl]-2-furancarboxamide;
2-methyl-N-{6-[5-(methylsulfonyl)-3-pyridinyl]-1H-indazol-4-yl}-1,3-thiazole-4-carboxamide;
2-methyl-N-[6-(4-methyl-3-pyridinyl)-1H-indazol-4-yl]-1,3-thiazole-4-carboxamide;
2-methyl-N-[6-(3-pyridinyl)-1H-indazol-4-yl]-1,3-thiazole-4-carboxamide;
2-methyl-N-[6-(2-oxo-1,2-dihydro-4-pyridinyl)-1H-indazol-4-yl]-1,3-thiazole-4-carboxamide;
2-methyl-N-[6-(4-pyridinyl)-1H-indazol-4-yl]-1,3-thiazole-4-carboxamide;
2-methyl-N-(6-{6-methyl-5-[(methylsulfonyl)amino]-3-pyridinyl}-1H-indazol-4-yl)-1,3-thiazole-4-carboxamide;
N-(6-{6-chloro-5-[(methylsulfonyl)amino]-3-pyridinyl}-1H-indazol-4-yl)-2-(4-morpholinylmethyl)-1,3-thiazole-4-carboxamide;
N-(6-{6-chloro-5-[(methylsulfonyl)amino]-3-pyridinyl}-1H-indazol-4-yl)-2-(1-piperidinylmethyl)-1,3-thiazole-4-carboxamide;
N-(6-{6-chloro-5-[(methylsulfonyl)amino]-3-pyridinyl}-1H-indazol-4-yl)-2-{[4-(1-methylethyl)-1-piperazinyl]methyl}-1,3-thiazole-4-carboxamide;
N-(6-{6-chloro-5-[(methylsulfonyl)amino]-3-pyridinyl}-1H-indazol-4-yl)-2-{[(2R,6S)-2,6-dimethyl-4-morpholinyl]methyl}-1,3-thiazole-4-carboxamide;
N-(6-{6-chloro-5-[(methylsulfonyl)amino]-3-pyridinyl}-1H-indazol-4-yl)-2-{[3-methyl-4-(1-methylethyl)-1-piperazinyl]methyl}-1,3-thiazole-4-carboxamide;
2-{[4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;
N-(6-{6-(methyloxy)-5-[(methylsulfonyl)amino]-3-pyridinyl}-1H-indazol-4-yl)-2-(4-morpholinylmethyl)-1,3-thiazole-4-carboxamide;
N-(6-{6-(methyloxy)-5-[(methylsulfonyl)amino]-3-pyridinyl}-1H-indazol-4-yl)-2-(1-piperidinylmethyl)-1,3-thiazole-4-carboxamide;
2-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-{6-[5-[(ethylsulfonyl)amino]-6-(methyloxy)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[3-(methyloxy)phenyl]sulfonyl}amino)-3-pyridinyl]-1H-indazol-4-yl}-1,3-thiazole-4-carboxamide;
N-{6-[5-[(cyclohexylsulfonyl)amino]-6-(methyloxy)-3-pyridinyl]-1H-indazol-4-yl}-2-{[(2R,6S)-2,6-dimethyl-4-morpholinyl]methyl}-1,3-thiazole-4-carboxamide;
2-{[(2R,6S)-2,6-dimethyl-4-morpholinyl]methyl}-N-{6-[5-{[(1-methylethyl)sulfonyl]amino}-6-(methyloxy)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[4-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-(6-{6-(methyloxy)-5-[(propylsulfonyl)amino]-3-pyridinyl}-1H-indazol-4-yl)-1,3-thiazole-4-carboxamide;

4-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;

3-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;

2-{[(2R,6S)-2,6-dimethyl-4-morpholinyl]methyl}-N-[6-(6-(methyloxy)-5-{[(3,3,3-trifluoropropyl)sulfonyl]amino}-3-pyridinyl)-1H-indazol-4-yl]-1,3-thiazole-4-carboxamide;

2-{[(2R,6S)-2,6-dimethyl-4-morpholinyl]methyl}-N-[6-(6-(methyloxy)-5-{[(2,2,2-trifluoroethyl)sulfonyl]amino}-3-pyridinyl)-1H-indazol-4-yl]-1,3-thiazole-4-carboxamide;

N-(6-{6-chloro-5-[(methylsulfonyl)amino]-3-pyridinyl}-1H-indazol-4-yl)-6-{[(2R,6S)-2,6-dimethyl-4-morpholinyl]methyl}-2-pyridinecarboxamide;

N-(6-{6-chloro-5-[(methylsulfonyl)amino]-3-pyridinyl}-1H-indazol-4-yl)-6-(4-morpholinylmethyl)-2-pyridinecarboxamide;

N-(6-{6-chloro-5-[(methylsulfonyl)amino]-3-pyridinyl}-1H-indazol-4-yl)-6-(1-piperidinylmethyl)-2-pyridinecarboxamide;

N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;

N-(6-{6-chloro-5-[(methylsulfonyl)amino]-3-pyridinyl}-1H-indazol-4-yl)-6-{[3-methyl-4-(1-methylethyl)-1-piperazinyl]methyl}-2-pyridinecarboxamide;

6-[(1,1-dioxido-4-thiomorpholinyl)methyl]-N-(6-{6-(methyloxy)-5-[(methylsulfonyl)amino]-3-pyridinyl}-1H-indazol-4-yl)-2-pyridinecarboxamide;

N-(6-{6-(methyloxy)-5-[(methylsulfonyl)amino]-3-pyridinyl}-1H-indazol-4-yl)-6-(1-piperidinylmethyl)-2-pyridinecarboxamide;

N-(6-{6-(methyloxy)-5-[(methylsulfonyl)amino]-3-pyridinyl}-1H-indazol-4-yl)-6-(4-morpholinylmethyl)-2-pyridinecarboxamide;

6-{[4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

6-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-2-pyridinecarboxamide;

6-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

N-{6-[5-[(cyclopropylsulfonyl)amino]-6-(methyloxy)-3-pyridinyl]-1H-indazol-4-yl}-2-methyl-1,3-thiazole-4-carboxamide;

N-{6-[5-{[(2,4-difluorophenyl)sulfonyl]amino}-6-(methyloxy)-3-pyridinyl]-1H-indazol-4-yl}-2-methyl-1,3-thiazole-4-carboxamide;

2-methyl-N-(6-{6-(methyloxy)-5-[(methylsulfonyl)amino]-3-pyridinyl}-1H-indazol-4-yl)-1,3-thiazole-4-carboxamide;

N-{6-[5-[(2-hydroxypropanoyl)amino]-6-(methyloxy)-3-pyridinyl]-1H-indazol-4-yl}-2-methyl-1,3-thiazole-4-carboxamide;

N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;

N-{6-[5-{[(2,4-difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-[(2-methyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

N-(6-{6-(methyloxy)-5-[(methylsulfonyl)amino]-3-pyridinyl}-1H-indazol-4-yl)-2-(tetrahydro-1,4-oxazepin-4(5H)-ylmethyl)-1,3-thiazole-4-carboxamide;

2-[(2-ethyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide;

N-{6-[5-{[(2,4-difluorophenyl)sulfonyl]amino}-6-(methyloxy)-3-pyridinyl]-1-methyl-1H-indazol-4-yl}-2-{[(2R,6S)-2,6-dimethyl-4-morpholinyl]methyl}-1,3-thiazole-4-carboxamide;

2-{[(2R,6S)-2,6-dimethyl-4-morpholinyl]methyl}-N-(6-{6-(methyloxy)-5-[(1H-pyrazol-4-ylsulfonyl)amino]-3-pyridinyl}-1H-indazol-4-yl)-1,3-thiazole-4-carboxamide;

N-{6-[5-{[(1,2-dimethyl-1H-imidazol-5-yl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-{[(2R,6S)-2,6-dimethyl-4-morpholinyl]methyl}-N-{6-[5-{[(2-methyl-1H-imidazol-4-yl)sulfonyl]amino}-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-(6-{6-(methyloxy)-5-[(2-thienylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-{6-[5-[(1H-imidazol-4-ylsulfonyl)amino]-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-{6-[6-(methyloxy)-5-({[2-(4-methyl-1-piperazinyl)ethyl]sulfonyl}amino)-3-pyridinyl]-1H-indazol-4-yl}-1,3-thiazole-4-carboxamide;

N-[6-(6-chloro-5-{[(2-methylphenyl)sulfonyl]amino}-3-pyridinyl)-1H-indazol-4-yl]-2-methyl-1,3-thiazole-4-carboxamide;

N-[6-(6-chloro-5-{[(5-fluoro-2-methylphenyl)sulfonyl]amino}-3-pyridinyl)-1H-indazol-4-yl]-2-methyl-1,3-thiazole-4-carboxamide;

N-[6-(6-chloro-5-{[(2,5-dimethylphenyl)sulfonyl]amino}-3-pyridinyl)-1H-indazol-4-yl]-2-methyl-1,3-thiazole-4-carboxamide;

N-(6-{6-(ethyloxy)-5-[(phenylsulfonyl)amino]-3-pyridinyl}-1H-indazol-4-yl)-2-methyl-1,3-thiazole-4-carboxamide;

N-(6-{6-chloro-5-[(methylsulfonyl)amino]-3-pyridinyl}-1-methyl-1H-indazol-4-yl)-6-methyl-2-pyridinecarboxamide;

N-(6-{6-chloro-5-[(methylsulfonyl)amino]-3-pyridinyl}-1H-indazol-4-yl)-6-methyl-2-pyridinecarboxamide;

N-{6-[6-chloro-5-({[5-methyl-2-(methyloxy)phenyl]sulfonyl}amino)-3-pyridinyl]-1H-indazol-4-yl}-2-methyl-1,3-thiazole-4-carboxamide;

N-(6-{6-chloro-5-[(cyclopropylsulfonyl)amino]-3-pyridinyl}-1H-indazol-4-yl)-2-methyl-1,3-thiazole-4-carboxamide;

N-[6-(2,3-diaminophenyl)-1H-indazol-4-yl]-2-methyl-1,3-thiazole-4-carboxamide;

2-methyl-N-(6-{5-[(methylsulfonyl)amino]-3-pyridinyl}-1H-indazol-4-yl)-1,3-thiazole-4-carboxamide;

N-{6-[4-(aminosulfonyl)phenyl]-1H-indazol-4-yl}-2-methyl-1,3-thiazole-4-carboxamide;

N-(6-{6-chloro-5-[(methylsulfonyl)amino]-3-pyridinyl}-1-methyl-1H-indazol-4-yl)-2-methyl-1,3-thiazole-4-carboxamide;
N-(6-{5-[(cyclopropylsulfonyl)amino]-6-hydroxy-3-pyridinyl}-1H-indazol-4-yl)-2-methyl-1,3-thiazole-4-carboxamide;
N-(6-{6-chloro-5-[(methylsulfonyl)amino]-3-pyridinyl}-1H-indazol-4-yl)-2-methyl-1,3-thiazole-4-carboxamide;
2-methyl-N-(6-{5-[(phenylsulfonyl)amino]-3-pyridinyl}-1H-indazol-4-yl)-1,3-thiazole-4-carboxamide;
N-[6-(5-hydroxy-3-pyridinyl)-1H-indazol-4-yl]-2-methyl-1,3-thiazole-4-carboxamide trifluoroacetate;
N-[6-(3-hydroxyphenyl)-1H-indazol-4-yl]-2-methyl-1,3-thiazole-4-carboxamide;
N-[6-(4-chloro-3-hydroxyphenyl)-1H-indazol-4-yl]-2-methyl-1,3-thiazole-4-carboxamide;
N-[6-(4-hydroxy-3-methylphenyl)-1H-indazol-4-yl]-2-methyl-1,3-thiazole-4-carboxamide;
N-[6-(3-hydroxy-4-methylphenyl)-1H-indazol-4-yl]-2-methyl-1,3-thiazole-4-carboxamide;
N-(6-{4-chloro-3-[(methylsulfonyl)amino]phenyl}-1H-indazol-4-yl)-2-methyl-1,3-thiazole-4-carboxamide;
2-methyl-N-(6-{5-[(methylamino)sulfonyl]-3-pyridinyl}-1H-indazol-4-yl)-1,3-thiazole-4-carboxamide;
N-(6-{5-[(diethylamino)sulfonyl]-3-pyridinyl}-1H-indazol-4-yl)-2-methyl-1,3-thiazole-4-carboxamide;
N-(6-{6-hydroxy-5-[(phenylsulfonyl)amino]-3-pyridinyl}-1H-indazol-4-yl)-2-methyl-1,3-thiazole-4-carboxamide;
N-(6-{6-chloro-5-[(methylsulfonyl)amino]-3-pyridinyl}-1-methyl-1H-indazol-4-yl)-2-{[(2R,6S)-2,6-dimethyl-4-morpholinyl]methyl}-1,3-thiazole-4-carboxamide; or
a salt thereof.

In another embodiment, the compound of the invention is:
6-bromo-N-[6-(4-hydroxyphenyl)-1H-indazol-4-yl]-2-pyridinecarboxamide;
N-[6-(3-hydroxyphenyl)-1H-indazol-4-yl]cyclohexanecarboxamide;
N-[6-(3-hydroxyphenyl)-1H-indazol-4-yl]-2-pyridinecarboxamide;
N-[6-(3-hydroxyphenyl)-1H-indazol-4-yl]-3-phenylpropanamide;
4-cyano-N-[6-(3-hydroxyphenyl)-1H-indazol-4-yl]benzamide;
3-(dimethylamino)-N-[6-(3-hydroxyphenyl)-1H-indazol-4-yl]benzamide;
(1R,2R)—N-[6-(3-hydroxyphenyl)-1H-indazol-4-yl]-2-phenylcyclopropanecarboxamide;
N-[6-(3-hydroxyphenyl)-1H-indazol-4-yl]-2-furancarboxamide;
N-[6-(3-hydroxyphenyl)-1H-indazol-4-yl]cyclopropanecarboxamide;
N-{6-[5-(aminosulfonyl)-3-pyridinyl]-1H-indazol-4-yl}-2-methyl-1,3-thiazole-4-carboxamide;
N-(6-{3-[(aminosulfonyl)methyl]phenyl}-1H-indazol-4-yl)-2-methyl-1,3-thiazole-4-carboxamide;
2-methyl-N-{6-[5-(methyloxy)-3-pyridinyl]-1H-indazol-4-yl}-1,3-thiazole-4-carboxamide;
3-(4-{[(2-methyl-1,3-thiazol-4-yl)carbonyl]amino}-1H-indazol-6-yl)benzoic acid;
N-(6-{6-chloro-5-[(phenylsulfonyl)amino]-3-pyridinyl}-1H-indazol-4-yl)-2-methyl-1,3-thiazole-4-carboxamide;
N-{6-[4-(acetylamino)phenyl]-1H-indazol-4-yl}-2-pyridinecarboxamide;
N-(6-{3-[(methylsulfonyl)amino]phenyl}-1H-indazol-4-yl)-2-pyridinecarboxamide;
N-[6-(3-{[(4-methylphenyl)sulfonyl]amino}phenyl)-1H-indazol-4-yl]-2-pyridinecarboxamide;
N-{6-[3,4-bis(methyloxy)phenyl]-1H-indazol-4-yl}-2-pyridinecarboxamide;
N-{6-[3-(4-morpholinyl)phenyl]-1H-indazol-4-yl}-2-pyridinecarboxamide;
N-(6-{3-[(methylamino)carbonyl]phenyl}-1H-indazol-4-yl)-2-pyridinecarboxamide;
N-{6-[3-(2-furanyl)phenyl]-1H-indazol-4-yl}-2-pyridinecarboxamide;
N-{6-[4-(2-furanyl)phenyl]-1H-indazol-4-yl}-2-pyridinecarboxamide;
N-{6-(3-{[(phenylmethyl)amino]sulfonyl}phenyl)-1H-indazol-4-yl]-2-pyridinecarboxamide;
N-[6-(3-cyanophenyl)-1H-indazol-4-yl]-2-methyl-1,3-thiazole-4-carboxamide;
2-methyl-N-{6-[3-(methylsulfonyl)phenyl]-1H-indazol-4-yl}-1,3-thiazole-4-carboxamide;
N-[6-(3-chloro-2-fluorophenyl)-1H-indazol-4-yl]-2-methyl-1,3-thiazole-4-carboxamide;
2-methyl-N-(6-{3-[(1-methylethyl)oxy]phenyl}-1H-indazol-4-yl)-1,3-thiazole-4-carboxamide;
N-{6-[3-(ethyloxy)-2-fluorophenyl]-1H-indazol-4-yl}-2-methyl-1,3-thiazole-4-carboxamide;
N-[6-(3-fluorophenyl)-1H-indazol-4-yl]-2-methyl-1,3-thiazole-4-carboxamide;
N-(6-{3-[(diethylamino)carbonyl]phenyl}-1H-indazol-4-yl)-2-methyl-1,3-thiazole-4-carboxamide;
N-(6-{3-[(dimethylamino)carbonyl]phenyl}-1H-indazol-4-yl)-2-methyl-1,3-thiazole-4-carboxamide;
2-methyl-N-(6-{3-[(methylamino)sulfonyl]phenyl}-1H-indazol-4-yl)-1,3-thiazole-4-carboxamide;
N-[6-(3-acetylphenyl)-1H-indazol-4-yl]-2-methyl-1,3-thiazole-4-carboxamide;
N-[6-(2,3-difluorophenyl)-1H-indazol-4-yl]-2-methyl-1,3-thiazole-4-carboxamide;
2-methyl-N-{6-[3-(4-morpholinylsulfonyl)phenyl]-1H-indazol-4-yl}-1,3-thiazole-4-carboxamide;
2-methyl-N-(6-{3-[(trifluoromethyl)oxy]phenyl}-1H-indazol-4-yl)-1,3-thiazole-4-carboxamide;
2-methyl-N-{6-[3-(1-pyrrolidinylcarbonyl)phenyl]-1H-indazol-4-yl}-1,3-thiazole-4-carboxamide;
2-methyl-N-{6-[3-(1-pyrrolidinylsulfonyl)phenyl]-1H-indazol-4-yl}-1,3-thiazole-4-carboxamide;
N-{6-[3-(acetylamino)phenyl]-1H-indazol-4-yl}-2-methyl-1,3-thiazole-4-carboxamide;
N-{6-[3-(aminocarbonyl)phenyl]-1H-indazol-4-yl}-2-methyl-1,3-thiazole-4-carboxamide;
N-(6-{3-[(cyclopropylamino)sulfonyl]phenyl}-1H-indazol-4-yl)-2-methyl-1,3-thiazole-4-carboxamide;
N-{6-[3-(dimethylamino)phenyl]-1H-indazol-4-yl}-2-methyl-1,3-thiazole-4-carboxamide;
N-[6-(3-methylphenyl)-1H-indazol-4-yl]cyclopropanecarboxamide;
N-[6-(4-hydroxyphenyl)-1H-indazol-4-yl]cyclopropanecarboxamide;
N-[6-(4-hydroxyphenyl)-1H-indazol-4-yl]cyclohexanecarboxamide;
N-[6-(4-hydroxyphenyl)-1H-indazol-4-yl]-2-pyridinecarboxamide;
3-(dimethylamino)-N-[6-(4-hydroxyphenyl)-1H-indazol-4-yl]benzamide;
N-[6-(4-hydroxyphenyl)-1H-indazol-4-yl]-3-phenylpropanamide;
(1R,2R)—N-[6-(4-hydroxyphenyl)-1H-indazol-4-yl]-2-phenylcyclopropanecarboxamide;
N-[6-(4-hydroxyphenyl)-1H-indazol-4-yl]-2-furancarboxamide;

2-methyl-N-{6-[5-(methylsulfonyl)-3-pyridinyl]-1H-indazol-4-yl}-1,3-thiazole-4-carboxamide;

2-methyl-N-[6-(4-methyl-3-pyridinyl)-1H-indazol-4-yl]-1,3-thiazole-4-carboxamide;

2-methyl-N-[6-(3-pyridinyl)-1H-indazol-4-yl]-1,3-thiazole-4-carboxamide;

2-methyl-N-[6-(2-oxo-1,2-dihydro-4-pyridinyl)-1H-indazol-4-yl]-1,3-thiazole-4-carboxamide;

2-methyl-N-[6-(4-pyridinyl)-1H-indazol-4-yl]-1,3-thiazole-4-carboxamide;

2-methyl-N-(6-{6-methyl-5-[(methylsulfonyl)amino]-3-pyridinyl}-1H-indazol-4-yl)-1,3-thiazole-4-carboxamide;

N-(6-{6-chloro-5-[(methylsulfonyl)amino]-3-pyridinyl}-1H-indazol-4-yl)-2-(4-morpholinylmethyl)-1,3-thiazole-4-carboxamide;

N-(6-{6-chloro-5-[(methylsulfonyl)amino]-3-pyridinyl}-1H-indazol-4-yl)-2-(1-piperidinylmethyl)-1,3-thiazole-4-carboxamide;

N-(6-{6-chloro-5-[(methylsulfonyl)amino]-3-pyridinyl}-1H-indazol-4-yl)-2-{[4-(1-methylethyl)-1-piperazinyl]methyl}-1,3-thiazole-4-carboxamide;

N-(6-{6-chloro-5-[(methylsulfonyl)amino]-3-pyridinyl}-1H-indazol-4-yl)-2-{[(2R,6S)-2,6-dimethyl-4-morpholinyl]methyl}-1,3-thiazole-4-carboxamide;

N-(6-{6-chloro-5-[(methylsulfonyl)amino]-3-pyridinyl}-1H-indazol-4-yl)-2-{[3-methyl-4-(1-methylethyl)-1-piperazinyl]methyl}-1,3-thiazole-4-carboxamide;

2-{[4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;

N-(6-{6-(methyloxy)-5-[(methylsulfonyl)amino]-3-pyridinyl}-1H-indazol-4-yl)-2-(4-morpholinylmethyl)-1,3-thiazole-4-carboxamide;

N-(6-{6-(methyloxy)-5-[(methylsulfonyl)amino]-3-pyridinyl}-1H-indazol-4-yl)-2-(1-piperidinylmethyl)-1,3-thiazole-4-carboxamide;

2-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-{6-[5-[(ethylsulfonyl)amino]-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-{6-[6-(methyloxy)-5-({[3-(methyloxy)phenyl]sulfonyl}amino)-3-pyridinyl]-1H-indazol-4-yl}-1,3-thiazole-4-carboxamide;

N-{6-[5-[(cyclohexylsulfonyl)amino]-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-{[(2R,6S)-2,6-dimethyl-4-morpholinyl]methyl}-N-{6-[5-{[(1-methylethyl)sulfonyl]amino}-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide;

2-{[(2R,6S)-2,6-dimethyl-4-morpholinyl]methyl}-N-{6-[6-(methyloxy)-5-({[4-(methyloxy)phenyl]sulfonyl}amino)-3-pyridinyl]-1H-indazol-4-yl}-1,3-thiazole-4-carboxamide;

2-{[(2R,6S)-2,6-dimethyl-4-morpholinyl]methyl}-N-(6-{6-(methyloxy)-5-[(propylsulfonyl)amino]-3-pyridinyl}-1H-indazol-4-yl)-1,3-thiazole-4-carboxamide;

4-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;

3-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;

2-{[(2R,6S)-2,6-dimethyl-4-morpholinyl]methyl}-N-[6-(6-(methyloxy)-5-{[(3,3,3-trifluoropropyl)sulfonyl]amino}-3-pyridinyl)-1H-indazol-4-yl]-1,3-thiazole-4-carboxamide;

2-{[(2R,6S)-2,6-dimethyl-4-morpholinyl]methyl}-N-[6-(6-(methyloxy)-5-{[(2,2,2-trifluoroethyl)sulfonyl]amino}-3-pyridinyl)-1H-indazol-4-yl]-1,3-thiazole-4-carboxamide;

N-(6-{6-chloro-5-[(methylsulfonyl)amino]-3-pyridinyl}-1H-indazol-4-yl)-6-{[(2R,6S)-2,6-dimethyl-4-morpholinyl]methyl}-2-pyridinecarboxamide;

N-(6-{6-chloro-5-[(methylsulfonyl)amino]-3-pyridinyl}-1H-indazol-4-yl)-6-(4-morpholinylmethyl)-2-pyridinecarboxamide;

N-(6-{6-chloro-5-[(methylsulfonyl)amino]-3-pyridinyl}-1H-indazol-4-yl)-6-(1-piperidinylmethyl)-2-pyridinecarboxamide;

N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;

N-(6-{6-chloro-5-[(methylsulfonyl)amino]-3-pyridinyl}-1H-indazol-4-yl)-6-{[3-methyl-4-(1-methylethyl)-1-piperazinyl]methyl}-2-pyridinecarboxamide;

6-[(1,1-dioxido-4-thiomorpholinyl)methyl]-N-(6-{6-(methyloxy)-5-[(methylsulfonyl)amino]-3-pyridinyl}-1H-indazol-4-yl)-2-pyridinecarboxamide;

N-(6-{6-(methyloxy)-5-[(methylsulfonyl)amino]-3-pyridinyl}-1H-indazol-4-yl)-6-(1-piperidinylmethyl)-2-pyridinecarboxamide;

N-(6-{6-(methyloxy)-5-[(methylsulfonyl)amino]-3-pyridinyl}-1H-indazol-4-yl)-6-(4-morpholinylmethyl)-2-pyridinecarboxamide;

6-{[4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

6-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-2-pyridinecarboxamide;

6-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

N-{6-[5-[(cyclopropylsulfonyl)amino]-6-(methyloxy)-3-pyridinyl]-1H-indazol-4-yl}-2-methyl-1,3-thiazole-4-carboxamide;

N-{6-[5-{[(2,4-difluorophenyl)sulfonyl]amino}-6-(methyloxy)-3-pyridinyl]-1H-indazol-4-yl}-2-methyl-1,3-thiazole-4-carboxamide;

2-methyl-N-(6-{6-(methyloxy)-5-[(methylsulfonyl)amino]-3-pyridinyl}-1H-indazol-4-yl)-1,3-thiazole-4-carboxamide;

N-{6-[5-[(2-hydroxypropanoyl)amino]-6-(methyloxy)-3-pyridinyl]-1H-indazol-4-yl}-2-methyl-1,3-thiazole-4-carboxamide;

N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;

N-{6-[5-{[(2,4-difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-[(2-methyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

N-(6-{6-(methyloxy)-5-[(methylsulfonyl)amino]-3-pyridinyl}-1H-indazol-4-yl)-2-(tetrahydro-1,4-oxazepin-4(5H)-ylmethyl)-1,3-thiazole-4-carboxamide;

2-[(2-ethyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide;

N-{6-[5-{[(2,4-difluorophenyl)sulfonyl]amino}-6-(methyloxy)-3-pyridinyl]-1-methyl-1H-indazol-4-yl}-2-{[(2R,6S)-2,6-dimethyl-4-morpholinyl]methyl}-1,3-thiazole-4-carboxamide; or a salt thereof.

In another embodiment, the compound of the invention is:

6-bromo-N-[6-(4-hydroxyphenyl)-1H-indazol-4-yl]-2-pyridinecarboxamide;

N-[6-(3-hydroxyphenyl)-1H-indazol-4-yl]cyclohexanecarboxamide;

N-[6-(3-hydroxyphenyl)-1H-indazol-4-yl]-2-pyridinecarboxamide;

N-[6-(3-hydroxyphenyl)-1H-indazol-4-yl]-3-phenylpropanamide;

4-cyano-N-[6-(3-hydroxyphenyl)-1H-indazol-4-yl]benzamide;

3-(dimethylamino)-N-[6-(3-hydroxyphenyl)-1H-indazol-4-yl]benzamide;

(1R,2R)—N-[6-(3-hydroxyphenyl)-1H-indazol-4-yl]-2-phenylcyclopropanecarboxamide;

N-[6-(3-hydroxyphenyl)-1H-indazol-4-yl]-2-furancarboxamide;

N-[6-(3-hydroxyphenyl)-1H-indazol-4-yl]cyclopropanecarboxamide;

N-{6-[5-(aminosulfonyl)-3-pyridinyl]-1H-indazol-4-yl}-2-methyl-1,3-thiazole-4-carboxamide;

N-(6-{3-[(aminosulfonyl)methyl]phenyl}-1H-indazol-4-yl)-2-methyl-1,3-thiazole-4-carboxamide;

2-methyl-N-{6-[5-(methyloxy)-3-pyridinyl]-1H-indazol-4-yl}-1,3-thiazole-4-carboxamide;

3-(4-{[(2-methyl-1,3-thiazol-4-yl)carbonyl]amino}-1H-indazol-6-yl)benzoic acid;

N-(6-{6-chloro-5-[(phenylsulfonyl)amino]-3-pyridinyl}-1H-indazol-4-yl)-2-methyl-1,3-thiazole-4-carboxamide;

N-{6-[4-(acetylamino)phenyl]-1H-indazol-4-yl}-2-pyridinecarboxamide;

N-(6-{3-[(methylsulfonyl)amino]phenyl}-1H-indazol-4-yl)-2-pyridinecarboxamide;

N-[6-(3-{[(4-methylphenyl)sulfonyl]amino}phenyl)-1H-indazol-4-yl]-2-pyridinecarboxamide;

N-{6-[3,4-bis(methyloxy)phenyl]-1H-indazol-4-yl}-2-pyridinecarboxamide;

N-{6-[3-(4-morpholinyl)phenyl]-1H-indazol-4-yl}-2-pyridinecarboxamide;

N-(6-{3-[(methylamino)carbonyl]phenyl}-1H-indazol-4-yl)-2-pyridinecarboxamide;

N-{6-[3-(2-furanyl)phenyl]-1H-indazol-4-yl}-2-pyridinecarboxamide;

N-{6-[4-(2-furanyl)phenyl]-1H-indazol-4-yl}-2-pyridinecarboxamide;

N-[6-(3-{[(phenylmethyl)amino]sulfonyl}phenyl)-1H-indazol-4-yl]-2-pyridinecarboxamide;

N-[6-(3-cyanophenyl)-1H-indazol-4-yl]-2-methyl-1,3-thiazole-4-carboxamide;

2-methyl-N-{6-[3-(methylsulfonyl)phenyl]-1H-indazol-4-yl}-1,3-thiazole-4-carboxamide;

N-[6-(3-chloro-2-fluorophenyl)-1H-indazol-4-yl]-2-methyl-1,3-thiazole-4-carboxamide;

2-methyl-N-(6-{3-[(1-methylethyl)oxy]phenyl}-1H-indazol-4-yl)-1,3-thiazole-4-carboxamide;

N-{6-[3-(ethyloxy)-2-fluorophenyl]-1H-indazol-4-yl}-2-methyl-1,3-thiazole-4-carboxamide;

N-[6-(3-fluorophenyl)-1H-indazol-4-yl]-2-methyl-1,3-thiazole-4-carboxamide;

N-(6-{3-[(diethylamino)carbonyl]phenyl}-1H-indazol-4-yl)-2-methyl-1,3-thiazole-4-carboxamide;

N-(6-{3-[(dimethylamino)carbonyl]phenyl}-1H-indazol-4-yl)-2-methyl-1,3-thiazole-4-carboxamide;

2-methyl-N-(6-{3-[(methylamino)sulfonyl]phenyl}-1H-indazol-4-yl)-1,3-thiazole-4-carboxamide;

N-[6-(3-acetylphenyl)-1H-indazol-4-yl]-2-methyl-1,3-thiazole-4-carboxamide;

N-[6-(2,3-difluorophenyl)-1H-indazol-4-yl]-2-methyl-1,3-thiazole-4-carboxamide;

2-methyl-N-{6-[3-(4-morpholinylsulfonyl)phenyl]-1H-indazol-4-yl}-1,3-thiazole-4-carboxamide;

2-methyl-N-(6-{3-[(trifluoromethyl)oxy]phenyl}-1H-indazol-4-yl)-1,3-thiazole-4-carboxamide;

2-methyl-N-{6-[3-(1-pyrrolidinylcarbonyl)phenyl]-1H-indazol-4-yl}-1,3-thiazole-4-carboxamide;

2-methyl-N-{6-[3-(1-pyrrolidinylsulfonyl)phenyl]-1H-indazol-4-yl}-1,3-thiazole-4-carboxamide;

N-{6-[3-(acetylamino)phenyl]-1H-indazol-4-yl}-2-methyl-1,3-thiazole-4-carboxamide;

N-{6-[3-(aminocarbonyl)phenyl]-1H-indazol-4-yl}-2-methyl-1,3-thiazole-4-carboxamide;

N-(6-{3-[(cyclopropylamino)sulfonyl]phenyl}-1H-indazol-4-yl)-2-methyl-1,3-thiazole-4-carboxamide;

N-{6-[3-(dimethylamino)phenyl]-1H-indazol-4-yl}-2-methyl-1,3-thiazole-4-carboxamide;

N-[6-(3-methylphenyl)-1H-indazol-4-yl]cyclopropanecarboxamide;

N-[6-(4-hydroxyphenyl)-1H-indazol-4-yl]cyclopropanecarboxamide;

N-[6-(4-hydroxyphenyl)-1H-indazol-4-yl]cyclohexanecarboxamide;

N-[6-(4-hydroxyphenyl)-1H-indazol-4-yl]-2-pyridinecarboxamide;

3-(dimethylamino)-N-[6-(4-hydroxyphenyl)-1H-indazol-4-yl]benzamide;

N-[6-(4-hydroxyphenyl)-1H-indazol-4-yl]-3-phenylpropanamide;

(1R,2R)—N-[6-(4-hydroxyphenyl)-1H-indazol-4-yl]-2-phenylcyclopropanecarboxamide;

N-[6-(4-hydroxyphenyl)-1H-indazol-4-yl]-2-furancarboxamide;

2-methyl-N-{6-[5-(methylsulfonyl)-3-pyridinyl]-1H-indazol-4-yl}-1,3-thiazole-4-carboxamide;

2-methyl-N-[6-(4-methyl-3-pyridinyl)-1H-indazol-4-yl]-1,3-thiazole-4-carboxamide;

2-methyl-N-[6-(3-pyridinyl)-1H-indazol-4-yl]-1,3-thiazole-4-carboxamide;

2-methyl-N-[6-(2-oxo-1,2-dihydro-4-pyridinyl)-1H-indazol-4-yl]-1,3-thiazole-4-carboxamide;

2-methyl-N-[6-(4-pyridinyl)-1H-indazol-4-yl]-1,3-thiazole-4-carboxamide;

2-methyl-N-(6-{6-methyl-5-[(methylsulfonyl)amino]-3-pyridinyl}-1H-indazol-4-yl)-1,3-thiazole-4-carboxamide; or a salt thereof.

In another embodiment, the compound of the invention is:
N-[6-(3-hydroxyphenyl)-1H-indazol-4-yl]-2-pyridinecarboxamide;
N-(6-{6-chloro-5-[(phenylsulfonyl)amino]-3-pyridinyl}-1H-indazol-4-yl)-2-methyl-1,3-thiazole-4-carboxamide;
N-[6-(4-hydroxyphenyl)-1H-indazol-4-yl]-2-pyridinecarboxamide;
2-methyl-N-[6-(2-oxo-1,2-dihydro-4-pyridinyl)-1H-indazol-4-yl]-1,3-thiazole-4-carboxamide;
2-methyl-N-(6-{6-methyl-5-[(methylsulfonyl)amino]-3-pyridinyl}-1H-indazol-4-yl)-1,3-thiazole-4-carboxamide; or
a salt thereof.

In another embodiment, the compound of the invention is:
2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-[6-(6-(methyloxy)-5-{[(2,2,2-trifluoroethyl)sulfonyl]amino}-3-pyridinyl)-1H-indazol-4-yl]-1,3-thiazole-4-carboxamide;
N-{6-[5-{[(2,4-difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;
2-{[(2R,6S)-2,6-dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide;
N-{6-[5-{[(2,4-difluorophenyl)sulfonyl]amino}-6-(methyloxy)-3-pyridinyl]-1-methyl-1H-indazol-4-yl}-2-{[(2R,6S)-2,6-dimethyl-4-morpholinyl]methyl}-1,3-thiazole-4-carboxamide; or
a salt thereof.

In another embodiment, the compound of the invention is:
2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-[6-(6-(methyloxy)-5-{[(2,2,2-trifluoroethyl)sulfonyl]amino}-3-pyridinyl)-1H-indazol-4-yl]-1,3-thiazole-4-carboxamide;
N-{6-[5-{[(2,4-difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;
2-{[(2R,6S)-2,6-dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide; or
a salt thereof.

In a further embodiment, the compound of the invention is:
2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide.

TERMS AND DEFINITIONS

"Alkyl" refers to a saturated hydrocarbon chain having the specified number of member atoms. For example, $C_{1-6}$alkyl refers to an alkyl group having from 1 to 6 member atoms. Similarly, $C_{1-4}$alkyl refers to an alkyl group having from 1 to 4 member atoms. Alkyl groups may be optionally substituted with one or more substituents if so defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl. In one embodiment, alkyl is methyl. In another embodiment, alkyl is ethyl. In a further embodiment, alkyl is isopropyl.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. In one embodiment, the cycloalkyl groups have 3 or 4 member atoms. In a further embodiment, the cycloalkyl groups have 5 or 6 member atoms. Cycloalkyl groups may be optionally substituted with one or more substituents if so defined herein. It will be appreciated that the substituent may be at any position on the ring, including the carbon atom which is the point of attachment to the rest of the molecule. Cycloalkyl includes cyclopropyl, cyclobutyl, cyclopentyl, and cyclohexyl. In one embodiment, cycloalkyl is cyclopropyl. In a further embodiment, cycloalkyl is cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, chloro, bromo, or iodo. In one embodiment, the halogen radical is fluoro, chloro or bromo.

"Heteroaryl", unless otherwise defined, refers to an aromatic ring containing 1 or 2 heteroatoms as member atoms in the ring. Heteroaryl groups containing more than one heteroatom may contain different heteroatoms. Heteroaryl groups may be optionally substituted with one or more substituents if so defined herein. The heteroaryl groups herein are monocyclic ring systems having 5 or 6 member atoms. Heteroaryl includes pyrrolyl, pyrazolyl, imidazolyl, oxazolyl, isoxazolyl, thiazolyl, isothiazolyl, furanyl, thienyl, pyridinyl, pyrimidinyl, pyridazinyl and pyrazinyl. In one embodiment, a 5-membered heteroaryl group having 1 or 2 heteroatoms is thiazolyl. In another embodiment, a 5-membered heteroaryl group having 1 or 2 heteroatoms is furanyl. In a further embodiment, a 6-membered heteroaryl group having 1 or 2 heteroatoms is pyridinyl.

"Heteroatom" refers to a nitrogen, sulphur, or oxygen atom.

"Heterocyclyl", unless otherwise defined, refers to a saturated or unsaturated ring containing 1 or 2 heteroatoms as member atoms in the ring. However, heterocyclyl rings are not aromatic. In certain embodiments, heterocyclyl is saturated. In other embodiments, heterocyclyl is unsaturated but not aromatic. Heterocyclyl groups containing more than one heteroatom may contain different heteroatoms. The heterocyclyl groups herein are monocyclic ring systems having 5, 6 or 7 member atoms. In one embodiment, the heterocyclyl groups herein are monocyclic ring systems having 5 or 6 member atoms. In another embodiment, the heterocyclyl groups herein are monocyclic ring systems having 7 member atoms. Heterocyclyl groups may be optionally substituted with one or more substituents if so defined herein. Monocyclic heterocyclyl includes pyrrolidinyl, pyrazolidinyl, imidazolidinyl, isoxazolidinyl, oxazolidinyl, isothiazolidinyl, thiazolidinyl, piperidinyl, piperazinyl, morpholinyl, thiamorpholinyl, hexahydro-1H-azepinyl and tetrahydro-1,4-oxazepin-4(5H)-yl. In one embodiment, monocyclic heterocyclyl includes pyrrolidinyl, oxazolidinyl, piperidinyl and morpholinyl. In another embodiment, monocyclic heterocyclyl includes piperazinyl, thiomorpholinyl and tetrahydro-1,4-oxazepin-4(5H)-yl. In one embodiment, heterocyclyl is pyrrolidinyl. In a further embodiment, heterocyclyl is morpholinyl. In one embodiment the heterocyclyl groups herein are bicyclic systems having 10 member atoms. Bicyclic heterocycyl includes octahydro-4H-1,4-benzoxazinyl and octahydro-2H-pyrido[1,2-a]pyrazinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as heteroaryl, may be unsubstituted or substituted with one or more substituents if so defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| aq | Aqueous |
| DCM | Dichloromethane |
| DIPEA | Diisopropylethylamine |
| DMF | N,N-Dimethylformamide |
| DMA | N,N-Dimethylacetamide |
| DMSO | Dimethylsulfoxide |
| $Et_3N$ | Triethylamine |
| EtOAc | Ethyl acetate |
| g | Grams |
| h or hr | Hour(s) |
| HATU | O-(7-Azabenzotriazol-1-yl)-N,N,N',N'-tetramethyluronium hexafluorophosphate |
| HCl | Hydrogen Chloride |
| HPLC | High performance liquid chromatography |
| IPA | Isopropanol |
| LC/MS | Liquid chromatography/mass spectroscopy |
| M | Molar |
| MDAP | Mass Directed Automated Preparative HPLC |
| MeOH | Methanol |
| MeCN | Acetonitrile |
| mg | Milligrams |
| min or mins | Minutes |
| ml | Milliliters |
| mmol | Millimoles |
| mp | Melting point |
| $Pd(dppf)Cl_2$ | [1,1'-Bis(diphenylphosphino)ferrocene]dichloropalladium(II) |
| $Pd(dppf)Cl_2$—$CH_2Cl_2$ | [1,1'-Bis(diphenylphosphino)ferrocene]dichloropalladium(II) dichloromethane adduct |
| $Pd(PPh_3)_4$ | Tetrakis(triphenylphosphine)palladium(0) |
| $R_t$ | Retention time |
| RT | room temperature |
| s | Seconds |
| SCX | Strong cation exchange |
| SPE | Solid Phase Extraction |
| THF | Tetrahydrofuran |
| TFA | Trifluoroacetic acid |

All references to brine are to a saturated aqueous solution of NaCl.

Included within the scope of the "compounds of the invention" are all solvates (including hydrates), complexes, polymorphs, prodrugs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making or recrystallising the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as 3H, 11C, 14C and 18F.

The compounds according to formula (I) may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formula (I), or in any chemical structure illustrated herein, is not specified the structure is intended to encompass any stereoisomer and all mixtures thereof. Thus, compounds according to formula (I) containing one or more chiral center may be used as racemic mixtures, enantiomerically enriched mixtures, or as enantiomerically pure individual stereoisomers.

Individual stereoisomers of a compound according to formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formula (I) may also contain centers of geometric asymmetry. Where the stereochemistry of a center of geometric asymmetry present in formula (I), or in any chemical structure illustrated herein, is not specified, the structure is intended to encompass the trans geometric isomer, the cis geometric isomer, and all mixtures thereof. Likewise, all tautomeric forms are also included in formula (I) whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to compounds of formula (I) as the free acid or free base. In another embodiment, the invention is directed to compounds of formula (I) and salts thereof. In a further embodiment, the invention is directed to compounds of formula (I) and pharmaceutically acceptable salts thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts impart greater stability or solubility to the molecule thereby facilitating formulation into a dosage form. Accordingly, the invention is further directed to compounds of formula (I) and pharmaceutically acceptable salts thereof.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Process a

Compounds of formula (I) wherein $R^1$, $R^2$, $R^3$ and $R^4$ are as defined above, and salts thereof, may be prepared from compounds of formula (II)

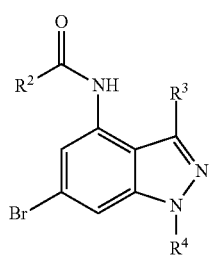

(II)

wherein $R^2$, $R^3$ and $R^4$ are as defined above, by a process comprising treatment with a suitable boronic acid ester such as 3-(methyloxy)-5-(4,4,5,5-tetramethyl-1,3,2-dioxaborolan-2-yl)pyridine (commercially available), under microwave irradiation, in the presence of a suitable palladium catalyst such as 1,1'-bis(diphenylphosphino)ferrocene palladium dichloride, in a suitable solvent such as 1,4-dioxane and water, in the presence of a suitable base such as sodium carbonate, and at a suitable temperature such as 60-150° C., for example about 150° C.

Compounds of formula (II) wherein $R^2$, $R^3$ and $R^4$ are as defined above, may be prepared from the compound of formula (III) (which is commercially available)

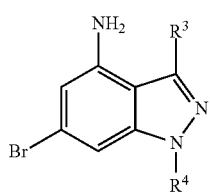

(III)

wherein $R^3$ and $R^4$ are H, by treatment either with (i) a suitable acid of formula $R^2COOH$, wherein $R^2$ is as defined above, or (ii) by treatment with an acid chloride of formula $R^2COCl$, wherein $R^2$ is as defined above. Suitable conditions for (i) include stirring an acid such as, for example, 2-methyl-1,3-thiazole-4-carboxylic acid (commercially available), in a suitable solvent such as N,N-dimethylformamide, at a suitable temperature such as room temperature, for example about 20° C., in the presence of a coupling reagent such as O-(7-azabenzotriazol-1-yl)-N,N,N',N'-tetramethyluronium hexafluorophosphate, and in the presence of a suitable base such as N,N-diisopropylethylamine. Alternatively, (ii) may be carried out by acylation with a suitable acylating agent such as an acid chloride, in a suitable solvent such as dichloromethane, in the presence of a suitable base such as N,N-diisopropylamine, and at a suitable temperature such as room temperature, for example about 20° C.

Process b

Compounds of formula (I) wherein $R^1$, $R^2$, $R^3$ and $R^4$ are as defined above, and salts thereof, may be prepared from compounds of formula (IV)

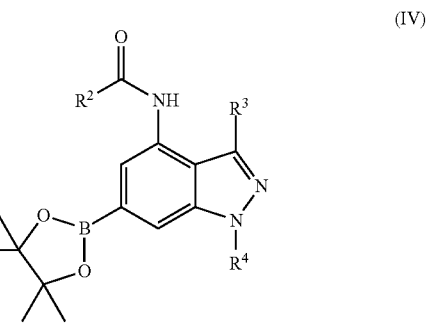

(IV)

wherein $R^2$, $R^3$ and $R^4$ are as defined above, by a process comprising treatment with a suitable halide such as 5-bromo-3-pyridinesulfonamide (commercially available), under microwave irradiation, in the presence of a suitable palladium catalyst such as tetrakis(triphenylphosphine)palladium (0), in a suitable solvent such as isopropanol, in the presence of a suitable base such as aqueous sodium bicarbonate, and at a suitable temperature such as between 60-150° C., for example about 120° C.

Compounds of formula (IV) wherein $R^2$, $R^3$ and $R^4$ are as defined above, may be prepared from compounds of formula (II) as defined above, by treatment with a suitable boronic acid ester such as 4,4,4',4',5,5,5',5'-octamethyl-2,2'-bi-1,3,2-dioxaborolane (commercially available), under microwave irradiation, in the presence of a suitable palladium catalyst such as 1,1'-bis(diphenylphosphino)ferrocene palladium dichloride, in a suitable solvent such as N,N-dimethylacetamide, in the presence of a suitable base such as potassium acetate, and at a suitable temperature such as 60-150° C., for example about 80° C.

Compounds of formula (II) wherein $R^2$, $R^3$ and $R^4$ are as defined above, may be prepared from the compound of formula (III) as described above.

Process c

Compounds of formula (I) wherein $R^1$, $R^2$ and $R^3$ are as defined above and $R^4$ is H, and salts thereof, may be prepared from compounds of formula (V)

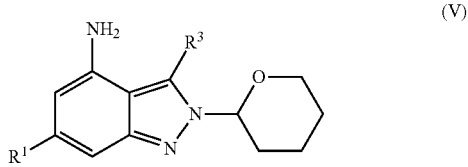

(V)

wherein $R^1$ and $R^3$ are as defined above, by a process comprising treatment either with (i) a suitable acid of formula $R^2COOH$, wherein $R^2$ is as defined above, followed by deprotection using a suitable acid, or (ii) treatment with an acid chloride of formula $R^2COCl$, wherein $R^2$ is as defined above, followed by deprotection by a suitable acid. Suitable conditions for (i) include stirring an acid such as, for example, 2-methyl-1,3-thiazole-4-carboxylic acid (commercially available), in a suitable solvent such as N,N-dimethylformamide, at a suitable temperature such as room temperature, for example about 20° C., in the presence of a coupling reagent such as O-(7-azabenzotriazol-1-yl)-N,N,N',N'-tetramethyluronium hexafluorophosphate, in the presence of a suitable base such as N,N-diisopropylethylamine, followed by treatment with a suitable acid such as hydrogen chloride in 1,4-dioxane. Alternatively, (ii) may be carried out by acylation with a suitable acylating agent such as an acid chloride, in a suitable solvent such as dichloromethane, in the presence of a suitable base such as N,N-diisopropylamine, and at a suitable temperature such as room temperature, for example about 20° C., followed by treatment with a suitable acid such as hydrogen chloride in 1,4-dioxane.

Compounds of formula (V) wherein $R^1$ and $R^3$ are as defined above, may be prepared from compounds of formula (VI)

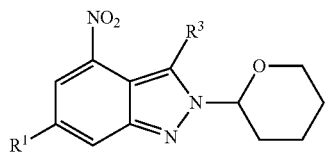

(VI)

wherein $R^1$ and $R^3$ are as described above, by hydrogenation in a Thales H-Cube®, in the presence of a suitable catalyst such as palladium on carbon, in a suitable solvent such as ethyl acetate, at a suitable temperature such as 20-40° C., for example about 30° C., and at a suitable pressure such as 1-50 bar, for example about 30 bar.

Compounds of formula (VI) wherein $R^1$ and $R^3$ are as defined above, may be prepared from compounds of formula (VII)

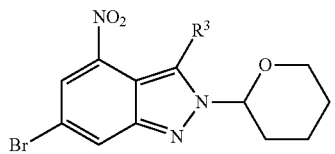

(VII)

wherein $R^3$ is as defined above, by treatment with a suitable boronic acid such as [4-(tetrahydro-2H-pyran-2-yloxy)phenyl]boronic acid, under microwave irradiation, in the presence of a suitable palladium catalyst such as 1,1'-bis(diphenylphosphino)ferrocene palladium dichloride, in a suitable solvent such as isopropanol, in the presence of a suitable base such as aqueous saturated sodium hydrogencarbonate, and at a suitable temperature such as 60-180° C., for example about 150° C.

Compounds of formula (VII) wherein $R^3$ is H, may be prepared from the compound of formula (VIII) (which is commercially available)

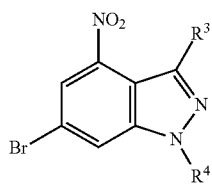

(VIII)

wherein $R^3$ and $R^4$ are H, by treatment with 3,4-dihydro-2H-pyran, in the presence of a suitable acid catalyst such as pyridinium p-toluene sulfonate, in a suitable solvent such as dichloromethane, and at a suitable temperature such as reflux temperature.

Process d

Compounds of formula (I) wherein $R^1$, $R^2$ and $R^3$ are as defined above and $R^4$ is H, and salts thereof, may be prepared from compounds of formula (IX)

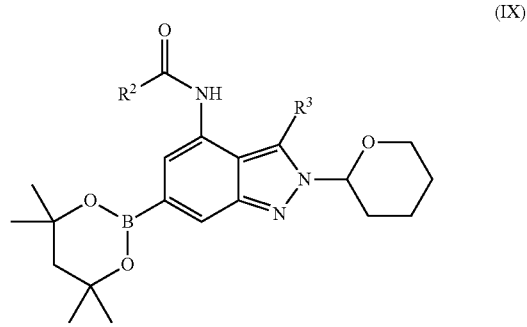

(IX)

wherein $R^2$ and $R^3$ are as defined above, by a process comprising treatment with a suitable halide such as 3-bromopyridine, under microwave irradiation, in the presence of a suitable palladium catalyst such as chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1), in a suitable solvent such as 1,4-dioxane, in the presence of a suitable base such as aqueous potassium triphosphate, and at a suitable temperature such as between 60-180° C., for example about 110° C.

Compounds of formula (IX) wherein $R^2$ and $R^3$ are as defined above, may be prepared from compounds of formula (X)

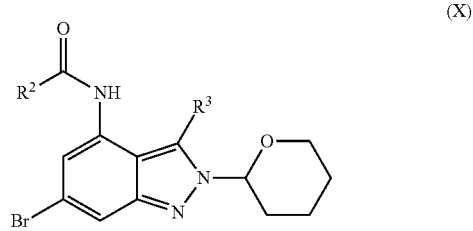

(X)

wherein $R^2$ and $R^3$ are as defined above, by treatment with a suitable boronate such as 4,4,4',4',6,6,6',6'-octamethyl-2,2'-bi-1,3,2-dioxaborinane, under microwave irradiation, in the presence of a suitable palladium catalyst such as 1,1'-bis(diphenylphosphino)ferrocene palladium dichloride, in a suitable solvent such as 1,4-dioxane, in the presence of a suitable base such as potassium acetate, and at a suitable temperature such as 60-150° C., for example about 80° C.

Compounds of formula (X) wherein $R^2$ and $R^3$ are as defined above, may be prepared from compounds of formula (XI)

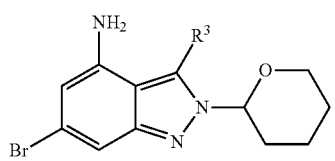

wherein R³ is as described above, by treatment either with (i) a suitable acid of formula R²COOH, wherein R² is as defined above, or (ii) by treatment with an acid chloride of formula R²COCl, wherein R² is as defined above. Suitable conditions for (i) include stirring an acid such as, for example, 2-methyl-1,3-thiazole-4-carboxylic acid (commercially available), in a suitable solvent such as N,N-dimethylformamide, at a suitable temperature such as room temperature, for example about 20° C., in the presence of a coupling reagent such as O-(7-azabenzotriazol-1-yl)-N,N,N'N' tetramethyluronium hexafluorophosphate, and in the presence of a suitable base such as N,N-diisopropylethylamine. Alternatively, (ii) may be carried out by acylation with a suitable acylating agent such as an acid chloride, in a suitable solvent such as dichloromethane, in the presence of a suitable base such as N,N-diisopropylamine, and at a suitable temperature such as room temperature, for example about 20° C.

Compounds of formula (XI) wherein R³ is as defined above, may be prepared from compounds of formula (VII) as described above, by treatment with a reducing agent such as iron filings and ammonium chloride, in a suitable solvent such as ethanol and water, and at a suitable temperature such as between 60-100° C., for example about 80° C.

Compounds of formula (VII), wherein R³ is as described above, may be prepared from the compound of formula (VIII) as described above.

Process e

Compounds of formula (I) wherein R¹, R² and R³ are as defined above and R⁴ is hydrogen, and salts thereof, may also be prepared by a process comprising deprotection of suitably protected derivatives of compounds of formula (IE). Examples of suitable protection groups and the means of their removal can be found in T. W. Greene and P. G. M. Wuts 'Protective Groups in Organic Synthesis' (3$^{rd}$ Ed., J. Wiley and Sons, 1999).

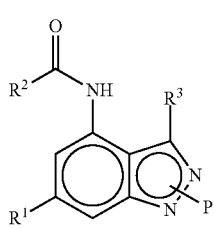

As a further example of this, compounds of formula (I) may be prepared from compounds of formula (IE) where the indazole ring nitrogen is protected (P), for example with 1-phenylsulphonyl, by deprotection under appropriate conditions, such as treating with a base, for example aqueous sodium hydroxide.

Compounds of formula (IE), wherein R¹, R² and R³ are as defined above, may be prepared from compounds of formula (XII)

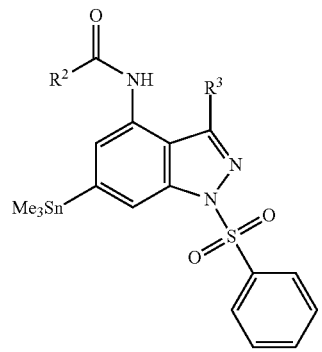

wherein R² and R³ are as defined above, by treatment with a suitable halide such as 4-bromo-1-(phenylsulphonyl)-1H-indole, in the presence of a suitable palladium catalyst such as tetrakis(triphenylphosphine) palladium (0), in a suitable solvent such as N,N-dimethylformamide, and at a suitable temperature such as 80-150° C., for example about 120° C.

Compounds of formula (XII) wherein R² and R³ are as defined above, may be prepared from compounds of formula (XIII)

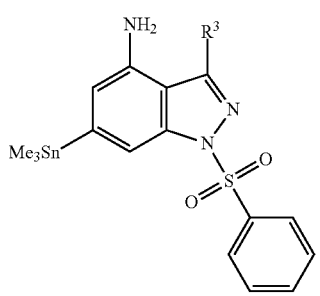

wherein R³ is defined as above, by (i) treatment with an acid of formula R²COOH, wherein R² is as defined above, or (ii) by treatment with an acid chloride of formula R²COCl, wherein R² is as defined above. Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (XIII) wherein R³ is as defined above, may be prepared from compounds of formula (XIV)

(XIV)

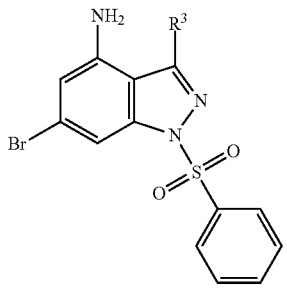

wherein $R^3$ is as defined above, by treatment with a suitable stannane such as hexamethyldistannane, under microwave irradiation, in the presence of a suitable palladium catalyst such as tetrakis(triphenylphosphine)palladium (0), in a suitable solvent such as toluene, in the presence of a suitable base such as triethylamine, and at a suitable temperature such as 80-150° C., for example about 120° C.

Process f

Compounds of formula (I) wherein $R^1$, $R^3$ and $R^4$ are as defined above and $R^2$ is 5-membered heteroaryl wherein the 5-membered heteroaryl contains one or two heteroatoms independently selected from oxygen, nitrogen and sulphur and is optionally substituted by —$(CH_2)_qNR^{25}R^{26}$, and salts thereof, may be prepared from compounds of formula (XVA) or (XVB)

(XVA)

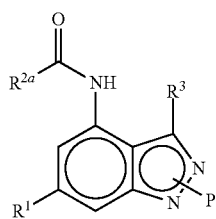

(XVB)

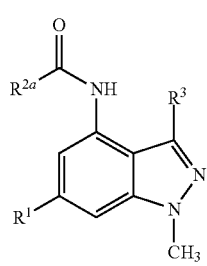

wherein $R^1$ and $R^3$ are as defined above and $R^{2a}$ is 5-membered heteroaryl wherein the 5-membered heteroaryl contains one or two heteroatoms independently selected from oxygen, nitrogen and sulphur and is optionally substituted by —$(CH_2)_qX$, wherein X is a leaving group, for example Cl, and wherein P is a protecting group, for example benzenesulphonyl, by a process comprising treatment with an amine of formula $NHR^{25}R^{26}$ in the presence of a suitable base such as DIPEA, a suitable activating agent such as sodium iodide and in a suitable solvent such as acetonitrile, heating to a suitable temperature such as 20° C.-120° C., for example about 70° C.

As the skilled person will appreciate, in the compound of formula (XVA), the protecting group P may be on the 1 or 2 position of the indazole. Following reaction with the amine, the protecting group P may be removed by deprotection under appropriate conditions.

Compounds of formula (XVA) and (XVB) wherein $R^1$ and $R^3$ are as defined above and $R^{2a}$ is 5-membered heteroaryl wherein the 5-membered heteroaryl contains one or two heteroatoms independently selected from oxygen, nitrogen and sulphur and is optionally substituted by —$(CH_2)_qX$, wherein X is a leaving group, for example Cl, and wherein P is a protecting group, for example benzenesulphonyl, may be prepared from compounds of formula (XVIA) or (XVIB)

(XVIA)

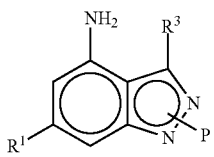

(XVIB)

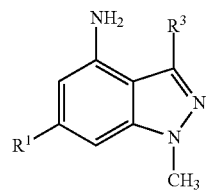

wherein $R^1$, $R^3$ and P are as defined above, by a process comprising treatment with an acid chloride of formula $R^{2a}COCl$, wherein $R^{2a}$ is as defined above, in the presence of a suitable base such as pyridine, in a suitable solvent such as DCM, and at a suitable temperature such as room temperature.

Compounds of formula $R^{2a}COCl$, wherein $R^{2a}$ is as defined above, can be prepared from compounds of formula $R^{2a}CO_2H$, wherein $R^{2a}$ is as defined above, by treatment with thionyl chloride in a suitable solvent such as chloroform, in the presence of DMF (catalytic quantity) and heating to a suitable temperature such as reflux.

Compounds of formula (IE) wherein $R^2$ and $R^3$ are as defined above, P is a protecting group, for example tetrahydropyran or benzenesulphonyl, and $R^1$ is pyridinyl substituted by —$NHSO_2R^{21}$ and further optionally substituted by a substituent $R^{37}$ which is $C_{1-6}$alkyl, —$OR^{17}$ or halo, and salts thereof, may be prepared from compounds of formula (XVII)

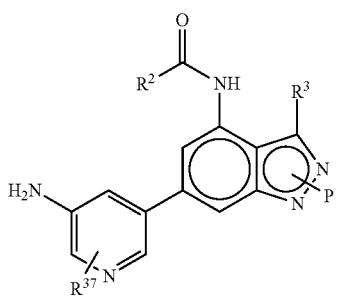
(XVII)

wherein $R^2$, $R^3$ and $R^{37}$ are as defined above and P is a protecting group, for example tetrahydropyran or benzenesulphonyl, by treatment with a sulphonyl chloride such as ethanesulfonyl chloride in the presence of a suitable base such as pyridine, in a suitable solvent such a chloroform, and at a suitable temperature such as room temperature.

Compounds of formula (XVII) wherein $R^2$, $R^3$ and $R^{37}$ are as defined above and P is a protecting group, for example tetrahydropyran or benzenesulphonyl, and salts thereof, may be prepared from compounds of formula (XVIII)

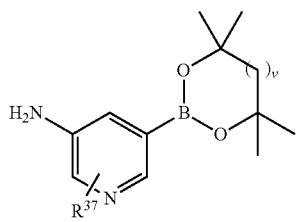
(XVIII)

wherein $R^2$ and $R^3$ are as defined above and P is a protecting group, for example tetrahydropyran or benzenesulphonyl, by treatment with a suitable boronic ester of formula (XIX) wherein $R^{37}$ is as defined above and v=0 or 1, under microwave irradiation, in the presence of a suitable palladium catalyst such as chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1), in a suitable solvent such as aqueous 1,4-dioxane, in the presence of a suitable base such as tripotassium phosphate, and at a suitable temperature such as 60-150° C., for example about 140° C.

(XIX)

Compounds of formula (XIX) wherein $R^{37}$ is as defined above and v=0 or 1, may be prepared from compounds of formula (XX) wherein $R^{37}$ is as defined above, for which a range of analogues are commercially available.

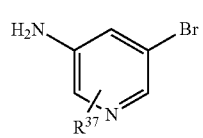
(XX)

In an alternative approach, compounds of formula (IE) wherein $R^2$ and $R^3$ are as defined above, P is a protecting group, for example tetrahydropyran or benzenesulphonyl, and $R^1$ is pyridinyl substituted by —$NHSO_2R^{21}$ and further optionally substituted by a substituent $R^{37}$ which is $C_{1-6}$alkyl, —$OR^{17}$ or halo, and salts thereof, may be prepared from compounds of formula (XVIII) above, by treatment with a boronic ester of formula (XXI)

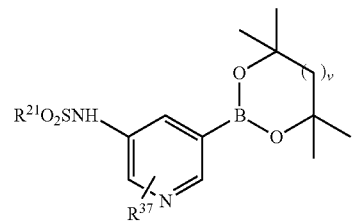
(XXI)

wherein $R^{37}$, $R^{21}$ and v are as defined above, under microwave irradiation, in the presence of a suitable palladium catalyst such as chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1), in a suitable solvent such as aqueous 1,4-dioxane, in the presence of a suitable base such as tripotassium phosphate, and at a suitable temperature such as 60-150° C., for example about 140° C.

Compounds of formula (XXI) wherein $R^{21}$ and $R^{37}$ are as defined above, and salts thereof, can be prepared from compounds of formula (XIX) above, by treatment with a sulphonyl chloride such as ethanesulfonyl chloride in the presence of a suitable base such as pyridine, in a suitable solvent such as chloroform, and at a suitable temperature such as room temperature.

Process g

Compounds of formula (I) wherein $R^1$ and $R^3$ are as defined above, $R^4$ is H and $R^2$ is 5-membered heteroaryl wherein the 5-membered heteroaryl contains one or two heteroatoms independently selected from oxygen, nitrogen and sulphur and is optionally substituted by —$(CH_2)_qNR^{25}R^{26}$, and salts thereof, may be prepared from compounds of formula (XXII) by deprotection of a suitable protecting group, for example 4-methylbenzenesulphonyl, as described above.

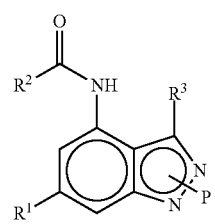
(XXII)

Compounds of formula (XXII) wherein $R^1$, $R^2$ and $R^3$ are as defined above, and compounds of formula (I) wherein $R^1$, $R^2$ and $R^3$ are as defined above and $R^4$ is methyl, may be may be prepared from compounds of formula (XXIIIA) or (XXIIIB)

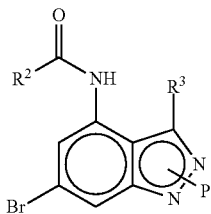
(XXIIIA)

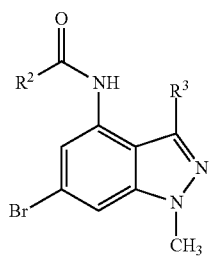
(XXIIIB)

wherein $R^2$, $R^3$ and P are as defined above, by a process comprising treatment with a suitable boronic ester, either under microwave irradiation or thermally, in the presence of a suitable palladium catalyst such as 1,1'-bis(diphenylphosphino)ferrocene palladium dichloride, in a suitable solvent such as aqueous 1,4-dioxane, in the presence of a suitable base such as sodium carbonate, and at a suitable temperature such as 60-140° C., for example about 80° C.

Compounds of formula (XXIIIA) and (XXIIIB) wherein $R^2$ and $R^3$ are as defined above, may be prepared from compounds of formula (XXIVA) and (XXIVB)

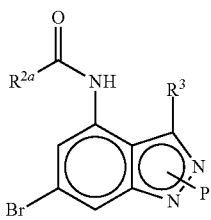
(XXIVA)

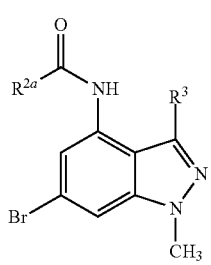
(XXIVB)

wherein $R^3$ is as defined above and $R^{2a}$ is 5-membered heteroaryl wherein the 5-membered heteroaryl contains one or two heteroatoms independently selected from oxygen, nitrogen and sulphur and is optionally substituted by —$(CH_2)_qX$, wherein X is a leaving group, for example Cl by a process comprising treatment with an amine of formula $NHR^{25}R^{26}$ and in a suitable solvent such as acetonitrile, heating to a suitable temperature such as 20° C.-120° C., for example about 80° C.

Compounds of formula (XXIVA) and (XXIVB) wherein $R^3$ is defined as above and $R^{2a}$ is 5-membered heteroaryl wherein the 5-membered heteroaryl contains one or two heteroatoms independently selected from oxygen, nitrogen and sulphur and is optionally substituted by —$(CH_2)_qX$, wherein X is a leaving group, for example Cl, may be prepared from compounds of formula (XXVA) and (XXVB)

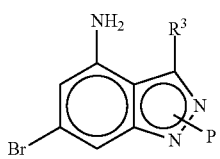
(XXVA)

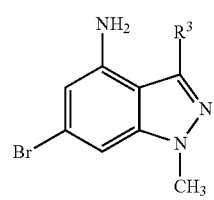
(XXVB)

wherein $R^3$ and P are as defined as above, by a process comprising treatment with an acid chloride of formula $R^{2a}COCl$, wherein $R^{2a}$ is as defined above, in the presence of a suitable base, such as pyridine, in a suitable solvent such as DCM, and at a suitable temperature such as room temperature.

Compounds of formula $R^{2a}COCl$, wherein $R^{2a}$ is as defined above, can be prepared from compounds of formula $R^{2a}CO_2H$, wherein $R^{2a}$ is as defined above, by treatment with thionyl chloride in a suitable solvent such as chloroform, in the presence of DMF (catalytic quantity) and heating to a suitable temperature such as reflux.

Thus, in one embodiment, the invention provides a process for preparing a compound of the invention comprising:

a) reacting a compound of formula (II)

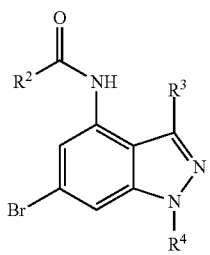
(II)

wherein $R^2$, $R^3$ and $R^4$ are as defined above, with a suitable boronic acid ester;

b) reacting a compound of fomula (IV)

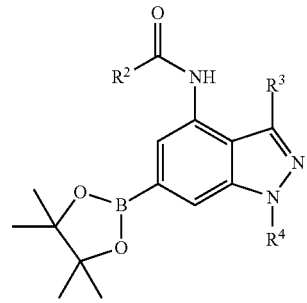
(IV)

wherein $R^2$, $R^3$ and $R^4$ are as defined above, with a suitable halide;

c) for a compound of formula (I) wherein $R^1$, $R^2$ and $R^3$ are as defined above and $R^4$ is H, or a salt thereof, reacting a compound of formula (V)

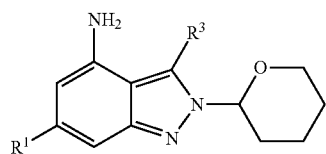
(V)

wherein $R^1$ and $R^3$ are as defined above, either with (i) a suitable acid of formula $R^2COOH$ wherein $R^2$ is as defined above, followed by deprotection using a suitable acid, or (ii) with an acid chloride of formula $R^2COCl$, wherein $R^2$ is as defined above, followed by deprotection by a suitable acid;

d) for a compound of formula (I) wherein $R^1$, $R^2$ and $R^3$ are as defined above and $R^4$ is H, or a salt thereof, reacting a compound of (IX)

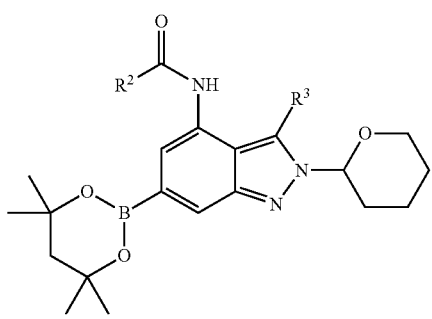
(IX)

wherein $R^2$ and $R^3$ are as defined above, with a suitable halide;

e) deprotection of a suitably protected derivative of a compound of formula (IE)

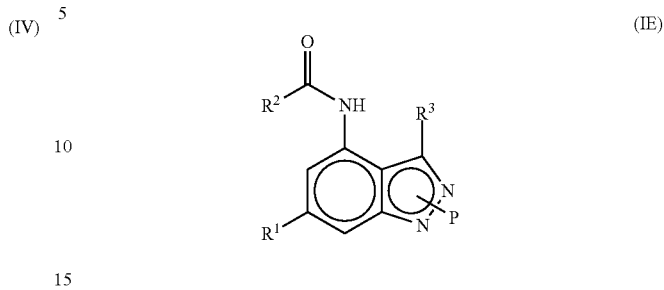
(IE)

f) for a compound of formula (I) wherein $R^1$, $R^3$ and $R^4$ are as defined above and $R^2$ is 5-membered heteroaryl wherein the 5-membered heteroaryl contains one or two heteroatoms independently selected from oxygen, nitrogen and sulphur and is optionally substituted by —$(CH_2)_qNR^{25}R^{26}$, and salts thereof, reacting a compound of formula (XVA) or (XVB)

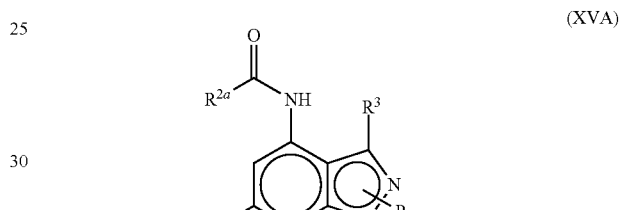
(XVA)

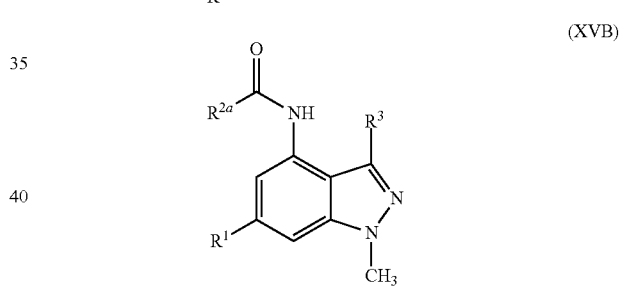
(XVB)

wherein $R^1$ and $R^3$ are as defined above and $R^{2a}$ is 5-membered heteroaryl wherein the 5-membered heteroaryl contains one or two heteroatoms independently selected from oxygen, nitrogen and sulphur and is optionally substituted by —$(CH_2)_qX$, wherein X is a leaving group, and wherein P is a protecting group, with an amine of formula $NHR^{25}R^{26}$, followed where necessary by deprotection; or g) reacting a compound of formula (XXIIIA) or (XXIIIB)

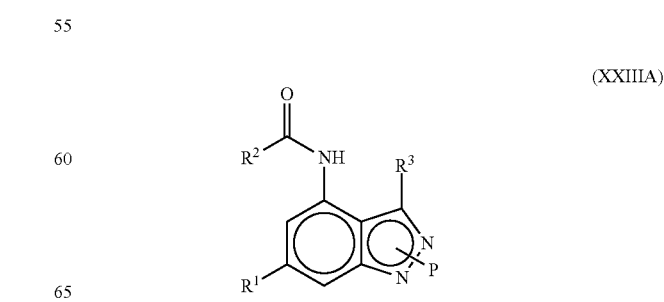
(XXIIIA)

-continued

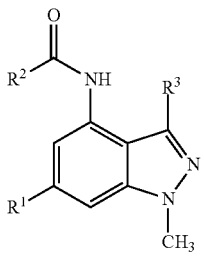

(XXIIIB)

wherein $R^2$, $R^3$ and P are as defined above, with a suitable boronic ester, followed where necessary by deprotection.

Methods of Use

The compounds of the invention are inhibitors of PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally. Preferably, the compounds of formula (I) or pharmaceutically acceptable salts thereof are administered by inhalation.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by inappropriate PI3-kinase activity comprising administering a safe and effective amount of a compound of formula (I) or a pharmaceutically acceptable salt thereof to a patient in need thereof.

In one embodiment, the disorder mediated by inappropriate PI3-kinase activity is selected from the group consisting of respiratory diseases (including asthma and chronic obstructive pulmonary disease (COPD)); allergic diseases (including allergic rhinitis and atopic dermatitis); autoimmune diseases (including rheumatoid arthritis and multiple sclerosis); inflammatory disorders (including inflammatory bowel disease); cardiovascular diseases (including thrombosis and atherosclerosis); hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain (including pain associated with rheumatoid arthritis or osteoarthritis, back pain, general inflammatory pain, post hepatic neuralgia, diabetic neuropathy, inflammatory neuropathic pain (trama), trigeminal neuralgia and central pain)

In one embodiment, the disorder mediated by inappropriate PI3-kinase activity is a respiratory disease. In a further embodiment, the disorder mediated by inappropriate PI3-kinase activity is asthma. In a further embodiment, the disorder mediated by inappropriate PI3-kinase activity is chronic obstructive pulmonary disease (COPD).

In one embodiment, the disorder mediated by inappropriate PI3-kinase activity is pain.

In one embodiment, the present invention provides a method of treating a respiratory disease comprising administering a safe and effective amount of 2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide or a pharmaceutically acceptable salt thereof to a patient in need thereof.

In one embodiment, the present invention provides a method of treating asthma comprising administering a safe and effective amount of 2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide or a pharmaceutically acceptable salt thereof to a patient in need thereof.

In one embodiment, the present invention provides a method of treating COPD comprising administering a safe and effective amount of 2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide or a pharmaceutically acceptable salt thereof to a patient in need thereof.

In one embodiment, the invention provides a compound of formula (I) or a pharmaceutically acceptable salt thereof for use in medical therapy. In another embodiment, the invention provides a compound of formula (I) or a pharmaceutically acceptable salt thereof for use in the treatment of a disorder mediated by inappropriate PI3-kinase activity. In a further embodiment, the invention provides the use of a compound of formula (I) or a pharmaceutically acceptable salt thereof in the manufacture of a medicament for use in the treatment of a disorder mediated by inappropriate PI3-kinase activity.

Compositions

The compounds of formula (I) and pharmaceutically acceptable salts thereof will normally, but not necessarily, be formulated into pharmaceutical compositions prior to administration to a patient. Accordingly, in another aspect the invention is directed to pharmaceutical compositions comprising a compound of formula (I) or a pharmaceutically acceptable salt thereof and one or more pharmaceutically-acceptable excipients.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or a pharmaceutically acceptable salt thereof and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration. Preferably, the compounds of formula (I) or pharmaceutically acceptable salts thereof will be formulated for inhaled administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example, as a dry powder, an aerosol, a suspension, or a solution composition. Preferably, the invention is directed to a dry powder composition adapted for inhalation comprising compound of formula (I) or a pharmaceutically acceptable salt thereof.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 μg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from about 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example of a bulk manufacturing method for preparing solution aerosol formulations, a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine.

Certain compounds of the invention may show selectivity for PI3K$\delta$ over other PI3-kinases. The invention thus provides, in a further aspect, a combination comprising a compound of formula (I) or a pharmaceutically acceptable salt thereof which is selective for PI3K$\delta$ together with a compound or pharmaceutically acceptable salt thereof which is selective for another PI3-kinase, for example PI3K$\gamma$.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 hrs or longer, are preferred.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (Sep. 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as Cl-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropyl-benzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or (endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003).

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

In a preferred aspect, the invention provides a combination comprising a compound of formula (I) or a pharmaceutically acceptable salt thereof together with a corticosteroid.

In a further preferred aspect, the invention provides a combination comprising a compound of formula (I) or a pharmaceutically acceptable salt thereof together with a $\beta_2$-adrenoreceptor agonist.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

In a preferred aspect, the invention provides a pharmaceutical composition comprising a combination of a compound of formula (I) or a pharmaceutically acceptable salt thereof together with a corticosteroid.

In a further preferred aspect, the invention provides a pharmaceutical composition comprising a combination of a compound of formula (I) or a pharmaceutically acceptable salt thereof together with a $\beta_2$-adrenoreceptor agonist.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

General Methods
LC/MS (Liquid Chromatography/Mass Spectroscopy)

LC/MS analysis was carried out using one of the methods listed below.

LC/MS Method A

Waters ZQ mass spectrometer operating in positive ion electrospray mode, mass range 100-1000 amu.
UV wavelength: 215-330 nm
Column: 3.3 cm×4.6 mm i.d., 3 µm ABZ+PLUS
Flow Rate: 3 ml/min
Injection Volume: 5 µl
Solvent A: 95% MeCN+0.05% of a 1% v/v solution of formic acid in water
Solvent B: 0.1% v/v solution of formic acid in 10 mmol ammonium acetate (aq)
Gradient: Mixtures of Solvent A and Solvent B are used according to the following gradient profiles (expressed as % Solvent A in the mixture): 0% A; 0.7 mins, 0-100% A; 3.5 mins, 100% A; 0.4 mins, 100-0% A; 0.2 mins.

LC/MS Method B

LC/MS instrumentation consists of the following:
Column: Acquity HPLC BEH $C_{18}$ 1.7 µm, 2.1 mm×50 mm.
Column oven at 40° C.
Solvent A: 0.1% formic acid in water containing 10 mmol ammonium acetate
Solvent B: MeCN:Water (95:5, v/v) containing 0.05% formic acid
Injection volume: 0.5 µl
Injection technique: Partial loop overfill
UV detection: 220-330 nm
UV sampling rate: 40 points/s
MS scan range: 100-1000 amu
MS scanning rate: 0.2 s/scan with a 0.1 s inter scan delay
MS scan function: Electrospray with pos neg switching
Cycle time: 150 s
Flow rate: 1 ml/min
Gradient:

| Time (mins) | % A | % B |
|---|---|---|
| 0 | 97 | 3 |
| 0.1 | 97 | 3 |
| 1.4 | 0 | 100 |

-continued

| Time (mins) | % A | % B |
|---|---|---|
| 1.9 | 0 | 100 |
| 2 | 97 | 3 |

LC/MS Method C

The HPLC analysis was conducted on a Sunfire C18 column (30 mm×4.6 mm i.d. 3.5 µm packing diameter) at 30 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
|---|---|---|---|
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

Mass Directed Automated Preparative HPLC

The methods for the mass-directed automated preparative HPLC used for the purification of compounds are described below:

Mass Directed Automated Preparative HPLC Column, Conditions and Eluent

Method A

Column

The column used is typically a Supelco LCABZ++ column with dimensions of 20 mm i.d. by 100 mm in length. The stationary phase particle size is 5 µm.

Solvents

A: Water containing 0.1% formic acid
B: MeCN:Water (95:5, v/v) containing 0.05% formic acid
Make up solvent: MeOH:Water (8:2, v/v)+50 mmol ammonium acetate
Needle rinse solvent=MeOH:Water:DMSO (8:1:1, v/v/v)

Methods

There are five methods used depending on the analytical retention time of the compound of interest.

They all have a 15 mins runtime, which comprises a 10 mins gradient followed by a 5 mins column flush and re-equilibration step.
compound retention time 1.5-2.2 mins=0-30% B
compound retention time 2.0-2.8 mins=5-30% B
compound retention time 2.5-3.0 mins=15-55% B
compound retention time 2.8-4.0 mins=30-80% B
compound retention time 3.8-5.5 mins=50-90% B Flow Rate All of the above methods have a flow rate of 20 ml/min
It is thought that basic compounds isolated by this method are formate salts.

Mass Directed Automated Preparative HPLC Column, Conditions and Eluent

Method B

Columns

Small Scale Preparative Column

Supelcosil ABZ+Plus column whose dimensions are 21.2 mm i.d. by 100 mm in length. The stationary phase particle size is 5 μm.

Large Scale Preparative Column

Supelcosil ABZ+Plus column whose dimensions are 30 mm i.d. by 150 mm in length. The stationary phase particle size is 12 μm.

Solvents

A: Water containing 0.1% formic acid
B: MeCN:Water (95:5, v/v) containing 0.05% formic acid
Make up solvent: MeOH:Water (4:1, v/v) containing 50 mmol ammonium acetate
Needle rinse solvent: MeOH:Water:DMSO (8:1:1, v/v/v)

Methods for Small Scale Prep for Up to 30 mg

There are ten methods available for use. The choice of method is dependant on the analytical retention time of the compound of interest.

Five methods have a 15 mins runtime, this comprises of a 10 mins gradient followed by a mins column flush and re-equilibration step. The other five have a 25 mins runtime. Here the methods have the same starting and end points for the organic content of B but the gradients have been extended over a 20 mins period to provide greater chromatographic resolution.

compound retention time 1.5-2.2 mins=0-30% B
compound retention time 2.0-2.8 mins=10-40% B
compound retention time 2.5-3.0 mins=15-55% B
compound retention time 2.8-4.0 mins=30-80% B
compound retention time 3.8-5.5 mins=60-90% B
Flow rates for the above methods are 20 ml/min Methods for Large Scale Prep for Up to 90 mg Due to the different column dimension and the phase particle size the percentage organic content varies slightly to the small scale methods. As for small scale there are ten methods available for use. The choice of method is dependant on the analytical retention time of the compound of interest.

Five methods have a 15 mins runtime, which comprises a 10 mins gradient followed by a 5 mins column flush and re-equilibration step. The other five have a 25 mins runtime. Here the methods have the same starting and end points for the organic content of B but the gradients have been extended over a 20 mins period to provide greater chromatographic resolution.

compound retention time 1.5-2.2 mins=0-30% B
compound retention time 2.0-2.8 mins=10-40% B
compound retention time 2.5-3.0 mins=25-55% B
compound retention time 2.8-4.0 mins=40-75% B
compound retention time 3.8-5.5 mins=60-90% B
Flow rates for the above methods are 40 ml/min It is thought that basic compounds isolated by this method are formate salts.

Mass Directed Automated Preparative HPLC Column, Conditions and Eluent

Method C

Column Details: XBRIDGE $C_{18}$ column (100 mm×19 mm i.d., 5 μm packing diameter)

Solvents:
A: 10 mmol ammonium bicarbonate (aq) adjusted to pH 10 with ammonia (aq)
B: MeCN The UV detection was an averaged signal from wavelength of 210 nm to 350 nm and mass spectra were recorded on a mass spectrometer using an alternate-scan positive and negative mode electrospray ionization.

Mass Directed Automated Preparative HPLC Column, Conditions and Eluent

Method D

Column Details: ATLANTIS dC18 5 um column (19×100 mm)

The solvents employed were:
A=0.1% v/v solution of Formic Acid in Water.
B=0.05% v/v solution of Formic Acid in 95% Acetonitrile plus 5% Water.

Gradient:

| Time (min) | Flow Rate (ml/min) | % A | % B |
|---|---|---|---|
| 0.0 | 20 | 90 | 10 |
| 1.0 | 20 | 90 | 10 |
| 9.0 | 20 | 1 | 99 |
| 9.6 | 20 | 1 | 99 |
| 9.7 | 20 | 90 | 10 |
| 11.7 | 20 | 90 | 10 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Mass Directed Automated Preparative HPLC Column, Conditions and Eluent

Method E

Stationary Phase

The stationary phase used for this purification was Sunfire C18 with a particle size of 5 μm.

Small Scale Preparative Column
Column Dimension: 100 mm×19 mm i.d.
Large Scale Preparative Column
Column Dimension: 150 mm×30 mm i.d.

Eluent

The eluents employed were:
A=0.1% v/v solution of formic acid in water.
B=0.1% v/v solution of formic acid in acetonitrile.

Methods for Small Scale Prep for Up to 30 mg of Crude Sample

There are ten focused small scale preparative methods available for use. The choice of method is dependent on two factors
1. The retention time of the component/s of interest on the generic analytical LCMS method.
2. The presence of closely eluting impurities to the component/s of interest.

From the analytical retention time the choice of one of five small scale focused prep methods was made. Small scale prep methods contain a 7 or 10 minute gradient over a specified organic range, followed by a 8 or 5 minute flush, respectively. The total run time is 15 minutes.

If there are closely eluting impurities to the component/s of interest then there are five extended small scale focused prep methods available using the same gradients over a longer time. Extended small scale prep methods contain a 20 or 14 minute gradient over the specified organic range followed by a 5 or 11 minute flush, respectively. The total run time is 25 minutes.

Flow rates for all small scale methods are 20 ml/min and the purification is performed at ambient temperature.

The injection volume for small scale prep is 500 μl.

The 5 small scale gradients are shown below.

5-30% B
15-55% B
30-85% B
50-99% B
80-99% B

Methods for Large Scale Prep for Up to 90 mg of Crude Sample

There are ten focused large scale prep methods available for use. The choice of method is dependent on the same two factors as for small scale prep. The run times (gradient and flush) are the same as for small scale prep methods.

Flow rates for all large scale methods are 40 ml/min and the purification is performed at ambient temperature.

The injection volume for large scale prep is 980 µl.

UV Detection

The UV detection for all methods is an averaged signal from all wavelengths from 210 nm to 350 nm.

MS Conditions

MS: Waters ZQ

Ionisation mode: Alternate-scan positive and negative electrospray

Scan range: 100 to 1000 amu

Scan time: 0.50 seconds

Inter scan delay: 0.20 seconds

Mass Directed Automated Preparative HPLC Column, Conditions and Eluent

Method F

Column Details: SUNFIRE C18 column (100 mm×19 mm id. 5 um)

The solvents employed were:

A=0.1% v/v solution of Trifluoroacetic Acid in Water.
B=0.1% v/v solution of Trifluoroacetic Acid in Acetonitrile.

Methods below are selected based on the analytical retention time of the compounds being purified.

Method 1

| Time (min) | Flow Rate (ml/min) | % A | % B |
|---|---|---|---|
| 0.0 | 20 | 95 | 5 |
| 1.0 | 20 | 95 | 5 |
| 10 | 20 | 70 | 30 |
| 10.5 | 20 | 5 | 95 |
| 12.5 | 20 | 5 | 95 |
| 13 | 20 | 95 | 5 |
| 14 | 20 | 95 | 5 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method 2

| Time (min) | Flow Rate (ml/min) | % A | % B |
|---|---|---|---|
| 0.0 | 20 | 85 | 15 |
| 1.0 | 20 | 85 | 15 |
| 10 | 20 | 45 | 55 |
| 10.5 | 20 | 5 | 95 |
| 12.5 | 20 | 5 | 95 |
| 13 | 20 | 85 | 15 |
| 14 | 20 | 85 | 15 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method 3

| Time (min) | Flow Rate (ml/min) | % A | % B |
|---|---|---|---|
| 0.0 | 20 | 70 | 30 |
| 1.0 | 70 | 70 | 30 |
| 10 | 20 | 15 | 85 |
| 10.5 | 20 | 5 | 95 |
| 12.5 | 20 | 5 | 95 |
| 13 | 20 | 70 | 30 |
| 14 | 20 | 70 | 30 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method 4

| Time (min) | Flow Rate (ml/min) | % A | % B |
|---|---|---|---|
| 0.0 | 20 | 50 | 50 |
| 1.0 | 20 | 50 | 50 |
| 10 | 20 | 1 | 99 |
| 12.5 | 20 | 1 | 99 |
| 13 | 20 | 50 | 50 |
| 14 | 20 | 50 | 50 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method 5

| Time (min) | Flow Rate (ml/min) | % A | % B |
|---|---|---|---|
| 0.0 | 20 | 20 | 80 |
| 1.0 | 20 | 20 | 80 |
| 7.0 | 20 | 1 | 99 |
| 12.5 | 20 | 1 | 99 |
| 13 | 20 | 20 | 80 |
| 14 | 20 | 20 | 80 |

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

INTERMEDIATES AND EXAMPLES

When the name of a commercial supplier is given after the name of a compound or a reagent, for instance "compound X (Aldrich)" or "compound X/Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

Similarly, when a literature or a patent reference is given after the name of a compound, for instance compound Y (EP 0 123 456), this means that the preparation of the compound is described in the named reference.

The names of the Examples have been obtained using a compound naming programme which matches name to structure (e.g. ACD/Name Batch v 9.0).

Intermediate 1

6-Bromo-4-nitro-2-(tetrahydro-2H-pyran-2-yl)-2H-indazole

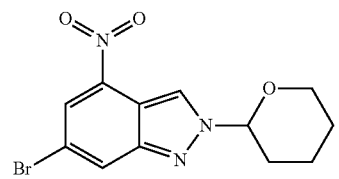

Method A:

6-Bromo-4-nitro-1H-indazole (10 g, 41 mmol), 3,4-dihydropyran (8.5 ml, 93 mmol) and pyridinium p-toluene sulfonate (125 mg, 0.496 mmol) in DCM (150 ml) were heated at reflux for 4.5 h. The reaction was cooled to RT and then poured onto saturated sodium bicarbonate (aq) (200 ml). The layers were separated and the aqueous layer extracted with DCM (2×100 ml). The combined organic layers were washed with 5% citric acid (aq) (100 ml) and brine (100 ml) and dried over magnesium sulphate. The solvent was removed in vacuo to give the title compound, 12.9 g, used without further purification.

LC/MS (Method A) $R_t$=3.42 mins, MH$^+$=328.

Method B:

To 6-bromo-4-nitro-1H-indazole (10 g, available from Sinova Ltd) in dihydropyran (100 ml) was added TFA (0.068 ml) and the reaction was heated for 1.5 hours at reflux. After cooling, 180 ml DCM and 50 ml saturated sodium bicarbonate solution was added and stirred for 10 minutes. The DCM was separated from the aqueous which was re-washed with DCM (70 ml). The combined organic layers were passed through a hydrophobic frit and evaporated to dryness. The residual solid was triturated with ether then filtered. The solid material was dissolved in DCM and purified by chromatography on silica on the ISCO Companion, using an isocratic gradient of DCM. Purified fractions were combined and evaporated to dryness to afford the title compound (7.78 g).

LCMS (Method A) $R_t$ 3.51 min, MH$^-$=326/328

Intermediate 2

4-Nitro-2-(tetrahydro-2H-pyran-2-yl)-6-[4-(tetrahydro-2H-pyran-2-yloxy)phenyl]-2H-indazole

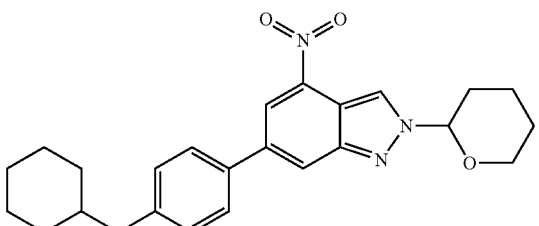

6-Bromo-4-nitro-2-(tetrahydro-2H-pyran-2-yl)-2H-indazole (500 mg, 1.53 mmol), Pd(dppf)Cl$_2$ (125 mg, 0.153 mmol), [4-(tetrahydro-2H-pyran-2-yloxy)phenyl]boronic acid (511 mg, 2.3 mmol), saturated sodium hydrogen carbonate (aq) (3 ml) and isopropyl alcohol (12 ml) were added to each of 5 microwave vessels. All 5 reactions were heated at 150° C. for 10 mins in a Biotage microwave. The reaction mixtures were combined and water (250 ml) and ethyl acetate (250 ml) were added. The mixture was filtered and the organic layer collected. The organic layer was washed with water, then brine, dried over magnesium sulphate, filtered and dried in vacuo. The residue was purified using silica gel chromatography, eluting with 0-25% ethyl acetate in cyclohexane. Appropriate fractions were combined and the solvent was removed in vacuo to give the title compound, 2.3 g.

LC/MS (Method A) $R_t$=3.85 mins, MH$^+$=424.

Intermediate 3

2-(Tetrahydro-2H-pyran-2-yl)-6-[4-(tetrahydro-2H-pyran-2-yloxy)phenyl]-2H-indazol-4-amine

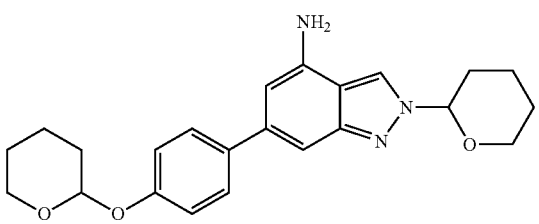

4-Nitro-2-(tetrahydro-2H-pyran-2-yl)-6-[3-(tetrahydro-2H-pyran-2-yloxy)phenyl]-2H-indazole (2.31 g, 5.45 mmol) was dissolved in ethyl acetate (109 ml) and the compound was reduced using the H-cube (available from ThalesNano) with a 10% Pd/C catalyst cartridge at 30° C. and 30 bar. The solvent was removed in vacuo and the residue was purified using silica gel chromatography eluting with 0-50% ethyl acetate in cyclohexane. Appropriate fractions were combined and the solvent was removed in vacuo to give the title compound, 963 mg.

LC/MS (Method A) $R_t$=3.22 mins, $MH^+$=394.

Intermediate 4

4-Nitro-2-(tetrahydro-2H-pyran-2-yl)-6-[3-(tetrahydro-2H-pyran-2-yloxy)phenyl]H-indazole

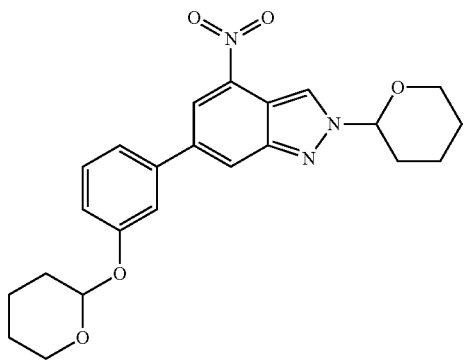

6-Bromo-4-nitro-2-(tetrahydro-2H-pyran-2-yl)-2H-indazole (500 mg, 1.53 mmol), Pd(dppf)Cl$_2$ (125 mg, 0.153 mmol), 2-{[3-(4,4,5,5-tetramethyl-1,3,2-dioxaborolan-2-yl)phenyl]oxy}tetrahydro-2H-pyran (700 mg, 2.3 mmol), saturated sodium hydrogen carbonate (aq) (2 ml) and isopropyl alcohol (8 ml) were added to each of 5 microwave vessels. All 5 reactions were heated at 150° C. for 10 mins in a Biotage Initiator microwave. Reaction mixtures 1, 4, 5 were combined and water (250 ml) and ethyl acetate (250 ml) were added. The separated organic layer was washed with water followed by brine, then dried over sodium sulphate. The solvent was removed in vacuo and the residue was purified using silica gel chromatography, eluting with 10-35% ethyl acetate in cyclohexane. Appropriate fractions were combined and the solvent was removed in vacuo. This process was then repeated on combined reaction mixtures 2 and 3. Finally, the residues were combined to give the title compound, 1.06 g.

LC/MS (Method A) $R_t$=3.86 mins, $MH^+$=424.

Intermediate 5

2-(Tetrahydro-2H-pyran-2-yl)-6-[3-(tetrahydro-2H-pyran-2-yloxy)phenyl]-2H-indazol-4-amine

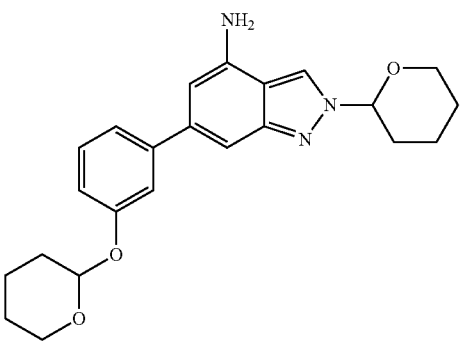

4-Nitro-2-(tetrahydro-2H-pyran-2-yl)-6-[3-(tetrahydro-2H-pyran-2-yloxy)phenyl]-2H-indazole (1.06 g, 2.5 mmol) was dissolved in ethyl acetate (100 ml) and 10% Pd/C (53 mg) was added. The reaction was stirred under an atmosphere of hydrogen gas (1 atm) at RT for 16 h. The reaction mixture was filtered through celite and the solvent was removed in vacuo to yield the title compound, 828 mg, used without further purification.

LC/MS (Method A) $R_t$=3.21 mins, $MH^+$=394.

Intermediate 6

2-Methyl-N-[6-(4,4,5,5-tetramethyl-1,3,2-dioxaborolan-2-yl)-1H-indazol-4-yl]-1,3-thiazole-4-carboxamide

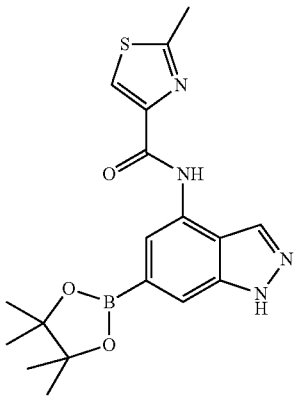

N-(6-Bromo-1H-indazol-4-yl)-2-methyl-1,3-thiazole-4-carboxamide (500 mg, 1.48 mmol), 4,4,4',4',5,5,5',5'-octamethyl-2,2'-bi-1,3,2-dioxaborolane (414 mg, 1.63 mmol), Pd(dppf)Cl$_2$—CH$_2$Cl$_2$ (121 mg, 0.148 mmol) and potassium acetate (437 mg, 4.45 mmol) were combined in DMA (19 ml) and the reaction mixture was degassed with nitrogen for 5 mins before heating in a Biotage microwave at 80° C. for 20 mins. Further Pd(dppf)Cl$_2$—CH$_2$Cl$_2$ (121 mg, 0.148 mmol) was added and the reaction was degassed with nitrogen for 5 mins before heating in a Biotage Initiator at 80° C. for 20 mins. The reaction mixture was partitioned between ethyl acetate (2×200 ml) and water (200 ml) using stirring to help the layers settle. The organic layers were combined, passed through a hydrophobic frit and evaporated in vacuo. The residue was purified using silica gel chromatography, eluting with 0-15% MeOH (containing 1% Et$_3$N) in DCM. Appropriate fractions were combined and evaporated in vacuo as was the purification waste. These residues were combined and further purified by silica gel chromatography eluting with 0-100% ethyl acetate in cyclohexane followed by 0-30% MeOH (containing 1% Et$_3$N) in ethyl acetate. Appropriate fractions were combined and evaporated in vacuo and the residue was further purified by flash chromatography, eluting with 0-100% ethyl acetate in DCM, followed by 0-20% MeOH (containing 1% Et$_3$N) in ethyl acetate. Appropriate fractions were combined and evaporated in vacuo to give the title compound, 23 mg.

LC/MS (Method B) R$_t$=1.11 min, MH$^+$=385.

Intermediate 7

N-(6-romo-1H-indazol-4-yl)-2-methyl-1,3-thiazole-4-carboxamide

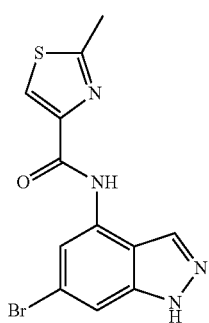

2-Methyl-1,3-thiazole-4-carboxylic acid (4.59 g, 32.1 mmol), HATU (13.4 g, 35.3 mmol) and DIPEA (16.8 ml, 96 mmol) were stirred in DMF (140 ml) for 30 mins at 20° C. 6-Bromo-1H-indazol-4-amine (3.40 g, 16.03 mmol) was added and the reaction stirred at 20° C. for 2 days. The solvent was reduced to ~40 ml and the reaction mixture applied to 5×70 g aminopropyl SPE cartridges and left to stand for 3 h. The cartridges were eluted with DCM:MeOH (1:1, v/v) and the solvent was evaporated in vacuo. The residue was purified by silica gel chromatography, eluting with 0-15% MeOH (containing 1% Et$_3$N) in DCM. Appropriate fractions were evaporated to give the title compound 1.02 g.

LC/MS (Method B) R$_t$=0.96 mins, MH$^+$=339.

Intermediate 8

1-[3-(4,4,5,5-Tetramethyl-1,3,2-dioxaborolan-2-yl)phenyl]methanesulfonamide

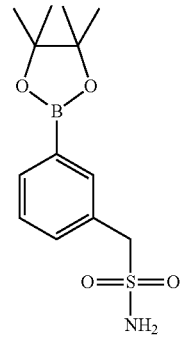

(3-Bromophenyl)methanesulfonyl chloride (49 g, 179 mmol) in 1,4-dioxane (15 ml) was added dropwise over 10 mins to 28% ammonia (aq) (500 ml) at −15° C. The reaction was warmed to RT and stirred overnight. The reaction was filtered, washed with water (30 ml) and hexane (30 ml), then dried to give a material assumed to be 1-(3-Bromophenyl)methanesulfonamide, 38.8 g, which was used directly in the next step without characterisation.

Crude 1-(3-bromophenyl)methanesulfonamide (32.5 g, 130 mmol), 4,4,4',4',5,5,5',5'-octamethyl-2,2'-bi-1,3,2-dioxaborolane (46.4 g, 180 mmol), potassium acetate (51 g, 520 mmol) and 1,4-dioxane (560 ml) were degassed for 10 mins with argon. Pd(dppf)Cl$_2$ (1.9 g, 2.6 mmol) was added and the reaction heated at 70° C. overnight. Additional Pd(dppf)Cl$_2$ (0.5 g, 0.68 mmol) was added and the mixture heated for 6 h. After cooling, the reaction mass was filtered through celite and the filtrates concentrated in vacuo. The residue was repeatedly refluxed with hexane (100 ml), then ground and dried to give title compound 37.8 g. GC: R$_t$=14.8 mins (GC system below), LC: R$_t$=1.58 mins (LC system below)

GC System:
Column: Varian VF5 ms column, 30 m×0.32 mm×0.25 μm
Conditions: 40° C. for 2 mins; 40-250° C. over 15 mins; 250° C. for 4 mins.

LC System:
Column: XBridge 2.1 mm×30 mm 5 μm C$_{18}$
Solvent A: 10 mM ammonium bicarbonate (aq)
Solvent B: MeCN
Gradient: 5% A to 95% B over 3.1 mins, hold for 0.8 mins.

Intermediate 9

N-(5-Bromo-2-chloro-3-pyridinyl)benzenesulfonamide

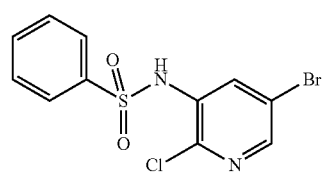

Benzenesulfonyl chloride (2.24 ml, 17.5 mmol) was added dropwise over 5-10 mins to a solution of 5-bromo-2-chloro-3-pyridinamine (2.5 g, 12.1 mmol) and pyridine (1.5 ml, 18.56 mmol) in DCM (25 ml). The reaction was stirred for 18 h at RT before evaporation to dryness in vacuo. The residue was split in two and purified by silica gel chromatography, eluting with 0-100% DCM in cyclohexane. Appropriate fractions were combined and evaporated to give title compound, 1.81 g.

LC/MS (Method B) $R_t$=1.09 mins, MH−=347.

Intermediate 10

6-(3-Methylphenyl)-4-nitro-2-(tetrahydro-2H-pyran-2-yl)-2H-indazole

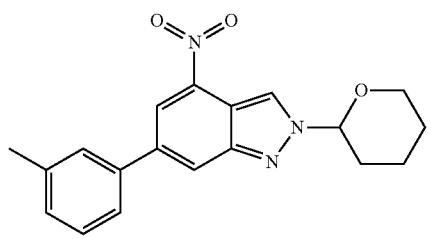

6-Bromo-4-nitro-2-(tetrahydro-2H-pyran-2-yl)-2H-indazole (500 mg, 1.53 mmol), Pd(dppf)Cl$_2$ (125 mg, 0.15 mmol), (3-methylphenyl)boronic acid (313 mg, 2.3 mmol), 1,4-dioxane (5 ml), 2 M sodium carbonate (aq) (2.3 ml) and water (5 ml) were combined and heated in a Biotage microwave at 150° C. for 30 mins. The crude reaction was combined with a separate reaction carried out at $1/10^{th}$ scale. The combined reactions were partitioned between water (100 ml) and ethyl acetate (100 ml), filtered and the separated organic layer was washed several times with water, followed by brine, before being dried over magnesium sulphate and the solvent removed in vacuo. The residue was purified by silica gel chromatography, eluting with 0-25% ethyl acetate in cyclohexane, to give the title compound, 422 mg.

LC/MS (Method A) $R_t$ 3.78 mins, MH$^+$=338.

Intermediate 11

6-(3-Methylphenyl)-2-(tetrahydro-2H-pyran-2-yl)-2H-indazol-4-amine

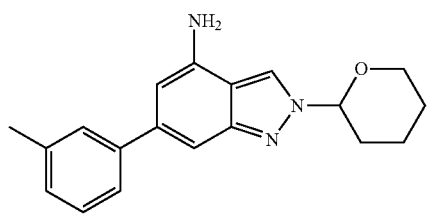

6-(3-Methylphenyl)-4-nitro-2-(tetrahydro-2H-pyran-2-yl)-2H-indazole (422 mg, 1.25 mmol) was dissolved in ethyl acetate (25 ml) and reduced using the H-cube (available from ThalesNano) with a Pd/C catalyst cartridge at a pressure of up to 80 bar. The solvent was removed in vacuo to give the title compound, 286 mg.

LC/MS (Method A) $R_t$ 3.13 mins, MH$^+$=308.

Intermediate 12

N-(6-Bromo-1H-indazol-4-yl)-2-pyridinecarboxamide

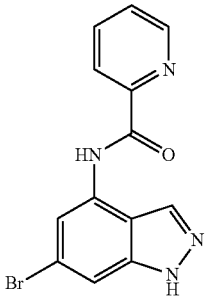

6-Bromo-1H-indazol-4-amine (100 mg, 0.47 mmol), 2-pyridinecarbonyl chloride hydrochloride (100 mg, 0.56 mmol) and DIPEA (0.164 ml, 0.94 mmol) were stirred in DCM (10 ml) at RT overnight. The reaction was concentrated in vacuo. The residue was purified by MDAP (Method B) and appropriate fractions were evaporated to give the title compound, 38 mg.

LC/MS (Method B) $R_t$=0.97 mins, MH$^+$=319.

Intermediate 13

6-Bromo-2-(tetrahydro-2H-pyran-2-yl)-2H-indazol-4-amine

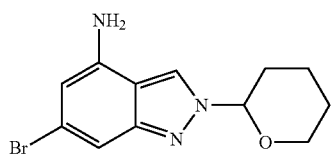

6-Bromo-4-nitro-2-(tetrahydro-2H-pyran-2-yl)-2H-indazole (6 g, 18.40 mmol), iron filings (3.29 g, 58.9 mmol) and ammonium chloride (0.492 g, 9.20 mmol) were weighed to a 250 ml round-bottomed flask and ethanol (60 ml) then water (18 ml) was added. The reaction was heated to 80° C. for 2.5 hr. The reaction mixture was cooled. 100 ml Ethyl acetate and 50 ml water was added. There was no visible separation of layers so the reaction was evaporated to remove the ethyl acetate and ethanol. 250 ml Ethyl acetate was then added and the organic layer was washed with a further 50 ml water, before passing through a hydrophobic frit. The organic layer was evaporated to dryness to give 6 g crude material. The aqueous layer was further extracted with DCM and then ethyl acetate. The DCM extract was evaporated to dryness to give a small amount of impure product that was discarded. The 6 g batch of crude material was purified by column chromatography on silica (120 g silica column, ISCO companion technology) eluting with a gradient of 1-2% methanol in DCM over 25 minutes. Fractions containing desired material were combined and evaporated to dryness to afford the title compound (3.95 g).

LC/MS (Method A) $R_t$=2.87 min, MH−=298.

Intermediate 14

N-[6-Bromo-2-(tetrahydro-2H-pyran-2-yl)-2H-indazol-4-yl]-1-(1-methylethyl)-1H-pyrazole-5-carboxamide

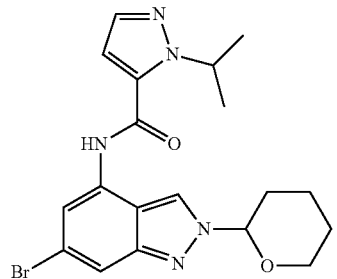

6-Bromo-2-(tetrahydro-2H-pyran-2-yl)-2H-indazol-4-amine (2.25 g, 7.59 mmol) was dissolved in DCM (40 ml) and DIPEA (2.85 ml, 16.34 mmol) was added. 1-(1-methylethyl)-1H-pyrazole-5-carbonyl chloride (1.41 g, 8.17 mmol) in DCM (10 ml) was added and the mixture left to stir at room temperature overnight. Water (50 ml) was added and the mixture vigorously stirred. The DCM layer was passed through a hydrophobic frit and evaporated to dryness. The material was combined with that obtained from a previous smaller scale reaction carried out in an identical manner but starting with 6-bromo-2-(tetrahydro-2H-pyran-2-yl)-2H-indazol-4-amine (0.2 g, 0.675 mmol). The combined crude materials were purified by chromatography on silica using a 50 g cartridge and eluting progressively with DCM, then 1-4% methanol in DCM. Product containing fractions were combined and evaporated to dryness to afford the title compound (2.8 g).

LC/MS (Method B) $R_t$=1.24 min, MH$^-$=434.

Similarly prepared was

Intermediate 16

1-(1-Methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide

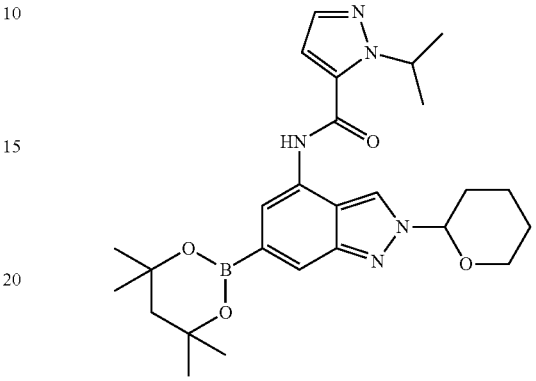

N-[6-Bromo-2-(tetrahydro-2H-pyran-2-yl)-2H-indazol-4-yl]-1-(1-methylethyl)-1H-pyrazole-5-carboxamide (500 mg, 1.16 mmol), Pd(dppf)Cl$_2$ DCM adduct (94 mg, 0.115 mmol), potassium acetate (341 mg, 3.47 mmol) and 4,4,4',4', 6,6,6',6'-octamethyl-2,2'-bi-1,3,2-dioxaborinane (978 mg, 3.47 mmol) were combined in a microwave vial. 1,4-Dioxane (8 ml) was added and the mixture was heated at 80° C. for 30 min. Analysis by LCMS showed incomplete reaction so the mixture was heated again under microwave conditions for 30 min at 80° C. Further Pd(dppf)Cl$_2$ DCM adduct (38 mg) was then added and the reaction heated for another 30 min at 80° C. The reaction mixture was applied to the top of a silica cartridge and washed through with methanol. After removal of solvent the residue was partitioned between DCM and water and the organics concentrated in vacuo. Purification was carried out by chromatography on silica (40 g) using a gradient of 40%-60% EtOAc in cyclohexane. Fractions containing desired product were combined, concentrated in vacuo and dried under vacuum to to afford the title compound as a pale yellow solid.

LC/MS $R_t$ 1.33 min m/z 494 [MH$^-$]. Method C

| Intermediate Number | Name | Structure | Acid chloride | LC/MS $R_t$ min | LC/MS MH$^+$ |
|---|---|---|---|---|---|
| 15 | N-[6-bromo-2-(tetrahydro-2H-pyran-2-yl)-2H-indazol-4-yl]-2-methyl-1,3-thiazole-4-carboxamide | 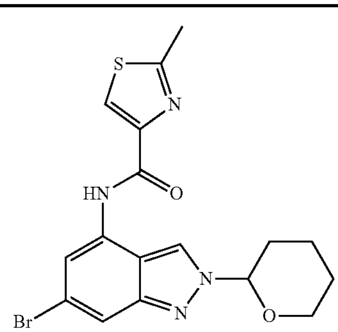 | 2-methyl-1,3-thiazole-4-carbonyl chloride | 1.18 | 423 |

Similarly prepared was:

| Intermediate Number | Name | Structure | Aryl bromide | LC/MS R$_t$ min | LC/MS MH$^+$ |
|---|---|---|---|---|---|
| 17 | 2-methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide | 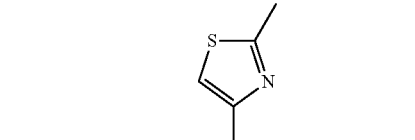 | N-[6-bromo-2-(tetrahydro-2H-pyran-2-yl)-2H-indazol-4-yl]-2-methyl-1,3-thiazole-4-carboxamide | 1.36 | 483 |

Intermediate 18

2-(Chloromethyl)-N-[6-{6-chloro-5-[(methylsulfonyl)amino]-3-pyridinyl}-1-(phenylsulfonyl)-1H-indazol-4-yl]-1,3-thiazole-4-carboxamide

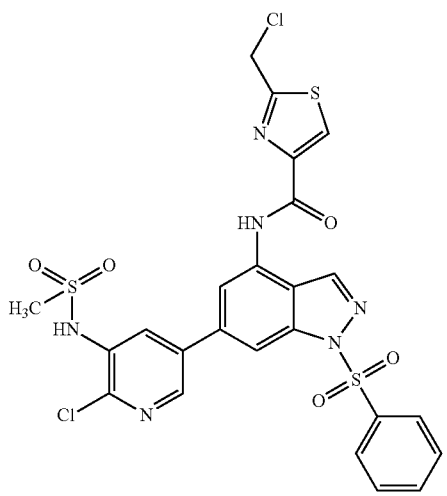

N-{5-[4-Amino-1-(phenylsulfonyl)-1H-indazol-6-yl]-2-chloro-3-pyridinyl}methanesulfonamide (780 mg, 1.632 mmol) was dissolved in DCM (32 ml) and pyridine (0.198 ml, 2.448 mmol) and cooled to 0° C. To this was added 2-(chloromethyl)-1,3-thiazole-4-carbonyl chloride (320 mg, 1.632 mmol) as a solution in DCM (6 ml) dropwise. The reaction was left to warm up and after final addition was stirred for a further 66 h at 20° C. Reaction was incomplete so the mixture was cooled again to 0° C. and a further portion of 2-(chloromethyl)-1,3-thiazole-4-carbonyl chloride (320 mg, 1.632 mmol) as a solution in DCM (6 ml) was added dropwise. The reaction was left to warm up and was stirred for a further 23 h at 20° C. Reaction still incomplete so, the mixture was cooled again to 0° C. and a further portion of 2-(chloromethyl)-1,3-thiazole-4-carbonyl chloride (320 mg, 1.632 mmol) as a solution in DCM (6 ml) was added dropwise. The reaction was left to warm up and was stirred for a further 23 h at 20° C. The solution was treated with DCM (25 ml) and saturated aqueous sodium bicarbonate (25 ml) and stirred vigorously for 10 mins. The organic phase was then separated, washed with dilute aqueous sodium chloride (30 ml), passed through a hydrophobic frit, and loaded directly onto a 100 g silica cartridge. This was eluted with 0-100% ethyl acetate/cyclohexane over 60 mins using the Flashmaster II. Appropriate fractions were combined and evaporated to give the title compound as a yellow solid (321 mg).

LCMS (Method B) R$_t$=1.13 min, MH$^+$=636.

Intermediate 19

N-{5-[4-Amino-1-(phenylsulfonyl)-1H-indazol-6-yl]-2-chloro-3-pyridinyl}methanesulfonamide

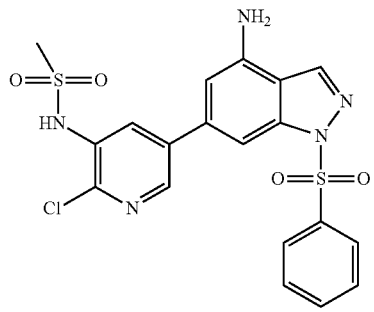

Four identical reactions were carried out in a 20 ml microwave vial, each using one quarter of the quantities stated. They were then combined for work-up and purification. A solution of a quarter of 1-(phenylsulfonyl)-6-(trimethylstannanyl)-1H-indazol-4-amine (4.329 g, 9.93 mmol) in a quarter of DMF (24 ml) was treated with a quarter of N-(5-bromo-2-chloro-3-pyridinyl)methanesulfonamide (3.26 g, 11.42 mmol) followed by a quarter of Pd(PPh$_3$)$_4$ (1.032 g, 0.893 mmol). Each vial was heated at 120° C. for 50 mins in a Biotage Initiator. The orange solutions were combined and loaded onto a 20 g silica cartridge, and the vials washed with methanol (10 ml) which was also loaded onto the cartridge which was then eluted with methanol. Then eluants were evaporated to leave an orange oil. This was diluted with DCM (10 ml) and loaded directly and evenly onto 2×100 g silica cartridges. These were eluted with 0-100% ethyl acetate/cyclohexane over 80 mins using the Flashmaster II. Appropriate pure fractions were combined and evaporated to give the title compound as a yellow solid (0.939 g).

LCMS (Method B) $R_t$=0.94 min, MH$^+$=478.

Intermediate 20

6-Bromo-1-(phenylsulfonyl)-1H-indazol-4-amine

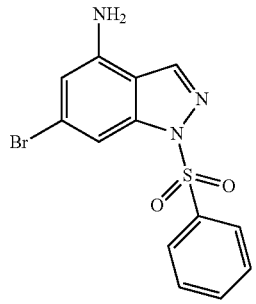

To sodium hydride (1.886 g, 47.2 mmol) in DMF (10 ml) stirring at 0° C. was added a solution of 6-bromo-1H-indazol-4-amine (10 g, 47.2 mmol, available from Sinova) in DMF (30 ml) dropwise. NOTE-gas evolution. Upon complete addition the mixture was treated with benzene sulphonyl chloride (6.08 ml, 47.2 mmol) dropwise. The resulting mixture was stirred for 2 hrs at room temperature then the mixture was poured onto ice water (300 ml). The mixture was then extracted with ethyl acetate and the layers separated. The aqueous was re-extracted with ethyl acetate. The organics were then combined and washed with brine, dried over magnesium sulfate then filtered and evaporated to yield a brown gum that was triturated using DCM to yield the title compound as a peachy solid (8.72 g).

LCMS (Method B) Rt=1.14 mins, MH+=352/354.

Intermediate 21

1-(Phenylsulfonyl)-6-(trimethylstannanyl)-1H-indazol-4-amine

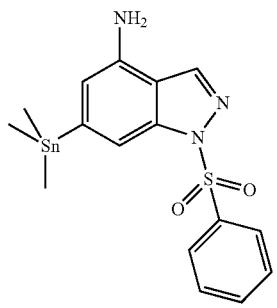

A stirred mixture of 6-bromo-1-(phenylsulfonyl)-1H-indazol-4-amine (1.3 g), hexamethylditin (2.4 g), triethylamine (1 ml) and Pd(PPh$_3$)$_4$ (0.2 g) in toluene (15 ml) was heated under microwave irradiation at 120° C. for 1 h. The reaction was applied to a silica cartridge using light petroleum 40-60° C. as eluent. This was changed to ether/light petroleum 40-60° C. The appropriate fractions were evaporated to give title compound (1.2 g).

LCMS (Method C) $R_t$=3.3 min, MH$^+$438.

Intermediate 22

2-(Chloromethyl)-N-[6-{6-(methyloxy)-5-[(methylsulfonyl)amino]-3-pyridinyl}-1-(phenylsulfonyl)-1H-indazol-4-yl]-1,3-thiazole-4-carboxamide

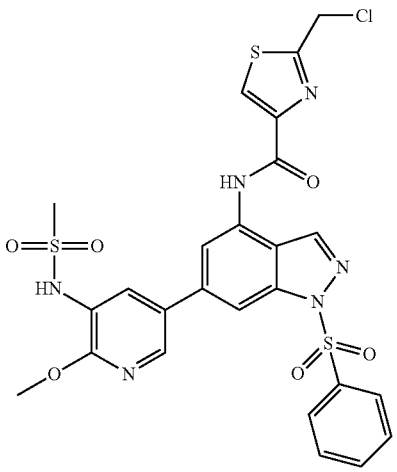

N-[5-[4-Amino-1-(phenylsulfonyl)-1H-indazol-6-yl]-2-(methyloxy)-3-pyridinyl]methanesulfonamide (700 mg, 1.478 mmol) was dissolved in DCM (30 ml) and cooled to 0° C. before pyridine (0.179 ml, 2.217 mmol) was added. To this mixture was added 2-(chloromethyl)-1,3-thiazole-4-carbonyl chloride (290 mg, 1.478 mmol) as a solution in DCM (10 ml) dropwise over 15 mins. The mixture was stirred at 0° C. for 30 min. Saturated aqueous sodium bicarbonate solution (20 ml) was added to the mixture and it was stirred vigorously for 10 mins. The organic layer was separated using a hydrophobic frit, washed with water (20 ml) and concentrated in vacuo to give the title compound as an orange solid (697 mg).

LCMS (Method B) $R_t$=1.14 min, MH$^+$=634.

Intermediate 23

N-[5-[4-Amino-1-(phenylsulfonyl)-1H-indazol-6-yl]-2-(methyloxy)-3-pyridinyl]methanesulfonamide

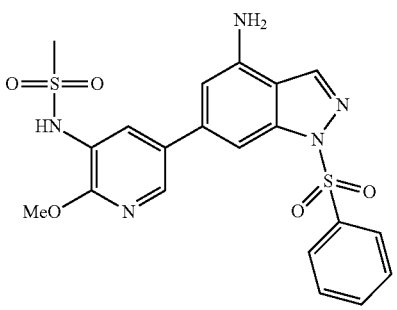

1-(Phenylsulfonyl)-6-(trimethylstannanyl)-1H-indazol-4-amine (4.2 g, 9.63 mmol), N-[5-bromo-2-(methyloxy)-3-pyridinyl]methanesulfonamide (3.25 g, 11.56 mmol) and Pd(PPh$_3$)$_4$ (1.113 g, 0.963 mmol) were weighed into a round-bottomed flask. DMF (30 ml) was added and the reaction was heated at 120° C. for 20 mins. The solvent was removed in vacuo and the crude material (9.8 g) was dissolved in DCM and loaded onto the top of a 750 g RediSep silica cartridge that was then eluted with 0-100% EtOAc/cyclohexane over 10 column volumes using the Companion XL. The product-containing fractions were combined and the solvent removed in vacuo to afford the title compound as a pale yellow solid (2.39 g).

LCMS (Method B) R$_t$=0.95 min, MH$^+$=474

Intermediate 24

N-[5-Bromo-2-(methyloxy)-3-pyridinyl]methanesulfonamide

Method A:

To N-[5-bromo-2-(methyloxy)-3-pyridinyl]-N-(methylsulfonyl)methanesulfonamide (4.64 g, 12.92 mmol) in a round-bottomed flask was added methanol (10 mL) and sodium hydroxide (10 mL, 12.92 mmol). The resulting suspension was stirred at room temperature for 1 hr. Methanol was removed in vacuo and the aqueous was acidified to ~pH 2 with 2M HCl (aq). The precipitate was collected by filtration and dried in a vacuum oven overnight to give a white solid. LCMS still showed some starting material to be present, so methanol (10 mL) and sodium hydroxide (10 mL, 12.92 mmol) were added and the mixture was stirred at room temperature for 1 hour. Further methanol (10 mL) and sodium hydroxide (10 mL, 12.92 mmol) were then added. After 30 mins the methanol was removed in vacuo and the aqueous was acidified to ~pH 3 with 2M HCl (aq). The precipitate was collected by filtration and dried in a vacuum oven for 2 hours to give the title compound as a white solid (3.28 g).

LCMS (Method B) R$_t$=0.83 min, MH$^+$=282.

Method B:

To 5-bromo-2-(methyloxy)-3-pyridinamine (3.11 g) in pyridine (30 ml) was added methanesulfonyl chloride (2.96 ml) and the reaction was stirred for 18 hours at room temperature. After this time, the mixture was adjusted to pH 7 with 2M HCl and extracted into DCM. The combined organic layers were evaporated to dryness. The residual solid was dissolved in methanol (15 ml) before 2M NaOH (15 ml) was added and the mixture stirred for 30 minutes at room temperature. The methanol was removed in vacuo and the aqueous mixture was washed with DCM. The DCM was separated from the aqueous which was then acidified to pH 2 with 2M HCl. The resulting precipitate was collected by vacuum filtration to afford the title compound (1.79 g).

LCMS (Method B) R$_t$=0.86 min, MH$^+$=282

Intermediate 25

2-(Methyloxy)-5-(4,4,6,6-tetramethyl-1,3,2-dioxaborinan-2-yl)-3-pyridinamine

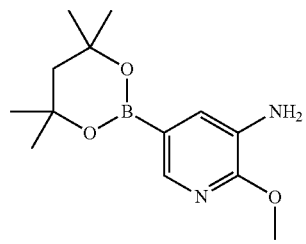

5-Bromo-2-(methyloxy)-3-pyridinamine (500 mg, 2.463 mmol), potassium acetate (725 mg, 7.39 mmol), 4,4,4',4',6,6,6',6'-octamethyl-2,2'-bi-1,3,2-dioxaborinane (1991 mg, 7.06 mmol) and Pd(dppf)Cl$_2$ (180 mg, 0.246 mmol) were weighed to a round bottomed flask and 1,4-Dioxane (20 mL) was added. The reaction mixture was heated at 80° C. overnight then passed through a 5 g silica cartridge which was washed with methanol, then evaporated on to dryness. The residue was partitioned between DCM and water. The DCM layer was passed through a hydrophobic frit then evaporated to dryness. The residue was triturated with ether then filtered. The ether was evaporated and the residue was triturated with hexane, then heated at 60° C. for 1 hour before evaporation to dryness. The residue was purified through a 10 g silica cartridge, eluting with DCM then 1-2% methanol in DCM. Pure fractions were combined and evaporated to dryness to afford the title compound (274 mg).

LCMS (Method B) R$_t$ 1.13 min, MH$^+$ 265.

Intermediate 26

N-[6-[5-Amino-6-(methyloxy)-3-pyridinyl]-2-(tetrahydro-2H-pyran-2-yl)-2H-indazol-4-yl]-2-{[(2R,6S)-2,6-dimethyl-4-morpholinyl]methyl}-1,3-thiazole-4-carboxamide

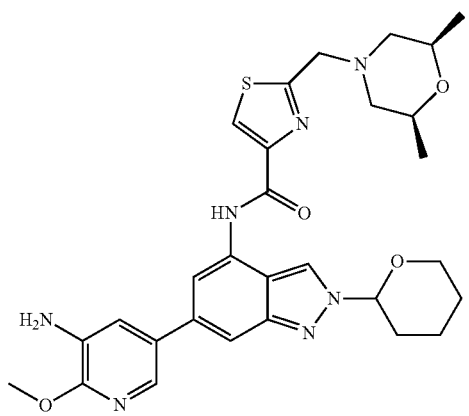

Tripotassium phosphate (910 mg, 4.29 mmol), chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (105 mg, 0.143 mmol) and 2-(methyloxy)-5-(4,4,6,6-tetramethyl-1,3,2-dioxaborinan-2-yl)-3-pyridinamine (453 mg, 1.715 mmol) were weighed to a 20 ml microwave vial. N-[6-Bromo-2-(tetrahydro-2H-pyran-2-yl)-2H-indazol-4-yl]-2-{[(2R,6S)-2,6-dimethyl-4-morpholinyl]methyl}-1,3-thiazole-4-carboxamide (764 mg, 1.429 mmol) was dissolved in 1,4-dioxane (10 mL) and added, followed by water (2.000 mL). The reaction was heated at 140° C. for 20 min. The reaction mixture was passed through a 10 g silica cartridge, eluting with methanol. The solvent was evaporated to dryness and the residue was partitioned between DCM 200 ml and water 200 ml. The DCM was collected and eluted through a hydrophobic frit, then evaporated to dryness. The residue was purified by chromatography on silica gel (100 g cartridge), eluting with 0-25% methanol in DCM over 40 mins, then on a further silica gel 100 g cartridge, eluting with 0-100% ethyl acetate in cyclohexane over 40 mins and then 0-25% methanol in DCM over 20 mins to afford the title compound (512 mg).

LCMS (Method B) $R_f$=0.84 min, MH$^+$ 578.

Intermediate 27

2-(Chloromethyl)-1,3-thiazole-4-carbonyl chloride

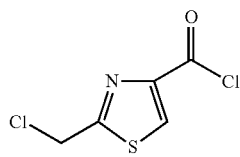

To a solution of 2-(hydroxymethyl)-1,3-thiazole-4-carboxylic acid (370 mg, 2.33 mmol) in chloroform (5 ml) and DMF (0.1 ml) was added thionyl chloride (1 ml, 13.70 mmol). The mixture was heated to reflux for 1 hr. The mixture was cooled and the solvent removed in vacuo. The residue was azeotroped with chloroform (5 ml) and dried on a high vacuum line for 30 mins to afford the title compound. LCMS was run as a solution in MeOH (Method B) $R_t$ 0.77 min, MH$^+$ 191. The material was not suitable for long term storage at room temperature so was either used immediately or stored at −20° C. for up to 2 weeks.

Intermediate 28

2-(Hydroxymethyl)-1,3-thiazole-4-carboxylic acid

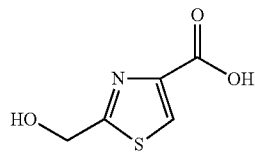

A solution of 2-{[(2,2-dimethylpropanoyl)oxy]methyl}-1,3-thiazole-4-carboxylic acid (3 g, 12.33 mmol, commercially available) and potassium carbonate (2.326 g, 16.83 mmol) in methanol (100 ml) and water (30 ml) was heated to reflux for 4 hr. The mixture was cooled and concentrated in vacuo to ~30 ml. It was then acidified with 2 M HCl (50 ml) and concentrated in vacuo. The resulting solid was treated with hot MeOH/EtOAc (2:1), washing well before filtering off the remaining solid. The filtrate was concentrated in vacuo to give a brown solid which was dissolved in MeOH and added to the top of 2×70 g aminopropyl cartridge that had been preconditioned with MeOH. The cartridges were both eluted with MeOH and then with 10% HCl in MeOH. The acidic fractions were combined and the solvent removed in vacuo to give the title compound as a brown oil (550 mg). LCMS (Method B) $R_f$=0.36 min, MH$^+$=160.

Intermediate 29

2-(Methyloxy)-5-(4,4,5,5-tetramethyl-1,3,2-dioxaborolan-2-yl)-3-pyridinamine

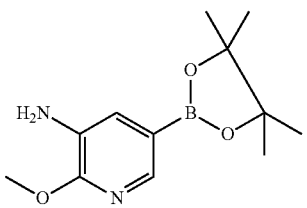

To 5-bromo-2-(methyloxy)-3-pyridinamine (18.93 g, 93 mmol, available from Asymchem) in a 1 L round-bottom flask was added nitrogen-purged 1,4-dioxane (500 mL) followed by 4,4,4',4',5,5,5',5'-octamethyl-2,2'-bi-1,3,2-dioxaborolane (47.4 g, 186 mmol), potassium acetate (27.5 g, 280 mmol) and Pd(dppf)Cl$_2$—CH$_2$Cl$_2$ adduct (7.61 g, 9.32 mmol). The mixture was then stirred at 80° C. under nitrogen for 2 hr. The reaction mixture was allowed to cool then partitioned between ethyl acetate and water. The mixture was filtered through a celite pad and the aqueous layer extracted further with ethyl acetate (2×). The combined organics were washed with water, brine and dried over magnesium sulphate overnight. The residue was purified on 1.5 Kg Silica cartridge, eluting a 0-50% ethyl acetate/DCM over 10 column volumes. The appropriate fractions were combined and evaporated to dryness. The residue was triturated with cyclohexane, the solid filtered off and dried in vacuo to leave the title compound as a light pink solid (11.1 g). A second crop was obtained from the above filtrate and after drying gave a further portion of the title compound as a light pink solid (2.95 g).

LCMS (Method B) Rt 0.91 mins, MH+ 251.

Intermediate 30

N-[2-(Methyloxy)-5-(4,4,5,5-tetramethyl-1,3,2-dioxaborolan-2-yl)-3-pyridinyl]methanesulfonamide

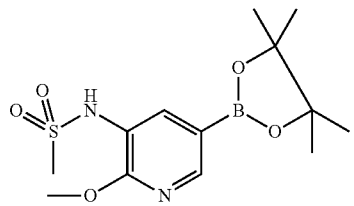

To a solution of 2-(methyloxy)-5-(4,4,5,5-tetramethyl-1,3,2-dioxaborolan-2-yl)-3-pyridinamine (0.5 g, 1.999 mmol) in pyridine (5 ml) was added methanesulphonyl chloride (0.309 ml, 4.00 mmol) and the mixture stirred at 20° C. for 18 hr

Intermediate 31

6-(Chloromethyl)-N-[6-{6-(methyloxy)-5-[(methyl-sulfonyl)amino]-3-pyridinyl}-1-(phenylsulfonyl)-1H-indazol-4-yl]-2-pyridinecarboxamide

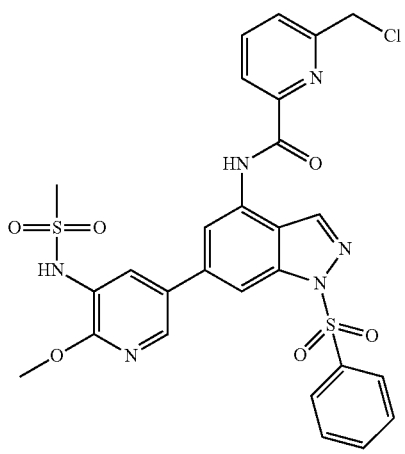

N-[5-[4-Amino-1-(phenylsulfonyl)-1H-indazol-6-yl]-2-(methyloxy)-3-pyridinyl]methanesulfonamide (750 mg, 1.584 mmol) was dissolved in DCM (20 ml), cooled to 0° C. before pyridine (0.192 mL, 2.376 mmol) was added. 6-(chloromethyl)-2-pyridinecarbonyl chloride (354 mg, 1.584 mmol) in DCM (10 ml) was then added dropwise over 15 mins and the reaction was stirred at 0° C. for 2 hr; ice was allowed to melt over this time. Saturated aqueous sodium bicarbonate solution (20 ml) was added to the mixture and it was stirred vigourously for 10 mins. The organic layer was separated using a hydrophobic frit, washed with water (20 ml) and concentrated in vacuo to give an orange oil. The oil was triturated with ether and the resulting solid was filtered off then pre-adsorbed onto silica. The silica was added to the top of a 50 g silica SPE cartridge that was subsequently eluted with 0-100% EtOAc/cyclohexane over 60 mins to afford the title compound as a pale yellow solid (253 mg).

LCMS (Method B) $R_t$=1.20 min, MH$^+$=628.

Intermediate 32

6-(Chloromethyl)-N-[6-{6-chloro-5-[(methylsulfonyl)amino]-3-pyridinyl}-1-(phenylsulfonyl)-1H-indazol-4-yl]-2-pyridinecarboxamide

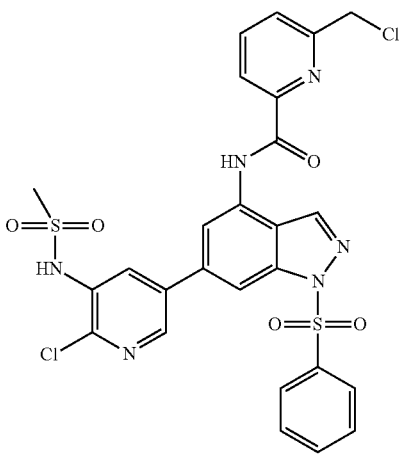

To a solution of 6-(hydroxymethyl)-2-pyridinecarboxylic acid (500 mg, 3.27 mmol) in chloroform (10 ml) and DMF (0.1 ml) was added thionyl chloride (1 ml, 13.70 mmol) and the mixture heated at 65° C. for 1 hr. Solvent was removed in vacuo and the residue was azeotroped with chloroform (5 ml) then dried on a high vacuum line for 30 mins to afford an orange oil (650 mg), presumed to be 6-(chloromethyl)-2-pyridinecarbonyl chloride. N-{5-[4-amino-1-(phenylsulfonyl)-1H-indazol-6-yl]-2-chloro-3-pyridinyl}methanesulphonamide (600 mg, 1.255 mmol) was dissolved in DCM (5 ml) and pyridine (0.122 mL, 1.506 mmol) was added followed by 6-(chloromethyl)-2-pyridinecarbonyl chloride (281 mg, 1.255 mmol) in DCM (5 ml). The reaction was stirred at 0° C. for 1 hr. A further portion of 6-(chloromethyl)-2-pyridinecarbonyl chloride (281 mg, 1.255 mmol) was added and the mixture stirred at 0° C. for 30 mins. The crude mixture was partitioned between saturated aqueous sodium bicarbonate solution (10 ml) and DCM (10 ml). The organic layer was separated using a hydrophobic frit, washed with water (10 ml) and concentrated in vacuo to give an orange solid which was purified by column chromatography (80 g silica RediSep column) eluting with 0-10% MeOH/DCM over 20 column volumes. Separation was incomplete, so all fractions were combined and the solvent was removed in vacuo. The resultant orange solid was re-purified by column chromatography on silica (80 g silica RediSep column) eluting with 50-100% EtOAc/cyclohexane over 40 mins on the ISCO Companion. Fractions containing desired material were combined to afford the title compound as a pale yellow solid (141 mg).

LCMS (Method B) $R_t$=1.19 min, MH+ 631.

--- when the solvent was removed in vacuo. The residue was partitioned between saturated sodium bicarbonate solution (10 ml) and DCM (20 ml), separated by hydrophobic frit and purified by silica (70 g) cartridge on Flashmaster II using a gradient of DCM and methanol to give the title compound as a brown solid (0.46 g).

LCMS (Method B) Rt 0.98 mins, MH+ 329.

Intermediate 33

N-{5-[4-Amino-1-(phenylsulfonyl)-1H-indazol-6-yl]-2-chloro-3-pyridinyl}methanesulfonamide

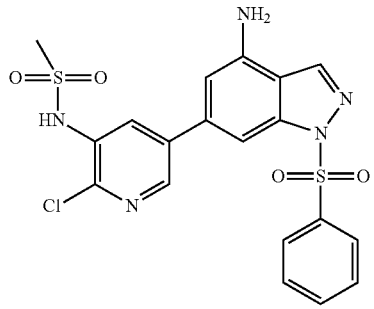

Four identical reactions were carried out in a 20 ml microwave vial, each using one quarter of the quantities stated. They were then combined for work-up and purification. A solution of a quarter of 1-(phenylsulfonyl)-6-(trimethylstannanyl)-1H-indazol-4-amine (4.329 g, 9.93 mmol) in a quarter of DMF (24 ml) was treated with a quarter of N-(5-bromo-2-chloro-3-pyridinyl)methanesulfonamide (3.26 g, 11.42 mmol) followed by a quarter of Pd(PPh$_3$)$_4$ (1.032 g, 0.893 mmol). Each vial was heated at 120° C. for 50 mins in a Biotage Initiator. The orange solutions were combined and loaded onto a 20 g silica cartridge, and the vials washed with methanol (10 ml) which was also loaded onto the cartridge which was then eluted with methanol. Then eluants were evaporated to leave an orange oil. This was diluted with DCM (10 ml) and loaded directly and evenly onto 2×100 g silica cartridges. These were eluted with 0-100% ethyl acetate/cyclohexane over 80 mins using the Flashmaster II. Appropriate pure fractions were combined and evaporated to give the title compound as a yellow solid (0.939 g).

LCMS (Method B) R$_t$=0.94 min, MH$^+$=478.

Intermediate 34

N-[5-Bromo-2-(methyloxy)-3-pyridinyl]cyclopropanesulfonamide

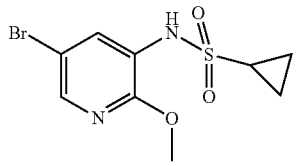

5-Bromo-2-(methyloxy)-3-pyridinamine (1.05 g, 5.17 mmol, available from Asymchem) was dissolved in pyridine (10 ml) and cyclopropanesulfonyl chloride (1.818 g, 12.93 mmol) was added dropwise. The reaction mixture was stirred at room temperature overnight, then acidified to ca. pH 2 with 2M HCl (aq) and extracted into DCM. The DCM was passed through a hydrophobic frit and the filtrate was evaporated to dryness to afford the title compound (1.48 g).

LCMS (Method B) R$_t$=0.99 min, MH$^+$=309.

Intermediate 35

N-[5-Bromo-2-(methyloxy)-3-pyridinyl]-2-hydroxypropanamide

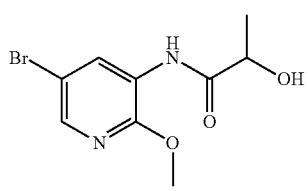

2-Hydroxypropanoic acid (444 mg, 4.93 mmol) was dissolved in DCM (10 ml) and (1-chloro-2-methyl-1-propen-1-yl)dimethylamine (0.652 ml, 4.93 mmol) was added. The mixture was stirred for 5 mins, then 5-bromo-2-(methyloxy)-3-pyridinamine (500 mg, 2.463 mmol, available from Asymchem) was added and the reaction mixture was diluted with further DCM (5 ml). Stirring was continued at room temperature, then after 3 hours a further portion of chloro-2-methyl-1-propen-1-yl)dimethylamine (0.652 mL, 4.93 mmol) was added and the reaction was left stirring at room temperature overnight. The mixture was quenched with water and the separated DCM layer was washed with saturated sodium bicarbonate (aq) before passing through a hydrophobic frit and evaporation to dryness. The residue was stirred with 2M NaOH (aq., 5 ml). After stirring for 4 hours the resulting precipitate was collected by filtration and then dissolved in DCM and washed with 2M HCl (aq). The DCM layer was separated. The remaining aqueous layer was washed with ethyl acetate and the combined organics were evaporated to dryness to afford the title compound (220 mg).

LCMS (Method B) R$_t$=0.89 min, MH$^+$=276.

Intermediate 36

N-[5-Bromo-2-(methyloxy)-3-pyridinyl]-2,4-difluorobenzenesulfonamide

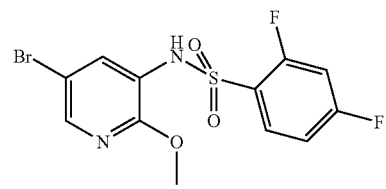

To a cooled (0° C.) solution of 5-bromo-2-(methyloxy)-3-pyridinamine (13.7 g, 67.5 mmol) in pyridine (200 ml) was added slowly 2,4-difluorobenzenesulfonyl chloride (14.37 g, 67.6 mmol) over 15 min (reaction became heterogeneous). The ice bath was removed and the reaction was stirred at ambient temperature for 16 h. Most of the pyridine was removed in vacuo and the residue diluted with water (500 ml). The solids were filtered off and washed with copious amounts of water to give 21 g of crude desired product. More solid appeared in the mother liquor and was filtered and washed with water to give an additional 1.5 g of desired material. The two batches were combined, triturated with DCM (70 ml) and dried in a vacuum oven at 50° C. to give the title compound (15 g).

LCMS (Method B) $R_t$=1.11 min, MH$^+$=378/380.

Intermediate 37

2-Methyl-N-[1-(phenylsulfonyl)-6-(trimethylstannanyl)-1H-indazol-4-yl]-1,3-thiazole-4-carboxamide

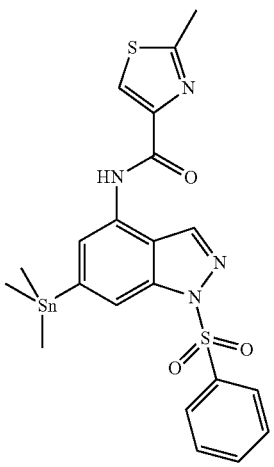

2-Methyl-1,3-thiazole-4-carbonyl chloride (350 mg) in DCM (4 ml) was added dropwise to 1-(phenylsulfonyl)-6-(trimethylstannanyl)-1H-indazol-4-amine (300 mg) in DCM (15 ml) and pyridine (0.167 ml). The reaction was stirred at room temperature overnight. Saturated sodium bicarbonate (aq) (25 ml) was added and the reaction vigorously stirred for 15 min. The DCM was passed through a hydrophobic frit then evaporated to dryness. The residue was dissolved in DCM and purified on a silica cartridge, preconditioned with cyclohexane, washing with cyclohexane followed by elution with ether. The ether was evaporated to give title compound (373 mg).

LCMS (Method B) $R_t$ 1.42 min, MH+ 563.

Intermediate 38

6-Bromo-1-[(4-methylphenyl)sulfonyl]-1H-indazol-4-amine

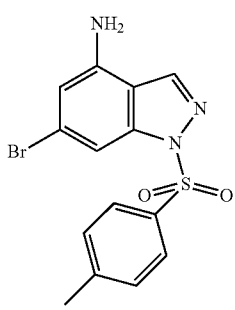

To a suspension of sodium hydride (5.66 g) in anhydrous DMF (75 ml) stirring at 0° C. was added a solution of 6-bromo-1H-indazol-4-amine (30 g), also in anhydrous DMF (125 ml), dropwise. The reaction mixture was stirred for 1 h at 0° C. then a solution of 4-methylbenzenesulfonyl chloride (27 g) in anhydrous DMF (100 ml) was added dropwise. The reaction was stirred for 2 h. A further portion of sodium hydride (0.57 g) was added followed by 4-methylbenzenesulfonyl chloride (2.70 g). The reaction mixture was left to stand overnight at room temperature, before pouring onto ice/water (1800 ml). A precipitate formed that was collected by filtration, triturated using diethyl ether:methanol (1:1, v/v), then re-collected by filtration and dried in vacuo at 40° C. over the weekend to give title compound, (26.5 g).

LCMS (Method B) $R_t$=1.16 min, MH$^+$=368.

Intermediate 39

N-{6-Bromo-1-[(4-methylphenyl)sulfonyl]-1H-indazol-4-yl}-2-(chloromethyl)-1,3-thiazole-4-carboxamide

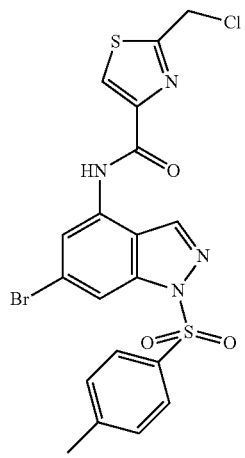

A three necked rounded bottomed flask was charged with 6-bromo-1-[(4-methylphenyl)sulfonyl]-1H-indazol-4-amine (12.7 g), anhydrous DCM (100 ml) and pyridine (7.5 ml) then placed under a nitrogen atmosphere and cooled to −10° C. A suspension of 2-(chloromethyl)-1,3-thiazole-4-carbonyl chloride (9.39 g) in anhydrous DCM (75 ml) was added in one portion. The reaction mixture was stirred at room temperature for ~4 hrs. Additional 2-(chloromethyl)-1,3-thiazole-4-carbonyl chloride (1.36 g) in anhydrous DCM was added in one portion and the reaction was stirred overnight. The suspension was filtered, washing sparingly with DCM, then dried on the vacuum pump to give title compound (15.8 g).

LCMS (Method B) $R_t$=1.34 min, MH$^+$=527.

Intermediate 40

N-{6-Bromo-1-[(4-methylphenyl)sulfonyl]-1H-indazol-4-yl}-2-{[(2R,6S)-2,6-dimethyl-4-morpholinyl]methyl}-1,3-thiazole-4-carboxamide

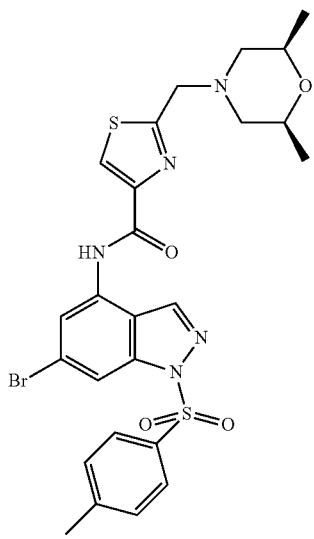

Acetonitrile (15 mL) and (2R,6S)-2,6-dimethylmorpholine (1.4 ml) were added to N-{6-bromo-1-[(4-methylphenyl)sulfonyl]-1H-indazol-4-yl}-2-(chloromethyl)-1,3-thiazole-4-carboxamide (2 g) and the reaction mixture was refluxed for 3 h. On cooling a solid precipitated. The mixture was diluted with acetonitrile (15 ml) and the solid was collected by filtration, washing with acetonitrile. The solid was dried on the vacuum pump overnight to give title compound (1.86 g).

LCMS Rt 1.18 min, MH+ 604/606.

Intermediate 41

N-{6-[5-{[(2,4-Difluorophenyl)sulfonyl]amino}-6-(methyloxy)-3-pyridinyl]-1-[(4-methylphenyl)sulfonyl]-1H-indazol-4-yl}-2-{[(2R,6S)-2,6-dimethyl-4-morpholinyl]methyl}-1,3-thiazole-4-carboxamide

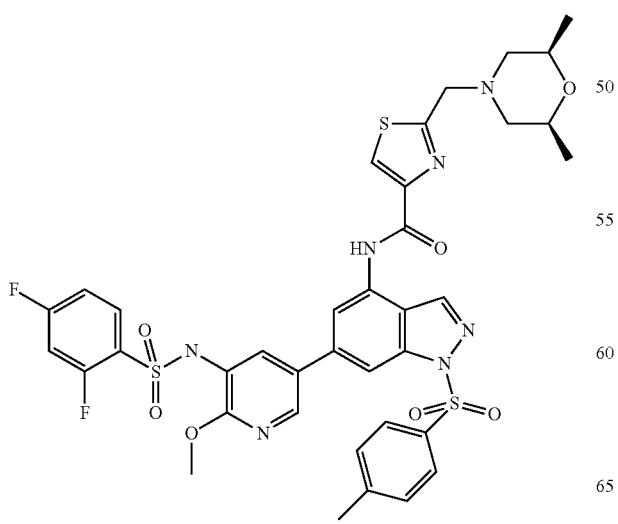

2,4-Difluoro-N-[2-(methyloxy)-5-(4,4,5,5-tetramethyl-1,3,2-dioxaborolan-2-yl)-3-pyridinyl]benzenesulfonamide (116 mg), N-{6-bromo-1-[(4-methylphenyl)sulfonyl]-1H-indazol-4-yl}-2-{[(2R,6S)-2,6-dimethyl-4-morpholinyl]methyl}-1,3-thiazole-4-carboxamide (150 mg), Pd(dppf)Cl$_2$ (18 mg), sodium carbonate (79 mg), 1,4-dioxane (5 ml) and water (5 ml) were combined and heated at 80° C. for 3 hours. The cooled reaction mixture was filtered through a 1 g silica cartridge, washing with methanol, then evaporated to dryness. The residue was dissolved in DCM and washed with water. The DCM was passed through a hydrophobic frit and evaporated to dryness. The residue was purified by ISCO companion, 12 g Silica cartridge using 0-5% MeOH in DCM over 16 mins. Pure fractions were combined and evaporated to give title compound, (105 mg).

LCMS (Method B) R$_t$=1.12 min, MH+=824.

Intermediate 42

2-{[(2R,6S)-2,6-Dimethyl-4-morpholinyl]methyl}-N-[1-methyl-6-(4,4,6,6-tetramethyl-1,3,2-dioxaborinan-2-yl)-1H-indazol-4-yl]-1,3-thiazole-4-crboxamide

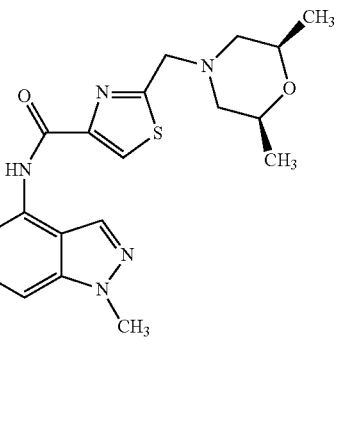

N-(6-Bromo-1-methyl-1H-indazol-4-yl)-2-{[(2R,6S)-2,6-dimethyl-4-morpholinyl]methyl}-1,3-thiazole-4-carboxamide (500 mg, 1.077 mmol), 4,4,4',4',6,6,6',6'-octamethyl-2,2'-bi-1,3,2-dioxaborinane (364 mg, 1.292 mmol), Pd(dppf)Cl$_2$ (79 mg, 0.108 mmol) and potassium acetate (423 mg, 4.31 mmol) were weighed to a microwave vial. Anhydrous 1,4-dioxane (5 ml) was added and the reaction heated in the microwave at 80° C. for 45 min. Further catalyst (50 mg) was added and the mixture heated at 100° C. for 30 mins. The solvent was removed and the residue was partitioned between water (20 ml) and (DCM 20 ml). The organic layer was collected using a hydrophobic frit and the solvent removed in vacuo. The residue was purified by chromatography on silica (50 g cartridge) eluting with 0-100% ethyl acetate in cyclohexane over 40 mins to give the title compound (356 mg).

LCMS (Method B) R$_t$=1.11 mins, MH+=526.

Intermediate 43

N-(6-Bromo-1-methyl-1H-indazol-4-yl)-2-{[(2R, 6S)-2,6-dimethyl-4-morpholinyl]methyl}-1,3-thiazole-4-carboxamide

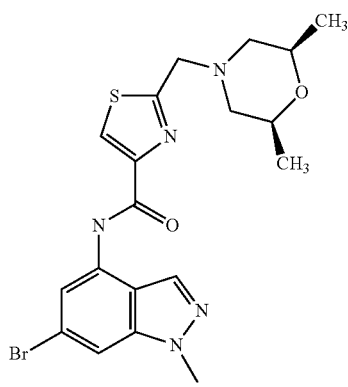

N-(6-Bromo-1-methyl-1H-indazol-4-yl)-2-(chloromethyl)-1,3-thiazole-4-carboxamide (860 mg, 2.230 mmol) was placed in dimethyl morpholine (3 ml, 2.230 mmol) and the mixture heated in a microwave at 90° C. for 15 mins. The solvent was blown off under a stream of nitrogen then the residue was partitioned between water (100 ml) and DCM (100 ml) and the organic layer collected, washed with water (2×75 ml), dried using a hydrophobic frit and the solvent removed in vacuo. Residual amine was still apparent so the residue was dissolved in DCM (20 ml) and methanol (20 ml) and then put on the buchi with the water bath at 60° C. for 3 hours to afford the title compound as a yellow/brown solid (1 g).

LCMS (Method B) $R_f$=0.88 min, MH$^+$=464/466.

Intermediate 44

N-(6-Bromo-1-methyl-1H-indazol-4-yl)-2-(chloromethyl)-1,3-thiazole-4-carboxamide

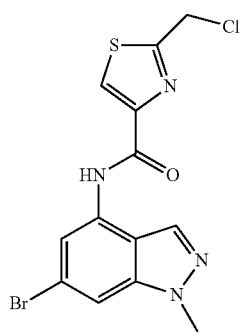

6-Bromo-1-methyl-1H-indazol-4-amine (1 g, 4.42 mmol) was dissolved in DCM (DCM) (10 ml) and pyridine (0.429 ml, 5.31 mmol) added. The mixture was cooled to 0° C. in an ice-water bath and 4-(chloromethyl)-1,3-thiazole-2-carbonyl chloride (0.867 g, 4.42 mmol) in DCM (10 ml) was added portionwise over 5 mins. The mixture was stirred for 2 hours and allowed to warm to room temperature. Saturated sodium bicarbonate solution (15 ml) was added and the mixture stirred vigorously for 10 mins. The mixture was diluted with water (50 ml) and DCM (50 ml), but a precipitate was still present. This was collected by filtration, washed with DCM and air dried to afford the title compound as a yellow/brown solid (860 mg).

LCMS (Method B) $R_f$ 1.11=mins, MH$^+$=385/387.

The organic layer was collected and the aqueous layer extracted with further DCM (50 ml). The combined organic layers were dried using a hydrophobic frit and the solvent removed in vacuo. The residue was suspended in DCM 5 ml and the resultant precipitate collected by filtration and air dried to give a further portion of the title compound (259 mg). Analytical data identical to that obtained above.

Intermediate 45

4-(Chloromethyl)-1,3-thiazole-2-carbonyl chloride

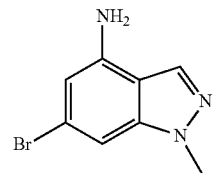

6-Bromo-1H-indazol-4-amine (5 g, 23.58 mmol) was added to THF (100 ml) and the mixture stirred in an ice-water bath. Then sodium hydride (1.037 g, 25.9 mmol)-(60% dispersion in mineral oil) was added portionwise to the mixture. After 10 minutes, iodomethane (1.622 ml, 25.9 mmol) was added to the flask. The mixture was stirred at 0° C. for 2 hours. Water (100 ml) was added and the mixture stirred for 30 mins. Then ethyl acetate (100 ml) was added. The organic layer was collected and the aqueous layer extracted with ethyl acetate (2×100 ml). The combined organic layers were dried using a hydrophobic frit and the solvent removed in vacuo. The residue was purified by chromatography on silica (2×100 g cartridges) eluting with 0-100% ethyl acetate in cylcohexane over 60 mins to afford the title compound as a yellow solid (2.96 g).

LCMS (Method B) $R_f$=0.83 min, MH$^+$=226/228.

Intermediate 46

N-[6-Bromo-2-(tetrahydro-2H-pyran-2-yl)-2H-indazol-4-yl]-2-(chloromethyl)-1,3-thiazole-4-carboxamide

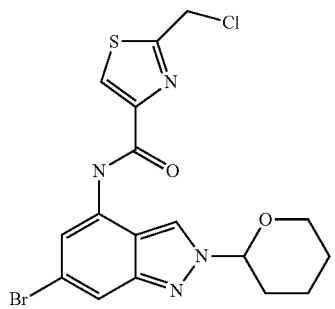

To 6-bromo-2-(tetrahydro-2H-pyran-2-yl)-2H-indazol-4-amine (1.47 g) in DCM (20 ml) was added pyridine (1 ml). The reaction mixture was stirred for 5 minutes at room temperature before 2-(chloromethyl)-1,3-thiazole-4-carbonyl chloride (1.21 g) in DCM (20 ml) was added dropwise over 10 minutes. The reaction mixture was stirred at room temperature for 18 hours. Saturated sodium bicarbonate solution (40 ml) was added and the reaction was stirred vigorously before the organic layer was separated using a hydrophobic frit. The aqueous layer was extracted with further DCM and the combined organic layers were evaporated to dryness. The residual solid was dried on a high vacuum line before triturating with cyclohexane to give the title compound (1.52 g).

LCMS (Method B) $R_t$=1.21 min, MH$^-$=453/455

Intermediate 47

N-[6-Bromo-2-(tetrahydro-2H-pyran-2-yl)-2H-indazol-4-yl]-2-{[(2R,6S)-2,6-dimethyl-4-morpholinyl]methyl}-1,3-thiazole-4-carboxamide

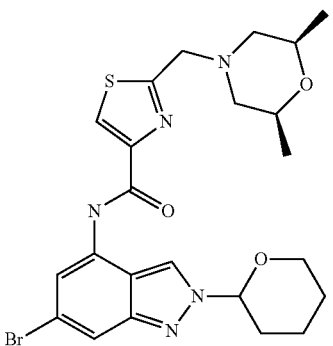

N-[6-Bromo-2-tetrahydro-2H-pyran-2-yl)-2H-indazol-4-yl]-2-(chloromethyl)-1,3-thiazole carboxamide (1 g) and (2R,6S)-2,6-dimethylmorpholine (3 ml) were combined in a microwave vial and heated under microwave irradiation at 90° C. for 15 minutes. DCM (100 ml) and water (100 ml) were added and the organic layer was separated by hydrophobic frit. The aqueous was washed further with DCM and the combined organic extracts were evaporated to dryness. The residual solid was purified by chromatography on silica (100 g cartridge) eluting with 0-100% ethyl acetate in cyclohexane over 40 mins to give the title compound.

LCMS (Method B) $R_t$ 1.07 min, MH$^-$=532/534

Intermediate 48

N-{6-[5-Amino-6-(methyloxy)-3-pyridinyl]-1-[(4-methylphenyl)sulfonyl]-1H-indazol-4-yl}-2-{[(2R,6S)-2,6-dimethyl-4-morpholinyl]methyl}-1,3-thiazole-4-carboxamide

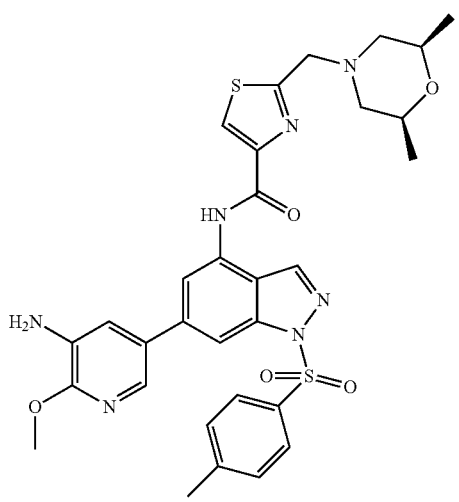

N-{6-Bromo-1-[(4-methylphenyl)sulfonyl]-1H-indazol-4-yl}-2-{[(2R,6S)-2,6-dimethyl-4-morpholinyl]methyl}-1,3-thiazole-4-carboxamide (4 g), 2-(methyloxy)-5-(4,4,5,5-tetramethyl-1,3,2-dioxaborolan-2-yl)-3-pyridinamine (1.8 g), sodium carbonate (2.8 g) and Pd(dppf)Cl$_2$ (0.48 g) were weighed to a 500 ml round-bottomed flask and 1,4-dioxane (150 ml) and water (150 ml) were added. The reaction was heated to 80° C. for 2 hours. The reaction was cooled then passed through a 10 g silica cartridge, washing with DCM: methanol. The reaction was concentrated to leave only the aqueous phase. DCM was added and the product extracted. The DCM was passed through a hydrophobic frit, then evaporated to dryness. The residue was purified on silica chromatography eluting with 0-6% methanol in DCM over 30 mins. Product containing fractions were combined and evaporated to dryness. The residue was repurified by silica chromatography using a gradient of 1.5-5% methanol in DCM over 30 mins. Product containing fractions were combined and evaporated to dryness to give title compound (1.9 g).

LCMS (Method B) $R_t$=0.95 min, MH$^+$=648.

Intermediate 49

2-{[(2R,6S)-2,6-Dimethyl-4-morpholinyl]methyl}-N-[6-[5-[(ethenylsulfonyl)amino]-6-(methyloxy)-3-pyridinyl]-2-(tetrahydro-2H-pyran-2-yl)-2H-indazol-4-yl]-1,3-thiazole-4-carboxamide

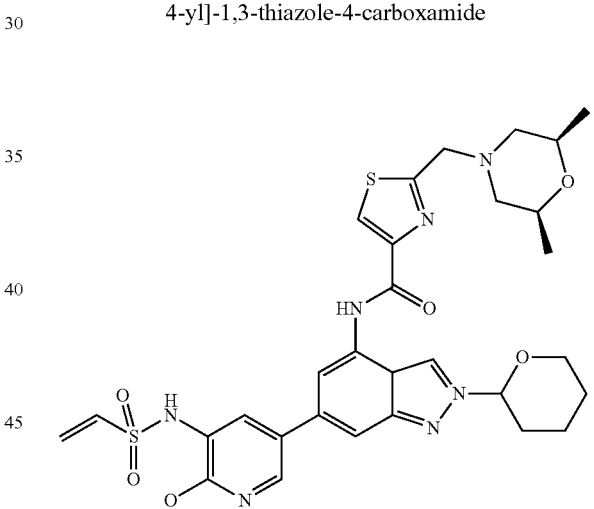

N-[6-[5-Amino-6-(methyloxy)-3-pyridinyl]-2-(tetrahydro-2H-pyran-2-yl)-2H-indazol-4-yl]-2-{[(2R,6S)-2,6-dimethyl-4-morpholinyl]methyl}-1,3-thiazole-4-carboxamide (250 mg) was dissolved in DCM (6 ml) and N-methylmorpholine (0.143 ml) was added. The reaction was cooled to 0° C. in an ice bath, then 2-chloroethanesulfonyl chloride (0.047 ml) was added dropwise. The reaction was left to warm to RT overnight. Reaction had blown dry, so was redissolved in DCM (6 ml). Further 2-chloroethanesulfonyl chloride (0.047 ml) was added and stirred at RT for 2 hours. Water (6 ml) was added to the reaction. The DCM was separated, passed through a hydrophobic frit, then evaporated to dryness to give crude title compound (250 mg) used directly in the next step without further purification.

LCMS (Method B) $R_t$=0.83 min, MH$^+$=668.

Intermediate 50

N-(5-Bromo-2-chloro-3-pyridinyl)methanesulfonamide

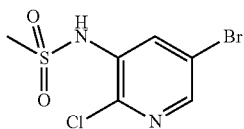

5-Bromo-2-chloro-3-pyridinamine (10 g) was dissolved in pyridine (75 ml) and methanesulfonyl chloride (7.5 ml) was added and stirred overnight. Further methanesulfonyl chloride (2.1 ml) was added and the reaction stirred at RT for 5 h. Further methanesulfonyl chloride (2.1 ml) was added and the mixture stirred at RT overnight. The ph was adjusted to ~6 by the addition of 2M HCl (aq). The mixture was then extracted with DCM (2×150 ml) and the combined organic layers were passed through a hydrophobic frit and the solvent removed in vacuo. The residue was suspended in methanol (200 ml) and 2M NaOH (50 ml) was added. The mixture was stirred for 1 hour and then the solvent removed in vacuo. The residue was dissolved in water (250 ml) and washed with DCM (150 ml). The aqueous layer was then acidified and the resulting precipitate collected by filtration. The solid was air dried overnight to give title compound (13.45 g) as an off white solid.

LCMS (Method B) $R_t$=0.81 min, MH$^-$=285.

Intermediate 51

{6-Chloro-5-[(methylsulfonyl)amino]-3-pyridinyl}boronic acid

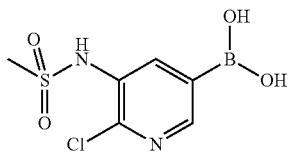

N-(5-Bromo-2-chloro-3-pyridinyl)methanesulfonamide (1 g), 4,4,4',4',5,5,5',5'-octamethyl-2,2'-bi-1,3,2-dioxaborolane (0.98 g), potassium acetate (1.03 g) and Pd(dppf)Cl$_2$ (0.256 g) were weighed to a 10-20 ml microwave vial and 1,4-dioxane (10 ml) was added. The reaction was heated at 80° C. for a total of 2 h in the microwave. Further 4,4,4',4',5,5,5',5'-octamethyl-2,2'-bi-1,3,2-dioxaborolane (0.489 g), potassium acetate (0.516 g) and Pd(dppf)Cl$_2$ (0.128 g) were added and the reaction was heated at 90° C. for a total of 1.5 h in the microwave. The reaction was filtered through a hydrophobic frit then evaporated to dryness. The residue was purified on the ISCO companion using an 80 g silica cartridge, and a gradient of 2-8% methanol in DCM (containing 1% ammonia) over 25 mins. Pure fractions were combined and evaporated to dryness, then dried on the vacuum line to give title compound (439 mg).

LCMS (Method B) $R_t$=0.46 min, MH$^+$=251.

Intermediate 52

N-[5-(4-Amino-1-methyl-1H-indazol-6-yl)-2-chloro-3-pyridinyl]methanesulfonamide

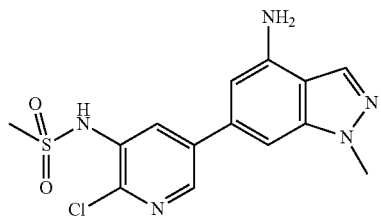

6-Bromo-1-methyl-1H-indazol-4-amine (340 mg), sodium carbonate (638 mg) and Pd(dppf)Cl$_2$ (110 mg) were weighed to a 10-20 ml microwave vial. {6-Chloro-5-[(methylsulfonyl)amino]-3-pyridinyl}boronic acid (377 mg) dissolved in 1,4-dioxane (6 ml) was added followed by water (6 ml). The reaction was heated for 15 min at 120° C. in the microwave. The reaction was passed through a 2 g silica cartridge, washing with methanol. The solvent was evaporated under nitrogen blow down. The residue was purified on the ISCO companion using a 40 g silica cartridge and a gradient of 2-8% methanol in DCM (containing 1% ammonia) over 15 mins at 40 ml/min. Product-containing fractions were combined and dried down to give title compound (158 mg).

LCMS (Method B) $R_t$=0.73 min, MH$^+$=352.

Intermediate 53

N-[6-(5-Amino-6-chloro-3-pyridinyl)-2-(tetrahydro-2H-pyran-2-yl)-2H-indazol-4-yl]-2-methyl-1,3-thiazole-4-carboxamide

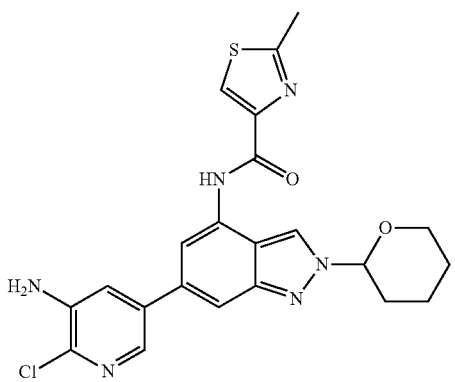

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (0.75 g), 5-bromo-2-chloro-3-pyridinamine (0.39 g), sodium carbonate (0.66 g) and Pd(dppf)Cl$_2$ (0.114 g) were weighed to a 10-20 ml microwave vial and 1,4-dioxane (8 ml) then water (8 ml) were added. The reaction was heated at 140° C. for 20 min. The reaction was passed through a 10 g silica cartridge, washing with methanol:DCM (1:1, v/v). The solvent was evaporated and the residue was purified on a 40 g ISCO companion silica cartridge, eluting with 1.5-7.5% methanol in DCM (containing 1% ammonia) at 40 ml/min. Pure fractions were combined and evaporated to dryness to give title compound (335 mg).

LCMS (Method B) $R_t$=1.05 min, MH$^+$=469/471.

Intermediate 54

N-(5-Bromo-2-chloro-3-pyridinyl)-2-methylbenzenesulfonamide

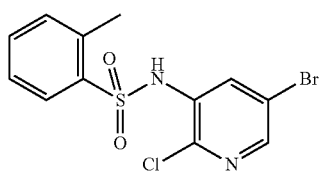

3-Amino-5-bromo-2-chloropyridine (767 mg) in dry pyridine (8 ml) was treated with 2-methylbenzenesulfonyl chloride (641 μl) then stirred at RT overnight. The reaction was purified by prep-HPLC. Desired fractions were combined, diluted with saturated sodium bicarbonate (aq) and brine and extracted into EtOAc. The solvent was dried over sodium sulfate and evaporated to give title compound (500 mg).

LCMS (Method B) $R_t$=1.1 min, MH$^+$=363.

Intermediate 55

N-(5-Bromo-2-chloro-3-pyridinyl)-5-fluoro-2-methylbenzenesulfonamide

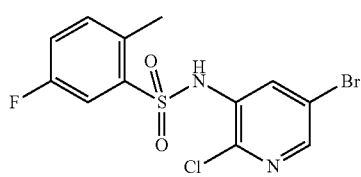

3-Amino-5-bromo-2-chloropyridine (797 mg) in dry pyridine (10 ml) was treated with 5-fluoro-2-methylbenzenesulfonyl chloride (962 mg) then stirred at RT over the weekend. The reaction was purified by prep-HPLC. Desired fractions were concentrated under reduced pressure, diluted with saturated sodium bicarbonate (aq) and brine and extracted into DCM. The solvent was dried over magnesium sulfate, filtered then evaporated to give title compound (865 mg).

LCMS (Method B) $R_t$=1.12 min, MH$^+$=381.

Intermediate 56

N-(5-Bromo-2-chloro-3-pyridinyl)-2,5-dimethylbenzenesulfonamide

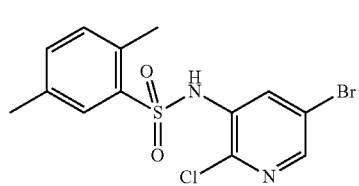

3-Amino-5-bromo-2-chloropyridine (510 mg) in dry pyridine (7 ml) was treated with 2,5-dimethylbenzenesulfonyl chloride (962 mg) then stirred at RT overnight. The reaction was purified by prep-HPLC. The combined fractions were concentrated to give a slurry, then filtered, rising with water and dried overnight to give title compound (441 mg).

LCMS (Method B) $R_t$=1.18 min, MH$^+$=377.

Intermediate 57

N-{5-[4-Amino-1-(phenylsulfonyl)-1H-indazol-6-yl]-3-pyridinyl}methanesulfonamide

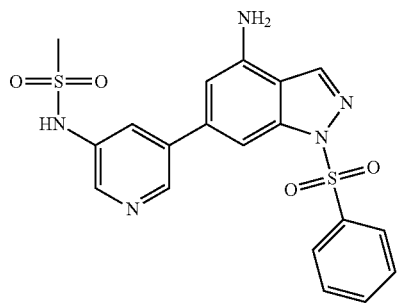

1-(Phenylsulfonyl)-6-(trimethylstannanyl)-1H-indazol-4-amine (700 mg), N-(5-bromo-3-pyridinyl)methanesulfonamide (484 mg) and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (45 mg) were dissolved in DMF (10 ml) and the reaction was heated under microwave irradiation 30 min at 120° C.

In a separate microwave vial, 1-(phenylsulfonyl)-6-(trimethylstannanyl)-1H-indazol-4-amine (50 mg), N-(5-bromo-3-pyridinyl)methanesulfonamide (35 mg) and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (3.2 mg) were dissolved in DMF (0.5 ml) and the reaction was heated under microwave irradiation for 30 min at 120° C.

The two reactions were combined and poured into water (350 ml) giving a precipitate that was filtered. The filtrate was extracted with EtOAc and evaporated to dryness. The precipitate and filtrate residue were separately dissolved in MeOH and adsorbed onto fluorosil then purified by column chromatography on silica, eluting with 50-100% EtOAc/cyclohexane then 0-5% MeOH/EtOAc. Combining the product-containing fractions and evaporating to dryness gave the title compound (314 mg).
LCMS (Method B) $R_t$=0.85 min, MH$^+$=444.

Intermediate 58

N-(5-Bromo-3-pyridinyl)methanesulfonamide

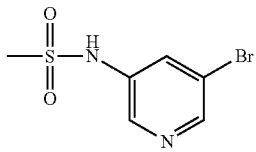

5-Bromo-3-pyridinamine (200 mg) was dissolved in pyridine (5 ml), cooled to 0° C. and stirred for 10 min. Methanesulfonyl chloride (0.05 ml) was added dropwise and the reaction continued stirring for 1 hr. 2M HCl (aq) (5 ml) was added and the reaction was extracted with DCM, passed through a hydrophobic frit and evaporated to dryness. The residue was dissolved in DCM and adsorbed onto fluorosil and purified by column chromatography on silica, eluting with 50% ether/cyclohexane then 0-10% MeOH/DCM to give the title compound (96 mg).
LCMS (Method B) $R_t$=0.68 min, MH$^+$=251/253.

Intermediate 59

N-{5-[4-Amino-1-(phenylsulfonyl)-1H-indazol-6-yl]-3-pyridinyl}benzenesulfonamide

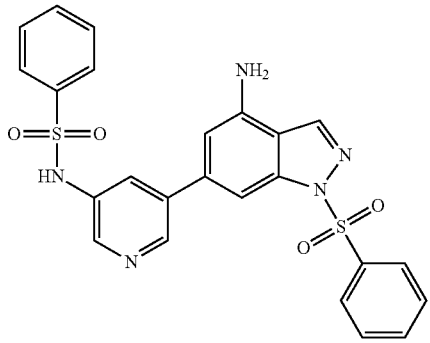

1-(Phenylsulfonyl)-6-(trimethylstannanyl)-1H-indazol-4-amine (500 mg), N-(5-bromo-3-pyridinyl)benzenesulfonamide (395 mg) and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (64 mg) were dissolved in DMF (10 ml) and heated under microwave irradiation at 120° C. for 15 min. The reaction was cooled to room temperature then heated under microwave irradiation for another 10 min at 120° C.
In a separate microwave vial, 1-(phenylsulfonyl)-6-(trimethylstannanyl)-1H-indazol-4-amine (50 mg), N-(5-bromo-3-pyridinyl)benzenesulfonamide (39.5 mg) and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (6.4 mg) were dissolved in DMF (1 ml) and the reaction was heated under microwave irradiation for 15 min at 120° C.

The two reactions were combined and partitioned between EtOAc (100 ml) and water (100 ml) before being evaporated to dryness. The residue was dissolved in DCM/MeOH and preadsorbed on fluorosil then purified by column chromatography on silica, eluting with 0-10% MeOH/DCM, to give the title compound (294 mg).
LCMS (Method B) $R_t$=1 min, MH$^+$=506.

Intermediate 60

N-(5-Bromo-3-pyridinyl)benzenesulfonamide

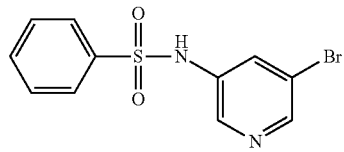

5-Bromo-3-pyridinamine (5 g) was dissolved in pyridine (150 ml) and the reaction was cooled to 0° C. in an ice-bath and stirred for 5 min. Benzenesulfonyl chloride (1.86 ml) was added dropwise and the reaction was stirred at 0° C. for 3 hr. Further benzenesulfonyl chloride (1.86 ml) was added and the reaction continued stirring for 1 hr. The reaction was neutralised with 2 M HCl and extracted with DCM (60 ml) then evaporated to dryness. The residue was dissolved in DCM and preadsorbed on fluorosil then purified by column chromatography on silica, eluting with 1-5% MeOH/DCM, to give the title compound (8 g).
LCMS (Method B) $R_t$=0.95 min, MH$^+$=313/315.

Intermediate 61

N-[5-Bromo-2-(ethyloxy)-3-pyridinyl]benzenesulfonamide

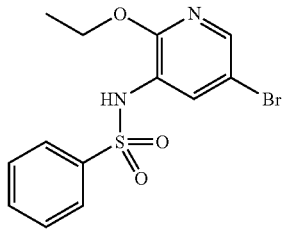

A solution of 5-bromo-2-(ethyloxy)-3-pyridinamine (1.45 g) in anhydrous pyridine (15 ml) was treated with benzenesulfonyl chloride (1.03 ml) then stirred at RT for 20 hr. The reaction was evaporated to dryness and the residue was purified by column chromatography on silica, eluting with 30% hexanes in DCM, to give the title compound (1.86 g).
$^1$H NMR: $\delta_H$ (DMSO-d$_6$, 400 MHz) 10.09 (1H, s), 8.03 (1H, d), 7.74 (1H, d), 7.71 (1H, d), 7.64 (1H, d), 7.57 (2H, d), 4.05 (2H, q), 1.07 (3H, t).

Intermediate 62

5-Bromo-2-(ethyloxy)-3-pyridinamine

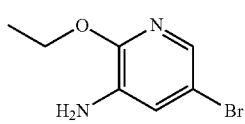

A solution of 5-bromo-2-(ethyloxy)-3-nitropyridine (15.5 g) in EtOAc (300 ml) was treated with tin(II) chloride anhydrate (56.6 g) then heated at reflux for 2.5 hr. The reaction was cooled to RT then evaporated to dryness. The residue was treated with 2M NaOH (aq) (500 ml) that was treated with anhydrous magnesium sulfate (~50 g) then slurried to give a filterable sludge. The filtrate was separated and the organic phase was washed with brine, dried over magnesium sulfate then evaporated to dryness. The residue was purified by column chromatography on silica, eluting with DCM, to give the title compound.

$^1$H NMR: $\delta_H$ (DMSO-d$_6$, 400 MHz) 7.37 (1H, d), 6.98 (1H, d), 5.24 (2H, br.s.), 4.27 (2H, q), 1.31 (3H, t).

Intermediate 63

5-Bromo-2-(ethyloxy)-3-nitropyridine

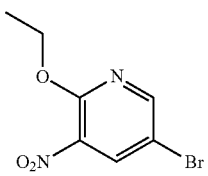

Sodium (3.22 g) was dissolved in absolute ethanol (100 ml) and added dropwise to a suspension of 5-bromo-2-chloro-3-nitropyridine (30.2 g) in ethanol (100 ml) at 0° C. over 10 mins. The cold bath was removed and the reaction stirred at RT for 18 h. The reaction was evaporated to approximately half its volume then diluted with saturated ammonium chloride (aq) (600 ml). The reaction was stirred at RT overnight then the solids were filtered and rinsed well with water. The solids were dissolved in hot ethanol (100 ml) then diluted with hot water (500 ml) and stirred with cooling to RT for 2 hr. The solids were collected and rinsed well with water then suction dried and vacuum dried to give the title compound (26.4 g) as a dark brown solid.

$^1$H NMR: $\delta_H$ (DMSO-d$_6$, 400 MHz) 8.68 (1H, d), 8.65 (1H, d), 4.48 (2H, q), 1.34 (3H, t).

Example 1

6-Bromo-N-[6-(4-hydroxyphenyl)-1H-indazol-4-yl]-2-pyridinecarboxamide

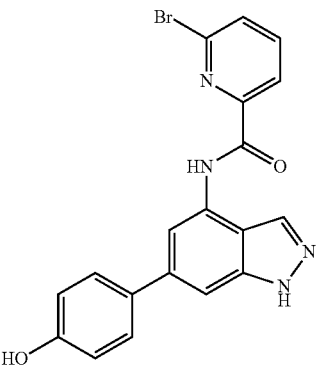

2-(Tetrahydro-2H-pyran-2-yl)-6-[4-(tetrahydro-2H-pyran-2-yloxy)phenyl]-2H-indazol-4-amine (500 mg, 1.27 mmol), 6-bromo-2-pyridinecarboxylic acid (272 mg, 1.35 mmol), HATU (531 mg, 1.35 mmol) and DIPEA (0.442 ml, 2.54 mmol) were combined in DMF (10 ml) and heated at 70° C. overnight. The solvent was removed in vacuo and the residue was purified by silica gel chromatography, eluting with DCM:MeOH:ammonia. Appropriate fractions were combined and the solvent was removed in vacuo. The residue was dissolved in Methanol (20 ml) and 4 M HCl in dioxane (2 ml) and stirred at RT for 5 days. A small amount of the reaction mixture was removed (2 ml), the solvent was removed in vacuo and the residue purified by MDAP (Method B) to give the title compound.

LC/MS (Method A) R$_t$=3.28 min, MH$^+$=411.

Example 2

N-[6-(3-Hydroxyphenyl)-1H-indazol-4-yl]cyclohexanecarboxamide

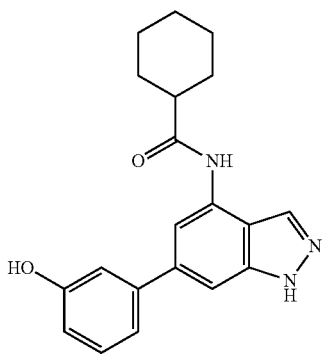

2-(Tetrahydro-2H-pyran-2-yl)-6-[3-(tetrahydro-2H-pyran-2-yloxy)phenyl]-2H-indazol-4-amine (50 mg, 0.127 mmol) was dissolved in DCM (1 ml) and DIPEA (0.111 ml, 0.635 mmol) and cyclohexanecarbonyl chloride (45 mg, 0.254 mmol) were added. The reaction was stirred at RT for 1 h. 2 M Sodium hydroxide (aq) (2 ml) was added and the reaction stirred at RT for 1 h, before the organic layer was passed through a hydrophobic frit. The aqueous layer was washed several times with DCM, which was passed through a hydrophobic frit. The combined organic layers were evaporated under a stream of nitrogen. The residue was dissolved in MeOH (2 ml) and 4 M HCl in dioxane was added (2 ml). The reaction was stirred at RT for 1 h. The solvent was removed under a stream of nitrogen and the residue was dissolved in DMSO:MeOH (1:1, v/v) and purified by MDAP (Method B). The residue was dissolved in 1,4-dioxane:water and freeze dried to produce the title compound.

LC/MS (Method A) $R_t$=3.16 mins, MH$^+$=336.

Similarly prepared were the following, using the appropriate amount of the appropriate acid chloride:

| Example number | Product Name | Structure | Starting Material Name | Starting Material (Acid chloride) | $R_t$ (mins) | MH$^+$ |
|---|---|---|---|---|---|---|
| 3 | N-[6-(3-hydroxyphenyl)-1H-indazol-4-yl]-2-pyridine-carboxamide | 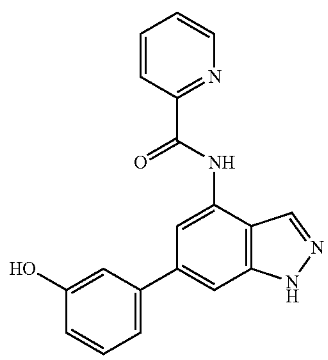 | 2-pyridine-carbonyl chloride hydrochloride | | 3.05 | 331 |
| 4 | N-[6-(3-hydroxyphenyl)-1H-indazol-4-yl]-3-phenyl-propanamide | 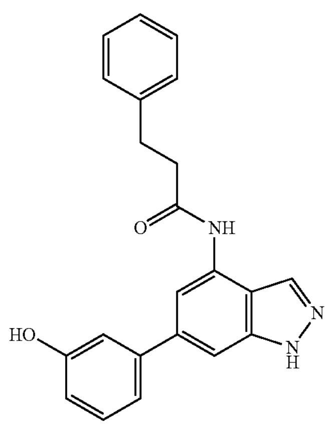 | 3-phenyl-propanoyl chloride | | 3.12 | 358 |
| 5 | 4-cyano-N-[6-(3-hydroxyphenyl)-1H-indazol-4-yl]benzamide | 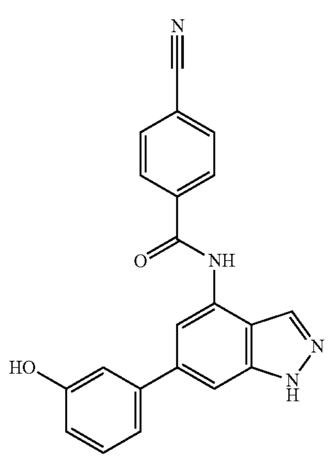 | 4-cyanobenzoyl chloride | | 2.98 | 355 |

-continued

| Example number | Product Name | Structure | Starting Material Name | Starting Material (Acid chloride) | R$_t$ (mins) | MH$^+$ |
|---|---|---|---|---|---|---|
| 6* | 3-(dimethyl-amino)-N-[6-(3-hydroxy-phenyl)-1H-indazol-4-yl]benzamide | 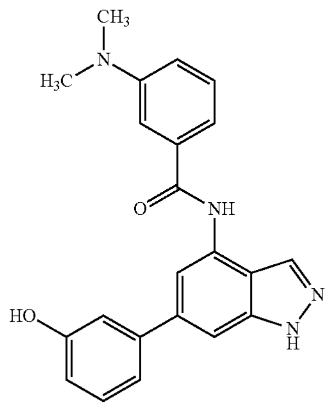 | 3-(dimethyl-amino) benzoyl chloride | | 3.11 | 373 |
| 7 | (1R,2R)-N-[6-(3-hydroxy-phenyl)-1H-indazol-4-yl]-2-phenyl-cyclopropane-carboxamide | 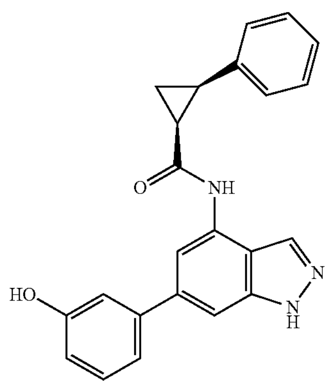 | (1R,2R)-2-phenylcyclo-propane-carbonyl chloride | | 3.28 | 370 |
| 8 | N-[6-(3-hydroxyphenyl)-1H-indazol-4-yl]-2-furan-carboxamide | 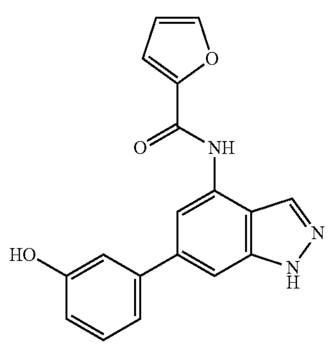 | 2-furan-carbonyl chloride | | 2.77 | 320 |
| 9 | N-[6-(3-hydroxyphenyl)-1H-indazol-4-yl]cyclo-propane-carboxamide | 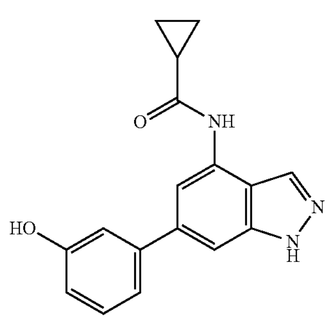 | cyclopropane-carbonyl chloride | | 2.76 | 294 |

*Further purified by HPLC using the following:
Solvent A: 0.1% Formic acid in water
Solvent B: 0.05% formic acid in MeCN
Gradient: 30-80% B over 20 mins.

Example 10

N-{6-[5-(Aminosulfonyl)-3-pyridinyl]-1H-indazol-4-yl}-2-methyl-1,3-thiazole-4-carboxamide

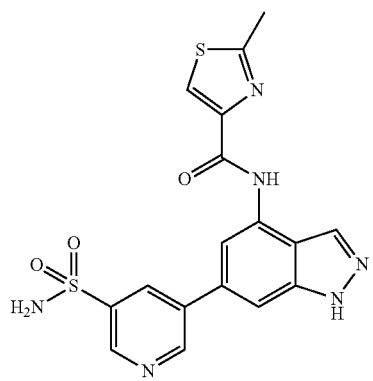

2-Methyl-N-[6-(4,4,5,5-tetramethyl-1,3,2-dioxaborolan-2-yl)-1H-indazol-4-yl]-1,3-thiazole-4-carboxamide (23 mg, 0.06 mmol), 5-bromo-3-pyridinesulfonamide (18 mg, 0.078 mmol) and Pd(PPh$_3$)$_4$ (7 mg, 0.006 mmol) were combined in IPA (0.5 ml) and 1 M sodium bicarbonate (aq) (0.18 ml). The reaction was heated in a Biotage microwave at 120° C. for 10 mins. After cooling the solvent was removed under a stream of nitrogen and the solid partitioned between water (10 ml) and ethyl acetate:DCM (3×10 ml, 1:1, v/v). A few drops of brine were added to aid separation. The organic layers were combined, passed through a hydrophobic frit and dried under a stream of nitrogen. The residue was dissolved in MeOH:DMSO (0.5 ml, 1:1, v/v) and purified by MDAP (Method B). The solvent was removed under a stream of nitrogen to give the title compound, 1.5 mg.

LC/MS (Method B) R$_t$=0.81 mins, MH$^+$=415.

Example 11

N-(6-{3-[(Aminosulfonyl)methyl]phenyl}-1H-indazol-4-yl)-2-methyl-1,3-thiazole-4-carboxamide

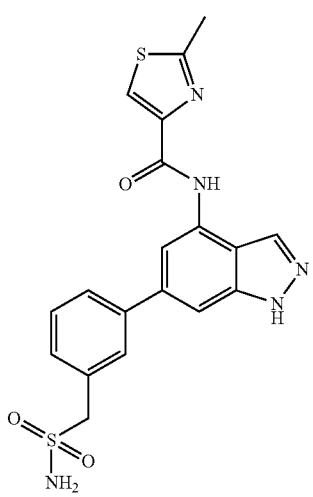

N-(6-Bromo-1H-indazol-4-yl)-2-methyl-1,3-thiazole-4-carboxamide (50 mg, 0.148 mmol), Pd(dppf)Cl$_2$ (12 mg, 0.015 mmol), 2 M sodium carbonate (aq) (0.222 ml, 0.444 mmol), 1,4-dioxane (1 ml) and water (1 ml) were added to 1-[3-(4,4,5,5-tetramethyl-1,3,2-dioxaborolan-2-yl)phenyl]methanesulfonamide (53 mg, 0.178 mmol). The reaction was heated in a Biotage microwave at 150° C. for 15 mins. The reaction mixture was extracted with DCM (2×20 ml) and the separated, combined organic layer was evaporated to dryness. The residue was dissolved in MeOH:DMSO (1 ml, 1:1, v/v) and purified by MDAP (Method B). Appropriate fractions were dried under a stream of nitrogen to give title compound, 5 mg.

LC/MS (Method B) R$_t$=0.86 mins, MH$^+$=428.

Example 12

2-Methyl-N-{6-[5-(methyloxy)-3-pyridinyl]-1H-indazol-4-yl}-1,3-thiazole-4-carboxamide

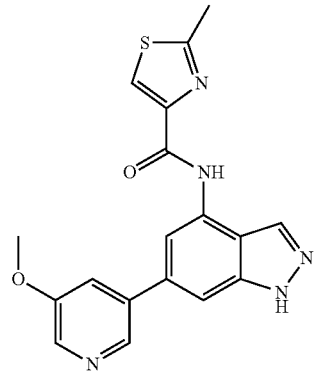

N-(6-Bromo-1H-indazol-4-yl)-2-methyl-1,3-thiazole-4-carboxamide (50 mg, 0.148 mmol), Pd(dppf)Cl$_2$ (12 mg, 0.015 mmol), 2 M sodium carbonate (aq) (0.222 ml, 0.444 mmol), 1,4-dioxane (1 ml) and water (1 ml) were added to 3-(methyloxy)-5-(4,4,5,5-tetramethyl-1,3,2-dioxaborolan-2-yl)pyridine (42 mg, 0.178 mmol). The reaction was heated in a Biotage microwave at 150° C. for 15 mins. The reaction mixture was extracted with DCM (2×20 ml) and the separated, combined organic layer was evaporated to dryness. The residue was dissolved in MeOH:DMSO (1 ml, 1:1, v/v) and purified by MDAP (Method B). Appropriate fractions were dried under a stream of nitrogen to give title compound, 11 mg. LC/MS (Method B) R$_t$=0.86 mins, MH$^+$=366.

Example 13

3-(4-{[(2-Methyl-1,3-thiazol-4-yl)carbonyl]amino}-1H-indazol-6-yl)benzoic acid

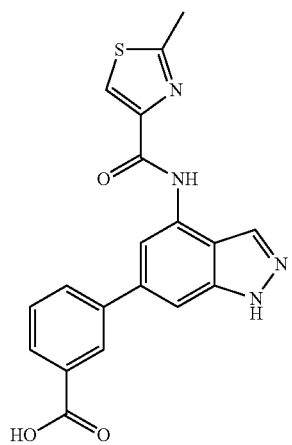

Material A:

N-(6-Bromo-1H-indazol-4-yl)-2-methyl-1,3-thiazole-4-carboxamide (80 mg, 0.237 mmol), 3-(4,4,5,5-tetramethyl-1,3,2-dioxaborolan-2-yl)benzoic acid (71 mg, 0.285 mmol), Pd(dppf)Cl$_2$ (19 mg, 0.024 mmol) and 2 M sodium carbonate (aq) (0.356 ml, 0.712 mmol) were combined in 1,4-dioxane (1 ml) and water (1 ml). The reaction was heated in a Biotage microwave at 150° C. for 15 mins. The pH was adjusted to ~2 with 2 M HCl (aq) and the solid formed was separated. The solid was extracted with 80% DCM in MeOH (3×25 ml) and the combined organic solvent was evaporated. The residue was dissolved in MeOH:DMSO (1 ml, 1:1, v/v) and purified by MDAP (Method B). The solvent of product-containing fractions was dried under a stream of nitrogen.

Material B:

Synthesis, scale, work up and purification was the same as Material A, except the solid was extracted with 50% DCM in ethyl acetate (4×25 ml) rather than 80% DCM in MeOH (2×25 ml).

Material A and B were combined and further purified by HPLC using the following system:
Column: 5 μm Phenomenex Luna C$_{18}$(2) 100×21.2 mm i.d.
Solvent A: 0.05% TFA in water
Solvent B: 0.05% TFA in MeCN:MeOH (1:1, v/v)
Flow rate: 20 ml/min
Gradient: Isocratic 46% B.

Purified fractions were dried, redissolved in MeCN, recombined and dried to give title compound, 5 mg. LC/MS (Method B) R$_t$=0.9 mins, M+NH$_4^+$=396.

Example 14

N-(6-{6-Chloro-5-[(phenylsulfonyl)amino]-3-pyridinyl}-1H-indazol-4-yl)-2-methyl-1,3-thiazole-4-carboxamide

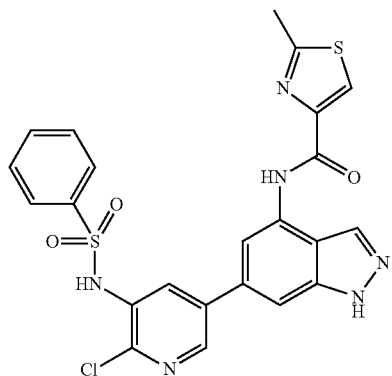

DMA (9 ml) was added to a Biotage microwave vial containing N-(6-bromo-1H-indazol-4-yl)-2-methyl-1,3-thiazole-4-carboxamide (175 mg, 0.519 mmol), Pd(dppf)Cl$_2$ (85 mg, 0.104 mmol), potassium acetate (153 mg, 1.56 mmol) and 4,4,4',4',5,5,5',5'-octamethyl-2,2'-bi-1,3,2-dioxaborolane (86 mg, 0.338 mmol). The vial was sealed, the solution was degassed with nitrogen, then heated in a Biotage Initiator at 80° C. for 20 mins. Pd(dppf)Cl$_2$ (85 mg, 0.104 mmol) was added to the reaction, the vial was sealed, degassed with nitrogen, then heated in a Biotage Initiator at 80° C. for 20 mins. Pd(PPh$_3$)$_4$ (30 mg, 0.026 mmol), N-(5-bromo-2-chloro-3-pyridinyl)benzenesulfonamide (361 mg, 1.038 mmol) and sodium bicarbonate (0.778 ml, 1.56 mmol) were added to the reaction, which was heated in a Biotage Initiator at 150° C. for 15 mins. Saturated sodium bicarbonate (100 ml) was added and the resulting suspension was washed with ethyl acetate (3×100 ml). Sodium chloride was added to improve separation. The organic layers were filtered through a hydrophobic frit, combined and dried under vacuum. The solid obtained was pre-adsorbed on silica and purified by silica chromatography (100 g cartridge) using 0-15% MeOH in DCM over 60 mins. Appropriate fractions were combined and dried under vacuum. The still crude compound was loaded onto an SPE (50 g) cartridge using DCM and the column was eluted with ethyl acetate:toluene:MeOH (200 ml, 14:5:1, v/v/v). Appropriate fractions were combined and the solvent was evaporated. The material obtained was dissolved in MeOH:DMSO (1 ml, 1:1, v/v) and further purified by HPLC as follows:

Column: Supelco ABZ+ Plus
Solvent A: 0.1% formic acid in water
Solvent B: 1% formic acid in MeCN:water (95:5, v/v)
Flow rate: 20 ml/min
Gradient: 35-65% B, over 25 mins.

Solvent from appropriate fractions was dried under a stream of nitrogen to give title compound, 3 mg.

LC/MS (Method B) R$_t$=1.04 mins, MH+=525.

Example 15

N-{6-[4-(Acetylamino)phenyl]-1H-indazol-4-yl}-2-pyridinecarboxamide

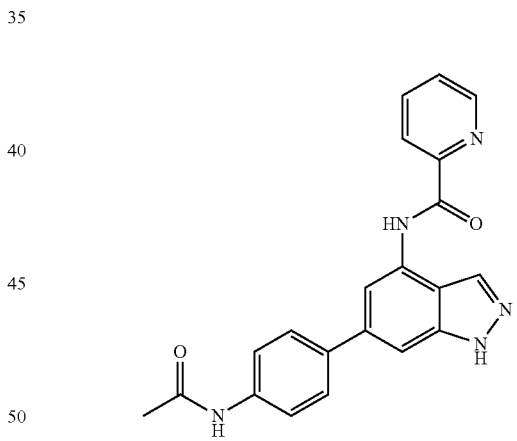

N-(6-Bromo-1H-indazol-4-yl)-2-pyridinecarboxamide (70 mg, 0.22 mmol), [4-(acetylamino)phenyl]boronic acid (47 mg, 0.26 mmol), Pd(dppf)Cl$_2$ (22 mg, 0.027 mmol) and 2 M sodium carbonate (aq) (0.328 ml, 0.656 mmol) in 1,4-dioxane (1.5 ml) and water (1.5 ml) were heated in a Biotage microwave at 150° C. for 30 mins. The reaction was washed through a silica cartridge eluting with MeOH. The solvent was removed in vacuo. The residue was purified by HPLC using the method described below to afford the title compound.

LC/MS (Method A) R$_t$=2.92 mins, MH$^+$=372.

Similarly prepared were the following, using the appropriate amount of the appropriate boronic acid/ester and purified using the appropriate method outlined below:

| Example number | Structure | Name | Monomer | Monomer name | R$_t$ (mins) | MH$^+$ |
|---|---|---|---|---|---|---|
| 16 | 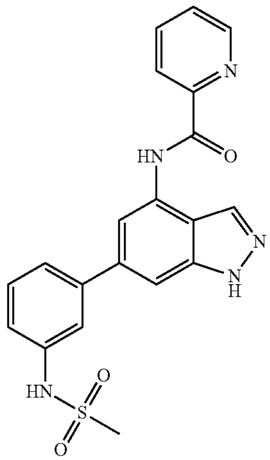 | N-(6-{3-[(methylsulfonyl)amino]phenyl}-1H-indazol-4-yl)-2-pyridinecarboxamide | | {3-[(methylsulfonyl)amino]phenyl}-boronic acid | 2.98 | 408 |
| 17 | 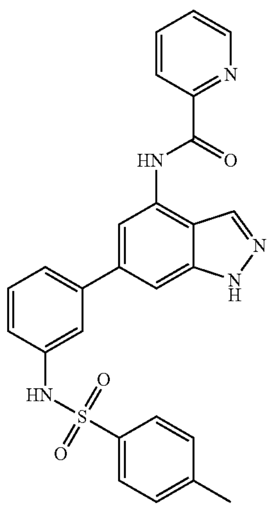 | N-[6-(3-{[(4-methylphenyl)sulfonyl]amino}phenyl)-1H-indazol-4-yl]-2-pyridinecarboxamide | | 4-methyl-N-[3-(4,4,5,5-tetramethyl-1,3,2-dioxaborolan-2-yl)phenyl]-benzenesulfonamide | 3.45 | 484 |
| 18 | 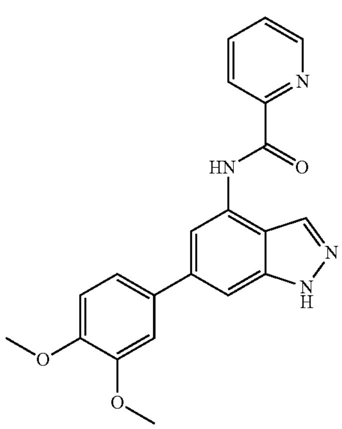 | N-{6-[3,4-bis(methyloxy)phenyl]-1H-indazol-4-yl}-2-pyridinecarboxamide | | [3,4-bis-(methyloxy)-phenyl]-boronic acid | 3.1 | 375 |

| Example number | Structure | Name | Monomer | Monomer name | $R_t$ (mins) | $MH^+$ |
|---|---|---|---|---|---|---|
| 19 | 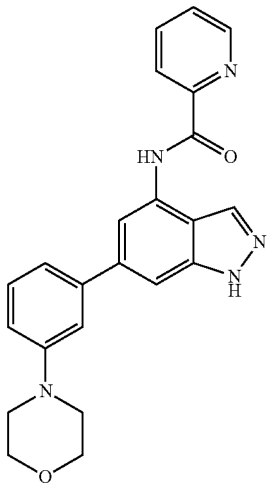 | N-{6-[3-(4-morpholinyl)-phenyl]-1H-indazol-4-yl}-2-pyridine-carboxamide | | (3-{ethyl[2-(methyloxy)-ethyl]amino}-phenyl)-boronic acid (available from Asymchem International Inc) | 3.47 | 411 |

HPLC Conditions:

Column:

(1) Waters Sunfire $C_{18}$ (100 mm×19 mm, 5 μm particle size), or;

(2) Supelco ABZ+ $C_{18}$ (100 mm×21.2 mm, 5 μm particle size)

Solvent A: Water (containing either 0.1% formic acid or 0.2% TFA)

Solvent B: MeCN:water (95:5, v/v) (containing either 0.05% formic acid or 0.1% TFA)

Flow Rate: 20 ml/min

Gradient A (used for examples 16, 17 and 18):

| Time (mins) | % A | % B |
|---|---|---|
| 0 | 75 | 25 |
| 1 | 75 | 25 |
| 12.5 | 1 | 99 |
| 13 | 1 | 99 |
| 13.5 | 75 | 25 |
| 15 | 75 | 25 |

Gradient B (Used for Example 15):

| Time (mins) | % A | % B |
|---|---|---|
| 0 | 80 | 20 |
| 1 | 80 | 20 |
| 10 | 35 | 65 |
| 12.5 | 1 | 99 |
| 13 | 1 | 99 |
| 13.5 | 80 | 20 |
| 15 | 80 | 20 |

Example 20

N-(6-{3-[(Methylamino)carbonyl]phenyl}-1H-indazol-4-yl)-2-pyridinecarboxamide

N-(6-Bromo-1H-indazol-4-yl)-2-pyridinecarboxamide (100 mg, 0.31 mmol), {3-[(methylamino)carbonyl]phenyl}boronic acid (66 mg, 0.37 mmol), Pd(dppf)Cl$_2$ (31 mg, 0.038 mmol) and 2 M sodium carbonate (aq) (0.468 ml, 0.936 mmol) in 1,4-dioxane (1.5 ml) and water (1 ml) were heated in a Biotage microwave at 150° C. for 30 mins. The reaction was purified by HPLC as follows to give title compound, 7 mg.

LC/MS (Method A) $R_t$=2.89 mins, $MH^+$=372.

Column: $C_{18}$ HPLC Supelcosil ABZ PLUS 100 mm×21.2 mm, 5 μm.

Solvent A: 0.1% TFA in water

Solvent B: 0.1% TFA in MeCN

Gradient: 20-60% B over 10 mins.

Similarly prepared were the following, using the appropriate amount of the appropriate boronic acid/ester and purified using a similar method, with differing gradients as shown:

| Example number | Structure | Name | Monomer | Monomer name | Gradient | R$_t$ (mins) | MH$^+$ |
|---|---|---|---|---|---|---|---|
| 21 | 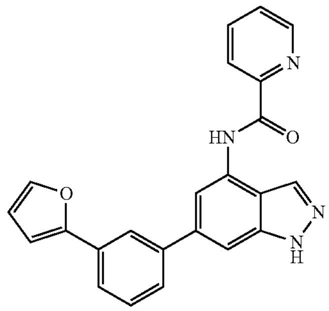 | N-{6-[3-(2-furanyl)-phenyl]-1H-indazol-4-yl}-2-pyridine-carboxamide | | 2-[3-(2-furanyl)-phenyl]-4,4,5,5-tetramethyl-1,3,2-dioxaborolane | 40-95% B | 3.72 | 381 |
| 22 | 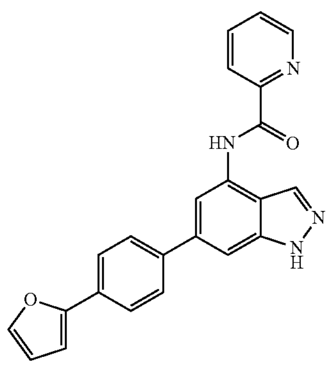 | N-{6-[4-(2-furanyl)phenyl]-1H-indazol-4-yl}-2-pyridine-carboxamide | | 2-[4-(2-furanyl)-phenyl]-4,4,5,5-tetramethyl-1,3,2-dioxaborolane | 40-95% B | 3.81 | 381 |
| 23 | 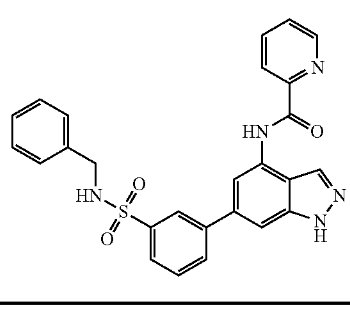 | N-[6-(3-{[(phenyl-methyl)ami-no]sulfon-yl}phenyl)-1H-indazol-4-yl]-2-pyridine-carboxamide | | (3-{[(phenyl-methyl)-amino]-sulfonyl}phenyl)-boronic acid (Combi-blocks) | 30-80% B | 3.41 | 484 |

Example 24

N-[6-(3-Cyanophenyl)-1H-indazol-4-yl]-2-methyl-1,3-thiazole-4-carboxamide

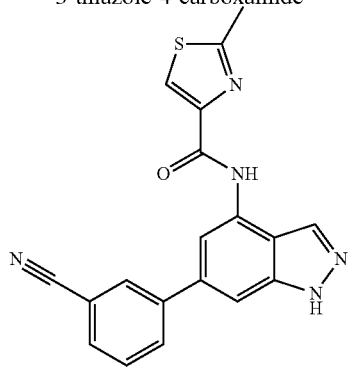

(3-Cyanophenyl)boronic acid (17 mg, 0.12 mmol), 0.6 M potassium carbonate (aq) (0.2 ml, 0.12 mmol) and Pd(dppf)Cl$_2$ (10 mg, 0.014 mmol) in 1,4-dioxane (1 ml) were treated with N-(6-bromo-1H-indazol-4-yl)-2-methyl-1,3-thiazole-4-carboxamide (40 mg, 0.12 mmol) in 1,4-dioxane (1 ml). The reaction was heated in a CEM Discover microwave at 150° C. for 30 mins. After cooling the solvent was removed in vacuo. The residue was dissolved in MeOH and loaded onto a C$_{18}$ SPE cartridge eluting with 0.1% TFA in MeCN (3×3 ml). The solvent was removed under a stream of nitrogen. The residue was purified by MDAP (Method C) to give the title compound.

LC/MS (Method B) R$_t$=0.97 min, MH$^+$=360.

Similarly prepared were the following:

| Example number | Structure | Name | Precursor boronic acid | R$_t$ (min) | MH$^+$ |
|---|---|---|---|---|---|
| 25 | 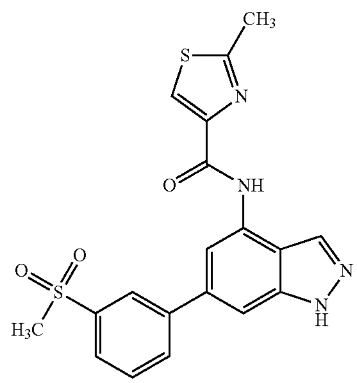 | 2-methyl-N-{6-[3-(methylsulfonyl)phenyl]-1H-indazol-4-yl}-1,3-thiazole-4-carboxamide | [3-(methylsulfonyl)phenyl]boronic acid | 0.86 | 413 |
| 26 | 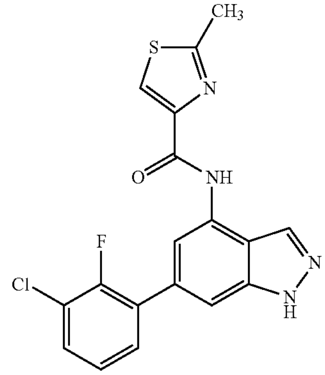 | N-[6-(3-chloro-2-fluorophenyl)-1H-indazol-4-yl]-2-methyl-1,3-thiazole-4-carboxamide | (3-chloro-2-fluorophenyl)boronic acid | 1.11 | 387 |

-continued

| Example number | Structure | Name | Precursor boronic acid | $R_t$ (min) | $MH^+$ |
|---|---|---|---|---|---|
| 27 | 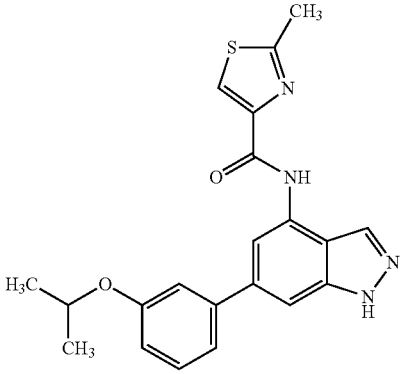 | 2-methyl-N-(6-{3-[(1-methylethyl)oxy]phenyl}-1H-indazol-4-yl)-1,3-thiazole-4-carboxamide | {3-[(1-methylethyl)oxy]phenyl}boronic acid | 1.14 | 393 |
| 28 | 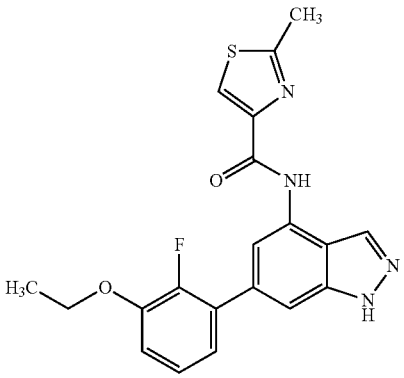 | N-{6-[3-(ethyloxy)-2-fluorophenyl]-1H-indazol-4-yl}-2-methyl-1,3-thiazole-4-carboxamide | [3-(ethyloxy)-2-fluoro-phenyl]boronic acid | 1.06 | 397 |
| 29 | 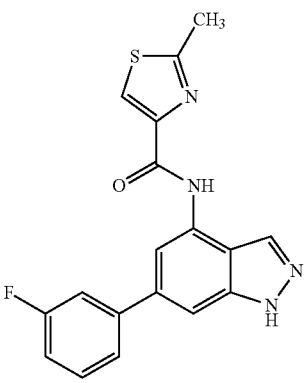 | N-[6-(3-fluorophenyl)-1H-indazol-4-yl]-2-methyl-1,3-thiazole-4-carboxamide | (3-fluoro-phenyl)boronic acid | 1.04 | 353 |
| 30 | 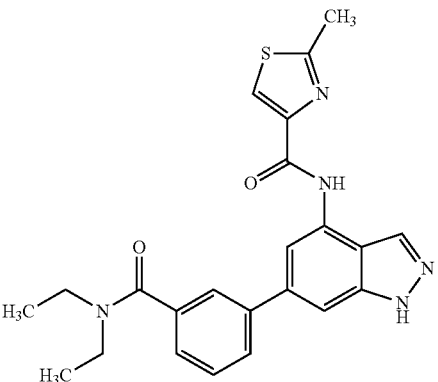 | N-(6-{3-[(diethylamino)carbonyl]phenyl}-1H-indazol-4-yl)-2-methyl-1,3-thiazole-4-carboxamide | {3-[(diethylamino)carbonyl]phenyl}boronic acid | 0.95 | 434 |

-continued

| Example number | Structure | Name | Precursor boronic acid | R$_t$ (min) | MH$^+$ |
|---|---|---|---|---|---|
| 31 | 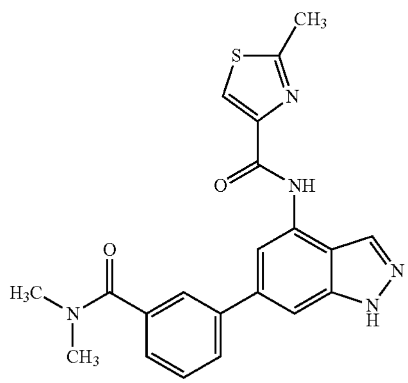 | N-(6-{3-[(dimethylamino)carbonyl]phenyl}-1H-indazol-4-yl)-2-methyl-1,3-thiazole-4-carboxamide | {3-[(dimethylamino)carbonyl]phenyl}boronic acid | 0.84 | 406 |
| 32 | 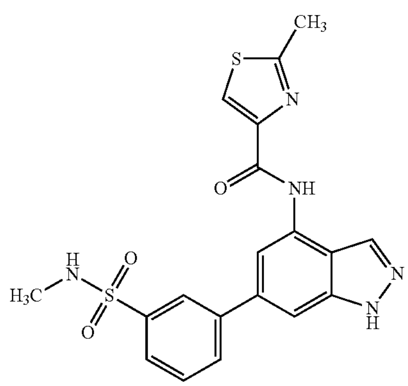 | 2-methyl-N-(6-{3-[(methylamino)sulfonyl]phenyl}-1H-indazol-4-yl)-1,3-thiazole-4-carboxamide | {3-[(methylamino)sulfonyl]phenyl}boronic acid | 0.87 | 428 |
| 33 | 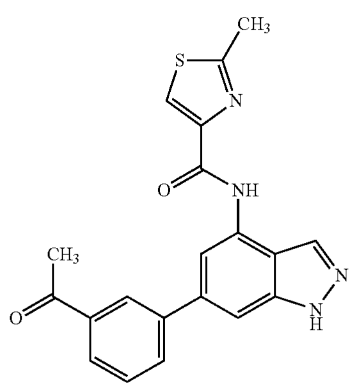 | N-[6-(3-acetylphenyl)-1H-indazol-4-yl]-2-methyl-1,3-thiazole-4-carboxamide | (3-acetylphenyl)boronic acid | 0.94 | 377 |
| 34 | 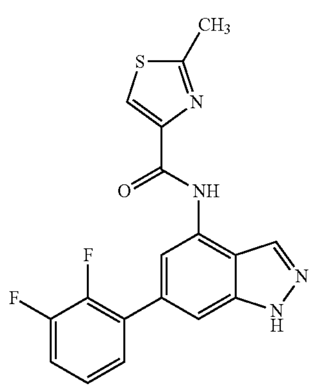 | N-[6-(2,3-difluorophenyl)-1H-indazol-4-yl]-2-methyl-1,3-thiazole-4-carboxamide | (2,3-difluorophenyl)boronic acid | 1.03 | 371 |

| Example number | Structure | Name | Precursor boronic acid | $R_t$ (min) | MH⁺ |
|---|---|---|---|---|---|
| 35§ | | 2-methyl-N-{6-[3-(4-morpholinyl-sulfonyl)phenyl]-1H-indazol-4-yl}-1,3-thiazole-4-carboxamide | 4-{[3-(4,4,5,5-tetramethyl-1,3,2-dioxaborolan-2-yl)phenyl]sulfonyl}morpholine | 3.12* | 484 |
| 36 | 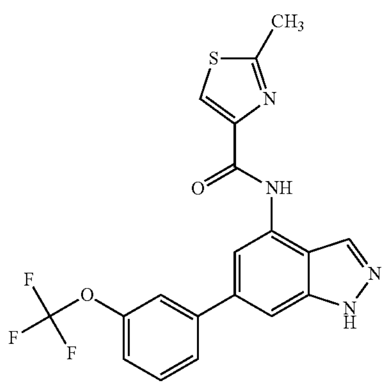 | 2-methyl-N-(6-{3-[(trifluoro-methyl)oxy]phenyl}-1H-indazol-4-yl)-1,3-thiazole-4-carboxamide | {3-[(trifluoro-methyl)oxy]phenyl}boronic acid | 1.18 | 419 |
| 37 | 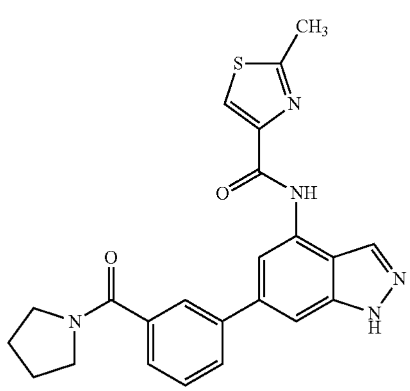 | 2-methyl-N-{6-[3-(1-pyrrolidinyl-carbonyl)phenyl]-1H-indazol-4-yl}-1,3-thiazole-4-carboxamide | [3-(1-pyrrolidinyl-carbonyl)phen-yl]boronic acid | 0.91 | 432 |

-continued

| Example number | Structure | Name | Precursor boronic acid | R$_t$ (min) | MH$^+$ |
|---|---|---|---|---|---|
| 38 | 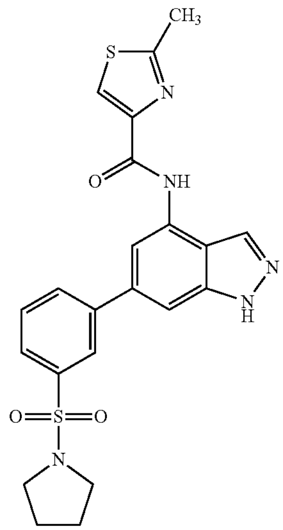 | 2-methyl-N-{6-[3-(1-pyrrolidinyl-sulfonyl)phenyl]-1H-indazol-4-yl}-1,3-thiazole-4-carboxamide | [3-(1-pyrrolidinyl-sulfonyl)phen-yl]boronic acid | 1.02 | 468 |
| 39 | 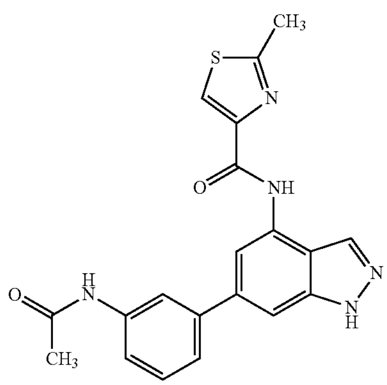 | N-{6-[3-(acetyl-amino)phenyl]-1H-indazol-4-yl}-2-methyl-1,3-thiazole-4-carboxamide | [3-(acetyl-ami-no)phenyl]-boronic acid | 0.84 | 392 |
| 40 | 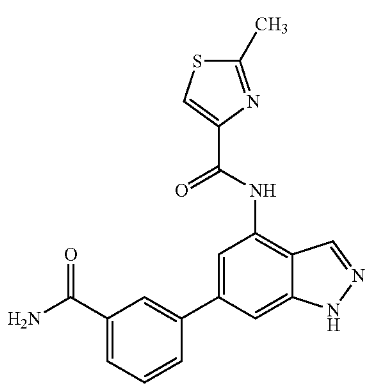 | N-{6-[3-(amino-carbonyl)phenyl]-1H-indazol-4-yl}-2-methyl-1,3-thiazole-4-carboxamide | [3-(aminocar-bonyl)phenyl]-boronic acid | 0.76 | 378 |

| Example number | Structure | Name | Precursor boronic acid | $R_t$ (min) | $MH^+$ |
|---|---|---|---|---|---|
| 41 | 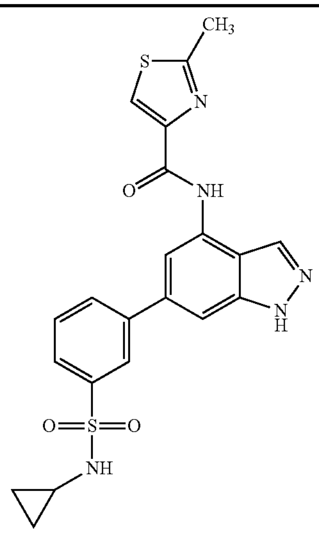 | N-(6-{3-[(cyclo-propylamino)sul-fonyl]phenyl}-1H-indazol-4-yl)-2-methyl-1,3-thiazole-4-carboxamide | {3-[(cyclopro-pylamino)sul-fonyl]phenyl}-boronic acid | 0.94 | 454 |
| 42 | 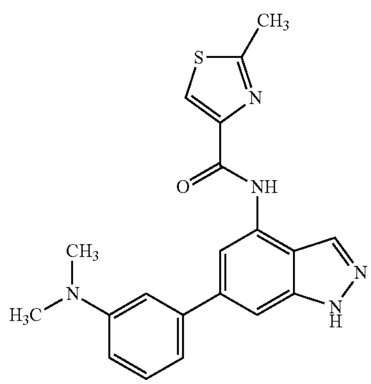 | N-{6-[3-(dimethylamino)phenyl]-1H-indazol-4-yl}-2-methyl-1,3-thiazole-4-carboxamide | [3-(dimethyl-amino)phen-yl]boronic acid | 0.82 | 378 |

*LC/MS Method A
§Further purified as shown:
Column: Supelco ABZ + plus 100 × 2.1 mm i.d.
Solvent A: 0.05% formic acid in water
Solvent B: 0.05% formic in MeCN
Flow rate: 20 ml/min.
Gradient: 40-60% B over 25 mins.

Example 43

N-[6-(3-Methylphenyl)-1H-indazol-4-yl]cyclopropanecarboxamide

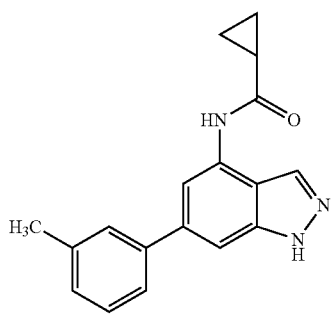

THF (1 ml), DIPEA (0.142 ml, 0.813 mmol) and cyclopropanecarbonyl chloride (34 mg, 0.325 mmol) were added to 6-(3-methylphenyl)-2-(tetrahydro-2H-pyran-2-yl)-2H-indazol-4-amine (50 mg, 0.163 mmol) and the reaction was stirred at RT for 1 h. The solvent was evaporated under a stream of nitrogen and 2 M sodium hydroxide (aq) (3 ml) was added and the reaction stirred for 1 h. DCM (3 ml) was added and the reaction stirred for a further 30 mins. The organic layer was passed through a hydrophobic frit and the aqueous layer extracted with DCM. The combined organic layers were concentrated. The residue was dissolved in MeOH (2 ml) and 4 M HCl in 1,4-dioxane (2 ml) was added. The reaction was stirred for 1 h then the solvent was removed in vacuo. The residue was purified by MDAP (Method A) then freeze dried to give title compound, 17 mg.

LC/MS (Method A) $R_t$=3.2 mins, $MH^+$=292.

Example 44

N-[6-(4-Hydroxyphenyl)-1H-indazol-4-yl]cyclopropanecarboxamide

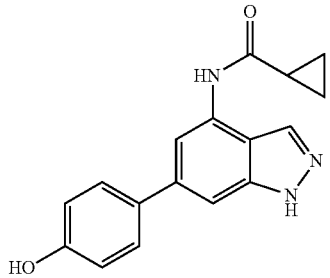

DIPEA (82 mg, 0.635 mmol) and cyclopropanecarbonyl chloride (15 mg, 0.14 mmol) were added to 2-(tetrahydro-2H-pyran-2-yl)-6-[4-(tetrahydro-2H-pyran-2-yloxy)phenyl]-2H-indazol-4-amine (50 mg, 0.127 mmol) in DCM (1 ml) and the reaction was stirred for 1 h. The solvent was removed under a stream of nitrogen. The residue was dissolved in MeOH (2 ml), 4 M HCl in 1,4-dioxane (2 ml) was added and the reaction was stirred for 1 h. The solvent was removed in vacuo. The residue was purified by MDAP (Method B), dried under a stream of nitrogen then freeze dried to give the title compound, 17 mg.

LC/MS (Method A) $R_t$=2.66 mins, $MH^+$=294.

Example 45

N-[6-(4-Hydroxyphenyl)-1H-indazol-4-yl]cyclohexanecarboxamide

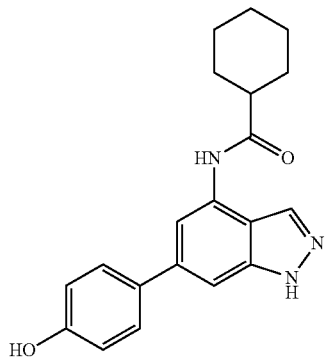

DIPEA (82 mg, 0.635 mmol) and cyclohexanecarbonyl chloride (37 mg, 0.254 mmol) were added to 2-(tetrahydro-2H-pyran-2-yl)-6-[4-(tetrahydro-2H-pyran-2-yloxy)phenyl]-2H-indazol-4-amine (50 mg, 0.127 mmol) in DCM (1 ml) and the reaction was stirred for 1 h. 2 M Sodium hydroxide (aq) (2 ml) was added and the reaction stirred for 1 h. The organic layer was passed through a hydrophobic frit and the aqueous layer was extracted with DCM. The organic layers were combined and the solvent removed under a stream of nitrogen. The residue was dissolved in MeOH (2 ml), 4 M HCl in 1,4-dioxane (2 ml) was added and the reaction was stirred at RT for 1 h. The solvent was removed under a stream of nitrogen. The residue was purified by MDAP using the following method:

Column: Sunfire C18 column (150 mm×30 mm i.d. 5 μm packing diameter) at ambient temperature.

The solvents employed were:

A=0.2% v/v solution of trifluoroacetic acid in water

B=0.1% v/v solution of trifluoroacetic acid in acetonitrile:water (95:5)

The gradient employed was:

| Time (min) | Flow Rate (ml/min) | % A | % B |
|---|---|---|---|
| 0 | 40 | 60 | 40 |
| 1 | 40 | 60 | 40 |
| 10 | 40 | 45 | 55 |
| 11 | 40 | 1 | 99 |
| 14 | 40 | 1 | 99 |
| 15 | 40 | 60 | 40 |

The UV detection was an averaged signal from wavelength of 210 nm to 350 nm and the mass spectra were recorded on a mass spectrometer using alternate-scan positive and negative mode electrospray ionization.

The residue was freeze dried to give the title compound, 16 mg. LC/MS (Method A) $R_t$=3.08 mins, $MH^+$=336.

Similarly prepared were the following:

| Example number | Product Name | Structure | Acid chloride | $R_t$ (mins) | $MH^+$ | Purification Comment |
|---|---|---|---|---|---|---|
| 46 | N-[6-(4-hydroxyphenyl)-1H-indazol-4-yl]-2-pyridinecarboxamide | 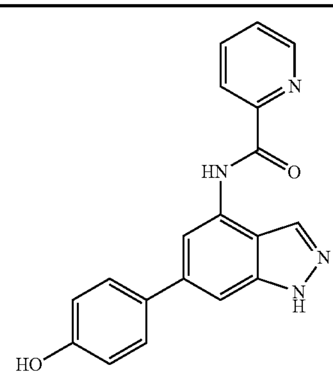 | 2-pyridinecarbonyl chloride hydrochloride | 2.97 | 331 | — |

| Example number | Product Name | Structure | Acid chloride | R$_t$ (mins) | MH$^+$ | Purification Comment |
|---|---|---|---|---|---|---|
| 47 | 3-(dimethylamino)-N-[6-(4-hydroxyphenyl)-1H-indazol-4-yl]benzamide | 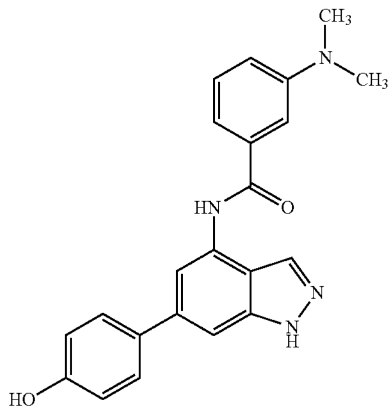 | 3-(dimethyl-amino)-benzoyl chloride | 3 | 373 | (a) |
| 48 | N-[6-(4-hydroxyphenyl)-1H-indazol-4-yl]-3-phenyl-propanamide | 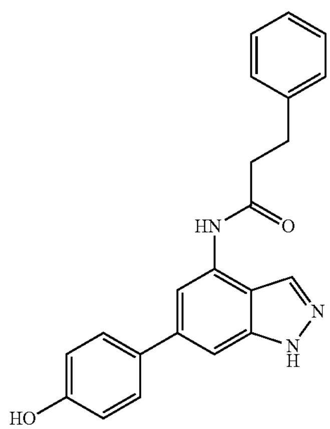 | 3-phenylpropanoyl chloride | 3.03 | 358 | (b) |
| 49 | (1R,2R)-N-[6-(4-hydroxyphenyl)-1H-indazol-4-yl]-2-phenylcyclo-propane-carboxamide | 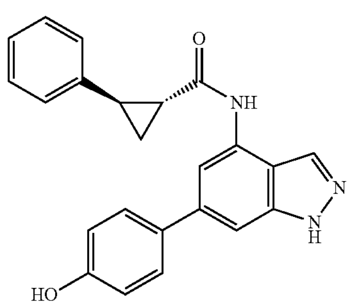 | (1R,2R)-2-phenylcyclo-propanecarbonyl chloride | 3.22 | 370 | (b) |

-continued

| Example number | Product Name | Structure | Acid chloride | R$_t$ (mins) | MH$^+$ | Purification Comment |
|---|---|---|---|---|---|---|
| 50 | N-[6-(4-hydroxyphenyl)-1H-indazol-4-yl]-2-furan-carboxamide | 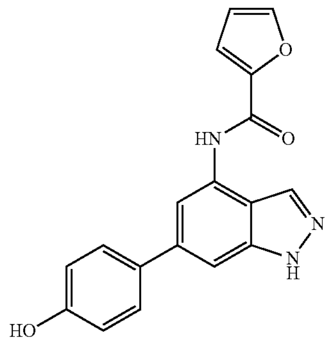 | 2-Furancarbonyl chloride | 2.69 | 320 | (c) |

(a) Required a second purification using MDAP using the following method:
  Column: Sunfire C18 column (150 mm×30 mm i.d. 5 μm packing diameter) at ambient temperature.
  The solvents employed were:
  A=0.2% v/v solution of trifluoroacetic acid in water
  B=0.1% v/v solution of trifluoroacetic acid in acetonitrile:water(95:5)
  The gradient employed was:

| Time (min) | Flow Rate (ml/min) | % A | % B |
|---|---|---|---|
| 0 | 40 | 75 | 25 |
| 1 | 40 | 75 | 25 |
| 20 | 40 | 45 | 55 |
| 21 | 40 | 1 | 99 |
| 24 | 40 | 1 | 99 |
| 25 | 40 | 75 | 25 |

The UV detection was an averaged signal from wavelength of 210 nm to 350 nm and the mass spectra were recorded on a mass spectrometer using alternate-scan positive and negative mode electrospray ionization.

(b) Purified by MDAP using the following method:
  Column: Sunfire C18 column (150 mm×30 mm i.d. 5 μm packing diameter) at ambient temperature.
  The solvents employed were:
  A=0.2% v/v solution of trifluoroacetic acid in water
  B=0.1% v/v solution of trifluoroacetic acid in acetonitrile/water (95:5)
  The gradient employed was:

| Time (min) | Flow Rate (ml/min) | % A | % B |
|---|---|---|---|
| 0 | 40 | 60 | 40 |
| 1 | 40 | 60 | 40 |
| 10 | 40 | 25 | 75 |
| 11 | 40 | 1 | 99 |
| 14 | 40 | 1 | 99 |
| 15 | 40 | 60 | 40 |

The UV detection was an averaged signal from wavelength of 210 nm to 350 nm and the mass spectra were recorded on a mass spectrometer using alternate-scan positive and negative mode electrospray ionization.

(c) Purified by MDAP using the following method:
  Column: Sunfire C18 column (150 mm×30 mm i.d. 5 μm packing diameter) at ambient temperature.
  The solvents employed were:
  A=0.2% v/v solution of trifluoroacetic acid in water
  B=0.1% v/v solution of trifluoroacetic acid in acetonitrile:water (95:5)
  The gradient employed was:

| Time (min) | Flow Rate (ml/min) | % A | % B |
|---|---|---|---|
| 0 | 40 | 85 | 15 |
| 1 | 40 | 85 | 15 |
| 10 | 40 | 55 | 45 |
| 12 | 40 | 1 | 99 |
| 14 | 40 | 1 | 99 |
| 15 | 40 | 85 | 15 |

The UV detection was an averaged signal from wavelength of 210 nm to 350 nm and the mass spectra were recorded on a mass spectrometer using alternate-scan positive and negative mode electrospray ionization.

Example 51

2-Methyl-N-{6-[5-(methylsulfonyl)-3-pyridinyl]-1H-indazol-4-yl}-1,3-thiazole-4-carboxamide

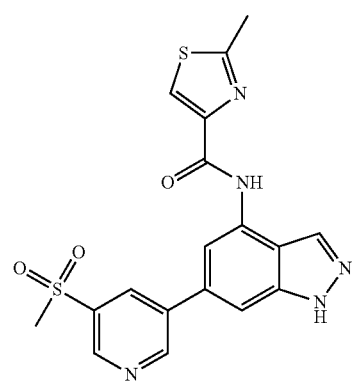

To a solution of 5-(methylsulfonyl)-3-pyridinylboronic acid (24 mg, 0.12 mmol, available from Combi-Blocks Inc.) in 1,4-dioxane (1 ml) was added a solution of N-(6-bromo- 1H-indazol-4-yl)-2-methyl-1,3-thiazole-4-carboxamide (34 mg, 0.10 mmol), also in 1,4-dioxane (1 ml). A solution of potassium carbonate (17 mg, 0.12 mmol) in water (0.2 ml) was then added, followed by Pd(dppf)Cl₂ (10 mg). The reaction vessel was sealed and heated in CEM Discover at 150° C. for 30 min. The mixture was cooled and the solvent was evaporated in vacuo using the Genevac to give the crude products. The sample was loaded in methanol and applied to reverse phase (C18) cartridge (500 mg) and eluted using MeCN/TFA 0.1% (3×3 ml). The appropriate fractions were combined and dried under a stream of nitrogen then the residue was dissolved in (3:1, DMSO:MeOH, 0.5 ml) and purified by MDAP (Method C) to afford the title compound, (2.4 mg).

LC/MS (Method A) $R_t$=0.77 mins, MH⁺=414.

Similarly prepared was:

| Example number | Product Name | Structure | Monomer boronic acid | $R_t$ (mins) | MH⁺ |
|---|---|---|---|---|---|
| 52 | 2-methyl-N-[6-(4-methyl-3-pyridinyl)-1H-indazol-4-yl]-1,3-thiazole-4-carboxamide | 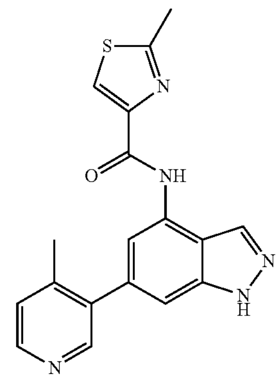 | (4-methyl-3-pyridinyl)-boronic acid (available from Frontier Scientific Ltd) | 0.57 | 350 |

Example 53

2-Methyl-N-[6-(3-pyridinyl)-1H-indazol-4-yl]-1,3-thiazole-4-carboxamide

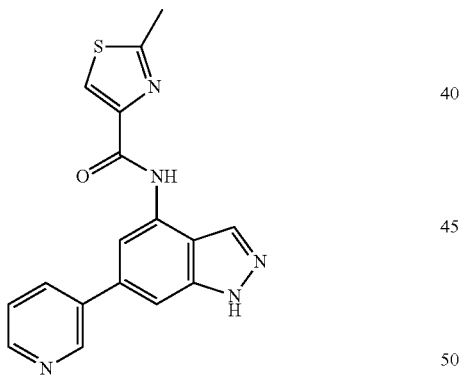

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (53 mg, 0.11 mmol) was dissolved in 1,4-Dioxane (0.4 ml) and added to 3-bromopyridine (16 mg, 0.1 mmol) in a microwave vessel. 1,4-Dioxane (0.4 ml) was added, followed by chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (Solvias catalyst, 2 mg, 0.004 mmol, (heaped microspatula) available from ABCR) and a solution of potassium triphosphate (0.2 g, 0.1 mmol) in water (0.2 ml). The vessel was sealed and heated in CEM Discover using initial 150 W to 110° C. for 20 min. After cooling the solution was loaded onto a C18 SPE cartridge (pre-conditioned with MeCN/0.1% TFA) and flushed through with a further 3 ml MeCN/0.1% TFA. Solvent was removed by blowdown under a stream of nitrogen. The residue was dissolved in MeOH (0.5 ml) and loaded onto a SCX-2 SPE cartridge (1 g) pre-conditioned with MeOH. The material was left on the column for 1 hr then eluted with 2M ammonia/MeOH and evaporated to dryness. The sample was purified by MDAP (Method C) to afford the title compound (4 mg).

LCMS (Method C) $R_t$=0.6 min, MH⁺=336.

Example 54

2-Methyl-N-[6-(2-oxo-1,2-dihydro-4-pyridinyl)-1H-indazol-4-yl]-1,3-thiazole-4-carboxamide

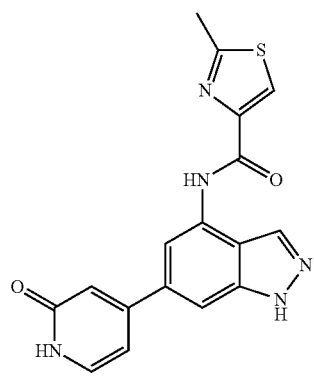

N-(6-Bromo-1H-indazol-4-yl)-2-methyl-1,3-thiazole-4-carboxamide (200 mg, 0.59 mmol), bis(pinacolato)diboron (166 mg, 0.652 mmol), Pd(dppf)Cl₂ (48 mg, 0.06 mmol) and potassium acetate (175 mg, 1.78 mmol) were combined in a microwave vial and DMA (10 ml) was added. The solution was degassed and then heated in a Biotage initiator at 80° C. for 20 minutes. More Pd(dppf)Cl₂ (48.4 mg, 0.059 mmol)

was added, the solution was degassed and heated again at 80° C. for 20 minutes. 4-Bromo-2-pyridone (206 mg, 1.19 mmol), Pd(PPh₃)₄ (34 mg, 0.03 mmol) and sodium bicarbonate (0.89 ml, 1.78 mmol) were added to the mixture, which was heated under microwave conditions at 150° C. for 15 minutes. Saturated sodium bicarbonate (100 ml) was added to the mixture. The resulting suspension was washed three times with ethyl acetate (100 ml each). A spatula of sodium chloride was added to improve layer separation. Organics were dried and filtered with a hydrophobic frit, combined and dried under vacuum. The solid obtained was preabsorbed on silica and purified on silica (Si) 100 g using a 0-15% methanol-DCM over 60 mins. Appropriate fractions were combined and dried under vacuum. The sample was dissolved in DMSO (1 ml) and purified by MDAP (Method B) eluting with solvents A/B (A: Water+0.1% Formic acid, B: MeCN:Water 95:5+0.05% Formic acid). Pure fractions were combined and dried under vacuum to afford the title compound (10 mg).

LCMS (Method B) $R_t$=0.73 min, MH⁺=352.

Example 55

2-Methyl-N-[6-(4-pyridinyl)-1H-indazol-4-yl]-1,3-thiazole-4-carboxamide

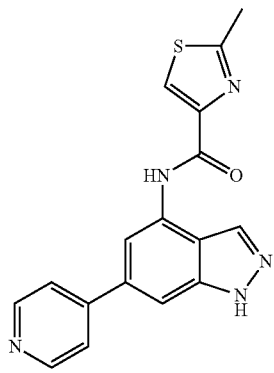

A microwave vial was charged with N-[6-bromo-2-(tetrahydro-2H-pyran-2-yl)-2H-indazol-4-yl]-2-methyl-1,3-thiazole-4-carboxamide (50 mg), Solvias catalyst (7 mg), tripotassium phosphate (76 mg), 4-pyridinylboronic acid (15 mg), 1,4-dioxane (0.5 ml) and water (0.1 ml). The mixture was heated under microwave irradiation for a total of 60 min at 80° C. 4-Pyridinylboronic acid (15 mg) was added and the mixture was heated for 30 min at 80° C., then 30 min at 120° C. The reaction mixture was passed through a silica cartridge preconditioned with methanol, washing with methanol, then dried in vacuo. The residue was extracted with DCM/water, dried through a hydrophobic frit and dried in vacuo. The residue was dissolved in DMSO:methanol (1 ml, 1:1, v/v) and purified by MDAP (method E). Appropriate fractions were dried under a stream of nitrogen. The residue was dissolved in methanol and a few drops of 2M HCl (aq) were added and the reaction was stirred for 30 min. The reaction mixture was passed through an aminopropyl cartridge, preconditioned with methanol, washing with methanol, then dried to give title compound, (19 mg).

LCMS (Method B) $R_t$=0.62 min, MH⁺=336.

Example 56

2-Methyl-N-(6-{6-methyl-5-[(methylsulfonyl)amino]-3-pyridinyl}-1H-indazol-4-yl)-1,3-thiazole-4-carboxamide

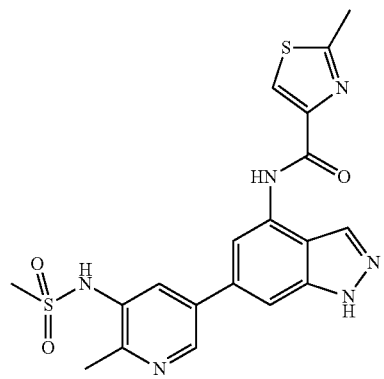

A microwave vial was charged with 1-(1-methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (70 mg), N-(5-bromo-2-methyl-3-pyridinyl)methanesulfonamide (39 mg), tripotassium phosphate (123 mg), Solvias catalyst (16 mg), 1,4-dioxane (0.5 ml) and water (0.1 ml). The mixture was heated under microwave irradiation 10 min at 120° C. The mixture was passed through a silica cartridge preconditioned with methanol, washing with methanol, then dried in vacuo. The residue was separated between DCM and water and the organic layer was passed through a hydrophobic frit and dried in vacuo. The residue was dissolved in DMSO:methanol (1 ml, 1:1, v/v) and purified by MDAP (Method E). Appropriate fractions were dried under a stream of nitrogen, redissolved in a minimum amount of methanol and a few drops of 2M HCl (aq) were added. The reaction mixture was left to stir for 30 min. The reaction was passed through an aminopropyl cartridge, preconditioned with methanol, washing with methanol, then dried under a stream of nitrogen to give title compound, (21 mg).

LCMS (Method B) $R_t$=0.71 min, MH⁺=443.

Example 57

Formic acid-N-(6-{6-chloro-5-[(methylsulfonyl)amino]-3-pyridinyl}-1H-indazol-4-yl)-2-(4-morpholinylmethyl)-1,3-thiazole-4-carboxamide (1:1)

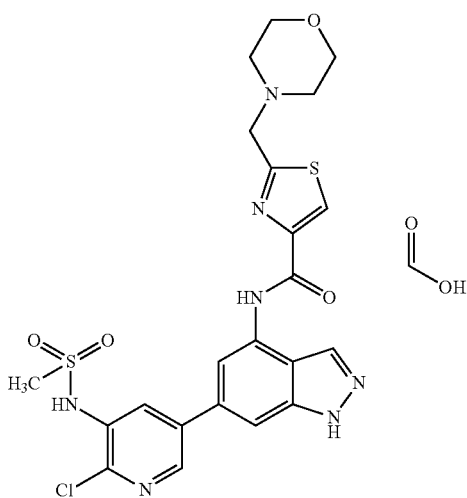

2-(Chloromethyl)-N-[6-{6-chloro-5-[(methylsulfonyl)amino]-3-pyridinyl}-1-(phenylsulfonyl)-1H-indazol-4-yl]-1,3-thiazole-4-carboxamide (50 mg, 0.078 mmol) was dissolved in MeCN (0.5 ml) and added to morpholine (0.1 mmol). DIPEA (0.026 ml, 0.15 mmol) was added followed by sodium iodide (0.015 g, 0.1 mmol) and the solutions was stirred for 18 hr at 70° C. Potassium trimethylsilanolate (64 mg, 0.5 mmol) was dissolved in THF (0.25 ml) and added to the reaction mixture which was heated to 50° C. for 24 hr. The solution was quenched with aqueous MeCN (50:50, 1 ml) and neutralised. Solvent was removed in a blowdown unit. The crude residue was dissolved in DMF (200 μl), Acetone (200 μl) and water (20 μl) and purified by MDAP (Method D). The solvent was removed in vacuo using the Genevac to give the title compound.

LCMS (Method B) $R_f$=0.6 min, MH$^+$=548.

Similarly prepared were:

| Example Number | Structure | Name | Monomer | MH$^+$ | LCMS Rt (min) |
|---|---|---|---|---|---|
| 58 | 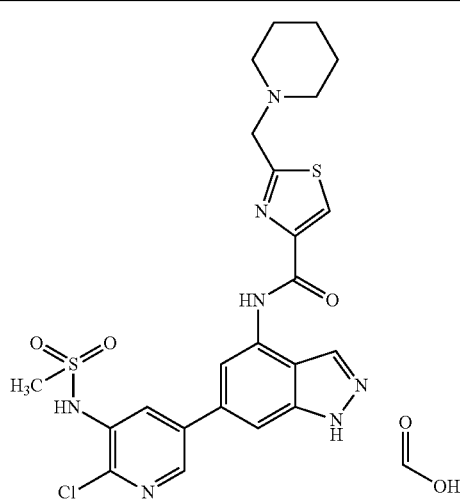 | formic acid-N-(6-{6-chloro-5-[(methylsulfonyl)-amino]-3-pyridinyl}-1H-indazol-4-yl)-2-(1-piperidinylmethyl)-1,3-thiazole-4-carboxamide (1:1) | piperidine | 576 | 0.69 |
| 59 | 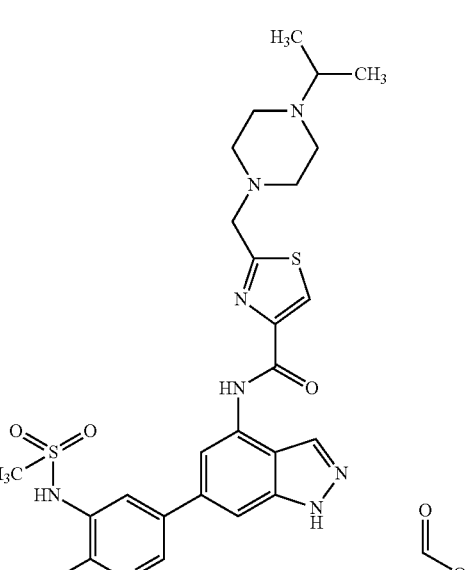 | formic acid-N-(6-{6-chloro-5-[(methylsulfonyl)-amino]-3-pyridinyl}-1H-indazol-4-yl)-2-{[4-(1-methylethyl)-1-piperazinyl]-methyl}-1,3-thiazole-4-carboxamide (1:1) | 4-(1-methyl-ethyl)-piperazine | 546 | 0.59 |

| Example Number | Structure | Name | Monomer | MH+ | LCMS Rt (min) |
|---|---|---|---|---|---|
| 60 | 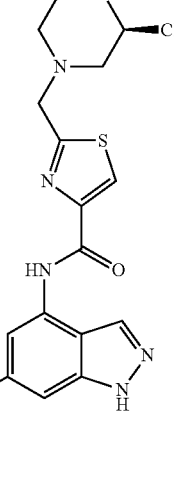 | formic acid-N-(6-{6-chloro-5-[(methylsulfonyl)-amino]-3-pyridinyl}-1H-indazol-4-yl)-2-{[(2R,6S)-2,6-dimethyl-4-morpholinyl]-methyl}-1,3-thiazole-4-carboxamide (1:1) | (2R,6S)-2,6-dimethyl-morpholine (available from Lancaster Synthesis) | 589 | 0.61 |
| 61 | 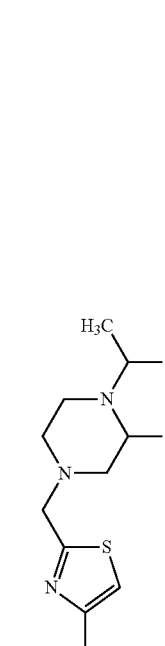 | formic acid-N-(6-{6-chloro-5-[(methylsulfonyl)amino]-3-pyridinyl}-1H-indazol-4-yl)-2-{3-methyl-4-(1-methylethyl)-1-piperazinyl]methyl}-1,3-thiazole-4-carboxamide (1:1) | 2-methyl-1-(1-methylethyl) piperazine (available from Fluorochem) | 603 | 0.63 |

Example 62

Formic acid-2-{[4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide (1:1)

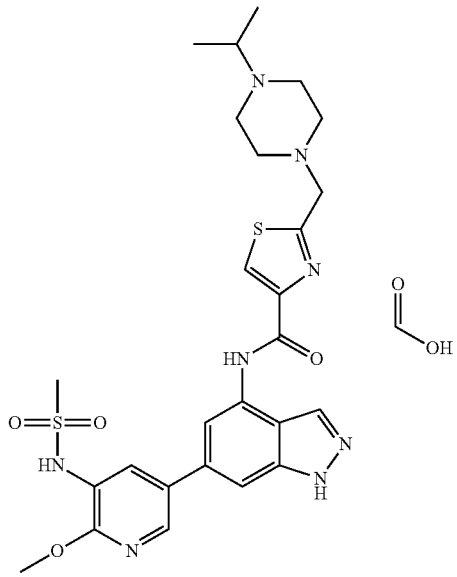

2-(Chloromethyl)-N-[6-{6-(methyloxy)-5-[(methylsulfonyl)amino]-3-pyridinyl}-1-(phenylsulfonyl)-1H-indazol-4-yl]-1,3-thiazole-4-carboxamide (50 mg, 0.08 mmol) was dissolved in MeCN (0.5 ml). 4-(1-Methylethyl)piperazine (13 mg, 0.1 mmol) was dissolved in MeCN (0.3 ml) and added to the mixture, followed by DIPEA (0.026 ml, 0.15 mmol) and sodium iodide (0.012 g, 0.078 mmol) (heaped microspatula). The solution was stirred and heated to 70° C. for 18 hr. Potassium trimethylsilanolate (64 mg, 0.5 mmol) was dissolved in THF (0.4 ml) and added to the mixture which was then heated at 50° C. for 5 hrs. The solution was quenched with aqueous MeCN (50:50, 1 ml) and neutralised, then the solvents were removed in a blowdown unit. The residue was dissolved in DMSO 0.5 ml and purified by MDAP (Method D). The solvent was evaporated using the Genevac to give the title compound (11 mg).

LCMS (Method B): $R_t$=0.62 min, MH$^+$=585.

Similarly prepared were:

| Example number | Structure | Name | Precursor amine | LCMS Rt (min) |
|---|---|---|---|---|
| 63 | 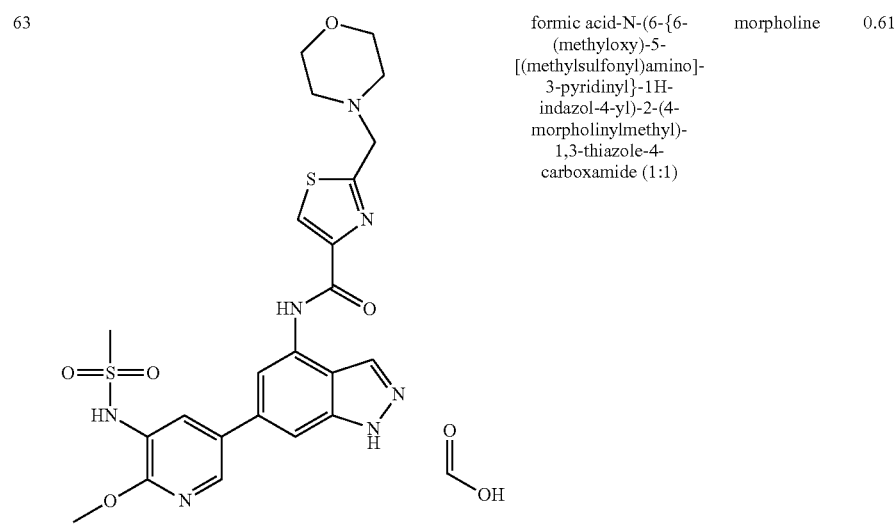 | formic acid-N-(6-{6-(methyloxy)-5-[(methylsulfonyl)amino]-3-pyridinyl}-1H-indazol-4-yl)-2-(4-morpholinylmethyl)-1,3-thiazole-4-carboxamide (1:1) | morpholine | 0.61 |

| Example number | Structure | Name | Precursor amine | LCMS Rt (min) |
|---|---|---|---|---|
| 64 | 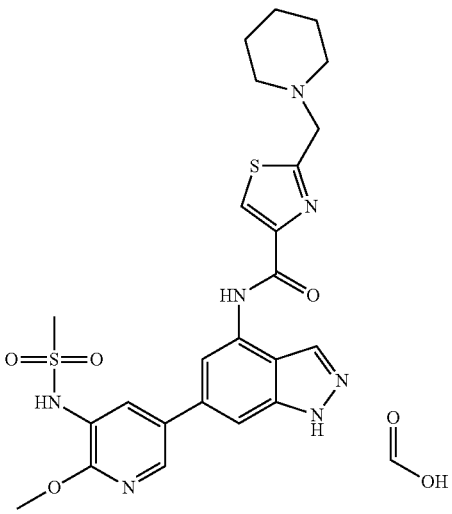 | formic acid-N-(6-{6-(methyloxy)-5-[(methylsulfonyl)amino]-3-pyridinyl}-1H-indazol-4-yl)-2-(1-piperidinylmethyl)-1,3-thiazole-4-carboxamide (1:1) | piperidine | 0.60 |
| 65 | 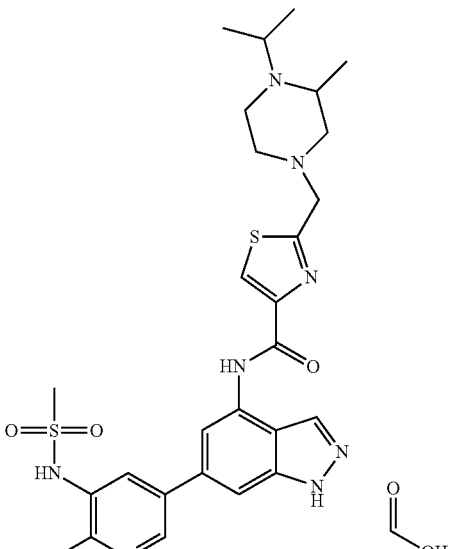 | formic acid-2-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide (1:1) | 2-methyl-1-(1-methylethyl)-piperazine (available from Fluorochem) | 0.64 |

Example 66

Formic acid-2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide (1:1)

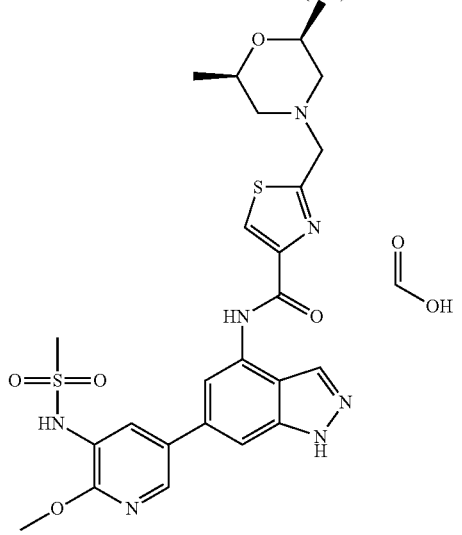

2-(Chloromethyl)-N-[6-{6-(methyloxy)-5-[(methylsulfonyl)amino]-3-pyridinyl}-1-(phenylsulfonyl)-1H-indazol-4-yl]-1,3-thiazole-4-carboxamide (50 mg, 0.08 mmol) was dissolved in MeCN (0.5 ml). (2R,6S)-2,6-Dimethylmorpholine (23 mg, 0.1 mmol, available from Lancaster Synthesis) was dissolved in MeCN (0.3 ml) and added to the mixture, followed by DIPEA (0.026 ml, 0.15 mmol) and sodium iodide (0.012 g, 0.078 mmol) (heaped microspatula). The solution was stirred and heated to 70° C. for 18 hr. Potassium trimethylsilanolate (64 mg, 0.5 mmol) was dissolved in THF (0.4 ml) and added to the mixture which was then heated at 50° C. for 5 hrs. The solution was quenched with aqueous MeCN (50:50, 1 ml) and neutralised, then the solvents were removed in a blowdown unit. The residue was dissolved in DMSO 0.5 ml and purified by MDAP (Method D). The solvent was evaporated using the Genevac to give the title compound (19 mg).

LCMS (Method B): $R_t$=0.69 min, MH$^+$=572.

$^1$H NMR: $\delta_H$ (DMSO-d$_6$, 600 MHz) 13.20 (1H, v.br.s, NH), 10.44 (1H, br.s, NH), 8.47 (1H, br.s, CH), 8.35 (1H, br.s, CH), 8.30 (1H, s, CH), 8.15 (1H, s, CH), 7.94 (1H, br.s, CH), 7.77 (1H, s, CH), 7.54 (1H, s, CH), 3.99 (3H, s, CH$_3$), 3.93 (2H, s, CH$_2$), 3.63 (2H, m, 2×CH), 1.91 (2H, t, 2×½ CH$_2$), 1.06 (6H, d, 2×CH$_3$).

Example 67

2-{[(2R,6S)-2,6-Dimethyl-4-morpholinyl]methyl}-N-{6-[5-[(ethylsulfonyl)amino]-6-(methyloxy)-3-pyridinyl]-1H-indazol-4-yl}-1,3-thiazole-4-carboxamide trifluoroacetate

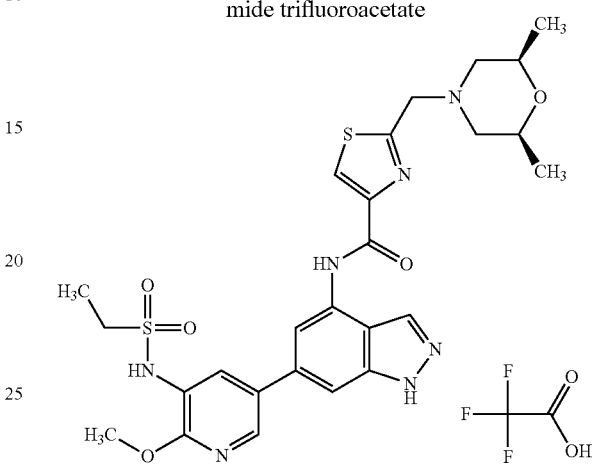

N-[6-[5-Amino-6-(methyloxy)-3-pyridinyl]-2-(tetrahydro-2H-pyran-2-yl)-2H-indazol-4-yl]-2-{[(2R,6S)-2,6-dimethyl-4-morpholinyl]methyl}-1,3-thiazole-4-carboxamide (0.043 mg, 0.075 mmol) was dissolved in chloroform (0.4 ml) and dispensed to a vessel containing ethanesulfonyl chloride (0.075 mmol). Pyridine (0.018 ml, 0.225 mmol) was then added and the solution was shaken and left for 18 hr at 22° C. Solvent was then removed in a blowdown unit under nitrogen. DCM (200 µl) was next added, followed by TFA (500 µl) and the solution was left for 2 hr. Solvent was removed in a blowdown unit under nitrogen. The sample was dissolved in DMSO (0.5 ml) and purified by MDAP (Method D). The solvent was concentrated by vacuum centrifugation to give the title compound (13 mg).

LCMS (Method C) $R_t$=1.75 min, MH$^+$=586.

Similarly prepared were:

| Example number | Structure | Name | Precursor amine | LCMS Rt (min) | MH+ |
|---|---|---|---|---|---|
| 68 | 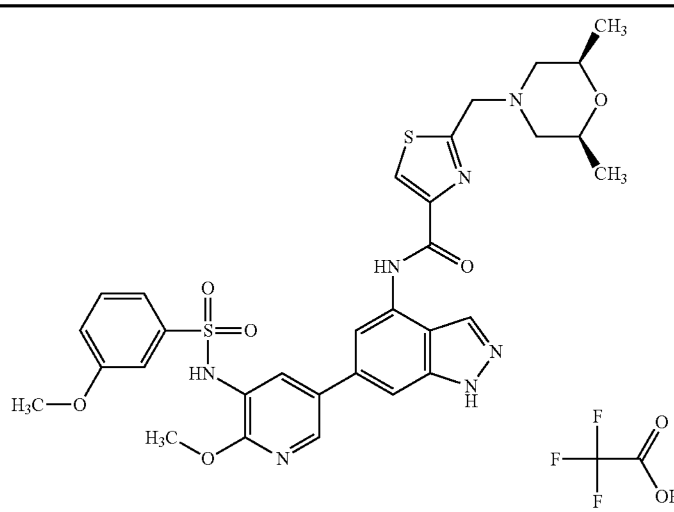 | 2-{[(2R,6S)-2,6-dimethyl-4-morpholinyl]-methyl}-N-{6-[6-(methyloxy)-5-({[3-(methyloxy)-phenyl]-sulfonyl}amino)-3-pyridinyl]-1H-indazol-4-yl}-1,3-thiazole-4-carboxamide trifluoroacetate | 3-(methyloxy)-benzene-sulfonyl chloride | 2.08 | 664 |

-continued

| Example number | Structure | Name | Precursor amine | LCMS Rt (min) | MH+ |
|---|---|---|---|---|---|
| 69 | 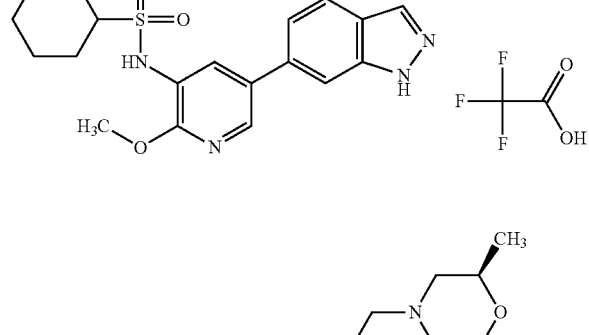 | N-{6-[5-[(cyclohexyl-sulfonyl)-amino]-6-(methyloxy)-3-pyridinyl]-1H-indazol-4-yl}-2-{[(2R,6S)-2,6-dimethyl-4-morpholinyl]-methyl}-1,3-thiazole-4-carboxamide trifluoroacetate | cyclohexane-sulfonyl chloride | 2.14 | 640 |
| 70 | 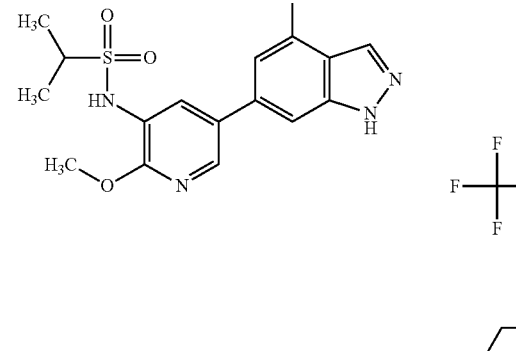 | 2-{[(2R,6S)-2,6-dimethyl-4-morpholinyl]-methyl}-N-{6-[5-{[(1-methylethyl)-sulfonyl]amino}-6-(methyloxy)-3-pyridinyl]-1H-indazol-4-yl}-1,3-thiazole-4-carboxamide trifluoroacetate | 2-propane-sulfonyl chloride | 1.84 | 600 |
| 72 | 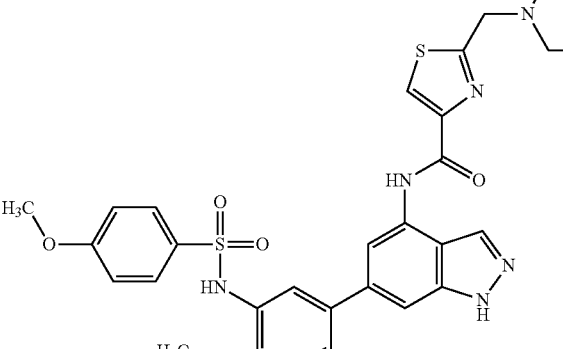 | 2-{[(2R,6S)-2,6-dimethyl-4-morpholinyl]-methyl}-N-{6-[6-(methyloxy)-5-({[4-(methyloxy)-phenyl]-sulfonyl}amino)-3-pyridinyl]-1H-indazol-4-yl}-1,3-thiazole-4-carboxamide trifluoroacetate | 4-(methyloxy)-benzene-sulfonyl chloride | 2.07 | 664 |

-continued

| Example number | Structure | Name | Precursor amine | LCMS Rt (min) | MH+ |
|---|---|---|---|---|---|
| 73 | 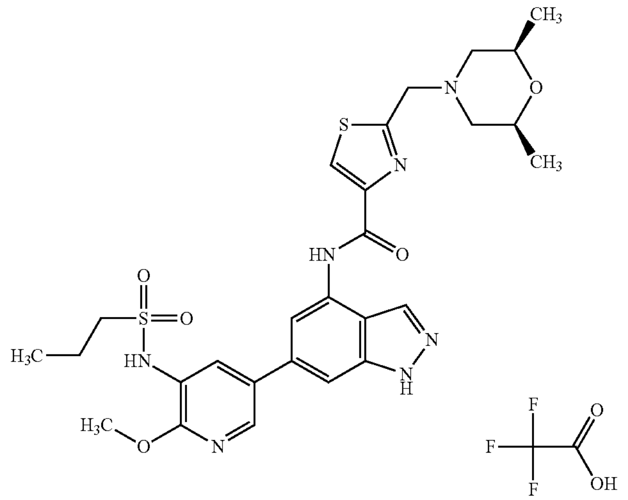 | 2-{[(2R,6S)-2,6-dimethyl-4-morpholinyl]-methyl}-N-(6-{6-(methyloxy)-5-[(propylsulfonyl)-amino]-3-pyridinyl}-1H-indazol-4-yl)-1,3-thiazole-4-carboxamide trifluoroacetate | 1-propane-sulfonyl chloride | 1.88 | 600 |
| 74 | 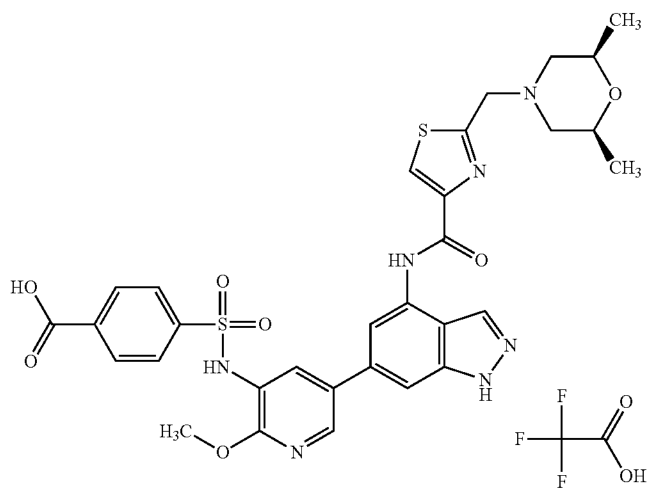 | 4-({[5-(4-{[(2-{[(2R,6S)-2,6-dimethyl-4-morpholinyl]-methyl}-1,3-thiazol-4-yl)carbonyl]amino}-1H-indazol-6-yl)-2-(methyloxy)-3-pyridinyl]-amino}-sulfonyl)-benzoic acid trifluoroacetate | 4-(chloro-sulfonyl)-benzoic acid | 1.86 | 678 |
| 75 | 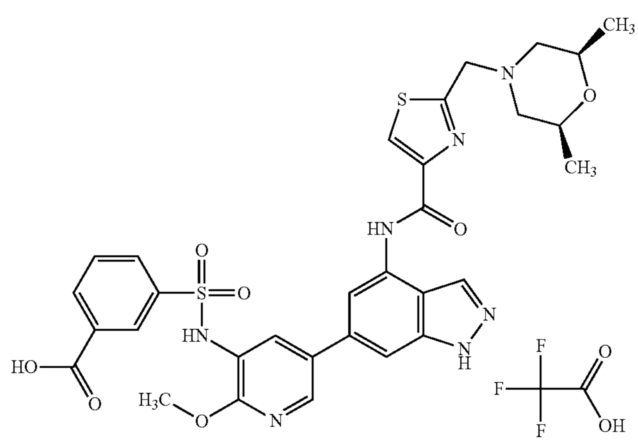 | 3-({[5-(4-{[(2-{[(2R,6S)-2,6-dimethyl-4-morpholinyl]-methyl}-1,3-thiazol-4-yl)carbonyl]-amino}-1H-indazol-6-yl)-2-(methyloxy)-3-pyridinyl]-amino}-sulfonyl)-benzoic acid trifluoroacetate | 3-(chloro-sulfonyl)-benzoic acid | 1.87 | 678 |

-continued

| Example number | Structure | Name | Precursor amine | LCMS Rt (min) | MH+ |
|---|---|---|---|---|---|
| 76 | 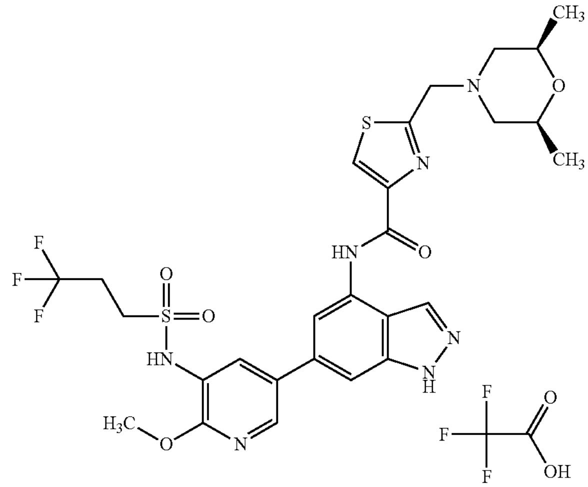 | 2-{[(2R,6S)-2,6-dimethyl-4-morpholinyl]methyl}-N-[6-(6-(methyloxy)-5-{[(3,3,3-trifluoropropyl)-sulfonyl]amino}-3-pyridinyl)-1H-indazol-4-yl]-1,3-thiazole-4-carboxamide trifluoroacetate | 3,3,3-trifluoro-1-propane-sulfonyl chloride | 2.04 | 654 |
| 77 | 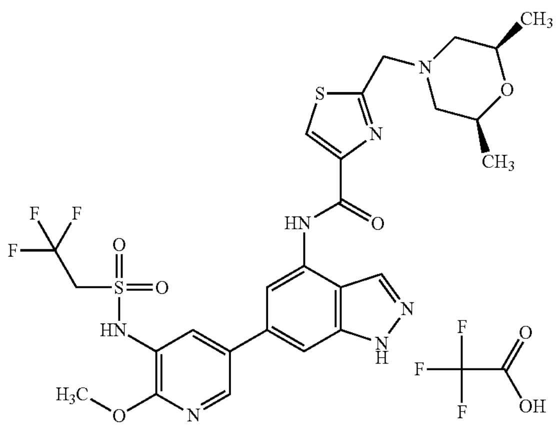 | 2-{[(2R,6S)-2,6-dimethyl-4-morpholinyl]methyl}-N-[6-(6-(methyloxy)-5-{[(2,2,2-trifluoroethyl)-sulfonyl]amino}-3-pyridinyl)-1H-indazol-4-yl]-1,3-thiazole-4-carboxamide trifluoroacetate | 2,2,2-trifluoro-ethane sulfonyl chloride | 1.96 | 640 |

Example 71

2-{[(2R,6S)-2,6-Dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide trifluoroacetate

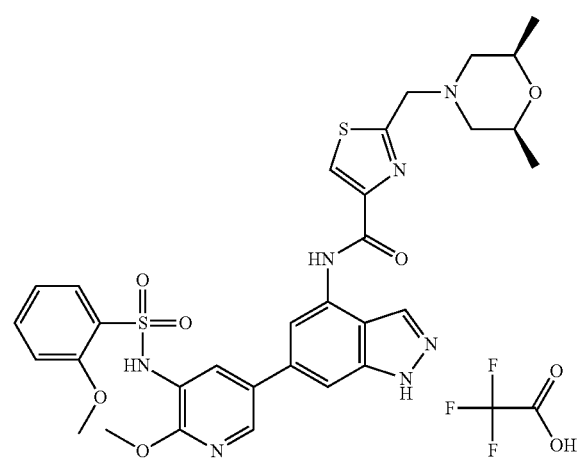

N-[6-[5-Amino-6-(methyloxy)-3-pyridinyl]-2-(tetrahydro-2H-pyran-2-yl)-2H-indazol-4-yl]-2-{[(2R,6S)-2,6-dimethyl-4-morpholinyl]methyl}-1,3-thiazole-4-carboxamide (0.043 g, 0.075 mmol) was dissolved in chloroform (0.4 ml) and dispensed to a vessel containing 2-(methyloxy)benzenesulfonyl chloride (15 mg, 0.075 mmol). Pyridine (0.018 ml, 0.225 mmol) was then added and the solution was shaken and left for 18 hr at 22° C. Solvent was removed in a blowdown unit under nitrogen. DCM (200 μl) was next added, followed by TFA (500 μl) and the solution was left for 2 hr. Solvent was removed in a blowdown unit under nitrogen. The sample was dissolved in DMSO (0.5 ml) and purified by MDAP (Method D). The solvent was concentrated by vacuum centrifugation to give the title compound (12 mg).

LCMS (Method C) $R_t$=2.06, MH+=664

$^1$H NMR: $\delta_H$ (DMSO-d$_6$, 600 MHz) 10.40 (1H, s, NH), 9.28 (1H, s, NH), 8.65 (1H, s, CH), 8.25 (1H, s, CH), 8.19 (1H, s, CH), 7.91 (1H, s, CH), 7.80 (1H, s, CH), 7.75 (1H, d, CH), 7.60 (1H, t, CH), 7.48 (1H, s, CH), 7.22 (1H, d, CH), 7.03 (1H, t, CH), 4.57 (2H, v.br.s, 2×CH), 3.90-3.80 (8H, 2×s+br.s, 2×CH$_3$+CH$_2$), 3.40 (2H, v.br.s, 2×½ CH$_2$), 2.60 (1H, br.m, 2×½ CH$_3$) 1.15 (6H, d, 2×CH$_3$).

161

Example 78

N-(6-{6-Chloro-5-[(methylsulfonyl)amino]-3-pyridinyl}-1H-indazol-4-yl)-6-{[(2R,6S)-2,6-dimethyl-4-morpholinyl]methyl}-2-pyridinecarboxamide

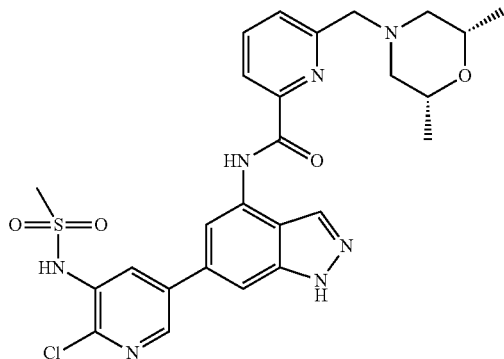

6-(Chloromethyl)-N-[6-{6-chloro-5-[(methylsulfonyl)amino]-3-pyridinyl}-1-(phenylsulfonyl)-1H-indazol-4-yl]-2-pyridinecarboxamide (80 mg, 0.127 mmol) was dissolved in MeCN (1 ml). (2R,6S)-2,6-Dimethylmorpholine (16.05 mg, 0.139 mmol) was added followed by DIPEA (0.033 mL, 0.190 mmol) and then sodium iodide (18.99 mg, 0.127 mmol). The mixture was heated at 70° C. for 1 h, then the solvent was removed in vacuo to give an orange oil. IPA (1 ml) was added to the crude residue followed by aqueous NaOH (2M, 1 ml) and the solution was stirred at room temperature for 1 h. The solution was neutralised with 2M aqueous HCl and concentrated in vacuo. The residue was dissolved in DMSO (2 ml) and purified by MDAP (Method E). The resulting pale yellow gum was dissolved in DCM/MeOH (1:1) and added to the top of a 500 mg silica SPE cartridge. This was eluted with cyclohexane and the solvent was removed under a stream of nitrogen to give the title compound (2.2 mg).

LCMS (Method B) $R_t$=0.63 min, MH$^+$=568.

Example 79

N-(6-{6-Chloro-5-[(methylsulfonyl)amino]-3-pyridinyl}-1H-indazol-4-yl)-6-(4-morpholinylmethyl)-2-pyridinecarboxamide

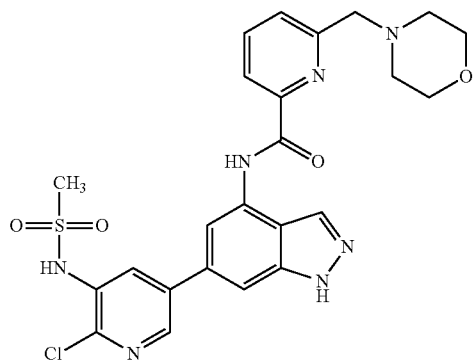

N-{2-Chloro-5-[4-({[6-(chloromethyl)-2-pyridinyl]carbonyl}amino)-1-(phenylsulfonyl)-1H-indazol-6-yl]-3-pyridinyl}-6-(chloromethyl)-N-(methylsulfonyl)-2-pyridinecarboxamide (60 mg, 0.061 mmol) and morpholine (0.5 ml, 5.74 mmol) were placed in a vial and heated in a microwave at 90° C. for 15 min. The mixture was concentrated by blow down under a stream of nitrogen. The crude residue was suspended in IPA (2 ml) and 2M NaOH (1 ml) added. The mixture was stirred at room temperature for 2 h. The solvent was removed by blow down and the residue purified by MDAP (Method E) (3×800 µl injections in DMSO, the insoluble salt was filtered off through a filter tube). Product-containing fractions were combined and the solvent removed in vacuo. The residue was dissolved in DCM:MeOH and added to the top of a 1 g silica cartridge that was subsequently eluted with 0-5% MeOH/DCM over 5 column volumes. No separation was observed, hence all fractions were combined and the solvent removed under a stream of nitrogen. The residue was dissolved in DMF/Acetone/Water (0.2 ml:0.2 ml:20 µl) and purified by MDAP (Method E). Product-containing fractions were combined and the solvent removed in vacuo. The resulting oil was triturated with ether to give the title compound as a cream solid (8 mg).

LCMS (Method B) $R_t$=0.59 min, MH$^+$ 543.

Example 80

Formic acid-N-(6-{6-chloro-5-[(methylsulfonyl)amino]-3-pyridinyl}-1H-indazol-4-yl)-6-(1-piperidinylmethyl)-2-pyridinecarboxamide (1:1)

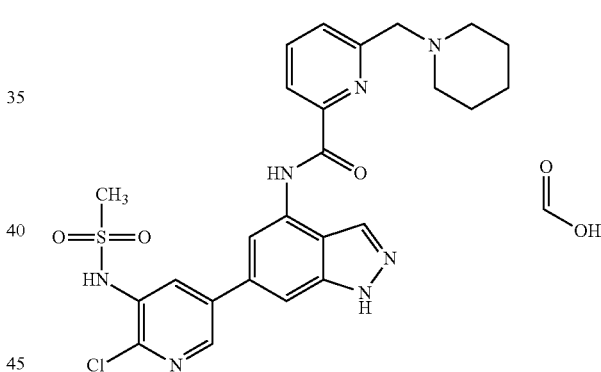

6-(Chloromethyl)-N-[6-{6-chloro-5-[(methylsulfonyl)amino]-3-pyridinyl}-1-(phenylsulfonyl)-1H-indazol-4-yl]-2-pyridinecarboxamide (50 mg, 0.079 mmol) and piperidine (0.5 ml, 5.05 mmol) were placed in a vial and heated in a microwave at 90° C. for 15 min. The amine was blown off under a stream of nitrogen to give an orange gum which was suspended in IPA (2 ml) and 2M NaOH (1 ml) was added. The mixture was stirred at room temperature for 2 hours then neutralised with 2M HCl (aq.) and the solvent was blown off under a stream of nitrogen. The residue was dissolved in DMF/Acetone/Water (0.3 ml:0.3 ml:30 µl) (the insoluble salt was filtered off through a filter tube) and purified by MDAP (Method E). A further purification was carried out by HPLC and following concentration of fractions containing desired material, the residue was dissolved in dioxane/water (1:1, 2 ml) and freeze dried to afford the title compound as a white solid (3 mg).

LCMS (Method B) $R_t$=0.63 min, MH$^+$=540.

Similarly prepared was:

| Example number | Structure | Name | Precursor amine | LCMS Rt (min) | MH+ |
|---|---|---|---|---|---|
| 81 | 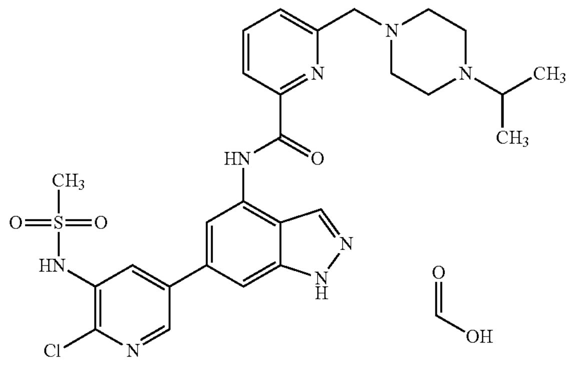 | formic acid-N-(6-{6-chloro-5-[(methyl-sulfonyl)-amino]-3-pyridinyl}-1H-indazol-4-yl)-6-{[4-(1-methylethyl)-1-piperazinyl]-methyl}-2-pyridine-carboxamide (1:1) | isopropyl piperazine | 0.63 | 583 |

Example 82

Formic acid-N-(6-{6-chloro-5-[(methylsulfonyl) amino]-3-pyridinyl}-1H-indazol-4-yl)-6-{[3-methyl-4-(1-methylethyl)-1-piperazinyl]methyl}-2-pyridinecarboxamide (1:1)

Example 83

Formic acid-6-[(1,1-dioxido-4-thiomorpholinyl)methyl]-N-(6-{6-(methyloxy)-5-[(methylsulfonyl) amino]-3-pyridinyl}-1H-indazol-4-yl)-2-pyridinecarboxamide (1:1)

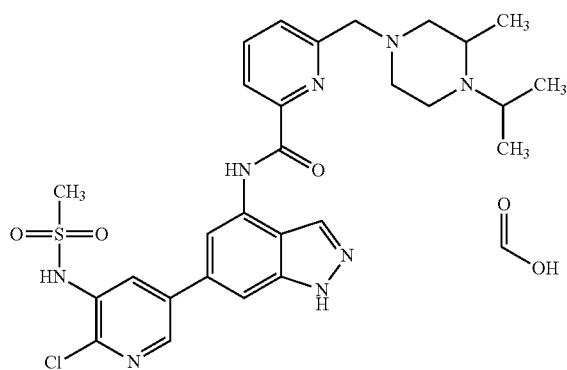

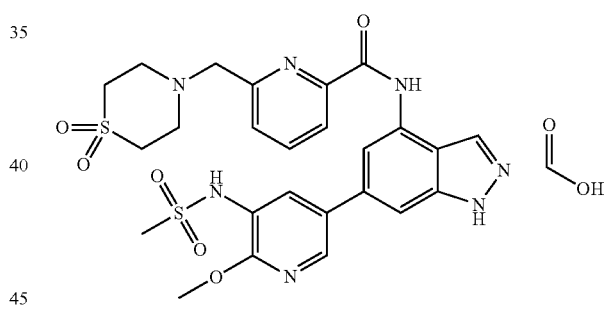

6-(Chloromethyl)-N-[6-{6-chloro-5-[(methylsulfonyl) amino]-3-pyridinyl}-1-(phenylsulfonyl)-1H-indazol-4-yl]-2-pyridinecarboxamide (50 mg, 0.079 mmol) and 2-methyl-1-(1-methylethyl)piperazine (0.5 ml, 0.047 mmol) were placed in a vial and heated in a microwave at 90° C. for 15 min. The amine was blown off under a stream of nitrogen to give an orange gum which was suspended in IPA (2 ml) and 2M NaOH (1 ml) was added. The mixture was stirred at room temperature for 2 hours then neutralised with 2M HCl (aq.) and the solvent was blown off under a stream of nitrogen. The residue was dissolved in DMSO (2 ml) (insoluble salt was filtered off through a filter tube) and purified by MDAP (Method E). The product-containing fractions were concentrated under a stream of nitrogen to give a white solid which was freeze dried to afford the title compound as a white solid (14 mg).

LCMS (Method B) $R_t$=0.65 min, MH+=597.

6-(Chloromethyl)-N-[6-{6-(methyloxy)-5-[(methylsulfonyl)amino]-3-pyridinyl}-1-(phenylsulfonyl)-1H-indazol-4-yl]-2-pyridinecarboxamide (50 mg, 0.08 mmol) was dissolved in MeCN (0.5 ml). Thiomorpholine 1,1-dioxide (available from TCI-Europe) (14 mg, 0.1 mmol) was dissolved in MeCN (0.3 ml) and added to the mixture, followed by DIPEA (0.026 ml, 0.15 mmol) and sodium iodide (0.012 g, 0.078 mmol) (heaped microspatula). The solution was stirred and heated to 70° C. for 18 hr. Potassium trimethylsilanolate (64 mg, 0.5 mmol) was dissolved in THF (0.4 ml) and added to the mixture which was then heated at 50° C. for 5 h. The solution was quenched with aqueous MeCN (50:50, 1 ml) and neutralised, then the solvents were removed in a blowdown unit. The residue was dissolved in DMSO (0.5 ml) and purified by MDAP (Method D). The solvent was evaporated using the Genevac to give the title compound (5 mg).

LCMS (Method B): $R_t$=0.77 min, MH+=586.

Similarly prepared were:

| Example number | Structure | Name | Precursor amine | LCMS R$_t$ (min) | MH$^+$ |
|---|---|---|---|---|---|
| 84 | 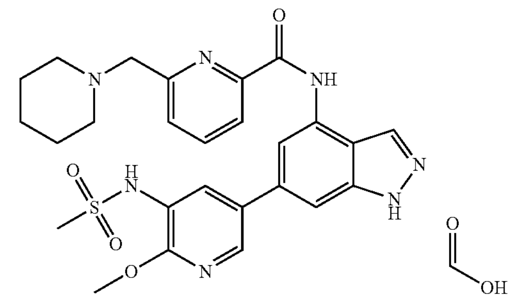 | formic acid-N-(6-{6-(methyloxy)-5-((methylsulfonyl)-amino]-3-pyridinyl}-1H-indazol-4-yl)-6-(1-piperidinylmethyl)-2-pyridinecarboxamide (1:1) | piperidine | 0.62 | 536 |
| 85 | 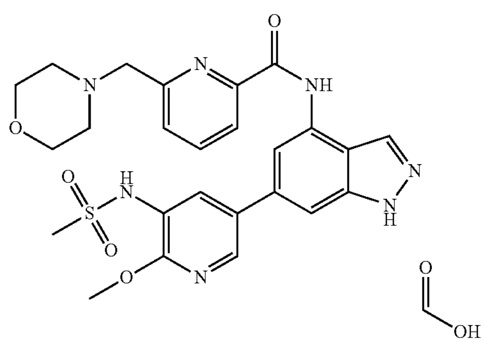 | formic acid-N-(6-{6-(methyloxy)-5-[(methylsulfonyl)-amino]-3-pyridinyl}-1H-indazol-4-yl)-6-(4-morpholinylmethyl)-2-pyridinecarboxamide (1:1) | morpholine | 0.58 | 538 |
| 86 | 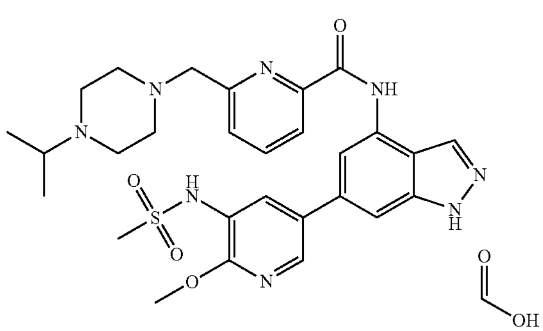 | formic acid-6-{[4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide (1:1) | 4-(1-Methyl-ethyl)piperazine | 0.63 | 579 |

| Example number | Structure | Name | Precursor amine | LCMS $R_t$ (min) | MH+ |
|---|---|---|---|---|---|
| 87 | 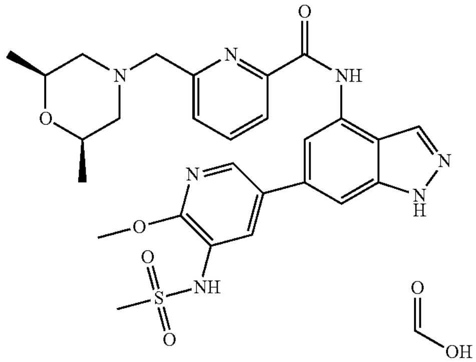 | formic acid-6-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-2-pyridinecarboxamide (1:1) | (2R,6S)-2,6-dimethyl-morpholine (available from Lancaster Synthesis) | 0.63 | 566 |
| 88 | 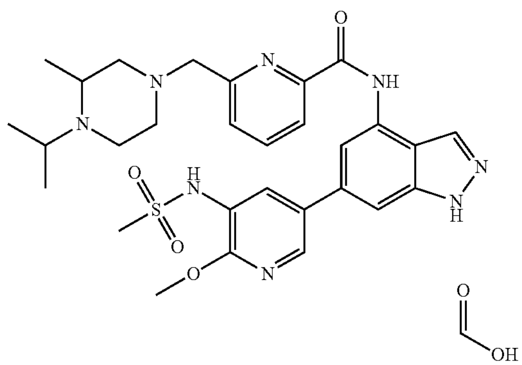 | formic acid-6-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide (1:1) | 2-methyl-1-(1-methylethyl)-piperazine (available from Fluorochem) | 0.65 | 593 |

Example 89

N-{6-[5-[(Cyclopropylsulfonyl)amino]-6-(methyloxy)-3-pyridinyl]-1H-indazol-4-yl}-2-methyl-1,3-thiazole-4-carboxamide

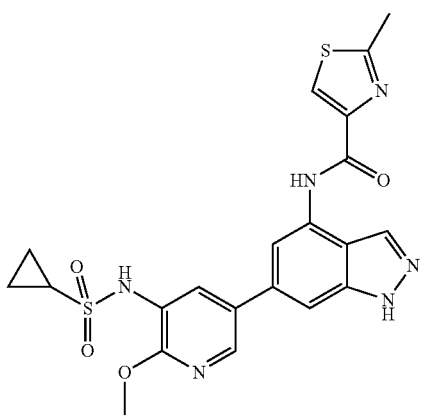

N-[5-Bromo-2-(methyloxy)-3-pyridinyl]cyclopropanesulfonamide (208 mg, 0.371 mmol), 2-methyl-N-[1-(phenylsulfonyl)-6-(trimethylstannanyl)-1H-indazol-4-yl]-1,3-thiazole-4-carboxamide (128 mg, 0.417 mmol) and Pd(PPh$_3$)$_4$ (43 mg, 0.037 mmol) were weighed to a microwave vial. DMF (3 ml) was added and the reaction was heated in the microwave at 120° C. for 30 min. LCMS showed incomplete reaction, therefore the mixture was reheated at 120° C. for a further 30 min. The residue was passed through a 1 g silica cartridge, pre-conditioned with methanol, washing with methanol. The solvent was evaporated in the blow down unit. The residue was purified on a 40 g silica cartridge on the ISCO Companion, using a 0.5-6% methanol in DCM gradient over 14 mins at a flow rate of 40 ml/min. Fractions containing desired material were combined and concentrated in vacuo, then subjected to further purification on the ISCO companion using a reverse phase 13 g column, with 0.1% TFA in MeCN and 0.1% TFA in water as eluents and a gradient of 15-65% MeCN over 14 mins. Fractions containing desired material were combined and concentrated in vacuo. The residue was dissolved in IPA (3 ml) and 2M NaOH (aq., 3 ml) was added and the reaction mixture left overnight. The IPA was evaporated and the aqueous was acidified using 2M HCl (aq). The precipitate was filtered, washing with water, then dissolved in 1 ml DMSO:methanol (1:1, v/v) and purified by MDAP (Method E) to afford the title compound (27 mg).

LCMS (Method B) Rt=0.90 min, MH+=485.

Example 90

N-{6-[5-{[(2,4-Difluorophenyl)sulfonyl]amino}-6-(methyloxy)-3-pyridinyl]-1H-indazol-4-yl}-2-methyl-1,3-thiazole-4-carboxamide

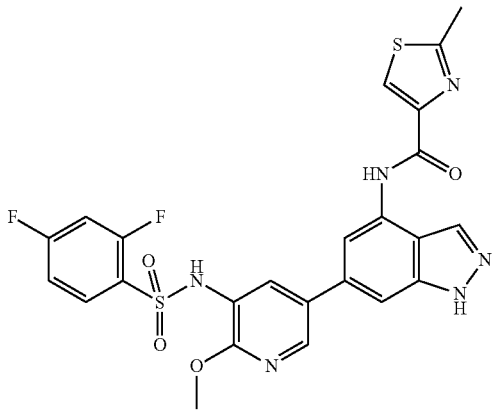

N-[5-Bromo-2-(methyloxy)-3-pyridinyl]-2,4-difluorobenzenesulfonamide (39 mg, 0.104 mmol), 2-methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg, 0.104 mmol), Pd(dppf)Cl$_2$ (8 mg, 10.36 μmol) and sodium carbonate (44 mg, 0.415 mmol) were added to a microwave vial, followed by 1,4-Dioxane (0.5 mL) and Water (0.5 mL) and the reaction mixture was heated in the microwave at 140° C. for 20 min. After cooling, the mixture was then passed through a 1 g silica cartridge and washed with DCM:methanol. The solvent was evaporated by blow down under nitrogen. The residue was dissolved in 1.6 ml DMSO:methanol (1:1, v/v) and passed through a 1 g C18 cartridge, washing with acetonitrile, then evaporated by blow down. The residue was dissolved in 1.6 ml DMSO:methanol (1:1, v/v) and purified by MDAP (Method E). This MDAP purification step was then repeated to afford the title compound (9 mg).

LCMS (Method B) Rt=1.07 min, MH+=557.

Example 91

2-Methyl-N-(6-{6-(methyloxy)-5-[(methylsulfonyl)amino]-3-pyridinyl}-1H-indazol-4-yl)-1,3-thiazole-4-carboxamide

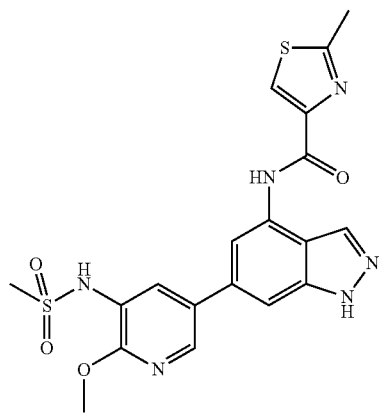

2-Methyl-N-[1-(phenylsulfonyl)-6-(trimethylstannanyl)-1H-indazol-4-yl]-1,3-thiazole-4-carboxamide (200 mg, 0.356 mmol), N-[5-bromo-2-(methyloxy)-3-pyridinyl]methanesulfonamide (120 mg, 0.428 mmol) and Pd(PPh$_3$)$_4$ (41 mg, 0.036 mmol) were weighed to a microwave vial. DMF (3 ml) was added and the reaction was heated in the microwave at 120° C. for 30 mins. The reaction mixture was passed through a 1 g silica cartridge (pre-conditioned with methanol), washing with methanol. The solvent was removed by blow down. The residue was dissolved in DCM and purified on the ISCO companion, using a 40 g Si cartridge, a gradient of 0-6% methanol in DCM containing 1% ammonia, over 14 mins and a 40 ml/min flow rate. LCMS showed still not pure, therefore the material was further purified by MDAP (Method E). The purified material was dissolved in IPA (3 ml) and 2M NaOH (aq, 3 ml) was added. The reaction mixture was left overnight then concentrated and acidified with 2M HCl (aq). The precipitate was filtered, re-dissolved in methanol and dried by blow down to afford the title compound (11 mg).

LCMS (Method B) R$_t$=0.83 min, MH$^+$=457.

Example 92

N-{6-[5-[(2-Hydroxypropanoyl)amino]-6-(methyloxy)-3-pyridinyl]-1H-indazol-4-yl}-2-methyl-1,3-thiazole-4-carboxamide

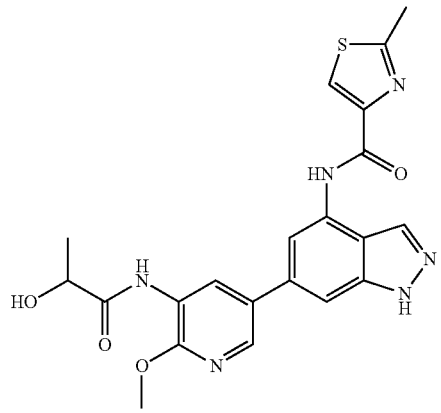

2-Methyl-N-[1-(phenylsulfonyl)-6-(trimethylstannanyl)-1H-indazol-4-yl]-1,3-thiazole-4-carboxamide (150 mg, 0.267 mmol), N-[5-bromo-2-(methyloxy)-3-pyridinyl]-2-hydroxypropanamide (88 mg, 0.321 mmol) and Pd(PPh$_3$)$_4$ (31 mg, 0.027 mmol) were weighed to a microwave vial. DMF (3 ml) was added and the reaction was heated in the microwave at 120° C. for 30 mins, then again at 120° C. for a further for 30 mins. The reaction mixture was passed through a 1 g silica cartridge, pre-conditioned with methanol, washing with methanol. The solvent was evaporated in the blow down. The residue was dissolved in DMSO:methanol (1 ml, 1:1, v/v) and purified by MDAP (Method E). Pure fraction was evaporated to dryness. The residue was dissolved in IPA and 2M NaOH (aq) and left overnight. The reaction was concentrated in vacuo, then neutralised using 2M HCl (aq) and the resultant precipitate was collected by filtration. The material was dissolved in DMSO:methanol (0.7 ml, 1:1, v/v) and purified by MDAP (Method E). Pure fractions were combined and evaporated to dryness to afford the title compound (10 mg).

LCMS (Method B) R$_t$=0.84 min, MH$^+$=451.

Example 93

Formic acid-N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide (1:1)

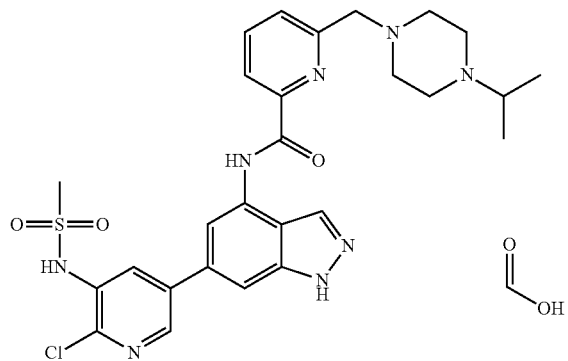

6-(Chloromethyl)-N-[6-{6-chloro-5-[(methylsulfonyl)amino]-3-pyridinyl}-1-(phenylsulfonyl)-1H-indazol-4-yl]-2-pyridinecarboxamide (50 mg, 0.079 mmol) and piperidine (0.5 ml, 5.05 mmol) were placed in a vial and heated in a microwave at 90° C. for 15 min. The piperidine was blown off under a stream of nitrogen to give a yellow gum. The crude residue was suspended in IPA (2 ml) and 2M NaOH (1 ml) added. The mixture was stirred at room temperature for 2 hours. The solution was neutralised with 2M HCl (aq.) and then the solvent was blown off under a stream of nitrogen. The residue was dissolved in DMF/Acetone/Water (0.3 ml:0.3 ml:30 μl) (the insoluble salt was filtered off through a filter tube) and purified by MDAP (Method E). The solvent was evaporated under a stream of nitrogen to give a brown oil which was not completely clean, so further HPLC purification was carried out. The residue was dissolved in dioxane/water (1:1, 2 ml) and freeze dried to give the title compound as a white solid (3 mg).

LCMS (Method B) Rt=0.63 min, MH$^+$540.

Example 94

N-{6-[5-{[(2,4-Difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide

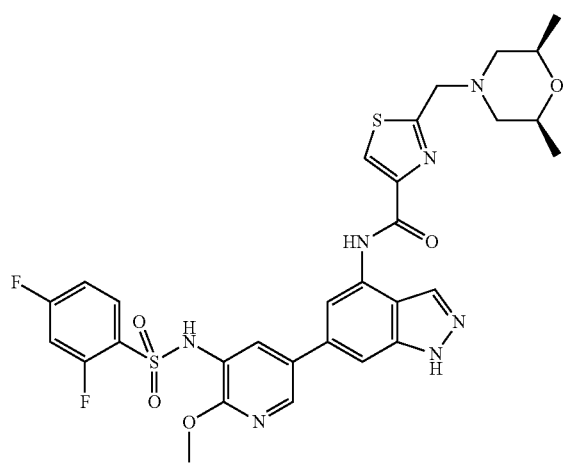

N-{6-[5-{[(2,4-Difluorophenyl)sulfonyl]amino}-6-(methyloxy)-3-pyridinyl]-1-[(4-methylphenyl)sulfonyl]-1H-indazol-4-yl}-2-{[(2R,6S)-2,6-dimethyl-4-morpholinyl]methyl}-1,3-thiazole-4-carboxamide (105 mg) was dissolved in IPA (1 mL) and 2M NaOH (aq) (1 mL) and stirred at room temperature overnight. The IPA was evaporated and the remaining aqueous phase was diluted with water (2 ml), then acidified to ca. pH 4 using 2M HCl (aq) to give a precipitate that was extracted into DCM, passed through a hydrophobic frit, then evaporated to dryness. The residue was purified by ISCO companion 12 g silica cartridge using a 0-6% methanol in DCM gradient over 16 mins at 30 ml/min. Product containing fractions were combined, evaporated to dryness then further dried on a vacuum line to give title compound, (53 mg).

LCMS (Method B) R$_t$=0.8 min, MH$^+$=670.

N-{6-[5-{[(2,4-Difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide was recrystallised from hot ethanol and crystallinity was confirmed by observation under a microscope (mp 211-212° C.).

Example 95

2-[(2-Methyl-4-morpholinyl)methyl]-N-(6-{6-(methyloxy)-5-[(methylsulfonyl)amino]-3-pyridinyl}-1H-indazol-4-yl)-1,3-thiazole-4-carboxamide

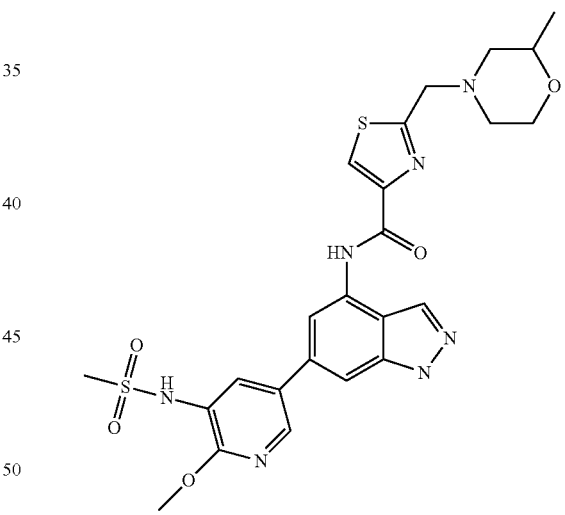

2-(Chloromethyl)-N-[6-{6-(methyloxy)-5-[(methylsulfonyl)amino]-3-pyridinyl}-1-(phenylsulfonyl)-1H-indazol-4-yl]-1,3-thiazole-4-carboxamide (50 mg, 0.079 mmol) was added to 2-methylmorpholine (0.5 ml, 0.079 mmol). The reaction mixture was heated in the microwave for 15 min at 90° C. The solvent was blown off under nitrogen. IPA (2 ml) and 2M NaOH (2 ml) were added to the mixture. The reaction mixture was stirred for 30 hours, then neutralised with 2M HCl aqueous to pH 7. The solvent was blown off under nitrogen. The mixture was dissolved in 2 ml of DMSO. Insoluble matter was removed by filtration and purification was carried out by MDAP (Method E) to afford the title compound (5 mg).

LCMS (Method B) R$_t$=0.58 min, MH$^+$=558.

Similarly prepared were:

| Example number | Structure | Name | Precursor amine | LCMS $R_t$ (min) | MH+ |
|---|---|---|---|---|---|
| 96 | 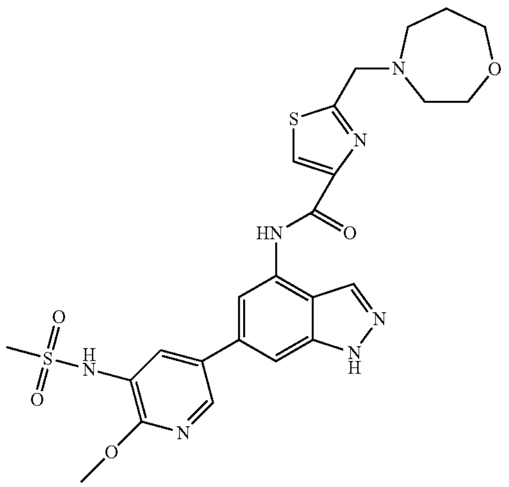 | N-(6-{6-(Methyloxy)-5-[(methylsulfonyl)amino]-3-pyridinyl}-1H-indazol-4-yl)-2-(tetrahydro-1,4-oxazepin-4(5H)-ylmethyl)-1,3-thiazole-4-carboxamide | Hexahydro-1,4-oxazepine | 0.51 | 558 |
| 97 | 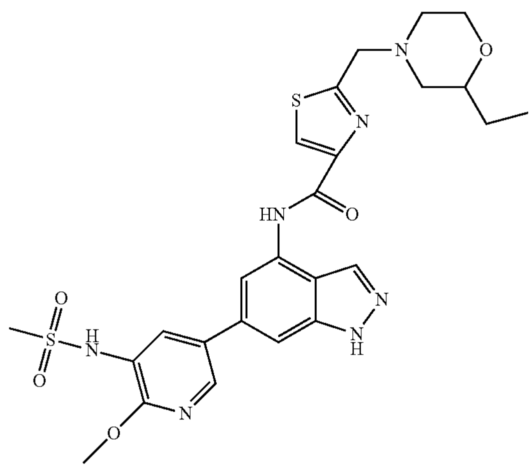 | 2-[(2-Ethyl-4-morpholinyl)methyl]-N-(6-{6-(methyloxy)-5-[(methylsulfonyl)amino]-3-pyridinyl}-1H-indazol-4-yl)-1,3-thiazole-4-carboxamide | 2-Ethylmorpholine | 0.64 | 572 |

Example 98

2-{[(2R,6S)-2,6-Dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide

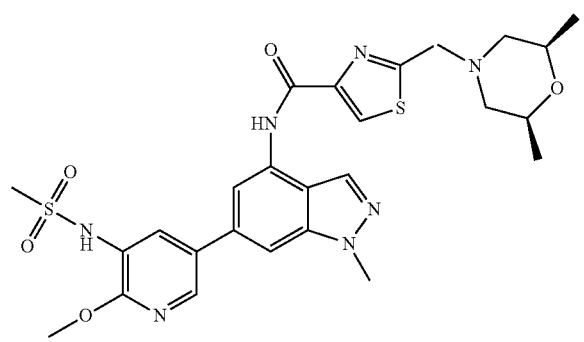

2-{[(2R,6S)-2,6-Dimethyl-4-morpholinyl]methyl}-N-[1-methyl-6-(4,4,6,6-tetramethyl-1,3,2-dioxaborinan-2-yl)-1H-indazol-4-yl]-1,3-thiazole-4-carboxamide (50 mg), N-[5-bromo-2-(methyloxy)-3-pyridinyl]methanesulfonamide (27 mg), tripotassium phosphate (61 mg) and Pd(dppf)Cl$_2$ (7 mg) were added to 1,4-dioxane (0.5 ml) and water (0.167 ml) in a 0.5-2 ml vial then put in the microwave for 10 min at 100° C. The solvent was removed under nitrogen. Purification was carried out using the Flash Master II (20 g Si cartridge, gradient: 0-100% EtOAc/cyclohexane, time: 30 min). The fractions containing product were collected and the solvent was removed to afford the title compound as a white solid (16 mg).

LCMS (Method B) $R_t$=0.76 min, MH+=586.

$^1$H NMR: $\delta_H$(DMSO-d$_6$, 600 MHz) 10.5 (1H, s, NH), 9.38 (1H, br.s, NH), 8.48 (1H, s, CH), 8.42 (1H, d, CH), 8.11 (1H, s, CH), 7.97 (1H, d, CH), 7.78 (1H, s, CH), 7.74 (1H, s, CH), 4.10 (3H, s, CH$_3$), 3.99 (3H, s, CH$_3$), 3.93 (2H, s, CH$_2$), 3.63 (2H, m, 2×CH), 3.09 (3H, s, CH$_3$), 2.86 (2H, d, 2×½ CH$_2$), 1.91 (2H, t, 2×½ CH$_2$) 1.07 (6H, d, 2×CH$_3$).

Example 99

N-{6-[5-{[(2,4-Difluorophenyl)sulfonyl]amino}-6-(methyloxy)-3-pyridinyl]-1-methyl-1H-indazol-4-yl}-2-{[(2R,6S)-2,6-dimethyl-4-morpholinyl]methyl}-1,3-thiazole-4-carboxamide

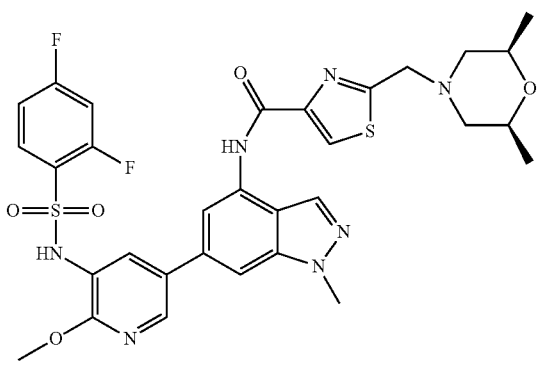

N-(6-Bromo-1-methyl-1H-indazol-4-yl)-2-{[(2R,6S)-2,6-dimethyl-4-morpholinyl]methyl}-1,3-thiazole-4-carboxamide (50 mg, 0.108 mmol), 2,4-difluoro-N-[2-(methyloxy)-5-(4,4,5,5-tetramethyl-1,3,2-dioxaborolan-2-yl)-3-pyridinyl]benzenesulfonamide (46 mg, 0.108 mmol), Pd(dppf)Cl$_2$ (16 mg, 0.022 mmol) and tripotassium phosphate (69 mg, 0.323 mmol) were added to 1,4-dioxane (1 ml) and water (0.25 ml) then put in the microwave. The reaction mixture was heated at 100° C. for 20 min. The solvent was blown down to give a brown oil which was dissolved in water (1 ml) and dioxane (1 ml), put in cardice for 15 min then put on freeze dryer to give a brown solid which was purified by MDAP (Method E) to give the title compound as a white solid (19 mg).

LCMS (Method B) R$_t$=0.88 min, MH$^+$=684.

Example 100

2-{[(2R,6S)-2,6-Dimethyl-4-morpholinyl]methyl}-N-(6-{6-(methyloxy)-5-[(1H-pyrazol-4-ylsulfonyl)amino]-3-pyridinyl}-1H-indazol-4-yl)-1,3-thiazole-4-carboxmide N-{6-[5-Amino-6-(methyloxy)-3-pyridinyl]-1-[(4-methylphenyl)sulfonyl]-1H-indazol-4-yl}-2-{[(2R,6S)-2,6-dimethyl-4-morpholinyl]methyl}-1,3-thiazole-4-carboxamide (65 mg) was dissolved in pyridine (2 ml) and 1H-pyrazole-4-sulfonyl chloride (25 mg) was added. The reaction was stirred at RT overnight. 2M HCl (aq) (12 ml) and DCM (12 ml) were added and the reaction was vigorously stirred. The solvent was passed through a hydrophobic frit then removed under nitrogen blow down. IPA (2 ml) and 2M NaOH (aq) (1 ml) were added and the reaction was stirred at RT. The reaction was evaporated to dryness and water (1 ml) and DCM (3 ml) were added, followed by 2M HCl (aq) (1 ml). A precipitate was observed. The mixture was evaporated to dryness. The residue was purified by MDAP using the following method:
Column: Waters Sunfire C18 (100 mm×19 mm I.D, 5 M)
Injection volume: 500 I, (DMSO:methanol, 1:1, v/v)
Mobile Phase A: 0.1% formic acid in water
Mobile Phase B: 0.1% formic acid in MeCN
Gradient: 15-40% B over 10 mins, 20 ml/min
LCMS (Method B) R$_t$=0.62 min, MH$^+$=624.
Similarly prepared were:

| Example number | Structure | Name | Precursor sulfonyl chloride | LCMS R$_t$ min | MH$^+$ |
|---|---|---|---|---|---|
| 101 | 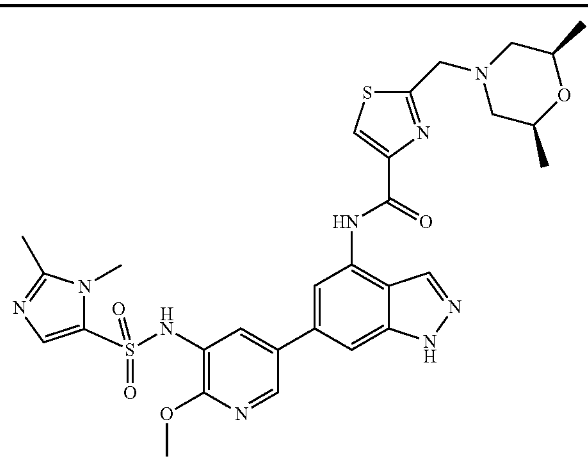 | N-{6-[5-{[(1,2-Dimethyl-1H-imidazol-5-yl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide | 1,2-Dimethyl-1H-imidazole-5-sulfonyl chloride | 0.58 | 652 |

| Example number | Structure | Name | Precursor sulfonyl chloride | LCMS R<sub>t</sub> min) | MH+ |
|---|---|---|---|---|---|
| 102 | 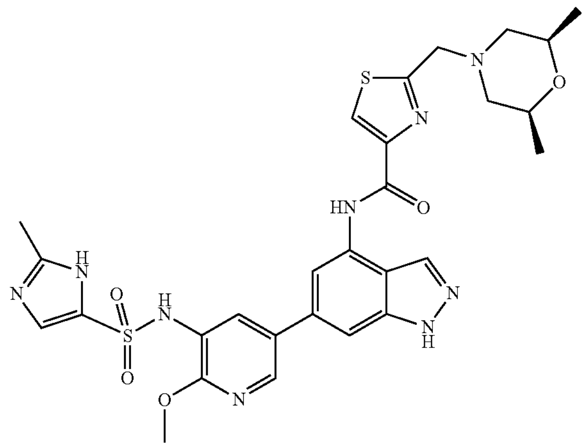 | 2-{[(2R,6S)-2,6-Dimethyl-4-morpholinyl]methyl}-N-{6-[5-{[(2-methyl-1H-imidazol-4-yl)sulfonyl]amino}-6-(methyloxy)-3-pyridinyl]-1H-indazol-4-yl}-1,3-thiazole-4-carboxamide | 2-Methyl-1H-imidazole-4-sulfonyl chloride | 0.6 | 638 |
| 103 | 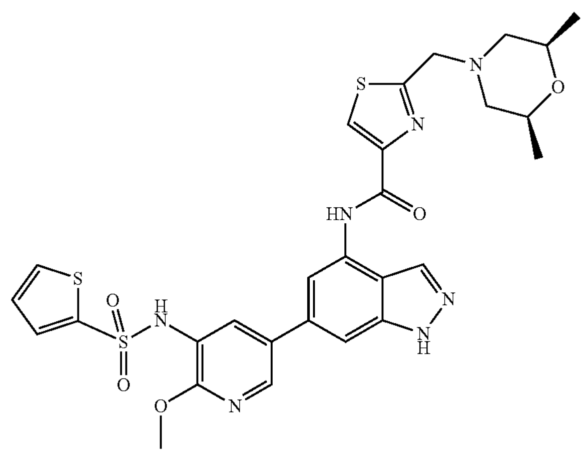 | 2-{[(2R,6S)-2,6-Dimethyl-4-morpholinyl]methyl}-N-(6-{6-(methyloxy)-5-[(2-thienylsulfonyl)amino]-3-pyridinyl}-1H-indazol-4-yl)-1,3-thiazole-4-carboxamide | 2-Thiophenesulfonyl chloride | 0.75 | 640 |
| 104 | 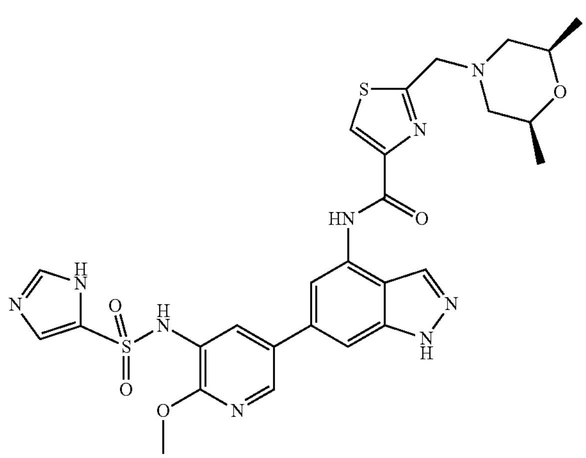 | 2-{[(2R,6S)-2,6-Dimethyl-4-morpholinyl]methyl}-N-{6-[5-[(1H-imidazol-4-ylsulfonyl)amino]-6-(methyloxy)-3-pyridinyl]-1H-indazol-4-yl}-1,3-thiazole-4-carboxamide | 1H-Imidazole-4-sulfonyl chloride | 0.6 | 624 |

Example 105

2-{[(2R,6S)-2,6-Dimethyl-4-morpholinyl]methyl}-N-{6-[6-(methyloxy)-5-({[2-(4-methyl-1-piperazinyl)ethyl]sulfonyl}amino)-3-pyridinyl]-1H-indazol-4-yl}-1,3-thiazole-4-carboxamide

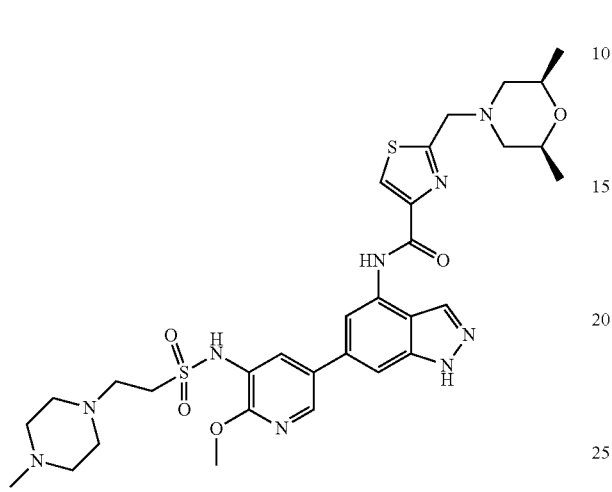

Acetonitrile (10 ml) was added to 2-{[(2R,6S)-2,6-dimethyl-4-morpholinyl]methyl}-N-[6-[5-[(ethenylsulfonyl)amino]-6-(methyloxy)-3-pyridinyl]-2-(tetrahydro-2H-pyran-2-yl)-2H-indazol-4-yl]-1,3-thiazole-4-carboxamide (250 mg) followed by 1-methylpiperazine (0.33 ml). The reaction was stirred at RT for 3 hours. The reaction was evaporated to dryness and the residue was separated between DCM and water. The DCM was passed through a hydrophobic frit then evaporated to dryness. The residue was dissolved in DMSO:methanol (1:1, v/v, 2 ml) and purified by MDAP (method E). Pure fractions were combined and evaporated to dryness. Analysis showed complete deprotection on drydown to give title compound (116 mg).

LCMS (Method B) $R_t$=0.52 min, MH$^+$=684.

Example 106

N-[6-(6-Chloro-5-{[(2-methylphenyl)sulfonyl]amino}-3-pyridinyl)-1H-indazol-4-yl]-2-methyl-1,3-thiazole-4-carboxamide

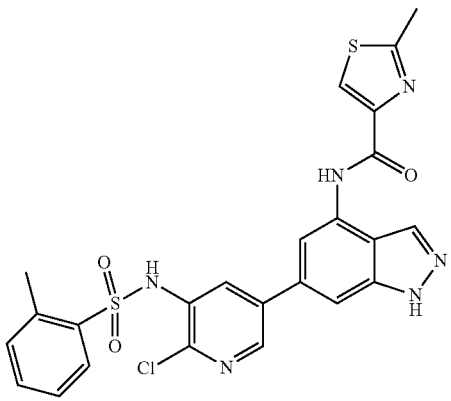

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg), Pd(dppf)Cl$_2$ (7.6 mg) and sodium carbonate (44 mg) were added to a 0.5-2 ml microwave vial. N-(5-Bromo-2-chloro-3-pyridinyl)-2-methylbenzenesulfonamide (37.5 mg) was added followed by 1,4-dioxane (0.5 ml) and water (0.5 ml). The reaction was heated at 140° C. for 20 min. The material was passed though a 1 g silica cartridge with DCM/methanol, then evaporated to dryness. The residue was dissolved in 1.6 ml DMSO:methanol (1:1, v/v), passed through a 1 g C18 cartridge, washing with acetonitrile and then evaporated in the blow down. The residue was dissolved in 1.6 ml DMSO:methanol (1:1, v/v) and purified by MDAP (method F). Pure fractions were combined, blown down, suspended in ca. 3 ml dioxane:water (1:1, v/v) and freeze-dried to give title compound (18 mg).

LCMS (Method B) $R_t$=1.09 min, MH$^+$=539.

Similarly prepared using the appropriate bromide were:

| Example number | Structure | Name | Precursor bromide | LCMS $R_t$ (min) | MH$^+$ |
|---|---|---|---|---|---|
| 107 | 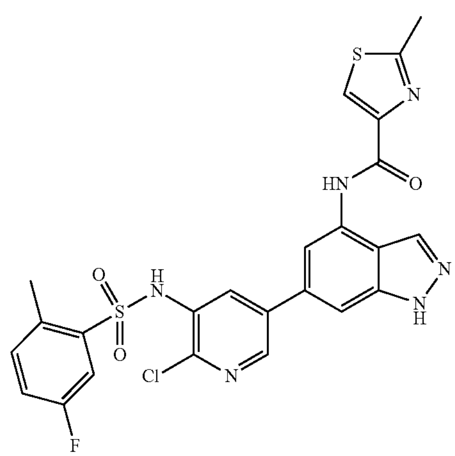 | N-[6-(6-Chloro-5-{[(5-fluoro-2-methylphenyl)sulfonyl]amino}-3-pyridinyl)-1H-indazol-4-yl]-2-methyl-1,3-thiazole-4-carboxamide | N-(5-Bromo-2-chloro-3-pyridinyl)-5-fluoro-2-methylbenzenesulfonamide | 1.09 | 557 |

| Example number | Structure | Name | Precursor bromide | LCMS $R_t$ (min) | MH+ |
|---|---|---|---|---|---|
| 108 | 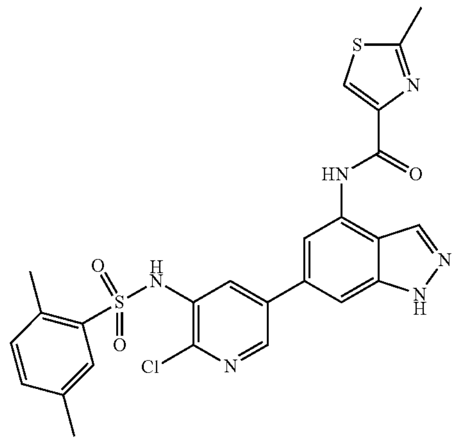 | N-[6-(6-Chloro-5-{[(2,5-dimethylphenyl)sulfonyl]amino}-3-pyridinyl)-1H-indazol-4-yl]-2-methyl-1,3-thiazole-4-carboxamide | N-(5-Bromo-2-chloro-3-pyridinyl)-2,5-dimethylbenzenesulfonamide | 1.14 | 553 |
| 109 | 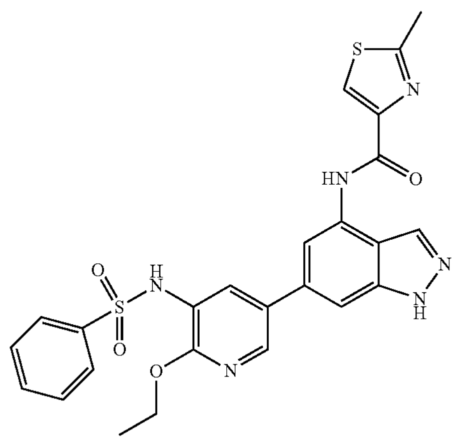 | N-(6-{6-(ethyloxy)-5-[(phenylsulfonyl)amino]-3-pyridinyl}-1H-indazol-4-yl)-2-methyl-1,3-thiazole-4-carboxamide | N-[5-Bromo-2-(ethyloxy)-3-pyridinyl]benzenesulfonamide | 1.09 | 535 |

Example 110

N-(6-{6-Chloro-5-[(methylsulfonyl)amino]-3-pyridinyl}-1-methyl-1H-indazol-4-yl)-6-methyl-2-pyridinecarboxamide

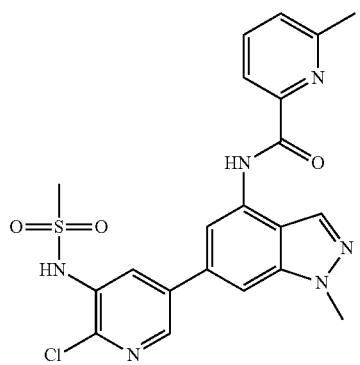

1-Chloro-N,N,2-trimethyl-1-propen-1-amine (0.042 ml) was added to 6-methyl-2-pyridinecarboxylic acid (44 mg) in DCM (1 ml). The reaction was stirred at RT for 20 mins. N-[5-(4-Amino-1-methyl-1H-indazol-6-yl)-2-chloro-3-pyridinyl]methanesulfonamide (75 mg) in DCM (2 ml) was added and the reaction stirred for 30 mins. Approximately 4 ml saturated sodium bicarbonate (aq) was added followed by DCM (3 ml). The reaction was stirred vigorously. The DCM was passed through a hydrophobic frit then evaporated to dryness. The residue was dissolved in DMSO:methanol (1 ml, 1:1, v/v) and purified by MDAP (method E). The pure fraction was evaporated to dryness to give title compound (6 mg)

LCMS (Method B) $R_t$=1.04 min, MH+=471.

Example 111

N-(6-{6-Chloro-5-[(methylsulfonyl)amino]-3-pyridinyl}-1H-indazol-4-yl)-6-methyl-2-pyridnecarboxamide

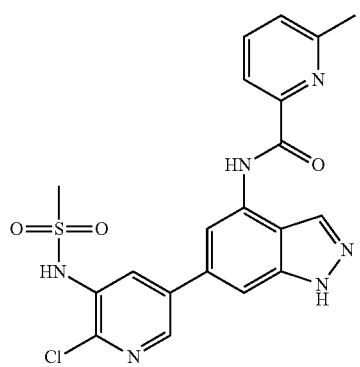

6-Methyl-2-pyridinecarboxylic acid (43 mg) was dissolved in DCM (2 ml) and 1-chloro-N,N,2-trimethyl-1-propen-1-amine (0.042 ml) was added. The reaction was stirred for 15 mins. N-{5-[4-Amino-1-(phenylsulfonyl)-1H-indazol-6-yl]-2-chloro-3-pyridinyl}methane sulfonamide (100 mg) in DCM (4 ml) was added and the reaction left at RT. The reaction was evaporated to dryness. IPA (3 ml) was added to the residue followed by 2M NaOH (aq) (3 ml) and the reaction was left overnight. The solution was neutralised using 2M HCl (aq) and then concentrated. The precipitate that formed was filtered then DMSO was added to the precipitate. Attempts to filter the solid failed so the reaction was blown down under a stream of nitrogen. The residue was redissolved in DMSO (0.5 ml) and purified by MDAP (method E). The pure fraction was evaporated to dryness to give title compound (40 mg).

LCMS (Method B) $R_t$=0.96 min, $MH^+$=457.

Example 112

N-{6-[6-Chloro-5-({[5-methyl-2-(methyloxy)phenyl]sulfonyl}amino)-3-pyridinyl]-1H-indazol-4-yl}-2-methyl-1,3-thiazole-4-carboxamde

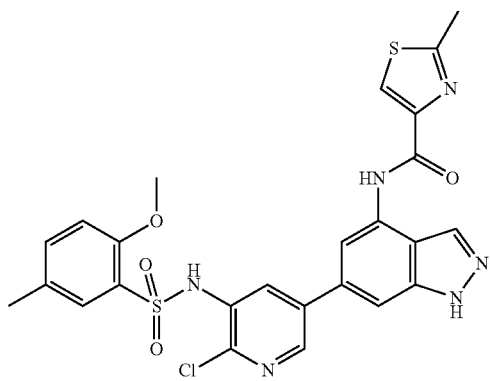

N-[6-(5-Amino-6-chloro-3-pyridinyl)-2-(tetrahydro-2H-pyran-2-yl)-2H-indazol-4-yl]-2-methyl-1,3-thiazole-4-carboxamide (50 mg) was dissolved in pyridine (1 ml) and 5-methyl-2-(methyloxy)benzenesulfonyl chloride (35 mg) was added. The reaction was stirred at RT overnight. Further 5-methyl-2-(methyloxy)benzenesulfonyl chloride (35 mg) was added and the reaction was stirred at RT for 4 h. DMAP (3 mg) followed by 5-methyl-2-(methyloxy)benzenesulfonyl chloride (20 mg) was added and the reaction was stirred at RT overnight. The reaction was neutralised with 2M HCl (aq) and extracted into DCM. The DCM was evaporated and the residue was dissolved in DMSO:methanol (1 ml, 8:1, v/v) and purified by MDAP (method E). The desired fraction was evaporated to dryness and methanol (3 ml) and a few drops of 2M HCl (aq) were added and the reaction stirred for 2 h. The reaction was evaporated to dryness to give title compound (39 mg).

LCMS (Method B) $R_t$=1.11 min, $MH^+$=569.

Example 113

N-(6-{6-Chloro-5-[(cyclopropylsulfonyl)amino]-3-pyridinyl}-1H-indazol-4-yl)-2-methyl-1,3-thiazole-4-carboxamide

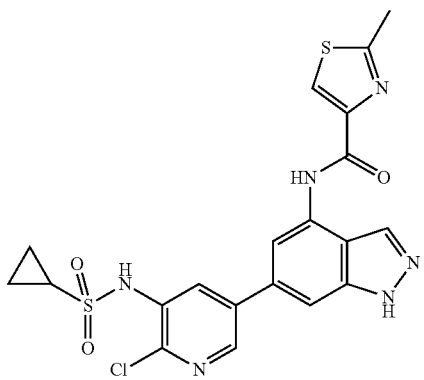

N-[6-(5-Amino-6-chloro-3-pyridinyl)-2-(tetrahydro-2H-pyran-2-yl)-2H-indazol-4-yl]-2-methyl-1,3-thiazole-4-carboxamide (40 mg) was dissolved in pyridine (1 ml) and cyclopropanesulfonyl chloride (24 mg) was added. The reaction was stirred at RT for 1 h. DMAP (3 mg) and cyclopropanesulfonyl chloride (24 mg) were added and the reaction was stirred for 1 h. Further cyclopropanesulfonyl chloride (48 mg) was added and the reaction stirred overnight. Further cyclopropanesulfonyl chloride (48 mg) was added and the reaction was stirred for 2 h. 2M HCl (aq) and DCM were added and the DCM was separated, passed through a hydrophobic frit and evaporated to dryness. The residue was dissolved in DMSO:methanol (1 ml, 7:3, v/v) and purified by MDAP (method E). The product fraction was evaporated to dryness and methanol (3 ml) and a few drops of 2M HCl (aq) were added and the reaction stirred for 2 h. The reaction was evaporated to dryness to give title compound (12 mg).

LCMS (Method B) $R_t$=0.94 min, $MH^+$=489.

Example 114

N-[6-(2,3-Diaminophenyl)-1H-indazol-4-yl]-2-methyl-1,3-thiazole-4-carboxamide

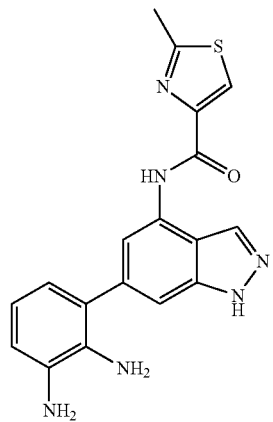

N-(6-Bromo-1H-indazol-4-yl)-2-methyl-1,3-thiazole-4-carboxamide (200 mg,), 3-(4,4,5,5-tetramethyl-1,3,2-dioxaborolan-2-yl)-1,2-benzenediamine (167 mg) (which may be prepared as described in WO2006005915), Pd(dppf)Cl$_2$ (43 mg) and sodium carbonate (890 μl) were added to a microwave vial followed by 1,4-dioxane (2 ml) and water (2 ml). The mixture was heated under microwave irradiation at 150° C. for 15 min. The reaction was diluted with DCM (30 ml) and the layers separated. The aqueous layer was extracted further with DCM (2×30 ml) and the combined organic extracts were evaporated to dryness to give the title compound (250 mg).

LCMS (Method B) R$_t$=0.81 min, MH$^+$=365.

Example 115

2-Methyl-N-(6-{5-[(methylsulfonyl)amino]-3-pyridinyl}-1H-indazol-4-yl)-1,3-thiazole-4-carboxamide

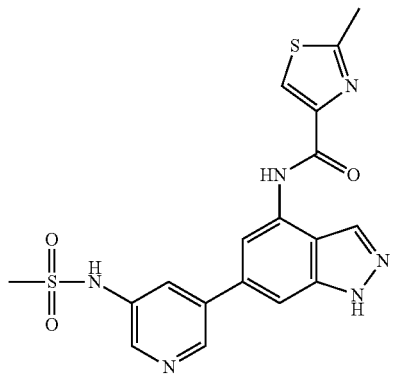

N-{5-[4-Amino-1-(phenylsulfonyl)-1H-indazol-6-yl]-3-pyridinyl}methanesulfonamide (50 mg) was dissolved in DCM (1 ml) and pyridine (0.014 ml) was added. A solution of 2-methyl-1,3-thiazole-4-carbonyl chloride (22 mg) in DCM (1 ml) was added to the reaction and the mixture was stirred at RT for 30 min. Further 2-methyl-1,3-thiazole-4-carbonyl chloride (10 mg) was added to the reaction and stirring continued for 30 min. Further 2-methyl-1,3-thiazole-4-carbonyl chloride (40 mg) was added then the reaction was quenched with water and passed through a hydrophobic frit. The organic layer was evaporated to dryness and the residue was dissolved in DMSO:MeOH (1 ml, 1:1, v/v) and purified by MDAP (method E). The compound was dissolved in MeOH containing a few drops of 2M NaOH and stirred for 5 mins at RT. The residue was dissolved in MeOH and loaded onto an SAX SPE cartridge pre-conditioned with MeOH. After eluting with MeOH and evaporating to dryness, the residue was dissolved in DMSO and purified by MDAP (method E) to give the title compound (9 mg).

LCMS (Method B) R$_t$=0.73 min, MH$^+$=429.

Example 116

N-{6-[4-(Aminosulfonyl)phenyl]-1H-indazol-4-yl}-2-methyl-1,3-thiazole-4-carboxamide

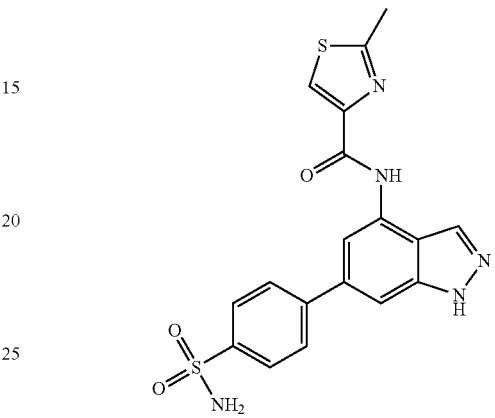

2-Methyl-N-[1-(phenylsulfonyl)-6-(trimethylstannanyl)-1H-indazol-4-yl]-1,3-thiazole-4-carboxamide (101 mg) was dissolved in DMF (0.4 ml) and added to 4-bromobenzenesulfonamide (42.5 mg) in DMF (0.4 ml). Chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (4 mg, heaped microspatula) was added to the reaction which was then heated under microwave irradiation at 135° C. for 20 min. The reaction was loaded onto a C18 SPE pre-conditioned with MeCN:0.1% TFA (aq), eluted with 3 ml MeCN: 0.1% TFA (aq) then evaporated to dryness. The residue was dissolved in DMSO (0.5 ml) and purified by MDAP (method C). The residue was then dissolved in IPA (0.3 ml) and 2M NaOH (0.3 ml) was added. The reaction was stirred at RT for 18 h then diluted with DMSO (0.6 ml) and purified by MDAP (method D) to give the title compound (5 mg).

LCMS (Method B) R$_t$=0.79 min, MH$^+$=414.

Similarly prepared was:

| Example number | Structure | Name | Precursor bromide | LCMS R$_t$ (min) | MH$^+$ |
|---|---|---|---|---|---|
| 117 | 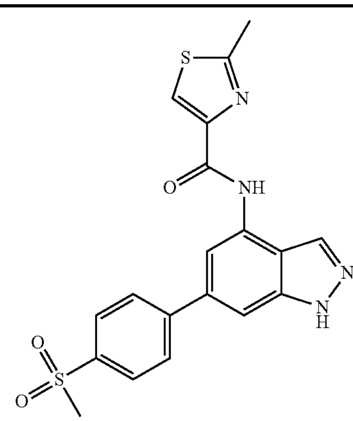 | 2-Methyl-N-{6-[4-(methylsulfonyl)-phenyl]-1H-indazol-4-yl}-1,3-thiazole-4-carboxamide | 4-Bromophenyl methyl sulfone | 0.86 | 414 |

Example 118

N-(6-{6-Chloro-5-[(methylsulfonyl)amino]-3-pyridinyl}-1-methyl-1H-indazol-4-yl)-2-methyl-1,3-thiazole-4-carboxamide

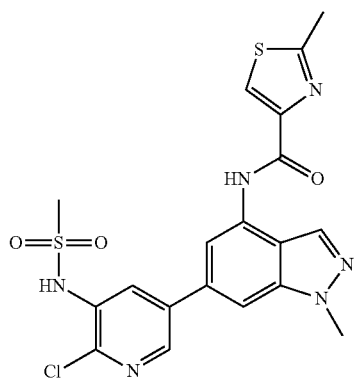

N-[5-(4-Amino-1-methyl-1H-indazol-6-yl)-2-chloro-3-pyridinyl]methanesulfonamide (75 mg) was dissolved in DCM (2 ml) and pyridine (0.052 ml) was added followed by 2-methyl-1,3-thiazole-4-carbonyl chloride (52 mg) in DCM (1 ml) as a suspension. The reaction was stirred at RT for 1 h. Saturated sodium bicarbonate solution was added followed by DCM (3 ml) and the reaction was stirred vigorously. The reaction was passed through a hydrophobic frit and evaporated to dryness. The residue was dissolved in DMSO:MeOH (1:1, v/v, 1 ml) and purified by MDAP (method E) to give the title compound (1.5 mg).

LCMS (Method B) $R_f$=0.95, MH$^+$=477.

Example 119

N-(6-{5-[(Cyclopropylsulfonyl)amino]-6-hydroxy-3-pyridinyl}-1H-indazol-4-yl)-2-methyl-1,3-thiazole-4-carboxamide

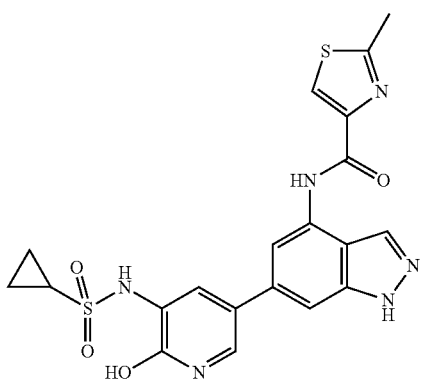

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (27.5 mg) was dissolved in 1,4-dioxane (0.5 ml) and N-(5-bromo-2-hydroxy-3-pyridinyl)cyclopropanesulfonamide (40 mg) was added. Sodium carbonate (48 mg) and Pd(dppf)Cl$_2$ (8.3 mg) were weighed before further 1,4-dioxane (0.5 ml) and water (1 ml) were added. The reaction was heated under microwave irradiation at 140° C. for 20 min. The reaction was added to a silica SPE cartridge that was eluted with MeOH. The MeOH was evaporated to dryness and the residue was dissolved in DMSO:MeOH (1.6 ml, 1:1, v/v) and purified by MDAP (method F) to give the title compound (11 mg).

LCMS (Method B) $R_f$=0.76, MH$^+$=471.

Example 120

N-(6-{6-Chloro-5-[(methylsulfonyl)amino]-3-pyridinyl}-1H-indazol-4-yl)-2-methyl-1,3-thiazole-4-carboxamide

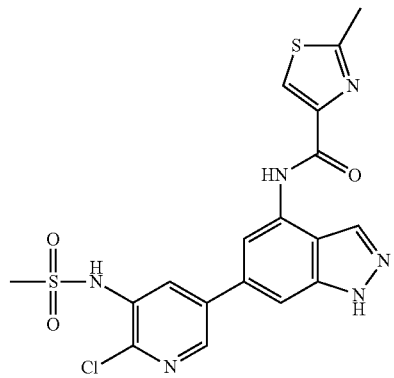

N-{5-[4-Amino-1-(phenylsulfonyl)-1H-indazol-6-yl]-2-chloro-3-pyridinyl}methane sulfonamide (100 mg) was dissolved in DCM (5 ml) and pyridine (0.02 ml) was added. 2-Methyl-1,3-thiazole-4-carbonyl chloride (41 mg) was added and the reaction stirred at RT for 1 h. The reaction was evaporated to dryness and the residue was stirred in MeOH:2M NaOH (aq) (5 ml, 1:1, v/v) for 15 min. The reaction was neutralised with 2M HCl and evaporated to dryness. The residue was dissolved in DMSO (1 ml), filtered and purified by MDAP (method E). The pure fraction was evaporated to dryness to give title compound (33 mg).

LCMS (Method B) $R_f$=0.87 min, MH$^+$=463.

Example 121

2-Methyl-N-(6-{5-[(phenylsulfonyl)amino]-3-pyridinyl}-1H-indazol-4-yl)-1,3-thiazole-4-carboxamide

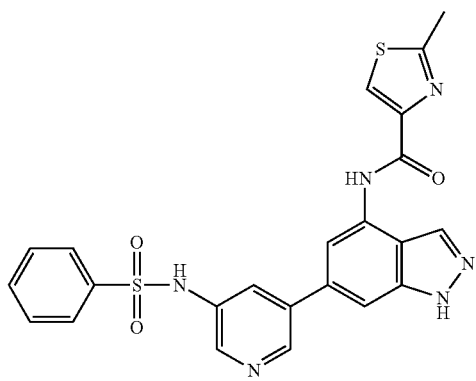

N-{5-[4-Amino-1-(phenylsulfonyl)-1H-indazol-6-yl]-3-pyridinyl}benzenesulfonamide (100 mg) was dissolved in DCM (5 ml) and pyridine (0.024 ml) was added. The reaction was stirred at RT for 2 min before 2-methyl-1,3-thiazole-4-carbonyl chloride (35 mg) was added. The reaction was stirred at RT for 18 h. Further 2-methyl-1,3-thiazole-4-carbonyl chloride (10 mg) was added and stirring continued for 2 h at RT. Further 2-methyl-1,3-thiazole-4-carbonyl chloride (35 mg) was added and the reaction stirred at RT for 18 h before being quenched with water. DCM was added and the reaction was passed through a hydrophobic frit and evaporated to dryness. The residue was dissolved in DMSO:MeOH (1:1, v/v, 1 ml) and purified by MDAP (method E). The desired dried intermediate was dissolved in MeOH and 2M NaOH (1 ml) was added. The reaction was stirred at RT for 30 min. The reaction was neutralised with 2M HCl (aq) then evaporated to dryness. The residue was dissolved in MeOH and loaded onto a SCX-2 SPE cartridge pre-conditioned with MeOH. After eluting with MeOH then 10% NH$_3$ in MeOH, the basic fraction was evaporated to dryness to give the title compound (22 mg).

LCMS (Method B) R$_t$=0.90, MH$^+$=491.

Example 122

N-[6-(5-Hydroxy-3-pyridinyl)-1H-indazol-4-yl]-2-methyl-1,3-thiazole-4-carboxamide trifluoroacetate

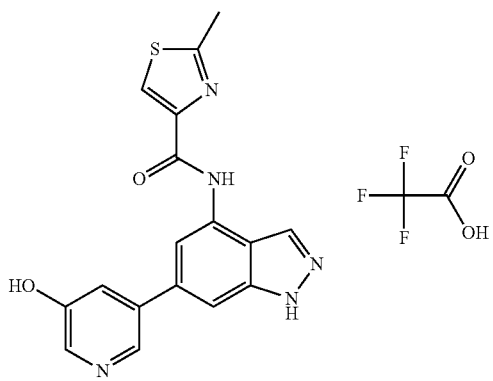

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg) and 5-bromo-3-pyridinol (18 mg) were added to a microwave vial. Pd(dppf)Cl$_2$ (8 mg) and 1,4-dioxane (1 ml) were added. Sodium carbonate (44 mg) in water (1 ml) was added and the reaction was heated under microwave irradiation at 140° C. for 20 min. The reaction was filtered through a 1 g silica SPE cartridge, washing with DCM:MeOH (3:1), the evaporated to dryness. The residue was dissolved in a mixture of DMSO (1.2 ml) and MeOH (0.4 ml) and purified by MDAP (method F). The product-containing fraction was left overnight then evaporated to dryness. The residue was dissolved in dioxane/water (1:1, v/v, 2 ml), frozen in cardice and freeze-dried overnight to give title compound (13 mg).

LCMS (Method B) R$_t$=0.64, MH$^-$=350.

Example 123

N-[6-(3-Hydroxyphenyl)-1H-indazol-4-yl]-2-methyl-1,3-thiazole-4-carboxamide

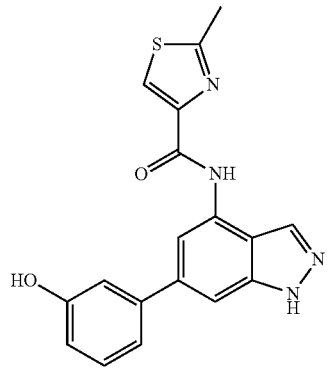

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg) and 3-bromophenol (18 mg) were added to a microwave vial. Pd(dppf)Cl$_2$ (8 mg) and 1,4-dioxane (1 ml) were then added. Sodium carbonate (44 mg) in water (1 ml) was added and the reaction was heated under microwave irradiation at 140° C. for 20 min. The reaction was filtered through a 1 g silica SPE cartridge, washing with DCM:MeOH (3:1) then evaporated to dryness. The residue was dissolved in a mixture of DMSO (1.2 ml) and MeOH (0.4 ml) and purified by MDAP (method F). The product-containing fraction was left overnight then evaporated to dryness. The residue was taken up in DCM and a few drops of TFA were added before sonicating the reaction overnight. The residue was dissolved in dioxane/water (1:1, v/v, 2 ml), frozen in cardice and freeze-dried overnight to give the title compound (2 mg).

LCMS (Method B) R$_t$=0.90, MH$^+$=351.

Similarly prepared were:

| Example number | Structure | Name | Precursor amine | LCMS Rt (min) | MH+ |
|---|---|---|---|---|---|
| 124 | 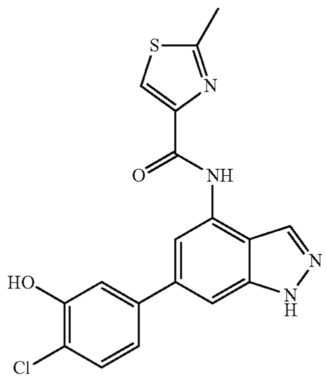 | N-[6-(4-Chloro-3-hydroxyphenyl)-1H-indazol-4-yl]-2-methyl-1,3-thiazole-4-carboxamide | 5-Bromo-2-chlorophenol | 1.00 | 385 |
| 125 | 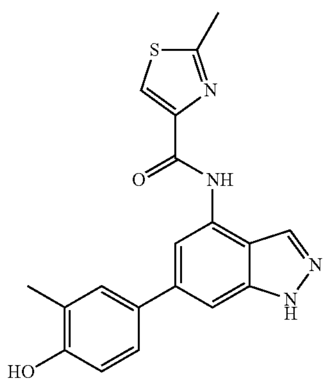 | N-[6-(4-Hydroxy-3-methylphenyl)-1H-indazol-4-yl]-2-methyl-1,3-thiazole-4-carboxamide | 4-Bromo-2-methylphenol | 0.93 | 365 |
| 126 | 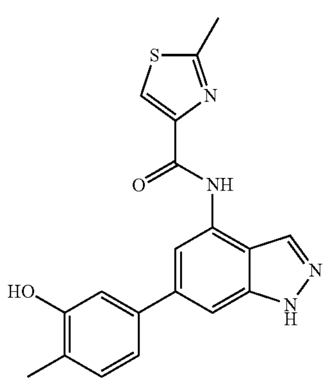 | N-[6-(3-Hydroxy-4-methylphenyl)-1H-indazol-4-yl]-2-methyl-1,3-thiazole-4-carboxamide | 5-Bromo-2-methylphenol | 0.98 | 365 |

Example 127

N-(6-{4-Chloro-3-[(methylsulfonyl)amino]phenyl}-1H-indazol-4-yl)-2-methyl-1,3-thiazole-4-carboxamide

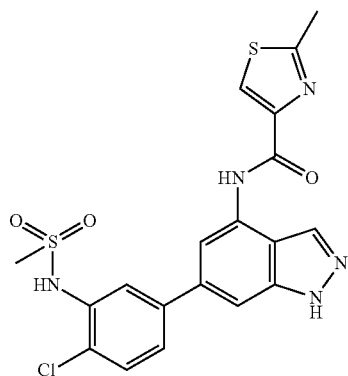

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (55 mg), N-(5-bromo-2-chlorophenyl)methanesulfonamide (39 mg), sodium carbonate (48 mg) and Pd(dppf)Cl$_2$ (8.3 mg) were weighed to a microwave vial. 1,4-Dioxane (0.5 ml) and water (0.5 ml) were added and the reaction was heated under microwave irradiation at 140° C. for 20 min. The reaction was passed through a 1 g silica SPE cartridge preconditioned with MeOH, washing with MeOH, the evaporated to dryness. The residue was dissolved in DMSO:MeOH (1:1, v/v, 1 ml) and purified by MDAP (method E). The residue obtained was dissolved in MeOH and a couple of drops of 2M HCl (aq) were added. The reaction was stirred for 2 h and evaporated to dryness to give the title compound (19 mg).

LCMS (Method B) R$_t$=0.98, MH$^+$=462.

Example 128

2-Methyl-N-(6-{5-[(methylamino)sulfonyl]-3-pyridinyl}-1H-indazol-4-yl)-1,3-thiazole-4-carboxamide

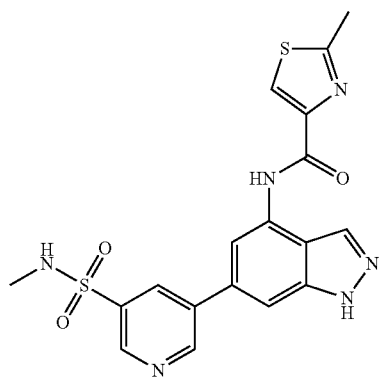

2-Methyl-N-[1-(phenylsulfonyl)-6-(trimethylstannanyl)-1H-indazol-4-yl]-1,3-thiazole-4-carboxamide (50 mg) was placed in microwave vial with Pd(PPh$_3$)$_4$ (10 mg) and 5-bromo-N-methyl-3-pyridinesulfonamide (24.6 mg) was added. DMF (2 ml) was added and the reaction was heated under microwave irradiation for 15 min at 120° C. The reaction was evaporated to dryness and the residue was dissolved in IPA (2 ml) and 2M NaOH (aq) (1 ml). The reaction was stirred at RT for 3 h then evaporated to dryness. The residue was purified by MDAP (method E) to give the title compound (1.5 mg).

LCMS (Method B) R$_t$=0.79, MH$^+$=429.

Example 129

N-(6-{5-[(Diethylamino)sulfonyl]-3-pyridinyl}-1H-indazol-4-yl)-2-methyl-1,3-thiazole-4-carboxamide

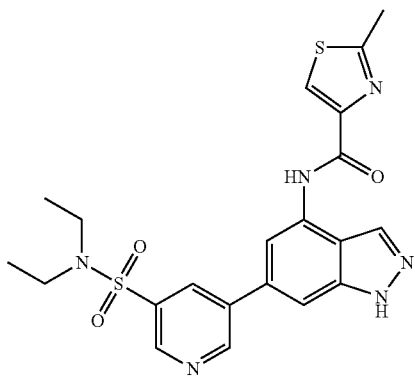

2-Methyl-N-[1-(phenylsulfonyl)-6-(trimethylstannanyl)-1H-indazol-4-yl]-1,3-thiazole-4-carboxamide (50 mg) was placed in a microwave vial with Pd(PPh$_3$)$_4$ (10 mg) and 5-bromo-N,N-diethyl-3-pyridinesulfonamide (29 mg) was added. DMF (2 ml) was added and the reaction was heated under microwave irradiation for 15 min at 120° C. The reaction was evaporated to dryness and the residue was dissolved in IPA (2 ml) and 2M NaOH (aq) (1 ml). The reaction was stirred at RT for 3 h then evaporated to dryness. The residue was purified by MDAP (method E). The residue obtained was further purified on silica, eluting with 0-100% EtOAc/cyclohexane over 15 min followed by 0-20% MeOH/DCM, to give the title compound (13 mg).

LCMS (Method B) R$_t$=0.98, MH$^+$=471.

Example 130

N-(6-{6-Hydroxy-5-[(phenylsulfonyl)amino]-3-pyridinyl}-1H-indazol-4-yl)-2-met3-thiazole-4-carboxamide

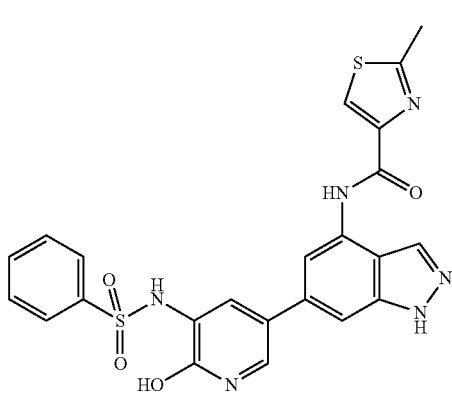

N-(6-{6-(Ethyloxy)-5-[(phenylsulfonyl)amino]-3-pyridinyl}-1H-indazol-4-yl)-2-methyl-1,3-thiazole-4-carboxamide (24 mg) was weighed to a microwave vial and acetic acid (0.25 ml) and concentrated HCl (0.25 ml) were added. The reaction was heated under microwave irradiation for 10 min at 100° C. The reaction was cooled to RT and then heated again under microwave irradiation for 10 min at 100° C. Water was added to the reaction and the resultant precipitate was collected by filtration. The precipitate was dissolved into MeOH:DCM then evaporated to dryness. The residue was then dissolved in DMSO:MeOH (0.8 ml, 1:1, v/v) and purified by MDAP (method F) to give the title compound (6.5 mg).

LCMS (Method B) $R_t$=0.86, MH$^-$=505.

Example 131

N-(6-{6-Chloro-5-[(methylsulfonyl)amino]-3-pyridinyl}-1-methyl-1H-indazol-4-yl)-2-{[(2R,6S)-2,6-dimethyl-4-morpholinyl]methyl}-1,3-thiazole-4-carboxamide

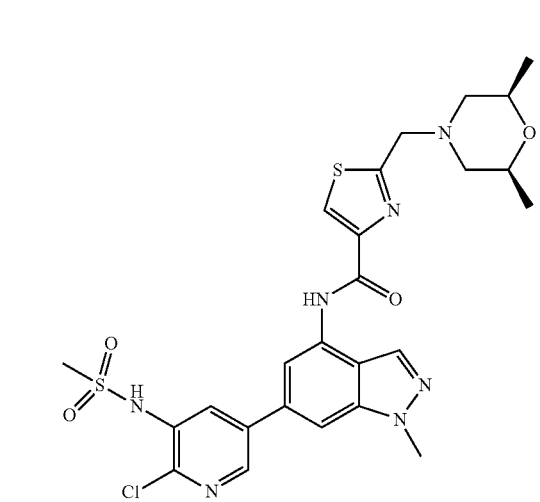

2-{[(2R,6S)-2,6-Dimethyl-4-morpholinyl]methyl}-N-[1-methyl-6-(4,4,6,6-tetramethyl-1,3,2-dioxaborinan-2-yl)-1H-indazol-4-yl]-1,3-thiazole-4-carboxamide (50 mg), N-(5-bromo-2-chloro-3-pyridinyl)methanesulfonamide (27 mg), tripotassium phosphate (61 mg) and Pd(dppf)Cl$_2$ (7 mg) were added to 1,4-dioxane (0.5 ml) and water (0.5 ml) and heated under microwave irradiation for 10 min at 100° C. The reaction was passed through a 2 g silica SPE cartridge, washing with MeOH then evaporating to dryness. The residue was purified on silica, eluting with 0-100% EtOAc/cyclohexane over 30 min to give the title compound (27 mg).

LCMS (Method B) $R_t$=0.76 min, MH$^+$=591.

Further compounds which were prepared include:

| Example number | Structure | Name |
|---|---|---|
| 132 | ![structure] | N-{6-[4-(4-Morpholinyl)phenyl]-1H-indazol-4-yl}-2-pyridinecarboxamide |

-continued

| Example number | Structure | Name |
|---|---|---|
| 133 | 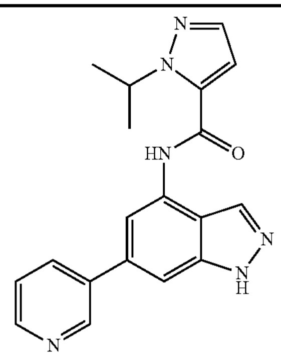 | 1-(1-Methylethyl)-N-[6-(3-pyridinyl)-1H-indazol-4-yl]-1H-pyrazole-5-carboxamide |

BIOLOGICAL DATA

PI3K Alpha, Beta, Delta and Gamma Assays

Assay Principle

The assay readout exploits the specific and high affinity binding of PIP3 to an isolated pleckstrin homology (PH) domain in the generation of a signal. Briefly, the PIP3 product is detected by displacement of biotinylated PIP3 from an energy transfer complex consisting of Europium (Eu)-labelled anti-GST monoclonal antibody, a GST-tagged PH domain, biotin-PIP3 and Streptavidin-APC. Excitation of Eu leads to a transfer of energy to APC and a sensitized fluorescence emission at 665 nm. PIP3 formed by PI3kinase activity competes for the binding site on the PH domain, resulting in a loss of energy transfer and a decrease in signal.

Assay Protocol

Solid compounds are typically plated with 0.1 µl of 100% DMSO in all wells (except column 6 and 18) of a 384-well, v bottom, low volume Greiner plate. The compounds are serially diluted (4-fold in 100% DMSO) across the plate from column 1 to column 12 and column 13 to column 24 and leave column 6 and 18 containing only DMSO to yield 11 concentrations for each test compound.

The assays are run using specific PI3 kinase kits from Millipore (Cat#33-001)

The assay kit consist of the following:
4×PI3K reaction buffer (Contains 200 mM Hepes pH 7, 600 mM NaCl, 40 mM Mgcl$_2$, <1% Cholate (w/v), <1% Chaps (w/v), 0.05% Sodium Azide (w/v))
PIP2 (1 mM)
3× Biotin PIP3 (50 µM)
Detection Mix C (Contains 267 mM KF)
Detection Mix A (Contains 60 µg/ml streptavadin-APC)
Detection Mix B (Contains 36 µg/ml Europium-anti-GST (Anti-GST-K) and 90 µg/ml GST-GRP1-PH-Domain and 1 mM DTT)
Stop Solution (Contains 150 mM EDTA)
Manually add 3 µl of Reaction buffer (contains 1 mM DTT) to column 18 only for 100% inhibition control (no activity)
Manually add 3 µl of 2× Enzyme solution to all wells except column 18. Preincubate with compound for 15 minutes.
Manually add 3 µl of 2× Substrate solution to all wells. (column 6 represents 0% inhibition control)
Leave plate for 1 hr (cover from light) (In the case of Gamma only a 50 min incubation is required)
Manually add 3 µl Stop/Detection solution to all wells
Leave plate for 1 hour (cover from light)
The assay is read upon the BMG Rubystar and the ratio data is utilised to calculate 11 point curves.
NB The substrate solution (concentrations) differ with each isoform (see below)
Alpha
 2× substrate solution containing 500 µM ATP, 16 µM PIP2 and 0.030 µM 3× biotin-PIP3.
Beta
 2× substrate solution containing 800 µM ATP, 16 µM PIP2 and 0.030 µM 3× biotin-PIP3.
Delta
 2× substrate solution containing 160 µM ATP, 10 µM PIP2 and 0.030 µM 3× biotin-PIP3.
Gamma
 2× substrate solution containing 30 µM ATP, 16 µM PIP2 and 0.030 µM 3× biotin-PIP3.
Analysis Method
 Data processed through the XC50 4-parameter logistic curve fit algorithm in Activity Base.
Normalise to % inhibition between the high and low controls (0% and 100% inhibition respectively)
Primary Module fit: Slope, Min and Max asymptotes varies
Secondary Module fits: (1) Fix Min asymptote, (2) Fix Max asymptote, (3) Fix Min and Max asymptotes
Curve Fit QC:pXC50 95% CL ratio>10
−20<Min asymptote<20
80<Max asymptote<120
 The compounds of Examples 1 to 116 and 118 to 131 were tested in one or more of the PI3K Alpha, Beta, Delta and/or Gamma assays above or similar assays and were found to have a mean pIC$_{50}$ of 5 or greater.
Inhibition of Interferon-Gamma (IFN-γ) or IL-5 Production in Human PBMC (Peripheral Blood Mononuclear Cell) Assay (MSD Technology)
 This assay is useful for demonstrating PI3K delta activity,
 A 96-well plate (96 MicroWell™ Plates Nunclon™— High Flange Design, Fisher Scientific UK, Loughborough, UK) is prepared by initially adding to column 1 ca. 10 mM of test compound dissolved in DMSO. For a more potent compound, a more diluted solution in DMSO may be used. The compound is further diluted with DMSO into columns 2 to 9 by 8 successive 4-fold dilutions using the Biomek® 2000 Laboratory Automation Workstation (Beckman Coulter, Inc., Fullerton, Calif.). Column 10 is used as a DMSO negative control (High Signal, 0% response), whilst column 11, which contains 10 mM of the pan-PI3K inhibitor wortmannin, is used as a positive control (Low Signal, 100% response). About 1 µl of compound is transferred to the compound plate using the Biomek® FX.

PBMC cells (peripheral blood mononuclear cells) are prepared from heparinised human blood (using 1% v/v Heparin Sodium 10001 U/ml Endotoxin Free, Leo Laboratories Ltd., Dublin. Ireland, Cat No: PL0043/0149) from normal volunteers using the Accuspin™ System-Histopaque®-1077 essentially (Sigma-Aldrich Company Ltd., Gillingham Dorset, UK). About 20 ml of blood is overlaid onto 15 ml Histopaque® in Accuspin™ tubes. The tube is then centrifuged at about 800 g for ca. 20 minutes. The cells are collected from the interface, washed by centrifugation (ca. 1300 g, ca. 10 minutes) and resuspended in assay medium (Low endotoxin RPMI1640 medium, Cat No: 31870-025, Invitrogen Corporation Invitrogen Ltd, Paisley, UK) containing 10% foetal calf serum (Invitrogen Corporation, Cat No: CT2507), 2 mM L-glutamine (Invitrogen Corporation, Cat No: 25030024), 10 U/ml penicillin and 10 µg/ml streptomycin (Invitrogen Corporation, Cat No: 15140-122). Viable cells are counted by trypan blue staining and diluted to $6.6 \times 10^5$ viable cells/ml. About 150 µl of diluted cells are then added to the compound plate and incubated 37 degrees C. for 1 hour prior to addition of 50 µl of 0.125% (v/v) CYTOSTIM (Cat No: 130-092-173, Miltenyi Biotec Ltd., Bisley, Surrey, UK) diluted in assay medium. The assay plate is then incubated at 37° C., 5% $CO_2$, for 20 hours. The supernatant is removed and the concentrations of IFN-γ and IL-5 are determined by electrochemiluminescence assay using the Meso Scale Discovery (MSD) technology (Meso Scale Discovery, Gaithersburg, Md., USA) as described below.

IFN-γ and IL-5 MSD Assay

Supernants were assayed using MSD (Meso Scale Discovery) technology using either the ultra sensitive IFN-γ single plex or the IFN-γ/IL-5 multiplex 96-well plates (MA6000). For the IL-5/IFNg multiplex, Human Serum Cytokine Assay Diluent (25 µl) is added to the plates precoated with anti-cytokine antibody and then incubated for 24 hours at 4° C. to prevent non-specific binding. This blocking step is not required for the Ultrasensitive IFN-γ plates. About 25 µl of supernatant from the PBMC plate is then transferred from columns 1-11 to columns 1-11 of the MSD plate using the Biomek FX. About 25 µl of standard (IFN-γ Cat No. Calibrator C0AE, IL-5 Cat No. Calibrator C01AJ, Meso Scale Discovery) are added to column 12 of the MSD plate to generate a standard calibration curve (about 0 to 10000 pg/ml final). Plates are washed after 2 hours shaking with a Skanwasher 300 version B (Skatron Instruments AS. PO Box 8, N-3401 Lier, Norway). About 25 µl of diluted sulfo-TAG cytokine detection antibody (IFN-γ antibody number D21AE alone or combined with IL-5 antibody number D21AJ ca. 1 µg/ml final) is added, the plates are shaken at room temperature for 1 hours, and the plates washed again as above. About 150 µl of Read Buffer T (2×) is added to the plates, which are then read on a MSD Sector 6000.

Data Analysis

Data analysis is performed with ActivityBase/XC50 module (ID Business Solutions Ltd., Guildford, Surrey, UK) or Bioassay (CambridgeSoft, Cambridge, UK). Data are normalized and expressed as % inhibition using the formula $100*((U-C1)/(C2-C1))$ where U is the unknown value, C1 is the average of the high signal (0%) control wells (column 10), and C2 is the average of the low signal (100%) control wells (column 11). Curve fitting is performed with a 4-parameter equation.

Preferred compounds, such as 2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide, 2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide, 2-{[(2R,6S)-2,6-dimethyl-4-morpholinyl]methyl}-N-[6-(6-(methyloxy)-5-{[(2,2,2-trifluoroethyl)sulfonyl]amino}-3-pyridinyl)-1H-indazol-4-yl]-1,3-thiazole-4-carboxamide, N-{6-[5-{[(2,4-difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide, 2-{[(2R,6S)-2,6-dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide, or a salt thereof, were tested in the human PBMC assay above or a similar assay and were found to have a mean $pIC_{50}$ of 5 or greater.

What is claimed is:

1. A compound of formula (I)

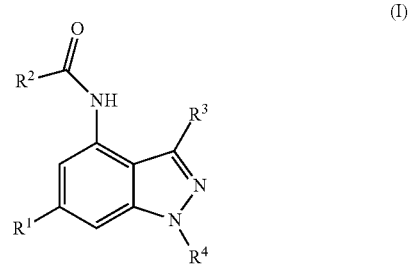

wherein
  $R^1$ is phenyl substituted by one or two substituents independently selected from $C_{1-6}$alkyl, —$OR^5$, halo, —CN, —$COR^6$, $CO_2R^7$, —$CONR^8R^9$, —$NR^{10}R^{11}$, —NHCOR$^{12}$, —$SO_2R^{13}$, —$(CH_2)_mSO_2NR^{14}R^{15}$, —$NHSO_2R^{16}$, and 5-membered heteroaryl wherein the 5-membered heteroaryl contains one or two heteroatoms independently selected from oxygen and nitrogen; or pyridinyl optionally substituted by one or two substituents independently selected from $C_{1-6}$alkyl, —$OR^{17}$, halo, —$SO_2R^{18}$, —$SO_2NR^{19}R^{20}$, —$NHSO_2R^{21}$ and —$NHCOR^{24}$;
  $R^2$ is —$(CH_2)_n$-phenyl optionally substituted by —CN or —$NR^{22}R^{23}$; 5- or 6-membered heteroaryl wherein the 5- or 6-membered heteroaryl contains one or two heteroatoms independently selected from oxygen, nitrogen and sulphur and is optionally substituted by $C_{1-6}$alkyl, halo or —$(CH_2)_qNR^{25}R^{26}$; or $C_{3-6}$cycloalkyl optionally substituted by phenyl;
  $R^3$ is hydrogen or fluoro;
  $R^4$ is hydrogen or methyl;
  $R^7$, $R^{17}$, $R^{19}$, $R^{20}$, $R^{22}$, $R^{23}$, $R^{27}$, $R^{28}$ and $R^{29}$ are each independently hydrogen or $C_{1-6}$alkyl;
  $R^5$ is hydrogen, $C_{1-6}$alkyl or —$CF_3$; $R^6$, $R^{12}$, $R^{13}$, $R^{18}$, $R^{33}$ and $R^{34}$ are each independently $C_{1-6}$alkyl;
  $R^8$ and $R^9$ are each independently hydrogen or $C_{1-6}$alkyl, or $R^8$ and $R^9$, together with the nitrogen atom to which they are attached, are linked to form a 5- or 6-membered heterocyclyl optionally containing an oxygen atom;
  $R^{10}$ and $R^{11}$ are each independently hydrogen or $C_{1-6}$alkyl, or $R^{10}$ and $R^{11}$, together with the nitrogen atom to which they are attached, are linked to form a 5- or 6-membered heterocyclyl optionally containing an oxygen atom;

$R^{14}$ and $R^{15}$ are each independently hydrogen, $C_{1-6}$alkyl, $C_{3-6}$cycloalkyl or —$(CH_2)_p$phenyl, or $R^{14}$ and $R^{15}$, together with the nitrogen atom to which they are attached, are linked to form a 5- or 6-membered heterocyclyl optionally containing an oxygen atom;

$R^{16}$ is $C_{1-6}$alkyl; or phenyl optionally substituted by $C_{1-6}$alkyl;

$R^{21}$ is $C_{3-6}$cycloalkyl; $C_{1-6}$alkyl optionally substituted by —$CF_3$; phenyl optionally substituted by one or two substituents independently selected from $C_{1-6}$alkyl, —$OR^{27}$, —$CO_2R^{28}$ and halo; —$(CH_2)_u NR^{35}R^{36}$; or 5-membered heteroaryl wherein the 5-membered heteroaryl contains one or two heteroatoms independently selected from oxygen, nitrogen and sulphur and is optionally substituted by one or two substituents independently selected from $C_{1-6}$alkyl;

$R^{24}$ is $C_{1-6}$alkyl optionally substituted by —$OR^{29}$;

$R^{25}$ and $R^{26}$, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl, $C_{3-6}$cycloalkyl, halo, oxo, phenyl optionally substituted by halo, pyridinyl, —$(CH_2)_rOR^{30}$, —$(CH_2)_sNR^{31}R^{32}$, —$COR^{33}$ and —$SO_2R^{34}$;

$R^{30}$ is hydrogen, $C_{1-6}$alkyl or —$(CH_2)_t$phenyl;

$R^{31}$ and $R^{32}$, together with the nitrogen atom to which they are attached, are linked to form a 6-membered heterocyclyl optionally containing an oxygen atom;

$R^{35}$ and $R^{36}$, together with the nitrogen atom to which they are attached, are linked to form a 5- or 6-membered heterocyclyl wherein the 5- or 6-membered heterocyclyl optionally contains an oxygen atom or a further nitrogen atom and is optionally substituted by one or two substituents independently selected from $C_{1-6}$alkyl;

m, n, p, q, r, s and t are each independently 0, 1 or 2; and u is 1 or 2;

or a salt thereof.

2. A compound of formula (I) according to claim 1 or a salt thereof wherein $R^1$ is pyridinyl optionally substituted by one or two substituents independently selected from $C_{1-6}$alkyl, —$OR^{17}$, halo and —$NHSO_2R^{21}$.

3. A compound of formula (I) according to claim 1 or a salt thereof wherein $R^1$ is pyridinyl substituted by —$OR^{17}$ and —$NHSO_2R^{21}$.

4. A compound of formula (I) according to claim 1 or a salt thereof wherein $R^2$ is 5- or 6-membered heteroaryl wherein the 5- or 6-membered heteroaryl contains one or two heteroatoms independently selected from oxygen, nitrogen and sulphur and is optionally substituted by $C_{1-6}$alkyl or —$(CH_2)_q NR^{25}R^{26}$.

5. A compound of formula (I) according to claim 1 or a salt thereof wherein $R^2$ is 5- or 6-membered heteroaryl wherein the 5- or 6-membered heteroaryl contains one or two heteroatoms independently selected from oxygen, nitrogen and sulphur and is substituted by —$(CH_2)_q NR^{25}R^{26}$.

6. A compound of formula (I) according to claim 1 or a salt thereof wherein $R^3$ is hydrogen.

7. A compound of formula (I) according to claim 1 or a salt thereof wherein $R^4$ is hydrogen.

8. A compound of formula (I) according to claim 1 which is:

6-bromo-N-[6-(4-hydroxyphenyl)-1H-indazol-4-yl]-2-pyridinecarboxamide;

N-[6-(3-hydroxyphenyl)-1H-indazol-4-yl]cyclohexanecarboxamide;

N-[6-(3-hydroxyphenyl)-1H-indazol-4-yl]-2-pyridinecarboxamide;

N-[6-(3-hydroxyphenyl)-1H-indazol-4-yl]-3-phenylpropanamide;

4-cyano-N-[6-(3-hydroxyphenyl)-1H-indazol-4-yl]benzamide;

3-(dimethylamino)-N-[6-(3-hydroxyphenyl)-1H-indazol-4-yl]benzamide;

(1R,2R)—N-[6-(3-hydroxyphenyl)-1H-indazol-4-yl]-2-phenylcyclopropanecarboxamide;

N-[6-(3-hydroxyphenyl)-1H-indazol-4-yl]-2-furancarboxamide;

N-[6-(3-hydroxyphenyl)-1H-indazol-4-yl]cyclopropanecarboxamide;

N-{6-[5-(aminosulfonyl)-3-pyridinyl]-1H-indazol-4-yl}-2-methyl-1,3-thiazole-4-carboxamide;

N-(6-{3-[(aminosulfonyl)methyl]phenyl}-1H-indazol-4-yl)-2-methyl-1,3-thiazole-4-carboxamide;

2-methyl-N-{6-[5-(methyloxy)-3-pyridinyl]-1H-indazol-4-yl}-1,3-thiazole-4-carboxamide;

3-(4-{[(2-methyl-1,3-thiazol-4-yl)carbonyl]amino}-1H-indazol-6-yl)benzoic acid;

N-(6-{6-chloro-5-[(phenylsulfonyl)amino]-3-pyridinyl}-1H-indazol-4-yl)-2-methyl-1,3-thiazole-4-carboxamide;

N-{6-[4-(acetylamino)phenyl]-1H-indazol-4-yl}-2-pyridinecarboxamide;

N-(6-{3-[(methylsulfonyl)amino]phenyl}-1H-indazol-4-yl)-2-pyridinecarboxamide;

N-[6-(3-{[(4-methylphenyl)sulfonyl]amino}phenyl)-1H-indazol-4-yl]-2-pyridinecarboxamide;

N-{6-[3,4-bis(methyloxy)phenyl]-1H-indazol-4-yl}-2-pyridinecarboxamide;

N-{6-[3-(4-morpholinyl)phenyl]-1H-indazol-4-yl}-2-pyridinecarboxamide;

N-(6-{3-[(methylamino)carbonyl]phenyl}-1H-indazol-4-yl)-2-pyridinecarboxamide;

N-{6-[3-(2-furanyl)phenyl]-1H-indazol-4-yl}-2-pyridinecarboxamide;

N-{6-[4-(2-furanyl)phenyl]-1H-indazol-4-yl}-2-pyridinecarboxamide;

N-[6-(3-{[(phenylmethyl)amino]sulfonyl}phenyl)-1H-indazol-4-yl]-2-pyridinecarboxamide;

N-[6-(3-cyanophenyl)-1H-indazol-4-yl]-2-methyl-1,3-thiazole-4-carboxamide;

2-methyl-N-{6-[3-(methylsulfonyl)phenyl]-1H-indazol-4-yl}-1,3-thiazole-4-carboxamide;

N-[6-(3-chloro-2-fluorophenyl)-1H-indazol-4-yl]-2-methyl-1,3-thiazole-4-carboxamide;

2-methyl-N-(6-{3-[(1-methylethyl)oxy]phenyl}-1H-indazol-4-yl)-1,3-thiazole-4-carboxamide;

N-{6-[3-(ethyloxy)-2-fluorophenyl]-1H-indazol-4-yl}-2-methyl-1,3-thiazole-4-carboxamide;

N-[6-(3-fluorophenyl)-1H-indazol-4-yl]-2-methyl-1,3-thiazole-4-carboxamide;

N-(6-{3-[(diethylamino)carbonyl]phenyl}-1H-indazol-4-yl)-2-methyl-1,3-thiazole-4-carboxamide;

N-(6-{3-[(dimethylamino)carbonyl]phenyl}-1H-indazol-4-yl)-2-methyl-1,3-thiazole-4-carboxamide;

2-methyl-N-(6-{3-[(methylamino)sulfonyl]phenyl}-1H-indazol-4-yl)-1,3-thiazole-4-carboxamide;

N-[6-(3-acetylphenyl)-1H-indazol-4-yl]-2-methyl-1,3-thiazole-4-carboxamide;

N-[6-(2,3-difluorophenyl)-1H-indazol-4-yl]-2-methyl-1,3-thiazole-4-carboxamide;

2-methyl-N-{6-[3-(4-morpholinylsulfonyl)phenyl]-1H-indazol-4-yl}-1,3-thiazole-4-carboxamide;
2-methyl-N-(6-{3-[(trifluoromethyl)oxy]phenyl}-1H-indazol-4-yl)-1,3-thiazole-4-carboxamide;
2-methyl-N-{6-[3-(1-pyrrolidinylcarbonyl)phenyl]-1H-indazol-4-yl}-1,3-thiazole-4-carboxamide;
2-methyl-N-{6-[3-(1-pyrrolidinylsulfonyl)phenyl]-1H-indazol-4-yl}-1,3-thiazole-4-carboxamide;
N-{6-[3-(acetylamino)phenyl]-1H-indazol-4-yl}-2-methyl-1,3-thiazole-4-carboxamide;
N-{6-[3-(aminocarbonyl)phenyl]-1H-indazol-4-yl}-2-methyl-1,3-thiazole-4-carboxamide;
N-(6-{3-[(cyclopropylamino)sulfonyl]phenyl}-1H-indazol-4-yl)-2-methyl-1,3-thiazole-4-carboxamide;
N-{6-[3-(dimethylamino)phenyl]-1H-indazol-4-yl}-2-methyl-1,3-thiazole-4-carboxamide;
N-[6-(3-methylphenyl)-1H-indazol-4-yl]cyclopropanecarboxamide;
N-[6-(4-hydroxyphenyl)-1H-indazol-4-yl]cyclopropanecarboxamide;
N-[6-(4-hydroxyphenyl)-1H-indazol-4-yl]cyclohexanecarboxamide;
N-[6-(4-hydroxyphenyl)-1H-indazol-4-yl]-2-pyridinecarboxamide;
3-(dimethylamino)-N-[6-(4-hydroxyphenyl)-1H-indazol-4-yl]benzamide;
N-[6-(4-hydroxyphenyl)-1H-indazol-4-yl]-3-phenylpropanamide;
(1R,2R)—N-[6-(4-hydroxyphenyl)-1H-indazol-4-yl]-2-phenylcyclopropanecarboxamide;
N-[6-(4-hydroxyphenyl)-1H-indazol-4-yl]-2-furancarboxamide;
2-methyl-N-{6-[5-(methylsulfonyl)-3-pyridinyl]-1H-indazol-4-yl}-1,3-thiazole-4-carboxamide;
2-methyl-N-[6-(4-methyl-3-pyridinyl)-1H-indazol-4-yl]-1,3-thiazole-4-carboxamide;
2-methyl-N-[6-(3-pyridinyl)-1H-indazol-4-yl]-1,3-thiazole-4-carboxamide;
2-methyl-N-[6-(2-oxo-1,2-dihydro-4-pyridinyl)-1H-indazol-4-yl]-1,3-thiazole-4-carboxamide;
2-methyl-N-[6-(4-pyridinyl)-1H-indazol-4-yl]-1,3-thiazole-4-carboxamide;
2-methyl-N-(6-{6-methyl-5-[(methylsulfonyl)amino]-3-pyridinyl}-1H-indazol-4-yl)-1,3-thiazole-4-carboxamide;
N-(6-{6-chloro-5-[(methylsulfonyl)amino]-3-pyridinyl}-1H-indazol-4-yl)-2-(4-morpholinylmethyl)-1,3-thiazole-4-carboxamide;
N-(6-{6-chloro-5-[(methylsulfonyl)amino]-3-pyridinyl}-1H-indazol-4-yl)-2-(1-piperidinylmethyl)-1,3-thiazole-4-carboxamide;
N-(6-{6-chloro-5-[(methylsulfonyl)amino]-3-pyridinyl}-1H-indazol-4-yl)-2-{[4-(1-methylethyl)-1-piperazinyl]methyl}-1,3-thiazole-4-carboxamide;
N-(6-{6-chloro-5-[(methylsulfonyl)amino]-3-pyridinyl}-1H-indazol-4-yl)-2-{[(2R,6S)-2,6-dimethyl-4-morpholinyl]methyl}-1,3-thiazole-4-carboxamide;
N-(6-{6-chloro-5-[(methylsulfonyl)amino]-3-pyridinyl}-1H-indazol-4-yl)-2-{[3-methyl-4-(1-methylethyl)-1-piperazinyl]methyl}-1,3-thiazole-4-carboxamide;
2-{[4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;
N-(6-{6-(methyloxy)-5-[(methylsulfonyl)amino]-3-pyridinyl}-1H-indazol-4-yl)-2-(4-morpholinylmethyl)-1,3-thiazole-4-carboxamide;
N-(6-{6-(methyloxy)-5-[(methylsulfonyl)amino]-3-pyridinyl}-1H-indazol-4-yl)-2-(1-piperidinylmethyl)-1,3-thiazole-4-carboxamide;
2-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-1,3-thiazole-4-carboxamide;
2-{[(2R,6S)-2,6-dimethyl-4-morpholinyl]methyl}-N-{6-[5-[(ethylsulfonyl)amino]-6-(methyloxy)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[3-(methyloxy)phenyl]sulfonyl}amino)-3-pyridinyl]-1H-indazol-4-yl}-1,3-thiazole-4-carboxamide;
N-{6-[5-[(cyclohexylsulfonyl)amino]-6-(methyloxy)-3-pyridinyl]-1H-indazol-4-yl}-2-{[(2R,6S)-2,6-dimethyl-4-morpholinyl]methyl}-1,3-thiazole-4-carboxamide;
2-{[(2R,6S)-2,6-dimethyl-4-morpholinyl]methyl}-N-{6-[5-{[(1-methylethyl)sulfonyl]amino}-6-(methyloxy)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[2-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-{6-[6-(methyloxy)-5-({[4-(methyloxy)phenyl]sulfonyl}amino)-3-pyridinyl]-1H-indazol-4-yl}-1,3-thiazole-4-carboxamide;
2-{[(2R,6S)-2,6-dimethyl-4-morpholinyl]methyl}-N-(6-{6-(methyloxy)-5-[(propylsulfonyl)amino]-3-pyridinyl}-1H-indazol-4-yl)-1,3-thiazole-4-carboxamide;
4-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;
3-({[5-(4-{[(2-{[(2R,6S)-2,6-dimethyl-4-morpholinyl]methyl}-1,3-thiazol-4-yl)carbonyl]amino}-1H-indazol-6-yl)-2-(methyloxy)-3-pyridinyl]amino}sulfonyl)benzoic acid;
2-{[(2R,6S)-2,6-dimethyl-4-morpholinyl]methyl}-N-[6-(6-(methyloxy)-5-{[(3,3,3-trifluoropropyl)sulfonyl]amino}-3-pyridinyl)-1H-indazol-4-yl]-1,3-thiazole-4-carboxamide;
2-{[(2R,6S)-2,6-dimethyl-4-morpholinyl]methyl}-N-[6-(6-(methyloxy)-5-{[(2,2,2-trifluoroethyl)sulfonyl]amino}-3-pyridinyl)-1H-indazol-4-yl]-1,3-thiazole-4-carboxamide;
N-(6-{6-chloro-5-[(methylsulfonyl)amino]-3-pyridinyl}-1H-indazol-4-yl)-6-{[(2R,6S)-2,6-dimethyl-4-morpholinyl]methyl}-2-pyridinecarboxamide;
N-(6-{6-chloro-5-[(methylsulfonyl)amino]-3-pyridinyl}-1H-indazol-4-yl)-6-(4-morpholinylmethyl)-2-pyridinecarboxamide;
N-(6-{6-chloro-5-[(methylsulfonyl)amino]-3-pyridinyl}-1H-indazol-4-yl)-6-(1-piperidinylmethyl)-2-pyridinecarboxamide;
N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;
N-(6-{6-chloro-5-[(methylsulfonyl)amino]-3-pyridinyl}-1H-indazol-4-yl)-6-{[3-methyl-4-(1-methylethyl)-1-piperazinyl]methyl}-2-pyridinecarboxamide;

6-[(1,1-dioxido-4-thiomorpholinyl)methyl]-N-(6-{6-(methyloxy)-5-[(methylsulfonyl)amino]-3-pyridinyl}-1H-indazol-4-yl)-2-pyridinecarboxamide;

N-(6-{6-(methyloxy)-5-[(methylsulfonyl)amino]-3-pyridinyl}-1H-indazol-4-yl)-6-(1-piperidinylmethyl)-2-pyridinecarboxamide;

N-(6-{6-(methyloxy)-5-[(methylsulfonyl)amino]-3-pyridinyl}-1H-indazol-4-yl)-6-(4-morpholinylmethyl)-2-pyridinecarboxamide;

6-{[4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

6-{[(2R,6S)-2,6-dimethyl-4-morpholinyl]methyl}-N-(6-{6-(methyloxy)-5-[(methylsulfonyl)amino]-3-pyridinyl}-1H-indazol-4-yl)-2-pyridinecarboxamide;

6-{[3-methyl-4-(1-methylethyl)-1-piperazinyl]methyl}-N-(6-{6-(methyloxy)-5-[(methylsulfonyl)amino]-3-pyridinyl}-1H-indazol-4-yl)-2-pyridinecarboxamide;

N-{6-[5-[(cyclopropylsulfonyl)amino]-6-(methyloxy)-3-pyridinyl]-1H-indazol-4-yl}-2-methyl-1,3-thiazole-4-carboxamide;

N-{6-[5-{[(2,4-difluorophenyl)sulfonyl]amino}-6-(methyloxy)-3-pyridinyl]-1H-indazol-4-yl}-2-methyl-1,3-thiazole-4-carboxamide;

2-methyl-N-(6-{6-(methyloxy)-5-[(methylsulfonyl)amino]-3-pyridinyl}-1H-indazol-4-yl)-1,3-thiazole-4-carboxamide;

N-{6-[5-[(2-hydroxypropanoyl)amino]-6-(methyloxy)-3-pyridinyl]-1H-indazol-4-yl}-2-methyl-1,3-thiazole-4-carboxamide;

N-(6-{6-chloro-5-[(methylsulfonyl)amino]-3-pyridinyl}-1H-indazol-4-yl)-6-{[4-(1-methylethyl)-1-piperazinyl]methyl}-2-pyridinecarboxamide;

N-{6-[5-{[(2,4-difluorophenyl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-[(2-methyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

N-(6-{6-(methyloxy)-5-[(methylsulfonyl)amino]-3-pyridinyl}-1H-indazol-4-yl)-2-(tetrahydro-1,4-oxazepin-4(5H)-ylmethyl)-1,3-thiazole-4-carboxamide;

2-[(2-ethyl-4-morpholinyl)methyl]-N-(6-{6-(methyloxy)-5-[(methylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-(1-methyl-6-{6-(methyloxy)-5-[(methylsulfonyl)amino]-3-pyridinyl}-1H-indazol-4-yl)-1,3-thiazole-4-carboxamide;

N-{6-[5-{[(2,4-difluorophenyl)sulfonyl]amino}-6-(methyloxy)-3-pyridinyl]-1-methyl-1H-indazol-4-yl}-2-{[(2R,6S)-2,6-dimethyl-4-morpholinyl]methyl}-1,3-thiazole-4-carboxamide;

2-{[(2R,6S)-2,6-dimethyl-4-morpholinyl]methyl}-N-(6-{6-(methyloxy)-5-[(1H-pyrazol-4-ylsulfonyl)amino]-3-pyridinyl}-1H-indazol-4-yl)-1,3-thiazole-4-carboxamide;

N-{6-[5-{[(1,2-dimethyl-1H-imidazol-5-yl)sulfonyl]amino}-6-(methyloxy)-3-pyridinyl]-1H-indazol-4-yl}-2-{[(2R,6S)-2,6-dimethyl-4-morpholinyl]methyl}-1,3-thiazole-4-carboxamide;

2-{[(2R,6S)-2,6-dimethyl-4-morpholinyl]methyl}-N-{6-[5-{[(2-methyl-1H-imidazol-4-yl)sulfonyl]amino}-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-(6-{6-(methyloxy)-5-[(2-thienylsulfonyl)amino]-3-pyridinyl}-1H-indazol-4-yl)-1,3-thiazole-4-carboxamide;

2-{[(2R,6S)-2,6-dimethyl-4-morpholinyl]methyl}-N-{6-[5-[(1H-imidazol-4-ylsulfonyl)amino]-6-(methyloxy)-3-pyridinyl]-1H-indazol-4-yl}-1,3-thiazole-4-carboxamide;

2-{[(2R,6S)-2,6-dimethyl-4-morpholinyl]methyl}-N-{6-[6-(methyloxy)-5-({[2-(4-methyl-1-piperazinyl)ethyl]sulfonyl}amino)-3-pyridinyl]-1H-indazol-4-yl}-1,3-thiazole-4-carboxamide;

N-[6-(6-chloro-5-{[(2-methylphenyl)sulfonyl]amino}-3-pyridinyl)-1H-indazol-4-yl]-2-methyl-1,3-thiazole-4-carboxamide;

N-[6-(6-chloro-5-{[(5-fluoro-2-methylphenyl)sulfonyl]amino}-3-pyridinyl)-1H-indazol-4-yl]-2-methyl-1,3-thiazole-4-carboxamide;

N-[6-(6-chloro-5-{[(2,5-dimethylphenyl)sulfonyl]amino}-3-pyridinyl)-1H-indazol-4-yl]-2-methyl-1,3-thiazole-4-carboxamide;

N-(6-{6-(ethyloxy)-5-[(phenylsulfonyl)amino]-3-pyridinyl}-1H-indazol-4-yl)-2-methyl-1,3-thiazole-4-carboxamide;

N-(6-{6-chloro-5-[(methylsulfonyl)amino]-3-pyridinyl}-1-methyl-1H-indazol-4-yl)-6-methyl-2-pyridinecarboxamide;

N-(6-{6-chloro-5-[(methylsulfonyl)amino]-3-pyridinyl}-1H-indazol-4-yl)-6-methyl-2-pyridinecarboxamide;

N-{6-[6-chloro-5-({[5-methyl-2-(methyloxy)phenyl]sulfonyl}amino)-3-pyridinyl]-1H-indazol-4-yl}-2-methyl-1,3-thiazole-4-carboxamide;

N-(6-{6-chloro-5-[(cyclopropylsulfonyl)amino]-3-pyridinyl}-1H-indazol-4-yl)-2-methyl-1,3-thiazole-4-carboxamide;

N-[6-(2,3-diaminophenyl)-1H-indazol-4-yl]-2-methyl-1,3-thiazole-4-carboxamide;

2-methyl-N-(6-{5-[(methylsulfonyl)amino]-3-pyridinyl}-1H-indazol-4-yl)-1,3-thiazole-4-carboxamide;

N-{6-[4-(aminosulfonyl)phenyl]-1H-indazol-4-yl}-2-methyl-1,3-thiazole-4-carboxamide;

N-(6-{6-chloro-5-[(methylsulfonyl)amino]-3-pyridinyl}-1-methyl-1H-indazol-4-yl)-2-methyl-1,3-thiazole-4-carboxamide;

N-(6-{5-[(cyclopropylsulfonyl)amino]-6-hydroxy-3-pyridinyl}-1H-indazol-4-yl)-2-methyl-1,3-thiazole-4-carboxamide;

N-(6-{6-chloro-5-[(methylsulfonyl)amino]-3-pyridinyl}-1H-indazol-4-yl)-2-methyl-1,3-thiazole-4-carboxamide;

2-methyl-N-(6-{5-[(phenylsulfonyl)amino]-3-pyridinyl}-1H-indazol-4-yl)-1,3-thiazole-4-carboxamide;

N-[6-(5-hydroxy-3-pyridinyl)-1H-indazol-4-yl]-2-methyl-1,3-thiazole-4-carboxamide trifluoroacetate;

N-[6-(3-hydroxyphenyl)-1H-indazol-4-yl]-2-methyl-1,3-thiazole-4-carboxamide;

N-[6-(4-chloro-3-hydroxyphenyl)-1H-indazol-4-yl]-2-methyl-1,3-thiazole-4-carboxamide;

N-[6-(4-hydroxy-3-methylphenyl)-1H-indazol-4-yl]-2-methyl-1,3-thiazole-4-carboxamide;

N-[6-(3-hydroxy-4-methylphenyl)-1H-indazol-4-yl]-2-methyl-1,3-thiazole-4-carboxamide;

N-(6-{4-chloro-3-[(methylsulfonyl)amino]phenyl}-1H-indazol-4-yl)-2-methyl-1,3-thiazole-4-carboxamide;

2-methyl-N-(6-{5-[(methylamino)sulfonyl]-3-pyridinyl}-1H-indazol-4-yl)-1,3-thiazole-4-carboxamide;

N-(6-{5-[(diethylamino)sulfonyl]-3-pyridinyl}-1H-indazol-4-yl)-2-methyl-1,3-thiazole-4-carboxamide;

N-(6-{6-hydroxy-5-[(phenylsulfonyl)amino]-3-pyridinyl}-1H-indazol-4-yl)-2-methyl-1,3-thiazole-4-carboxamide; or N-(6-{6-chloro-5-[(methylsulfonyl)amino]-3-pyridinyl}-1-methyl-1H-indazol-4-yl)-2-{[(2R,6S)-2,6-dimethyl-4-morpholinyl]methyl}-1,3-thiazole-4-carboxamide; or a salt thereof.

9. A compound of formula (I) according to claim 1 in the form of a pharmaceutically acceptable salt thereof.

10. A pharmaceutical composition comprising a compound of formula (I) as defined in claim 1, or a pharmaceutically acceptable salt thereof, and one or more pharmaceutically acceptable excipients.

11. A method of treating a patient suffering from asthma or COPD comprising administering to said patient an effective amount of a compound of formula (I) according to claim 1, or a pharmaceutically acceptable salt thereof, neat or admixed with a pharmaceutically acceptable excipient.

* * * * *